United States Patent
Burns et al.

(10) Patent No.: US 12,084,445 B2
(45) Date of Patent: Sep. 10, 2024

(54) BROAD-SPECTRUM CARBAPENEMS

(71) Applicant: VenatoRx Pharmaceuticals, Inc., Malvern, PA (US)

(72) Inventors: Christopher J. Burns, Malvern, PA (US); Guo-Hua Chu, Exton, PA (US); Jodie Hamrick, New Holland, PA (US); Steven A. Boyd, Chester Springs, PA (US); Stephen M. Condon, Glenmoore, PA (US)

(73) Assignee: VenatoRx Pharmaceuticals, Inc., Malvern, PA (US)

( * ) Notice: Subject to any disclaimer, the term of this patent is extended or adjusted under 35 U.S.C. 154(b) by 873 days.

(21) Appl. No.: 17/057,594

(22) PCT Filed: May 29, 2019

(86) PCT No.: PCT/US2019/034402
§ 371 (c)(1),
(2) Date: Nov. 20, 2020

(87) PCT Pub. No.: WO2019/232053
PCT Pub. Date: Dec. 5, 2019

(65) Prior Publication Data
US 2021/0188851 A1 Jun. 24, 2021

Related U.S. Application Data

(60) Provisional application No. 62/678,151, filed on May 30, 2018.

(51) Int. Cl.
| | |
|---|---|
| *A61K 31/403* | (2006.01) |
| *A61K 45/06* | (2006.01) |
| *A61P 31/04* | (2006.01) |
| *C07D 477/20* | (2006.01) |
| *A61K 31/407* | (2006.01) |

(52) U.S. Cl.
CPC .......... *C07D 477/20* (2013.01); *A61K 31/403* (2013.01); *A61K 45/06* (2013.01); *A61P 31/04* (2018.01); *A61K 31/407* (2013.01)

(58) Field of Classification Search
CPC ..... A61K 31/403; A61K 31/407; A61P 31/04; C07D 477/20
See application file for complete search history.

(56) References Cited

U.S. PATENT DOCUMENTS

| | | | | |
|---|---|---|---|---|
| 5,783,703 | A * | 7/1998 | Hayashi | ............... C07D 417/04 548/193 |
| 2011/0118229 | A1 | 5/2011 | Choi et al. | |
| 2023/0127944 | A1 | 4/2023 | Burns et al. | |

FOREIGN PATENT DOCUMENTS

| | | | | |
|---|---|---|---|---|
| CN | 101328180 | A | 12/2008 | |
| CN | 102731503 | A | 10/2012 | |
| CN | 102757430 | A | 10/2012 | |
| CN | 103012406 | A | 4/2013 | |
| CN | 103113374 | A | 5/2013 | |
| CN | 103275081 | A | 9/2013 | |
| CN | 107501268 | A | 12/2017 | |
| EP | 1113016 | A1 * | 7/2001 | ........... C07D 477/20 |
| EP | 1561748 | A1 | 8/2005 | |
| EP | 1580191 | A1 | 9/2005 | |
| JP | 2003183281 | A | 7/2003 | |
| JP | 2007291048 | A | 11/2007 | |
| TW | 200621778 | A | 7/2006 | |
| WO | WO-2009066917 | A2 | 5/2009 | |
| WO | WO-2010065110 | A2 | 6/2010 | |
| WO | WO-2019232053 | A1 | 12/2019 | |
| WO | WO-2021101620 | A1 | 5/2021 | |

OTHER PUBLICATIONS

Hanaki et al. TOC-39, a novel parenteral broad-spectrum cephalosporin with excellent activity against methicillin-resistant *Staphylococcus aureus*. Antimicrobial Agents and Chemotherapy 39(5):1120-1126 (1995).

Payne et al. Comparative activities of clavulanic acid, sulbactam, and tazobactam against clinically important beta-lactamases. Antimicrob Agents Chemother 38(4):767-72 (1994).

PCT/US2019/034402 International Search Report and Written Opinion dated Sep. 16, 2019.

PCT/US2020/051163 International Search Report and Written Opinion dated Mar. 17, 2021.

PubChem-SID-172127013, Modify Date: Feb. 10, 2014 (Feb. 10, 2014).

Yilmaz et al. Synthesis, structures and anticancer potentials of platinum(II) saccharinate complexes of tertiary phosphines with phenyl and cyclohexyl groups targeting mitochondria and DNA. Eur J Med Chem 155:609-622 (2018).

\* cited by examiner

*Primary Examiner* — Craig D Ricci
*Assistant Examiner* — Janet L Coppins
(74) *Attorney, Agent, or Firm* — WILSON SONSINI GOODRICH & ROSATI

(57) ABSTRACT

The present disclosure provides broad-spectrum carbapenem derivatives and pharmaceutical compositions useful in the treatment of bacterial infections and methods for treating such infections using such derivatives and/or compositions.

12 Claims, No Drawings

BROAD-SPECTRUM CARBAPENEMS

STATEMENT AS TO FEDERALLY SPONSORED RESEARCH

This patent application is a national stage entry of PCT/US2019/034402, filed on May 29, 2019, which claims the benefit of U.S. Provisional Application No. 62/678,151, filed May 30, 2018, which are incorporated herein by reference in their entirety.

CROSS-REFERENCE

This application claims the benefit of U.S. Provisional Application Ser. No. 62/678,151 filed May 30, 2018 which is hereby incorporated by reference in its entirety.

BACKGROUND OF THE INVENTION

Antibiotics are the most effective drugs for curing bacteria-related infectious diseases clinically. They are incredibly valuable therapeutic options that are currently losing efficacy due to the evolution and spread of drug resistance genes. A dramatic increase in the prevalence of infections caused by Multi Drug Resistant (MDR) Gram positive and Gram negative microorganisms is now occurring, both in the hospital and in the community. Carbapenem beta-lactams face two important issues with regard to their utility: (1) inactivity against MDR Gram positive bacteria (e.g. methicillin-resistant *Staphylococcus aureus* (MRSA), vancomycin-resistant *Staphylococcus aureus* (VRSA)), and (2) clinical failure due to spread of beta-lactamase-producing Gram negative Enterobacteriaceae and *Pseudomonas aeruginosa*. There is a growing consensus on the need for agents with activity against these MDR bacteria as first-line empiric treatment of many nosocomial infections, such as pneumonia, skin and soft tissue, intra-abdominal, and complicated urinary tract infections. These infections are caused by either Gram positive or negative pathogens, or a polymicrobial mix potentially including anaerobes. There is a significant need to develop a safe and bactericidal agent with the widest known spectrum of activity, including against MDR Gram-positives, Gram-negatives, and anaerobes, to treat empirically this wide range of infections.

SUMMARY OF THE INVENTION

Described herein are carbapenem compounds that provide significant antibacterial activity in vitro against a range of Gram positive and Gram negative bacteria.

Described herein are compounds of Formula (I), or a pharmaceutically acceptable salt, solvate, or stereoisomer thereof:

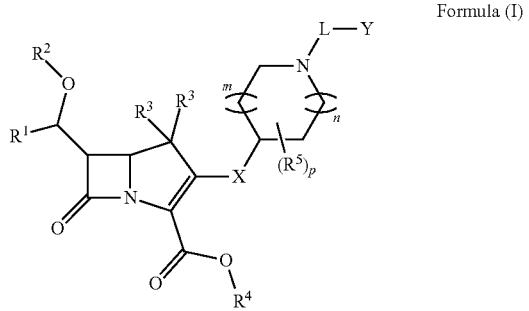

Formula (I)

wherein
Y is
(a) heterocycloalkyl selected from the group consisting of aziridinyl, azetidinyl, pyrrolidinyl, piperidinyl, piperazinyl, morpholinyl, thiomorpholinyl, azepanyl, and homopiperazinyl, each optionally substituted with one, two, or three substituents each independently selected from the group consisting of oxo, optionally substituted $C_1$-$C_6$ alkyl, optionally substituted $C_2$-$C_6$ alkenyl, optionally substituted $C_2$-$C_6$ alkynyl, $-OR^{10}$, $-(CR^{12}R^{13})_{v1}OR^{10}$, $-CN$, $-NO_2$, halogen, $-S(=O)_2R^{14}$, $-(CR^{12}R^{13})_{v1}S(=O)_2R^{14}$, $-S(=O)_2NR^{10}R^{11}$, $-(CR^{12}R^{13})_{v1}S(=O)_2NR^{10}R^{11}$, $-C(=O)OR^{10}$, $-(CR^{12}R^{13})_{v1}C(=O)OR^{10}$, $-C(=O)NR^{10}R^{11}$, $-C(=O)(CR^{12}R^{13})_{v1}NR^{10}R^{11}$, $-(CR^{12}R^{13})_{v1}C(=O)NR^{10}R^{11}$, $-NR^{10}R^{11}$, $-NR^{10}(CR^{12}R^{13})_{w1}NR^{10}R^{11}$, $-NR^{10}C(=NR^{11})NR^{10}R^{11}$, $-C(=NR^{10})NR^{10}R^{11}$, $-C(=NR^{10})R^{10}$, $-N(R^{10})C(=NR^{n})R^{10}$, $-(CR^{12}R^{13})_{v1}NR^{10}R^{11}$, $-(CR^{12}R^{13})_{v1}N(R^{10})C(=NR^{11})NR^{10}R^{11}$, $-(CR^{12}R^{13})_{v1}NR^{10}(CR^{12}R^{13})_{w1}NR^{10}R^{11}$, $-NR^{11}C(=NR^{11})NR^{10}(CR^{12}R^{13})_{w1}NR^{10}R^{11}$, $-NR^{10}(CR^{12}R^{13})_{w1}N(R^{10})C(=NR^{11})NR^{10}R^{11}$, $-(CR^{12}R^{13})_{v1}C(=NR^{11})NR^{10}R^{11}$, $-NR^{10}(CR^{12}R^{13})_{v1}B(OR^{15})_2$, and $-(CR^{12}R^{13})_{v1}NR^{10}(CR^{12}R^{13})_{v1}B(OR^{15})_2$; or
(b) heteroaryl selected from the group consisting of pyridyl, pyrimidinyl, pyridazinyl, and pyrazinyl each optionally substituted with one, two, or three substituents each independently selected from optionally substituted $C_1$-$C_6$ alkyl, optionally substituted $C_2$-$C_6$ alkenyl, optionally substituted $C_2$-$C_6$ alkynyl, $-OR^{20}$, $-(CR^{22}R^{23})_{v2}OR^{20}$, $-CN$, $-NO_2$, halogen, $-S(=O)_2R^{24}$, $-(CR^{22}R^{23})_{v2}S(=O)_2R^{24}$, $-S(=O)_2NR^{20}R^{21}$, $-(CR^{22}R^{23})_{v2}S(=O)_2NR^{20}R^{21}$, $-C(=O)OR^{20}$, $-(CR^{22}R^{23})_{v2}C(=O)OR^{20}$, $-C(=O)NR^{20}R^{21}$, $-C(=O)(CR^{22}R^{23})_{v2}NR^{20}R^{21}$, $-(CR^{22}R^{23})_{v2}C(=O)NR^{20}R^{21}$, $-NR^{20}R^{21}$, $-NR^{20}(CR^{22}R^{23})_{w2}NR^{20}R^{21}$, $-NR^{20}C(=NR^{21})NR^{20}R^{21}$, $-C(=NR^{20})NR^{20}R^{21}$, $-C(=NR^{20})R^{20}$, $-N(R^{20})C(=NR^{21})R^{20}$, $-(CR^{22}R^{23})_{v2}NR^{20}R^{21}$, $-(CR^{22}R^{23})_{v2}N(R^{20})C(=NR^{21})NR^{20}R^{21}$, $-(CR^{22}R^{23})_{v2}NR^{20}(CR^{22}R^{23})_{w2}NR^{20}R^{21}$, $-NR^{21}C(=NR^{21})NR^{20}(CR^{22}R^{23})_{w2}NR^{20}R^{21}$, $-NR^{20}(CR^{22}R^{23})_{w2}N(R^{20})C(=NR^{21})NR^{20}R^{21}$, $-(CR^{22}R^{23})_{v2}C(=NR^{21})NR^{20}R^{21}$, $-NR^{20}(CR^{22}R^{23})_{v2}B(OR^{25})_2$, and $-(CR^{22}R^{23})_{v2}NR^{20}(CR^{22}R^{23})_{v2}B(OR^{25})_2$; provided that at least one of the optional substituent is not $-O(C_3$ alkenyl) when $R^4$ is $C_3$ alkenyl; or
(c) $-NR^{30}R^{31}$, $-NR^{30}(CR^{32}R^{33})_{w3}NR^{30}R^{31}$, $-NR^{30}C(=NR^{31})NR^{30}R^{31}$, $-C(=NR^{30})NR^{30}R^{31}$, $-C(=NR^{30})R^{30}$, $-N(R^{30})C(=NR^{31})R^{30}$, $-(CR^{32}R^{33})_{v3}NR^{30}R^{31}$, $-NR^{31}C(=NR^{31})NR^{30}(CR^{32}R^{33})_{w3}NR^{30}R^{31}$, $-NR^{30}(CR^{32}R^{33})_{w3}N(R^{30})C(=NR^{31})NR^{30}R^{31}$, or $-NR^{30}(CR^{32}R^{33})_{v3}B(OR^{35})_2$ provided that z is not 0;
X is $-O-$, $-S-$, $-S(=O)-$, $-S(=O)_2-$, or $-NR^7-$;
L is $-(CR^8R^9)_z-$ or $-(CR^{18}R^{19})_yC(=O)-$;
$R^1$ is optionally substituted $C_1$-$C_6$ alkyl, optionally substituted $C_2$-$C_6$ alkenyl, or optionally substituted $C_2$-$C_6$ alkynyl; $R^2$ is hydrogen, optionally substituted $C_1$-$C_6$ alkyl, optionally substituted $C_2$-$C_6$ alkenyl, optionally substituted $C_2$-$C_6$ alkynyl, or $-Si(R^c)_3$;
each $R^3$ is independently hydrogen, optionally substituted $C_1$-$C_6$ alkyl, optionally substituted $C_2$-$C_6$ alkenyl, optionally substituted $C_2$-$C_6$ alkynyl, or $-OR^a$;

R⁴ is hydrogen, optionally substituted $C_1$-$C_6$ alkyl, optionally substituted $C_2$-$C_6$ alkenyl, optionally substituted $C_2$-$C_6$ alkynyl, optionally substituted aryl, optionally substituted heteroaryl, optionally substituted $C_3$-$C_8$ cycloalkyl, optionally substituted $C_2$-$C_8$ heterocycloalkyl, optionally substituted —($C_1$-$C_6$ alkyl)($C_3$-$C_8$ cycloalkyl), optionally substituted —($C_1$-$C_6$ alkyl)($C_2$-$C_8$ heterocycloalkyl), optionally substituted —($C_1$-$C_6$ alkyl)(aryl), or optionally substituted —($C_1$-$C_6$ alkyl)(heteroaryl);

each $R^5$ is independently hydrogen, halogen, optionally substituted $C_1$-$C_6$ alkyl, optionally substituted $C_2$-$C_6$ alkenyl, optionally substituted $C_2$-$C_6$ alkynyl, —$OR^{40}$, —$(CR^{42}R^{43})_{v4}OR^{40}$, —CN, —$NO_2$, —$S(=O)_2R^{44}$, —$(CR^{42}R^{43})_{v4}S(=O)_2R^{44}$, —$S(=O)_2NR^{40}R^{41}$, —$(CR^{42}R^{43})_{v4}S(=O)_2NR^{40}R^{41}$, —$C(=O)OR^{40}$, —$(CR^{42}R^{43})_{v4}C(=O)OR^{40}$, —$(CR^{42}R^{43})_{v4}C(=O)NR^{40}R^{41}$, —$NR^{40}R^{41}$, —$NR^{40}(CR^{42}R^{43})_{w4}NR^{40}R^{41}$, —$NR^{40}C(=NR^{41})NR^{40}R^{41}$, —$C(=NR^{40})NR^{40}R^{41}$, —$C(=NR^{40})R^{40}$, —$N(R^{40})C(=NR^{41})R^{40}$, —$(CR^{42}R^{43})_{v4}NR^{40}R^{41}$, —$(CR^{42}R^{43})_{v4}OR^{40}$, —$(CR^{42}R^{43})_{v4}N(R^{40})C(=NR^{41})NR^{40}R^{41}$, —$(CR^{42}R^{43})_{v4}NR^{40}(CR^{42}R^{43})_{w4}NR^{40}R^{41}$, —$NR^{41}C(=NR^{41})NR^{40}(CR^{42}R^{43})_{w4}NR^{40}R^{41}$, —$NR^{40}(CR^{42}R^{43})_{w4}N(R^{40})C(=NR^{41})NR^{40}R^{41}$, —$(CR^{42}R^{43})_{v4}C(=NR^{41})NR^{40}R^{41}$, —$NR^{40}(CR^{42}R^{43})_{v4}B(OR^{45})_2$, or —$(CR^{42}R^{43})_{v4}NR^{40}(CR^{42}R^{43})_{v4}B(OR^{45})_2$;

$R^7$ is hydrogen, optionally substituted $C_1$-$C_6$ alkyl, —$S(=O)_2R^c$, or —$S(=O)_2NR^aR^b$;

each $R^8$ and $R^9$ is independently hydrogen, halogen, —CN, optionally substituted $C_1$-$C_6$ alkyl, optionally substituted $C_2$-$C_6$ alkenyl, optionally substituted $C_2$-$C_6$ alkynyl, —$OR^a$, —$NR^aR^b$, —$C(=O)OR^a$, —$C(=O)NR^aR^b$, —$S(=O)_2R^c$, or —$S(=O)_2NR^aR^b$;

each $R^{18}$ and $R^{19}$ is independently hydrogen, halogen, —CN, optionally substituted $C_1$-$C_6$ alkyl, optionally substituted $C_2$-$C_6$ alkenyl, optionally substituted $C_2$-$C_6$ alkynyl, —$OR^a$, —$NR^aR^b$, —$C(=O)OR^a$, —$C(=O)NR^aR^b$, —$S(=O)_2R^c$, or —$S(=O)_2NR^aR^b$;

each $R^{10}$, $R^{11}$, $R^{20}$, $R^{21}$, $R^{30}$, $R^{31}$, $R^{40}$, and $R^{41}$ is independently selected from the group consisting of hydrogen, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, $C_2$-$C_8$ optionally substituted heterocycloalkyl, optionally substituted aryl, optionally substituted heteroaryl, optionally substituted —($C_1$-$C_6$ alkyl)($C_3$-$C_8$ cycloalkyl), optionally substituted —($C_1$-$C_6$ alkyl)($C_2$-$C_8$ heterocycloalkyl), optionally substituted —($C_1$-$C_6$ alkyl)(aryl), and optionally substituted —($C_1$-$C_6$ alkyl)(heteroaryl);

or $R^{10}$ and $R^{11}$, or $R^{20}$ and $R^{21}$, or $R^{30}$ and $R^{31}$, or $R^{40}$ and $R^{41}$ are taken together with the nitrogen to which they are attached to form an optionally substituted $C_2$-$C_8$ heterocycloalkyl;

each $R^{12}$, $R^{13}$, $R^{22}$, $R^{23}$, $R^{32}$, $R^{33}$, $R^{42}$, and $R^{43}$ is independently selected from the group consisting of hydrogen, halogen, —CN, —$OR^a$, —$NR^aR^b$, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, optionally substituted $C_2$-$C_8$ heterocycloalkyl, optionally substituted aryl, and optionally substituted heteroaryl;

$R^{14}$, $R^{24}$, and $R^{44}$ are independently optionally substituted $C_1$-$C_6$ alkyl, optionally substituted $C_2$-$C_6$ alkenyl, optionally substituted $C_2$-$C_6$ alkynyl, optionally substituted aryl, optionally substituted heteroaryl, optionally substituted $C_3$-$C_8$ cycloalkyl, optionally substituted $C_2$-$C_8$ heterocycloalkyl, optionally substituted —($C_1$-$C_6$ alkyl)($C_3$-$C_8$ cycloalkyl), optionally substituted —($C_1$-$C_6$ alkyl)($C_2$-$C_8$ heterocycloalkyl), optionally substituted —($C_1$-$C_6$ alkyl)(aryl), or optionally substituted —($C_1$-$C_6$ alkyl)(heteroaryl);

each $R^{15}$, $R^{25}$, $R^{35}$, and $R^{45}$ is independently hydrogen or optionally substituted $C_1$-$C_6$ alkyl;

or two $R^{15}$, or two $R^{25}$, or two $R^{35}$, or two $R^{45}$ are taken together with the atoms to which there are attached to form a cyclic boronate ester;

$R^a$ and $R^b$ are independently hydrogen or optionally substituted $C_1$-$C_6$ alkyl;

or $R^a$ and $R^b$ are taken together with the nitrogen to which they are attached to form an optionally substituted $C_2$-$C_8$ heterocycloalkyl;

each $R^c$ is independently optionally substituted $C_1$-$C_6$ alkyl, optionally substituted $C_2$-$C_6$ alkenyl, or optionally substituted $C_2$-$C_6$ alkynyl;

n is 0-2;
m is 0-2;
p is 0-4;
v1, v2, v3, or v4 are independently 1-4;
w1, w2, w3, or w4 are independently 2-4;
y is 1-4; and
z is 0-5.

Also described herein are compounds of Formula (III), or a pharmaceutically acceptable salt, solvate, or stereoisomer thereof:

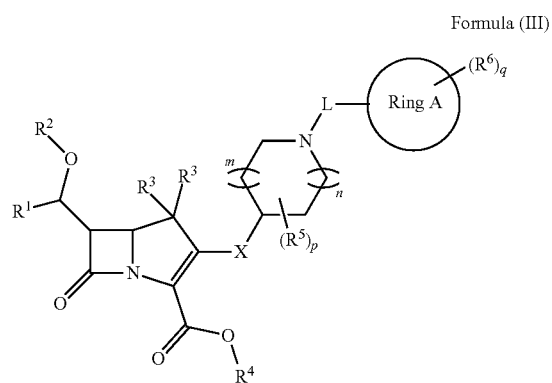

Formula (III)

wherein

Ring A is aryl, heteroaryl, cycloalkyl, or heterocycloalkyl; each optionally substituted with one, two, or three substituents each independently selected from the group consisting of oxo (when Ring A is cycloalkyl or heterocycloalkyl), optionally substituted $C_1$-$C_6$ alkyl, optionally substituted $C_2$-$C_6$ alkenyl, optionally substituted $C_2$-$C_6$ alkynyl, —$OR^{50}$, —$(CR^{52}R^{53})_{v5}OR^{50}$, —CN, —$NO_2$, halogen, —$S(=O)_2R^{54}$, —$(CR^{52}R^{53})_{v5}S(=O)_2R^{54}$, —$S(=O)_2NR^{50}R^{51}$, —$(CR^{52}R^{53})_{v5}S(=O)_2NR^{50}R^{51}$, —$C(=O)OR^{50}$, —$(CR^{52}R^{53})_{v5}C(=O)OR^{10}$, —$C(=O)NR^{50}R^{51}$, and —$(CR^{52}R^{53})_{v5}C(=O)NR^{50}R^{51}$;

X is —O—, —S—, —S(=O)—, —$S(=O)_2$—, or —$NR^7$—;

L is —$(CR^8R^9)_z$— or —$(CR^{18}R^{19})_yC(=O)$—;

$R^1$ is optionally substituted $C_1$-$C_6$ alkyl, optionally substituted $C_2$-$C_6$ alkenyl, or optionally substituted $C_2$-$C_6$ alkynyl;

$R^2$ is hydrogen, optionally substituted $C_1$-$C_6$ alkyl, optionally substituted $C_2$-$C_6$ alkenyl, optionally substituted $C_2$-$C_6$ alkynyl, or —Si($R^c$)$_3$;

each $R^3$ is independently hydrogen, optionally substituted $C_1$-$C_6$ alkyl, optionally substituted $C_2$-$C_6$ alkenyl, optionally substituted $C_2$-$C_6$ alkynyl, or —O$R^a$;

$R^4$ is hydrogen, optionally substituted $C_1$-$C_6$ alkyl, optionally substituted $C_2$-$C_6$ alkenyl, optionally substituted $C_2$-$C_6$ alkynyl, optionally substituted aryl, optionally substituted heteroaryl, optionally substituted $C_3$-$C_8$ cycloalkyl, optionally substituted $C_2$-$C_8$ heterocycloalkyl, optionally substituted —($C_1$-$C_6$ alkyl)($C_3$-$C_8$ cycloalkyl), optionally substituted —($C_1$-$C_6$ alkyl)($C_2$-$C_8$ heterocycloalkyl), optionally substituted —($C_1$-$C_6$ alkyl)(aryl), or optionally substituted —($C_1$-$C_6$ alkyl)(heteroaryl);

each $R^5$ is independently hydrogen, halogen, optionally substituted $C_1$-$C_6$ alkyl, optionally substituted $C_2$-$C_6$ alkenyl, optionally substituted $C_2$-$C_6$ alkynyl, —O$R^{40}$, —(C$R^{42}R^{43}$)$_{v4}$O$R^{40}$, —CN, —NO$_2$, —S(=O)$_2R^{44}$, —(C$R^{42}R^{43}$)$_{v4}$S(=O)$_2R^{44}$, —S(=O)$_2$N$R^{40}R^{41}$, —(C$R^{42}R^{43}$)$_{v4}$S(=O)$_2$N$R^{40}R^{41}$, —C(=O)O$R^{40}$, —(C$R^{42}R^{43}$)$_{v4}$C(=O)O$R^{40}$, —(C$R^{42}R^{43}$)$_{v4}$C(=O)N$R^{40}R^{41}$, —N$R^{40}R^{41}$, —N$R^{40}$(C$R^{42}R^{43}$)$_{v4}$N$R^{40}R^{41}$, —N$R^{40}$C(=N$R^{41}$)N$R^{40}R^{41}$, —C(=N$R^{40}$)N$R^{40}R^{41}$, —C(=N$R^{40}$)$R^{40}$, —N($R^{40}$)C(=N$R^{41}$)$R^{40}$, —(C$R^{42}R^{43}$)$_{v4}$N$R^{40}R^{41}$, —(C$R^{42}R^{43}$)$_{v4}$O$R^{40}$, —(C$R^{42}R^{43}$)$_{v4}$N($R^{40}$)C(=N$R^{41}$)N$R^{40}R^{41}$, —(C$R^{42}R^{43}$)$_{v4}$N$R^{40}$(C$R^{42}R^{43}$)$_{w4}$N$R^{40}R^{41}$, —N$R^{41}$C(=N$R^{41}$)N$R^{40}$(C$R^{42}R^{43}$)$_{w4}$N$R^{40}R^{41}$, —N$R^{40}$(C$R^{42}R^{43}$)$_{w4}$N($R^{40}$)C(=N$R^{41}$)N$R^{40}R^{41}$, —(C$R^{42}R^{43}$)$_{v4}$C(=N$R^{41}$)N$R^{40}R^{41}$, —N$R^{40}$(C$R^{42}R^{43}$)$_{v4}$B(O$R^{45}$)$_2$, or —(C$R^{42}R^{43}$)$_{v4}$N$R^{40}$(C$R^{42}R^{43}$)$_{v4}$B(O$R^{45}$)$_2$;

each $R^6$ is independently a basic substituent;

$R^7$ is hydrogen, optionally substituted $C_1$-$C_6$ alkyl, —S(=O)$_2R^c$, or —S(=O)$_2$N$R^aR^b$;

each $R^8$ and $R^9$ is independently hydrogen, halogen, —CN, optionally substituted $C_1$-$C_6$ alkyl, optionally substituted $C_2$-$C_6$ alkenyl, optionally substituted $C_2$-$C_6$ alkynyl, —O$R^a$, —N$R^aR^b$, —C(=O)O$R^a$, —C(=O)N$R^aR^b$, —S(=O)$_2R^c$, or —S(=O)$_2$N$R^aR^b$;

each $R^{18}$ and $R^{19}$ is independently hydrogen, halogen, —CN, optionally substituted $C_1$-$C_6$ alkyl, optionally substituted $C_2$-$C_6$ alkenyl, optionally substituted $C_2$-$C_6$ alkynyl, —O$R^a$, —N$R^aR^b$, —C(=O)O$R^a$, —C(=O)N$R^aR^b$, —S(=O)$_2R^c$, or —S(=O)$_2$N$R^aR^b$;

each $R^{40}$, $R^{41}$, $R^{50}$, and $R^{51}$ is independently selected from the group consisting of hydrogen, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, $C_2$-$C_8$ optionally substituted heterocycloalkyl, optionally substituted aryl, optionally substituted heteroaryl, optionally substituted —($C_1$-$C_6$ alkyl)($C_3$-$C_8$ cycloalkyl), optionally substituted —($C_1$-$C_6$ alkyl)($C_2$-$C_8$ heterocycloalkyl), optionally substituted —($C_1$-$C_6$ alkyl)(aryl), and optionally substituted —($C_1$-$C_6$ alkyl)(heteroaryl);

or $R^{40}$ and $R^{41}$, or $R^{50}$ and $R^{51}$ are taken together with the nitrogen to which they are attached to form an optionally substituted $C_2$-$C_8$ heterocycloalkyl;

each $R^{42}$, $R^{43}$, $R^{52}$, and $R^{53}$ is independently selected from the group consisting of hydrogen, halogen, —CN, —O$R^a$, —N$R^aR^b$, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, optionally substituted $C_2$-$C_8$ heterocycloalkyl, optionally substituted aryl, and optionally substituted heteroaryl;

each $R^{44}$ and $R^{54}$ is independently optionally substituted $C_1$-$C_6$ alkyl, optionally substituted $C_2$-$C_6$ alkenyl, optionally substituted $C_2$-$C_6$ alkynyl, optionally substituted aryl, optionally substituted heteroaryl, optionally substituted $C_3$-$C_8$ cycloalkyl, optionally substituted $C_2$-$C_8$ heterocycloalkyl, optionally substituted —($C_1$-$C_6$ alkyl)($C_3$-$C_8$ cycloalkyl), optionally substituted —($C_1$-$C_6$ alkyl)($C_2$-$C_8$ heterocycloalkyl), optionally substituted —($C_1$-$C_6$ alkyl)(aryl), or optionally substituted —($C_1$-$C_6$ alkyl)(heteroaryl);

each $R^{45}$ is independently hydrogen or optionally substituted $C_1$-$C_6$ alkyl;

or two $R^{45}$ are taken together with the atoms to which there are attached to form a cyclic boronate ester;

$R^a$ and $R^b$ are independently hydrogen or optionally substituted $C_1$-$C_6$ alkyl;

or $R^a$ and $R^b$ are taken together with the nitrogen to which they are attached to form an optionally substituted $C_2$-$C_8$ heterocycloalkyl;

each $R^c$ is independently optionally substituted $C_1$-$C_6$ alkyl, optionally substituted $C_2$-$C_6$ alkenyl, or optionally substituted $C_2$-$C_6$ alkynyl;

n is 0-2;

m is 0-2;

p is 0-4;

q is 1-4;

v4 and v5 are independently 1-4;

w4 is 2-4;

y is 1-4; and z is 1-5.

Disclosed herein are pharmaceutical compositions comprising a compound disclosed herein, or a pharmaceutically acceptable salt, solvate, or stereoisomer thereof and a pharmaceutically acceptable excipient.

Disclosed herein are pharmaceutical compositions comprising a compound disclosed herein, or a pharmaceutically acceptable salt, solvate, or stereoisomer thereof; a β-lactamase inhibitor; and a pharmaceutically acceptable excipient.

Disclosed herein are methods of treating a bacterial infection in a subject, comprising administering to the subject an effective amount of a compound disclosed herein, or a pharmaceutically acceptable salt, solvate, or stereoisomer thereof.

Disclosed herein are methods of treating a bacterial infection in a subject, comprising administering to the subject an effective amount of a compound disclosed herein, or a pharmaceutically acceptable salt, solvate, or stereoisomer thereof, in combination with a β-lactamase inhibitor.

Described herein are methods of treating a bacterial infection in a subject, comprising administering to the subject a pharmaceutical composition comprising a compound disclosed herein, or a pharmaceutically acceptable salt, solvate, or stereoisomer thereof, and a pharmaceutically acceptable excipient.

Described herein are methods of treating a bacterial infection in a subject, comprising administering to the subject an effective amount of a compound disclosed herein, or a pharmaceutically acceptable salt, solvate, or stereoisomer thereof in combination with a β-lactamase inhibitor.

In some embodiments, the bacterial infection is caused by gram-negative bacteria. In some embodiments, the bacterial infection is caused by gram-positive bacteria. In some embodiments, the bacterial infection is caused by multidrug-resistant (MDR) bacteria. In some embodiments, the bacterial infection is caused by carbapenem resistant Enterobacteriaceae (CRE).

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Decades of clinical use of antibiotics have led to a dramatic increase in the prevalence of infections caused by Multi Drug Resistant (MDR) bacteria. For gram-positive pathogens, methicillin resistant *Staphylococcus aureus* (MRSA) and Penicillin-Resistant pneumococcus (PRP) are increasingly prevalent. For gram-negatives, the extensive use of β-lactam antibiotics has pressured bacteria to develop several mechanisms of resistance, the most widely diffused and efficient of which is the production of Extended Spectrum β-lactamase enzymes (ESBFs) and Ambler Class C cephalosporinases. Because MRSA and ESBF producing gram-negative bacteria frequently demonstrate cross-resistance to other antibiotic classes (e.g., aminoglycosides, quinolones) the choice for treatment of infections has diminished. In addition, the spread of Class A/D (serine) and B (metallo) carbapenemases is now eroding efficacy of carbapenems, which is regarded as the most potent sub class of β-lactams.

Novel carbapenems with activity against MRSA, ESBL and Class C producing Enterobacteriaceae, and *Pseudomonas aeruginosa* would represent a major advance in the treatment of many nosocomial infections. These novel carbapenems may also be paired with a proprietary pan-β-lactamase inhibitor to include even broader coverage of infections from carbapenem resistant Enterobacteriaceae (CRE). These ultra-broad spectrum carbapenems would provide coverage that usually requires co-administration of two or even three antibacterials. This would provide a single product first-line empiric therapy for either gram-positive or negative pathogens, a polymicrobial mix, and/or anaerobes. The present disclosure is directed to certain carbapenem compounds which are antibacterials active against the bacterial Penicillin Binding Proteins (PBPs). Some embodiments include compounds, compositions, pharmaceutical compositions, use and preparation thereof.

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The term "antibiotic" refers to a compound or composition which decreases the viability of a microorganism, or which inhibits the growth or proliferation of a microorganism. The phrase "inhibits the growth or proliferation" means increasing the generation time (i.e., the time required for the bacterial cell to divide or for the population to double) by at least about 2-fold. Examples antibiotics are those which can increase the generation time by at least about 10-fold or more (e.g., at least about 100-fold or even indefinitely, as in total cell death). As used in this disclosure, an antibiotic is further intended to include an antimicrobial, bacteriostatic, or bactericidal agent. Examples of antibiotics suitable for use with respect to the present invention include penicillins, cephalosporins, and carbapenems.

The term "β-lactam antibiotic" refers to a compound with antibiotic properties that contains a β-lactam functionality. Non-limiting examples of β-lactam antibiotics useful with respect to the invention include penicillins, cephalosporins, penems, carbapenems, and monobactams.

The term "β-lactamase" denotes a protein capable of inactivating a β-lactam antibiotic. The β-lactamase can be an enzyme which catalyzes the hydrolysis of the β-lactam ring of a β-lactam antibiotic. Of particular interest herein are microbial β-lactamases. The β-lactamase may be, for example, a serine β-lactamase or a metallo-β-lactamase.

The terms below, as used herein, have the following meanings, unless indicated otherwise:

"Alkyl" refers to a straight or branched chain hydrocarbon monoradical, which is fully saturated, having from one to about ten carbon atoms, or from one to six carbon atoms. Examples of alkyls include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl, and the like. Whenever it appears herein, a numerical range such as "$C_1$-$C_6$ alkyl" or "$C_{1-6}$ alkyl" means that the alkyl group consists of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_1$-$C_{10}$ alkyl, a $C_4$-$C_9$ alkyl, a $C_1$-$C_8$ alkyl, a $C_4$-$C_7$ alkyl, a $C_1$-$C_6$ alkyl, a $C_1$-$C_5$ alkyl, a $C_1$-$C_4$ alkyl, a $C_4$-$C_3$ alkyl, a $C_1$-$C_2$ alkyl, or a $C_1$ alkyl. Unless stated otherwise specifically in the specification, an alkyl group is optionally substituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, the alkyl is optionally substituted with oxo, halogen, —CN, —CF$_3$, —OH, —OMe, —NH$_2$, or —NO$_2$. In some embodiments, the alkyl is optionally substituted with oxo, halogen, —CN, —CF$_3$, —OH, or —OMe. In some embodiments, the alkyl is optionally substituted with halogen.

"Alkenyl" refers to an optionally substituted straight-chain, or optionally substituted branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to ethenyl (—CH=CH$_2$), 1-propenyl (—CH$_2$CH=CH$_2$), isopropenyl [—C(CH$_3$)=CH$_2$], butenyl, 1,3-butadienyl and the like. Whenever it appears herein, a numerical range such as "C$_2$-C$_6$ alkenyl" or "C$_{2-6}$ alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. Unless stated otherwise specifically in the specification, an alkenyl group may be optionally substituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, an alkenyl is optionally substituted with oxo, halogen, —CN, —CF$_3$, —OH, —OMe, —NH$_2$, or —NO$_2$. In some embodiments, an alkenyl is optionally substituted with oxo, halogen, —CN, —CF$_3$, —OH, or —OMe. In some embodiments, the alkenyl is optionally substituted with halogen.

"Alkynyl" refers to an optionally substituted straight-chain or optionally substituted branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "C$_2$-C$_6$ alkynyl" or "C$_{2-6}$ alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. Unless stated otherwise specifically in the specification, an alkynyl group may be optionally substituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, an alkynyl is optionally substituted with oxo, halogen, —CN, —CF$_3$, —OH, —OMe, —NH$_2$, or —NO$_2$. In some embodiments, an alkynyl is optionally substituted with oxo, halogen, —CN, —CF$_3$, —OH, or —OMe. In some embodiments, the alkynyl is optionally substituted with halogen.

"Alkylene" refers to a straight or branched divalent hydrocarbon chain. Unless stated otherwise specifically in the specification, an alkylene group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkylene is optionally substituted with oxo, halogen, —CN, —CF$_3$, —OH, —OMe, —NH$_2$, or —NO$_2$. In some embodiments, an alkylene is optionally substituted with oxo, halogen, —CN, —CF$_3$, —OH, or —OMe. In some embodiments, the alkylene is optionally substituted with halogen.

"Alkoxy" refers to a radical of the formula —OR$_a$ where R$_a$ is an alkyl radical as defined. Unless stated otherwise specifically in the specification, an alkoxy group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkoxy is optionally substituted with oxo, halogen, —CN, —CF$_3$, —OH, —OMe, —NH$_2$, or —NO$_2$. In some embodiments, an alkoxy is optionally substituted with oxo, halogen, —CN, —CF$_3$, —OH, or —OMe. In some embodiments, the alkoxy is optionally substituted with halogen.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl. Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In some embodiments, the aryl is phenyl. Unless stated otherwise specifically in the specification, an aryl may be optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, an aryl is optionally substituted with halogen, methyl, ethyl, —CN, —CF$_3$, —OH, —OMe, —NH$_2$, or —NO$_2$. In some embodiments, an aryl is optionally substituted with halogen, methyl, ethyl, —CN, —CF$_3$, —OH, or —OMe. In some embodiments, the aryl is optionally substituted with halogen.

"Cycloalkyl" refers to a partially or fully saturated, monocyclic or polycyclic carbocyclic ring, which may include fused (when fused with an aryl or a heteroaryl ring, the cycloalkyl is bonded through a non-aromatic ring atom) or bridged ring systems. Representative cycloalkyls include, but are not limited to, cycloalkyls having from three to fifteen carbon atoms (C$_3$-C$_{15}$ cycloalkyl), from three to ten carbon atoms (C$_3$-C$_{10}$ cycloalkyl), from three to eight carbon atoms (C$_3$-C$_8$ cycloalkyl), from three to six carbon atoms (C$_3$-C$_6$ cycloalkyl), from three to five carbon atoms (C$_3$-C$_5$ cycloalkyl), or three to four carbon atoms (C$_3$-C$_4$ cycloalkyl). In some embodiments, the cycloalkyl is a 3- to 6-membered cycloalkyl. In some embodiments, the cycloalkyl is a 5- to 6-membered cycloalkyl. Monocyclic cycloalkyls include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a cycloalkyl is optionally substituted with oxo, halogen, methyl, ethyl, —CN, —CF$_3$, —OH, —OMe, —NH$_2$, or —NO$_2$. In some embodiments, a cycloalkyl is optionally substituted with oxo, halogen, methyl, ethyl, —CN, —CF$_3$, —OH, or —OMe. In some embodiments, the cycloalkyl is optionally substituted with halogen.

"Halo" or "halogen" refers to bromo, chloro, fluoro or iodo. In some embodiments, halogen is fluoro or chloro. In some embodiments, halogen is fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Heterocycloalkyl" refers to a 3- to 24-membered partially or fully saturated ring radical comprising 2 to 23 carbon atoms and from one to 8 heteroatoms selected from nitrogen, oxygen, phosphorous, and sulfur. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon or sulfur atoms in the heterocycloalkyl radical may be optionally oxidized; the nitrogen atom may be optionally quaternized. In some embodiments, the heterocycloalkyl is a 3- to 6-membered heterocycloalkyl. In some embodiments, the heterocycloalkyl is a 5- to 6-membered heterocycloalkyl. Examples of such heterocycloalkyl radicals include, but are not limited to, aziridinyl, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heterocycloalkyl is optionally substituted with oxo, halogen, methyl, ethyl, —CN, —CF$_3$, —OH, —OMe, —NH$_2$, or —NO$_2$. In some embodiments, a heterocycloalkyl is optionally substituted with oxo, halogen, methyl, ethyl, —CN, —CF$_3$, —OH, or —OMe. In some embodiments, the heterocycloalkyl is optionally substituted with halogen.

"Heteroalkyl" refers to an alkyl group in which one or more skeletal atoms of the alkyl are selected from an atom other than carbon, e.g., oxygen, nitrogen (e.g. —NH—, —N(alkyl)-), sulfur, or combinations thereof. A heteroalkyl is attached to the rest of the molecule at a carbon atom of the heteroalkyl. In one aspect, a heteroalkyl is a C$_1$-C$_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, or combinations thereof wherein the heteroalkyl is attached to the rest of the molecule at a carbon atom of the heteroalkyl. Unless stated otherwise specifically in the specification, a heteroalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —CF$_3$, —OH, —OMe, —NH$_2$, or —NO$_2$. In some embodiments, a heteroalkyl is optionally substituted with oxo, halogen, methyl, ethyl, —CN, —CF$_3$, —OH, or —OMe. In some embodiments, the heteroalkyl is optionally substituted with halogen.

"Heteroaryl" refers to a 5- to 14-membered ring system radical comprising hydrogen atoms, one to thirteen carbon atoms, one to six heteroatoms selected from nitrogen, oxygen, phosphorous, and sulfur, and at least one aromatic ring. The heteroaryl radical may be a monocyclic, bicyclic, tricyclic or tetracyclic ring system, which may include fused (when fused with a cycloalkyl or heterocycloalkyl ring, the heteroaryl is bonded through an aromatic ring atom) or bridged ring systems; and the nitrogen, carbon or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl is optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroaryl is optionally substituted with halogen, methyl, ethyl, —CN, —CF$_3$, —OH, —OMe, —NH$_2$, or —NO$_2$. In some embodiments, a heteroaryl is optionally substituted with halogen, methyl, ethyl, —CN, —CF$_3$, —OH, or —OMe. In some embodiments, the heteroaryl is optionally substituted with halogen.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and monosubstituted (e.g., —CH$_2$CHF$_2$, —CH$_2$CF$_3$, —CF$_2$CH$_3$, —CFHCHF$_2$, etc.). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons.

An "effective amount" or "therapeutically effective amount" refers to an amount of a compound administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. In some embodiments, treatment includes administration of a pharmaceutical composition, subsequent to the initiation of a pathologic event or contact with an etiologic agent and includes stabilization of the condition (e.g., condition does not worsen) or alleviation of the condition. In some embodiments, treatment also includes prophylactic treatment (e.g., administration of a composition described herein when an individual is suspected to be suffering from a bacterial infection).

Compounds

Described herein are compounds, or a pharmaceutically acceptable salt, solvate, or stereoisomer thereof, useful in the treatment of bacterial infections. In some embodiments, the bacterial infection is an upper or lower respiratory tract infection, a urinary tract infection, an intra-abdominal infection, a skin infection or septicemia.

Described herein are compounds of Formula (I), or a pharmaceutically acceptable salt, solvate, or stereoisomer thereof:

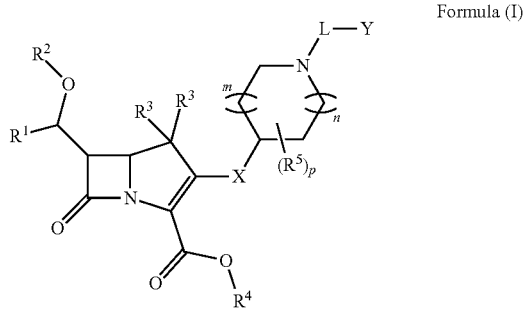

Formula (I)

wherein
Y is
(a) heterocycloalkyl selected from the group consisting of aziridinyl, azetidinyl, pyrrolidinyl, piperidinyl, piperazinyl, morpholinyl, thiomorpholinyl, azepanyl, and homopiperazinyl, each optionally substituted with one, two, or three substituents each independently selected from the group consisting of oxo, optionally substituted C$_1$-C$_6$ alkyl, optionally substituted C$_2$-C$_6$ alkenyl, optionally substituted C$_2$-C$_6$ alkynyl, —OR$^{10}$, —(CR$^{12}$R$^{13}$)$_{v1}$OR$^{10}$, —CN, —NO$_2$, halogen, —S(=O)$_2$R$^{14}$, —(CR$^{12}$R$^{13}$)$_{v1}$S(=O)$_2$R$^{14}$, —S(=O)$_2$NR$^{10}$R$^{11}$, —(CR$^{12}$R$^{13}$)$_{v1}$S(=O)$_2$NR$^{10}$R$^{11}$, —C(=O)OR$^{10}$, —(CR$^{12}$R$^{13}$)$_{v1}$C(=O)OR$^{10}$, —C(=O)NR$^{10}$R$^{11}$, —C(=O)(CR$^{12}$R$^{13}$)$_{v1}$NR$^{10}$R$^{11}$, —(CR$^{12}$R$^{13}$)$_{v1}$C(=O)NR$^{10}$R$^{11}$, —NR$^{10}$R$^{11}$, —NR$^{10}$(CR$^{12}$R$^{13}$)$_{w1}$NR$^{10}$R$^{11}$, —NR$^{10}$C(=NR$^{11}$)NR$^{10}$R$^{11}$, —C(=NR$^{10}$)NR$^{10}$R$^{11}$, —C(=NR$^{10}$)R$^{10}$, —N(R$^{10}$)C(=NR$''$)R$^{10}$, —(CR$^{12}$R$^{13}$)$_{v1}$NR$^{10}$R$^{11}$, —(CR$^{12}$R$^{13}$)$_{v1}$N(R$^{10}$)C(=NR$^{11}$)NR$^{10}$R$^{11}$, —(CR$^{12}$R$^{13}$)$_{v1}$NR$^{10}$(CR$^{12}$R$^{13}$)$_{w1}$NR$^{10}$R$^{11}$, —NR$^{11}$C(=NR$^{11}$)NR$^{10}$(CR$^{12}$R$^{13}$)$_{w1}$NR$^{10}$R$^{11}$, —NR$^{10}$(CR$^{12}$R$^{13}$)$_{w1}$N(R$^{10}$)C(=NR$^{11}$)NR$^{10}$R$^{11}$, —(CR$^{12}$R$^{13}$)$_{v1}$C(=NR$^{11}$)NR$^{10}$R$^{11}$, —NR$^{10}$(CR$^{12}$R$^{13}$)$_{v1}$B(OR$^{15}$)$_2$, and —(CR$^{12}$R$^{13}$)$_{v1}$NR$^{10}$(CR$^{12}$R$^{13}$)$_{v1}$B(OR$^{15}$)$_2$; or (b) heteroaryl selected from the group consisting of pyridyl, pyrimidinyl, pyridazinyl, and pyrazinyl each optionally substituted with one, two, or three substituents each independently selected from the group consisting of optionally substituted C$_1$-C$_6$ alkyl, optionally substituted C$_2$-C$_6$ alkenyl, optionally substituted C$_2$-C$_6$ alkynyl, —OR$^{20}$, —(CR$^{22}$R$^{23}$)$_{v2}$OR$^{20}$, —CN, —NO$_2$, halogen, —S(=O)$_2$R$^{24}$, —(CR$^{22}$R$^{23}$)$_{v2}$S(=O)$_2$R$^{24}$, —S(=O)$_2$NR$^{20}$R$^{21}$, —(CR$^{22}$R$^{23}$)$_{v2}$S(=O)$_2$NR$^{20}$R$^{21}$, —C(=O)OR$^{20}$, —(CR$^{22}$R$^{23}$)$_{v2}$C(=O)OR$^{20}$, —C(=O)NR$^{20}$R$^{21}$, —C(=O)(CR$^{22}$R$^{23}$)$_{v2}$NR$^{20}$R$^{21}$, —(CR$^{22}$R$^{23}$)$_{v2}$C(=O)NR$^{20}$R$^{21}$, —NR$^{20}$R$^{21}$, —NR$^{20}$(CR$^{22}$R$^{23}$)$_{w2}$NR$^{20}$R$^{21}$, —NR$^{20}$C(=NR$^{21}$)NR$^{20}$R$^{21}$, —C(=NR$^{20}$)NR$^{20}$R$^{21}$, —C(=NR$^{20}$)R$^{20}$, —N(R$^{20}$)C(=NR$^{21}$)R$^{20}$, —(CR$^{22}$R$^{23}$)$_{v2}$NR$^{20}$R$^{21}$, —(CR$^{22}$R$^{23}$)$_{v2}$N(R$^{20}$)C(=NR$^{21}$)NR$^{20}$R$^{21}$, —(CR$^{22}$R$^{23}$)$_{v2}$NR$^{20}$(CR$^{22}$R$^{23}$)$_{w2}$NR$^{20}$R$^{21}$, —NR$^{21}$C(=NR$^{21}$)NR$^{20}$(CR$^{22}$R$^{23}$)$_{w2}$NR$^{20}$R$^{21}$, —NR$^{20}$(CR$^{22}$R$^{23}$)$_{w2}$N(R$^{20}$)C(=NR$^{21}$)NR$^{20}$R$^{21}$, —(CR$^{22}$R$^{23}$)$_{v2}$C(=NR$^{21}$)NR$^{20}$R$^{21}$, —NR$^{20}$(CR$^{22}$R$^{23}$)$_{v2}$B(OR$^{25}$)$_2$, and —(CR$^{22}$R$^{23}$)$_{v2}$NR$^{20}$(CR$^{22}$R$^{23}$)$_{v2}$B(OR$^{25}$)$_2$; provided that at least one of the optional substituent is not —O(C$_3$ alkenyl) when R$^4$ is C$_3$ alkenyl; or (c) —NR$^{30}$R$^{31}$, —NR$^{30}$(CR$^{32}$R$^{33}$)$_{w3}$NR$^{30}$R$^{31}$, —NR$^{30}$C(=NR$^{31}$)NR$^{30}$R$^{31}$, —C(=NR$^{30}$)NR$^{30}$R$^{31}$, —C(=NR$^{30}$)R$^{30}$, —N(R$^{30}$)C(=NR$^{31}$)R$^{30}$, —(CR$^{32}$R$^{33}$)$_{v3}$NR$^{30}$R$^{31}$, —NR$^{31}$C(=NR$^{31}$)NR$^{30}$(CR$^{32}$R$^{33}$)$_{w3}$NR$^{30}$R$^{31}$, —NR$^{30}$(CR$^{32}$R$^{33}$)$_{w3}$N(R$^{30}$)C(=NR$^{31}$)NR$^{30}$R$^{31}$, or —NR$^{30}$(CR$^{32}$R$^{33}$)$_{v3}$B(OR$^{35}$)$_2$ provided that z is not 0;

X is —O—, —S—, —S(=O)—, —S(=O)$_2$—, or —NR$^7$—;

L is —(CR$^8$R$^9$)$_z$— or —(CR$^{18}$R$^{19}$)$_y$C(=O)—;

R$^1$ is optionally substituted C$_1$-C$_6$ alkyl, optionally substituted C$_2$-C$_6$ alkenyl, or optionally substituted C$_2$-C$_6$ alkynyl;

R$^2$ is hydrogen, optionally substituted C$_1$-C$_6$ alkyl, optionally substituted C$_2$-C$_6$ alkenyl, optionally substituted C$_2$-C$_6$ alkynyl, or —Si(R$^c$)$_3$;

each R$^3$ is independently hydrogen, optionally substituted C$_1$-C$_6$ alkyl, optionally substituted C$_2$-C$_6$ alkenyl, optionally substituted C$_2$-C$_6$ alkynyl, or —OR$^a$;

R$^4$ is hydrogen, optionally substituted C$_1$-C$_6$ alkyl, optionally substituted C$_2$-C$_6$ alkenyl, optionally substituted C$_2$-C$_6$ alkynyl, optionally substituted aryl, optionally substituted heteroaryl, optionally substituted C$_3$-C$_8$ cycloalkyl, optionally substituted C$_2$-C$_8$ heterocycloalkyl, optionally substituted —(C$_1$-C$_6$ alkyl)(C$_3$-C$_8$ cycloalkyl), optionally substituted —(C$_1$-C$_6$ alkyl)(C$_2$-

C$_8$ heterocycloalkyl), optionally substituted —(C$_1$-C$_6$ alkyl)(aryl), or optionally substituted —(C$_1$-C$_6$ alkyl)(heteroaryl);

each R$^5$ is independently hydrogen, halogen, optionally substituted C$_1$-C$_6$ alkyl, optionally substituted C$_2$-C$_6$ alkenyl, optionally substituted C$_2$-C$_6$ alkynyl, —OR$^{40}$, —(CR$^{42}$R$^{43}$)$_{v4}$OR$^{40}$, —CN, —NO$_2$, —S(═O)$_2$R$^{44}$, —(CR$^{42}$R$^{43}$)$_{v4}$S(═O)$_2$R$^{44}$, —S(═O)$_2$NR$^{40}$R$^{41}$, —(CR$^{42}$R$^{43}$)$_{v4}$S(═O)$_2$NR$^{40}$R$^{41}$, —C(═O)OR$^{40}$, —(CR$^{42}$R$^{43}$)$_{v4}$C(═O)OR$^{40}$, —(CR$^{42}$R$^{43}$)$_{v4}$C(═O)NR$^{40}$R$^{41}$, —NR$^{40}$R$^{41}$, —NR$^{40}$(CR$^{42}$R$^{43}$)$_{w4}$NR$^{40}$R$^{41}$, —NR$^{40}$C(═NR$^{41}$)NR$^{40}$R$^{41}$, —C(═NR$^{40}$)NR$^{40}$R$^{41}$, —C(═NR$^{40}$)R$^{40}$, —N(R$^{40}$)C(═NR$^{41}$)R$^{40}$, —(CR$^{42}$R$^{43}$)$_{v4}$NR$^{40}$R$^{41}$, —(CR$^{42}$R$^{43}$)$_{v4}$OR$^{40}$, —(CR$^{42}$R$^{43}$)$_{v4}$N(R$^{40}$)C(═NR$^{41}$)NR$^{40}$R$^{41}$, —(CR$^{42}$R$^{43}$)$_{v4}$NR$^{40}$(CR$^{42}$R$^{43}$)$_{w4}$NR$^{40}$R$^{41}$, —NR$^{41}$C(═NR$^{41}$)NR$^{40}$(CR$^{42}$R$^{43}$)$_{w4}$NR$^{40}$R$^{41}$, —NR$^{40}$(CR$^{42}$R$^{43}$)$_{w4}$N(R$^{40}$)C(═NR$^{41}$)NR$^{40}$R$^{41}$, —(CR$^{42}$R$^{43}$)$_{v4}$C(═NR$^{41}$)NR$^{40}$R$^{41}$, —NR$^{40}$(CR$^{42}$R$^{43}$)$_{v4}$B(OR$^{45}$)$_2$, or —(CR$^{42}$R$^{43}$)$_{v4}$NR$^{40}$(CR$^{42}$R$^{43}$)$_{v4}$B(OR$^{45}$)$_2$;

R$^7$ is hydrogen, optionally substituted C$_1$-C$_6$ alkyl, —S(═O)$_2$R$^c$, or —S(═O)$_2$NR$^a$R$^b$;

each R$^8$ and R$^9$ is independently hydrogen, halogen, —CN, optionally substituted C$_1$-C$_6$ alkyl, optionally substituted C$_2$-C$_6$ alkenyl, optionally substituted C$_2$-C$_6$ alkynyl, —OR$^a$, —NR$^a$R$^b$, —C(═O)OR$^a$, —C(═O)NR$^a$R$^b$, —S(═O)$_2$R$^c$, or —S(═O)$_2$NR$^a$R$^b$;

each R$^{18}$ and R$^{19}$ is independently hydrogen, halogen, —CN, optionally substituted C$_1$-C$_6$ alkyl, optionally substituted C$_2$-C$_6$ alkenyl, optionally substituted C$_2$-C$_6$ alkynyl, —OR$^a$, —NR$^a$R$^b$, —C(═O)OR$^a$, —C(═O)NR$^a$R$^b$, —S(═O)$_2$R$^c$, or —S(═O)$_2$NR$^a$R$^b$;

each R$^{10}$, R$^{11}$, R$^{20}$, R$^{21}$, R$^{30}$, R$^{31}$, R$^{40}$, and R$^{41}$ is independently selected from the group consisting of hydrogen, optionally substituted C$_1$-C$_6$ alkyl, optionally substituted C$_2$-C$_6$ alkenyl, optionally substituted C$_2$-C$_6$ alkynyl, optionally substituted C$_3$-C$_8$ cycloalkyl, C$_2$-C$_8$ optionally substituted heterocycloalkyl, optionally substituted aryl, optionally substituted heteroaryl, optionally substituted —(C$_1$-C$_6$ alkyl)(C$_3$-C$_8$ cycloalkyl), optionally substituted —(C$_1$-C$_6$ alkyl)(C$_2$-C$_8$ heterocycloalkyl), optionally substituted —(C$_1$-C$_6$ alkyl)(aryl), and optionally substituted —(C$_1$-C$_6$ alkyl)(heteroaryl);

or R$^{10}$ and R$^{11}$, or R$^{20}$ and R$^{21}$, or R$^{30}$ and R$^{31}$, or R$^{40}$ and R$^{41}$ are taken together with the nitrogen to which they are attached to form an optionally substituted C$_2$-C$_8$ heterocycloalkyl;

each R$^{12}$, R$^{13}$, R$^{22}$, R$^{23}$, R$^{32}$, R$^{33}$, R$^{42}$, and R$^{43}$ is independently selected from the group consisting of hydrogen, halogen, —CN, —OR$^a$, —NR$^a$R$^b$, optionally substituted C$_1$-C$_6$ alkyl, optionally substituted C$_2$-C$_6$ alkenyl, optionally substituted C$_2$-C$_6$ alkynyl, optionally substituted C$_3$-C$_8$ cycloalkyl, optionally substituted C$_2$-C$_8$ heterocycloalkyl, optionally substituted aryl, and optionally substituted heteroaryl;

R$^{14}$, R$^{24}$, and R$^{44}$ are independently optionally substituted C$_1$-C$_6$ alkyl, optionally substituted C$_2$-C$_6$ alkenyl, optionally substituted C$_2$-C$_6$ alkynyl, optionally substituted aryl, optionally substituted heteroaryl, optionally substituted C$_3$-C$_8$ cycloalkyl, optionally substituted C$_2$-C$_8$ heterocycloalkyl, optionally substituted —(C$_1$-C$_6$ alkyl)(C$_3$-C$_8$ cycloalkyl), optionally substituted —(C$_1$-C$_6$ alkyl)(C$_2$-C$_8$ heterocycloalkyl), optionally substituted —(C$_1$-C$_6$ alkyl)(aryl), or optionally substituted —(C$_1$-C$_6$ alkyl)(heteroaryl);

each R$^{15}$, R$^{25}$, R$^{35}$, and R$^{45}$ is independently hydrogen or optionally substituted C$_1$-C$_6$ alkyl;

or two R$^{15}$, or two R$^{25}$, or two R$^{35}$, or two R$^{45}$ are taken together with the atoms to which there are attached to form a cyclic boronate ester;

R$^a$ and R$^b$ are independently hydrogen or optionally substituted C$_1$-C$_6$ alkyl;

or R$^a$ and R$^b$ are taken together with the nitrogen to which they are attached to form an optionally substituted C$_2$-C$_8$ heterocycloalkyl;

each R$^c$ is independently optionally substituted C$_1$-C$_6$ alkyl, optionally substituted C$_2$-C$_6$ alkenyl, or optionally substituted C$_2$-C$_6$ alkynyl;

n is 0-2;

m is 0-2;

p is 0-4;

v1, v2, v3, and v4 are independently 1-4;

w1, w2, w3, and w4 are independently 2-4;

y is 1-4; and z is 0-5.

In some embodiments of a compound of Formula (I), X is —S—. In some embodiments of a compound of Formula (I), X is —O—. In some embodiments of a compound of Formula (I), X is —S(═O)—. In some embodiments of a compound of Formula (I), X is —S(═O)$_2$—. In some embodiments of a compound of Formula (I), X is —NR$^7$—. In some embodiments of a compound of Formula (I), X is —NR$^7$— and R$^7$ is hydrogen.

In some embodiments of a compound of Formula (I), R$^1$ is C$_1$-C$_6$ alkyl. In some embodiments of a compound of Formula (I), R$^1$ is methyl. In some embodiments of a compound of Formula (I), R$^1$ is C$_2$-C$_6$ alkenyl. In some embodiments of a compound of Formula (I), R$^1$ is C$_2$-C$_6$ alkynyl.

In some embodiments of a compound of Formula (I) R$^2$ is hydrogen. In some embodiments of a compound of Formula (I), R$^2$ is C$_1$-C$_6$ alkyl. In some embodiments of a compound of Formula (I), R$^2$ is methyl. In some embodiments of a compound of Formula (I), R$^2$ is C$_2$-C$_6$ alkenyl. In some embodiments of a compound of Formula (I), R$^2$ is C$_2$-C$_6$ alkynyl. In some embodiments of a compound of Formula (I), R$^2$ is —Si(R$^c$)$_3$.

In some embodiments of a compound of Formula (I), each R$^3$ is hydrogen. In some embodiments of a compound of Formula (I), each R$^3$ is independently hydrogen or C$_1$-C$_6$ alkyl. In some embodiments of a compound of Formula (I), each R$^3$ is independently hydrogen, C$_1$-C$_6$ alkyl, or OR$^a$. In some embodiments of a compound of Formula (I), each R$^3$ is independently hydrogen, C$_1$-C$_6$ alkyl, or OH. In some embodiments of a compound of Formula (I), each R$^3$ is independently C$_1$-C$_6$ alkyl. In some embodiments of a compound of Formula (I), one R$^3$ is methyl and the other R$^3$ is hydrogen. In some embodiments of a compound of Formula (I), each R$^3$ is independently hydrogen or C$_2$-C$_6$ alkenyl. In some embodiments of a compound of Formula (I), each R$^3$ is independently hydrogen or C$_2$-C$_6$ alkynyl.

In some embodiments of a compound of Formula (I), R$^4$ is hydrogen. In some embodiments of a compound of Formula (I), R$^4$ is C$_1$-C$_6$ alkyl. In some embodiments of a compound of Formula (I), R$^4$ is C$_2$-C$_6$ alkenyl. In some embodiments of a compound of Formula (I), R$^4$ is not C$_3$ alkenyl. In some embodiments of a compound of Formula (I), R$^4$ is C$_2$-C$_6$ alkynyl. In some embodiments of a compound of Formula (I), R$^4$ is optionally substituted —(C$_1$-C$_6$ alkyl)(aryl). In some embodiments of a compound of Formula (I), R$^4$ is —(C$_1$-C$_6$ alkyl)(aryl) substituted with alkyl or —NO$_2$.

In some embodiments a compound of Formula (I), or a pharmaceutically acceptable salt, solvate, or stereoisomer thereof, is of Formula (Ia), or a pharmaceutically acceptable salt, solvate, or stereoisomer thereof:

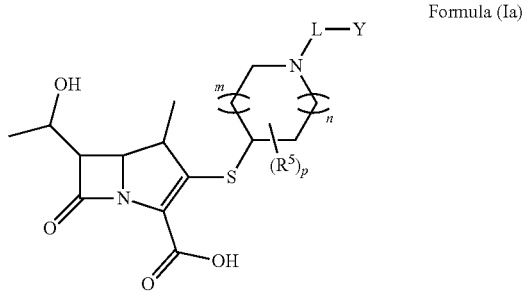

Formula (Ia)

wherein
Y is
(a) heterocycloalkyl selected from the group consisting of aziridinyl, azetidinyl, pyrrolidinyl, piperidinyl, piperazinyl, morpholinyl, thiomorpholinyl, azepanyl, and homopiperazinyl, each optionally substituted with one, two, or three substituents each independently selected from the group consisting of oxo, optionally substituted $C_1$-$C_6$ alkyl, optionally substituted $C_2$-$C_6$ alkenyl, optionally substituted $C_2$-$C_6$ alkynyl, —$OR^{10}$, —$(CR^{12}R^{13})_{v1}OR^{10}$, —CN, —$NO_2$, halogen, —$S(=O)_2R^{14}$, —$(CR^{12}R^{13})_{v1}S(=O)_2R^{14}$, —$S(=O)_2NR^{10}R^{11}$, —$(CR^{12}R^{13})_{v1}S(=O)_2NR^{10}R^{11}$, —$C(=O)OR^{10}$, —$(CR^{12}R^{13})_{v1}C(=O)OR^{10}$, —$C(=O)NR^{10}R^{11}$, —$C(=O)(CR^{12}R^{13})_{v1}NR^{10}R^{11}$, —$(CR^{12}R^{13})_{v1}C(=O)NR^{10}R^{11}$, —$NR^{10}R^{11}$, —$NR^{10}(CR^{12}R^{13})_{w1}NR^{10}R^{11}$, —$NR^{10}C(=NR^{11})NR^{10}R^{11}$, —$C(=NR^{10})NR^{10}R^{11}$, —$C(=NR^{10})R^{10}$, —$N(R^{10})C(=NR^{11})R^{10}$, —$(CR^{12}R^{13})_{v1}NR^{10}R^{11}$, —$(CR^{12}R^{13})_{v1}N(R^{10})C(=NR^{11})NR^{10}R^{11}$, —$(CR^{12}R^{13})_{v1}NR^{10}(CR^{12}R^{13})_{w1}NR^{10}R^{11}$, —$NR^{11}C(=NR^{11})NR^{10}(CR^{12}R^{13})_{w1}NR^{10}R^{11}$, —$NR^{10}(CR^{12}R^{13})_{w1}N(R^{10})C(=NR^{11})NR^{10}R^{11}$, —$(CR^{12}R^{13})_{v1}C(=NR^{11})NR^{10}R^{11}$, —$NR^{10}(CR^{12}R^{13})_{v1}B(OR^{15})_2$, and —$(CR^{12}R^{13})_{v1}NR^{10}(CR^{12}R^{13})_{v1}B(OR^{15})_2$; or (b) heteroaryl selected from the group consisting of pyridyl, pyrimidinyl, pyridazinyl, and pyrazinyl each optionally substituted with one, two, or three substituents each independently selected from the group consisting of optionally substituted $C_1$-$C_6$ alkyl, optionally substituted $C_2$-$C_6$ alkenyl, optionally substituted $C_2$-$C_6$ alkynyl, —$OR^{20}$, —$(CR^{22}R^{23})_{v2}OR^{20}$, —CN, —$NO_2$, halogen, —$S(=O)_2R^{24}$, —$(CR^{22}R^{23})_{v2}S(=O)_2R^{24}$, —$S(=O)_2NR^{20}R^{21}$, —$(CR^{22}R^{23})_{v2}S(=O)_2NR^{20}R^{21}$, —$C(=O)OR^{20}$, —$(CR^{22}R^{23})_{v2}C(=O)OR^{20}$, —$C(=O)NR^{20}R^{21}$, —$C(=O)(CR^{22}R^{23})_{v2}NR^{20}R^{21}$, —$(CR^{22}R^{23})_{v2}C(=O)NR^{20}R^{21}$, —$NR^{20}R^{21}$, —$NR^{20}(CR^{22}R^{23})_{w2}NR^{20}R^{21}$, —$NR^{20}C(=NR^{21})NR^{20}R^{21}$, —$C(=NR^{20})NR^{20}R^{21}$, —$C(=NR^{20})R^{20}$, —$N(R^{20})C(=NR^{21})R^{20}$, —$(CR^{22}R^{23})_{v2}NR^{20}R^{21}$, —$(CR^{22}R^{23})_{v2}N(R^{20})C(=NR^{21})NR^{20}R^{21}$, —$(CR^{22}R^{23})_{v2}NR^{20}(CR^{22}R^{23})_{w2}NR^{20}R^{21}$, —$NR^{21}C(=NR^{21})NR^{20}(CR^{22}R^{23})_{w2}NR^{20}R^{21}$, —$NR^{20}(CR^{22}R^{23})_{w2}N(R^{20})C(=NR^{21})NR^{20}R^{21}$, —$(CR^{22}R^{23})_{v2}C(=NR^{21})NR^{20}R^{21}$, —$NR^{20}(CR^{22}R^{23})_{v2}B(OR^{25})_2$, and —$(CR^{22}R^{23})_{v2}NR^{20}(CR^{22}R^{23})_{v2}B(OR^{25})_2$; or (c) —$NR^{30}R^{31}$, —$NR^{30}(CR^{32}R^{33})_{w3}NR^{30}R^{31}$, —$NR^{30}C(=NR^{31})NR^{30}R^{31}$, —$C(=NR^{30})NR^{30}R^{31}$, —$C(=NR^{30})R^{30}$, —$N(R^{30})C(=NR^{31})R^{30}$, —$(CR^{32}R^{33})_{v3}NR^{30}R^{31}$, —$NR^{31}C(=NR^{31})NR^{30}(CR^{32}R^{33})_{w3}NR^{30}R^{31}$, —$NR^{30}(CR^{32}R^{33})_{w3}N(R^{30})C(=NR^{31})NR^{30}R^{31}$, or —$NR^{30}(CR^{32}R^{33})_{v3}B(OR^{35})_2$ provided that z is not 0;

L is —$(CR^8R^9)_z$— or —$(CR^{18}R^{19})_xC(=O)$—;
each $R^5$ is independently hydrogen, halogen, optionally substituted $C_1$-$C_6$ alkyl, optionally substituted $C_2$-$C_6$ alkenyl, optionally substituted $C_2$-$C_6$ alkynyl, —$OR^{40}$, —$(CR^{42}R^{43})_{v4}OR^{40}$, —CN, —$NO_2$, —$S(=O)_2R^{44}$, —$(CR^{42}R^{43})_{v4}S(=O)_2R^{44}$, —$S(=O)_2NR^{40}R^{41}$, —$(CR^{42}R^{43})_{v4}S(=O)_2NR^{40}R^{41}$, —$C(=O)OR^{40}$, —$(CR^{42}R^{43})_{v4}C(=O)OR^{40}$, —$(CR^{42}R^{43})_{v4}C(=O)NR^{40}R^{41}$, —$NR^{40}R^{41}$, —$NR^{40}(CR^{42}R^{43})_{w4}NR^{40}R^{41}$, —$NR^{40}C(=NR^{41})NR^{40}R^{41}$, —$C(=NR^{40})NR^{40}R^{41}$, —$C(=NR^{40})R^{40}$, —$N(R^{40})C(=NR^{41})R^{40}$, —$(CR^{42}R^{43})_{v4}NR^{40}R^{41}$, —$(CR^{42}R^{43})_{v4}OR^{40}$, —$(CR^{42}R^{43})_{v4}N(R^{40})C(=NR^{41})NR^{40}R^{41}$, —$(CR^{42}R^{43})_{w4}NR^{40}(CR^{42}R^{43})_{w4}NR^{40}R^{41}$, —$NR^{41}C(=NR^{41})NR^{40}(CR^{42}R^{43})_{w4}NR^{40}R^{41}$, —$NR^{40}(CR^{42}R^{43})_{w4}N(R^{40})C(=NR^{41})NR^{40}R^{41}$, —$(CR^{42}R^{43})_{v4}C(=NR^{41})NR^{40}R^{41}$, —$NR^{40}(CR^{42}R^{43})_{v4}B(OR^{45})_2$, or —$(CR^{42}R^{43})_{v4}NR^{40}(CR^{42}R^{43})_{v4}B(OR^{45})_2$;

each $R^8$ and $R^9$ is independently hydrogen, halogen, —CN, optionally substituted $C_1$-$C_6$ alkyl, optionally substituted $C_2$-$C_6$ alkenyl, optionally substituted $C_2$-$C_6$ alkynyl, —$OR^a$, —$NR^aR^b$, —$C(=O)OR^a$, —$C(=O)NR^aR^b$, —$S(=O)_2R^c$, or —$S(=O)_2NR^aR^b$;

each $R^{18}$ and $R^{19}$ is independently hydrogen, halogen, —CN, optionally substituted $C_1$-$C_6$ alkyl, optionally substituted $C_2$-$C_6$ alkenyl, optionally substituted $C_2$-$C_6$ alkynyl, —$OR^a$, —$NR^aR^b$, —$C(=O)OR^a$, —$C(=O)NR^aR^b$, —$S(=O)_2R^c$, or —$S(=O)_2NR^aR^b$;

each $R^{10}$, $R^{11}$, $R^{20}$, $R^{21}$, $R^{30}$, $R^{31}$, $R^{40}$, and $R^{41}$ is independently selected from the group consisting of hydrogen, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, $C_2$-$C_8$ optionally substituted heterocycloalkyl, optionally substituted aryl, optionally substituted heteroaryl, optionally substituted —$(C_1$-$C_6$ alkyl)($C_3$-$C_8$ cycloalkyl), optionally substituted —$(C_1$-$C_6$ alkyl)($C_2$-$C_8$ heterocycloalkyl), optionally substituted —$(C_1$-$C_6$ alkyl)(aryl), and optionally substituted —$(C_1$-$C_6$ alkyl)(heteroaryl);

or $R^{10}$ and $R^{11}$, or $R^{20}$ and $R^{21}$, or $R^{30}$ and $R^{31}$, or $R^{40}$ and $R^{41}$ are taken together with the nitrogen to which they are attached to form an optionally substituted $C_2$-$C_8$ heterocycloalkyl;

each $R^{12}$, $R^{13}$, $R^{22}$, $R^{23}$, $R^{32}$, $R^{33}$, $R^{42}$, and $R^{43}$ is independently selected from the group consisting of hydrogen, halogen, —CN, —$OR^a$, —$NR^aR^b$, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, optionally substituted $C_2$-$C_8$ heterocycloalkyl, optionally substituted aryl, and optionally substituted heteroaryl;

$R^{14}$, $R^{24}$, and $R^{44}$ are independently optionally substituted $C_1$-$C_6$ alkyl, optionally substituted $C_2$-$C_6$ alkenyl, optionally substituted $C_2$-$C_6$ alkynyl, optionally substituted aryl, optionally substituted heteroaryl, optionally substituted $C_3$-$C_8$ cycloalkyl, optionally substituted $C_2$-$C_8$ heterocycloalkyl, optionally substituted —$(C_1$-$C_6$ alkyl)($C_3$-$C_8$ cycloalkyl), optionally substituted —$(C_1$-$C_6$ alkyl)($C_2$-$C_8$ heterocycloalkyl), optionally substituted —$(C_1$-$C_6$ alkyl)(aryl), or optionally substituted —$(C_1$-$C_6$ alkyl)(heteroaryl);

each $R^{15}$, $R^{25}$, $R^{35}$, and $R^{45}$ is independently hydrogen or optionally substituted $C_1$-$C_6$ alkyl;

or two $R^{15}$, or two $R^{25}$, or two $R^{35}$, or two $R^{45}$ are taken together with the atoms to which there are attached to form a cyclic boronate ester;

$R^a$ and $R^b$ are independently hydrogen or optionally substituted $C_1$-$C_6$ alkyl;

or $R^a$ and $R^b$ are taken together with the nitrogen to which they are attached to form an optionally substituted $C_2$-$C_8$ heterocycloalkyl;

each $R^c$ is independently optionally substituted $C_1$-$C_6$ alkyl, optionally substituted $C_2$-$C_6$ alkenyl, or optionally substituted $C_2$-$C_6$ alkynyl;

n is 0-2;
m is 0-2;
p is 0-4;
v1, v2, v3, and v4 are independently 1-4;
w1, w2, w3, and w4 are independently 2-4; and
z is 0-5.

In some embodiments of a compound of Formula (I) or (Ia), or a pharmaceutically acceptable salt, solvate, or stereoisomer thereof, is of Formula (Ia-1), or a pharmaceutically acceptable salt, solvate, or stereoisomer thereof:

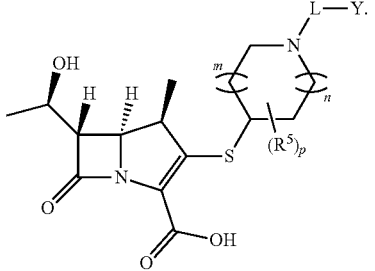

Formula (Ia-1)

In some embodiments of a compound of Formula (I), (Ia), or (Ia-1), n is 1 or 2 and m is 0-2. In some embodiments of a compound of Formula (I), (Ia), or (Ia-1), n is 0 or 1 and m is 0 or 1.

In some embodiments of a compound of Formula (I), (Ia), or (Ia-1), n is 0 and m is 0. In some embodiments of a compound of Formula (I), (Ia), or (Ia-1), n is 0 and m is 1. In some embodiments of a compound of Formula (I), (Ia), or (Ia-1), n is 0 and m is 2.

In some embodiments of a compound of Formula (I), (Ia), or (Ia-1), n is 1 and m is 0. In some embodiments of a compound of Formula (I), (Ia), or (Ia-1) n is 1 and m is 1. In some embodiments of a compound of Formula (I), (Ia), or (Ia-1), n is 1 and m is 2.

In some embodiments of a compound of Formula (I), (Ia), or (Ia-1), n is 2 and m is 0. In some embodiments of a compound of Formula (I), (Ia), or (Ia-1) n is 2 and m is 1. In some embodiments of a compound of Formula (I), (Ia), or (Ia-1) n is 2 and m is 2.

In some embodiments of a compound of Formula (I), (Ia), or (Ia-1), n is 0 and m is 0 or n is 1 and m is 0.

In some embodiments of a compound of Formula (I), (Ia), or (Ia-1), L is —(CR$^8$R$^9$)$_z$—. In some embodiments of a compound of Formula (I), (Ia), or (Ia-1), z is 0. In some embodiments of a compound of Formula (I), (Ia), or (Ia-1), z is not 0. In some embodiments of a compound of Formula (I), (Ia), or (Ia-1), z is 0-5. In some embodiments of a compound of Formula (I), (Ia), or (Ia-1), z is 0-4. In some embodiments of a compound of Formula (I), (Ia), or (Ia-1), z is 0-3. In some embodiments of a compound of Formula (I), (Ia), or (Ia-1), z is 0-2. In some embodiments of a compound of Formula (I), (Ia), or (Ia-1), z is 0 or 1. In some embodiments of a compound of Formula (I), (Ia), or (Ia-1), z is 1-3. In some embodiments of a compound of Formula (I), (Ia), or (Ia-1), z is 1 or 2. In some embodiments of a compound of Formula (I), (Ia), or (Ia-1), z is 1. In some embodiments of a compound of Formula (I), (Ia), or (Ia-1), z is 2. In some embodiments of a compound of Formula (I), (Ia), or (Ia-1), z is 3. In some embodiments of a compound of Formula (I), (Ia), or (Ia-1), z is 4. In some embodiments of a compound of Formula (I), (Ia), or (Ia-1), z is 5. In some embodiments of a compound of Formula (I), (Ia), or (Ia-1), each $R^8$ and $R^9$ is independently hydrogen, halogen, —CN, optionally substituted $C_1$-$C_6$ alkyl, —OR$^a$, or —NR$^a$R$^b$. In some embodiments of a compound of Formula (I), (Ia), or (Ia-1), each $R^8$ and $R^9$ is independently hydrogen, halogen, —CN, $C_1$-$C_6$ alkyl, $C_1$-$C_6$ haloalkyl, —OR$^a$, or —NR$^a$R$^b$. In some embodiments of a compound of Formula (I), (Ia), or (Ia-1), each $R^8$ and $R^9$ is independently hydrogen, halogen, $C_1$-$C_6$ alkyl, or $C_1$-$C_6$ haloalkyl. In some embodiments of a compound of Formula (I), (Ia), or (Ia-1), each $R^8$ and $R^9$ are independently hydrogen, halogen, or $C_1$-$C_6$ alkyl. In some embodiments of a compound of Formula (I), (Ia), or (Ia-1), each $R^8$ and $R^9$ is independently hydrogen or $C_1$-$C_6$ alkyl. In some embodiments of a compound of Formula (I), (Ia), or (Ia-1), each $R^8$ and $R^9$ is independently hydrogen or methyl. In some embodiments of a compound of Formula (I), (Ia), or (Ia-1), each $R^8$ and $R^9$ is independently hydrogen or halogen. In some embodiments of a compound of Formula (I), (Ia), or (Ia-1), each $R^8$ and $R^9$ is hydrogen.

In some embodiments of a compound of Formula (I), (Ia), or (Ia-1), L is —(CR$^{18}$R$^{19}$)$_y$C(=O)—. In some embodiments of a compound of Formula (I), (Ia), or (Ia-1), y is 1-3. In some embodiments of a compound of Formula (I), (Ia), or (Ia-1), y is 1 or 2. In some embodiments of a compound of Formula (I), (Ia), or (Ia-1), y is 1. In some embodiments of a compound of Formula (I), (Ia), or (Ia-1), y is 2. In some embodiments of a compound of Formula (I), (Ia), or (Ia-1), y is 3. In some embodiments of a compound of Formula (I), (Ia), or (Ia-1), y is 4. In some embodiments of a compound of Formula (I), (Ia), or (Ia-1), each $R^{18}$ and $R^{19}$ is independently hydrogen, halogen, —CN, optionally substituted $C_1$-$C_6$ alkyl, —OR$^a$, or —NR$^a$R$^b$. In some embodiments of a compound of Formula (I), (Ia), or (Ia-1), each $R^{18}$ and $R^{11}$ is independently hydrogen, halogen, or $C_1$-$C_6$ alkyl. In some embodiments of a compound of Formula (I), (Ia), or (Ia-1), each $R^{18}$ and $R^{19}$ is independently hydrogen or $C_1$-$C_6$ alkyl. In some embodiments of a compound of Formula (I), (Ia), or (Ia-1), each $R^{18}$ and $R^{19}$ is independently hydrogen or methyl. In some embodiments of a compound of Formula (I), (Ia), or (Ia-1), each $R^{18}$ and $R^{19}$ is independently hydrogen or halogen. In some embodiments of a compound of Formula (I), (Ia), or (Ia-1), each $R^{18}$ and $R^{19}$ is hydrogen.

In some embodiments of a compound of Formula (I), (Ia), or (Ia-1), p is 0. In some embodiments of a compound of Formula (I), (Ia), or (Ia-1), p is 1. In some embodiments of a compound of Formula (I), (Ia), or (Ia-1), p is 2. In some embodiments of a compound of Formula (I), (Ia), or (Ia-1), p is 3. In some embodiments of a compound of Formula (I), (Ia), or (Ia-1), p is 4. In some embodiments of a compound of Formula (I), (Ia), or (Ia-1), each $R^5$ is independently hydrogen, halogen, optionally substituted $C_1$-$C_6$ alkyl, —OR$^{40}$, —(CR$^{42}$R$^{43}$)$_{v4}$OR$^{40}$, —CN, —NO$_2$, or —NR$^{40}$R$^{41}$. In some embodiments of a compound of Formula (I), (Ia), or (Ia-1), each $R^5$ is independently hydrogen, halogen, or $C_1$-$C_6$ alkyl. In some embodiments of a compound of Formula (I), (Ia), or (Ia-1), each $R^5$ is hydrogen. In some embodiments of a compound of Formula (I), (Ia), or (Ia-1), each $R^5$ is independently halogen or optionally substituted $C_1$-$C_6$ alkyl. In some embodiments of a compound of Formula (I), (Ia), or (Ia-1), each $R^5$ is independently optionally substituted $C_1$-$C_6$ alkyl. In some embodiments of a compound of Formula (I), (Ia), or (Ia-1), each $R^5$ is optionally substituted methyl. In some embodiments of a compound of Formula (I), (Ia), or (Ia-1), each $R^5$ is independently $C_1$-$C_6$ alkyl or $C_1$-$C_6$ hydroxyalkyl. In some embodiments of a compound of Formula (I), (Ia), or (Ia-1), each $R^5$ is independently methyl or —$CH_2OH$. In some embodiments of a compound of Formula (I), (Ia), or (Ia-1), Y is heterocycloalkyl selected from the group consisting of aziridinyl, azetidinyl, pyrrolidinyl, piperidinyl, piperazinyl, morpholinyl, thiomorpholinyl, azepanyl, and homopiperazinyl, each optionally substituted with one, two, or three substituents each independently selected from the group consisting of oxo, optionally substituted $C_1$-$C_6$ alkyl, optionally substituted $C_2$-$C_6$ alkenyl, optionally substituted $C_2$-$C_6$ alkynyl, —$OR^{10}$, —$(CR^{12}R^{13})_{v1}OR^{10}$, —CN, —$NO_2$, halogen, —$S(=O)_2R^{14}$, —$(CR^{12}R^{13})_{v1}S(=O)_2R^{14}$, —$S(=O)_2NR^{10}R^{11}$, —$(CR^{12}R^{13})_{v1}S(=O)_2NR^{10}R^{11}$, —$C(=O)OR^{10}$, —$(CR^{12}R^{13})_{v1}C(=O)OR^{10}$, —$C(=O)NR^{10}R^{11}$, —$C(=O)(CR^{12}R^{13})_{v1}NR^{10}R^{11}$, —$(CR^{12}R^{13})_{v1}C(=O)NR^{10}R^{11}$, —$NR^{10}R^{11}$, —$NR^{10}(CR^{12}R^{13})_{w1}NR^{10}R^{11}$, —$NR^{10}C(=NR^{11})NR^{10}R^{11}$, —$C(=NR^{10})NR^{10}R^{11}$, —$C(=NR^{10})R^{10}$, —$N(R^{10})C(=NR'')R^{10}$, —$(CR^{12}R^{13})_{v1}NR^{10}R^{11}$, —$(CR^{12}R^{13})_{v1}N(R^{10})C(=NR^{11})NR^{10}R^{11}$, —$(CR^{12}R^{13})_{v1}NR^{10}(CR^{12}R^{13})_{w1}NR^{10}R^{11}$, —$NR^{11}C(=NR^{11})NR^{10}(CR^{12}R^{13})_{w1}NR^{10}R^{11}$, —$NR^{10}(CR^{12}R^{13})_{w1}N(R^{10})C(=NR^{11})NR^{10}R^{11}$, —$(CR^{12}R^{13})_{v1}C(=NR^{11})NR^{10}R^{11}$, —$NR^{10}(CR^{12}R^{13})_{v1}B(OR^{15})_2$, and —$(CR^{12}R^{13})_{v1}NR^{10}(CR^{12}R^{13})_{v1}B(OR^{15})_2$.

In some embodiments of a compound of Formula (I), (Ia), or (Ia-1), Y is optionally substituted heterocycloalkyl selected from the group consisting of aziridinyl, azetidinyl, pyrrolidinyl, piperidinyl, piperazinyl, morpholinyl, thiomorpholinyl, azepanyl, and homopiperazinyl.

In some embodiments of a compound of Formula (I), (Ia), or (Ia-1), Y is optionally substituted pyrrolidinyl, optionally substituted piperidinyl, optionally substituted piperazinyl, or optionally substituted morpholinyl. In some embodiments of a compound of Formula (I), (Ia), or (Ia-1), Y is optionally substituted piperidinyl. In some embodiments of a compound of Formula (I), (Ia), or (Ia-1), Y is optionally substituted pyrrolidinyl. In some embodiments of a compound of Formula (I), (Ia), or (Ia-1), Y is optionally substituted piperazinyl. In some embodiments of a compound of Formula (I), (Ia), or (Ia-1), Y is optionally substituted morpholinyl.

In some embodiments of a compound of Formula (I), (Ia), or (Ia-1), Y is pyrrolidinyl, piperidinyl, piperazinyl, or morpholinyl, each optionally substituted with one, two, or three substituents each independently selected from the group consisting of $C_1$-$C_6$ alkyl, $C_1$-$C_6$ haloalkyl, halogen, —$S(=O)_2R^{14}$, —$NR^{10}R^{11}$, —$(CR^{12}R^{13})_{v1}NR^{10}R^{11}$, —$C(=NR^{10})NR^{10}R^{11}$, —$NR^{10}C(=NR^{11})NR^{10}R^{11}$, —$C(=NR^{10})R^{10}$, —$C(=O)NR^{10}R^{11}$, —$C(=O)(CR^{12}R^{13})_{v1}NR^{10}R^{11}$, —$(CR^{12}R^{13})_{v1}C(=O)NR^{10}R^{11}$, —$(CR^{12}R^{13})_{v1}OR^{10}$, and —$NR^{10}(CR^{12}R^{13})_{v1}B(OR^{15})_2$. In some embodiments of a compound of Formula (I), (Ia), or (Ia-1), Y is pyrrolidinyl or piperidinyl, each optionally substituted with one, two, or three substituents each independently selected from the group consisting of $C_1$-$C_6$ alkyl, $C_1$-$C_6$ haloalkyl, halogen, —$S(=O)_2R^{14}$, —$NR^{10}R^{11}$, —$(CR^{12}R^{13})_{v1}NR^{10}R^{11}$, —$C(=NR^{10})NR^{10}R^{11}$, —$NR^{10}C(=NR^{11})NR^{10}R^{11}$, —$C(=NR^{10})R^{10}$, —$C(=O)NR^{10}R^{11}$, —$C(=O)(CR^{12}R^{13})_{v1}NR^{10}R^{11}$, —$(CR^{12}R^{13})_{v1}C(=O)NR^{10}R^{11}$, —$(CR^{12}R^{13})_{v1}OR^{10}$, and —$NR^{10}(CR^{12}R^{13})_{v1}B(OR^{15})_2$.

In some embodiments of a compound of Formula (I), (Ia), or (Ia-1), Y is pyrrolidinyl, piperidinyl, piperazinyl, or morpholinyl, each optionally substituted with one, two, or three substituents each independently selected from the group consisting of $C_1$-$C_6$ alkyl, $C_1$-$C_6$ haloalkyl, halogen, —$S(=O)_2R^{14}$, —$NR^{10}R^{11}$, —$(CR^{12}R^{13})_{v1}NR^{10}R^{11}$, —$C(=NR^{10})NR^{10}R^{11}$, —$C(=NR^{10})R^{10}$, —$C(=O)NR^{10}R^{11}$, —$C(=O)(CR^{12}R^{13})_{v1}NR^{10}R^{11}$, —$(CR^{12}R^{13})_{v1}C(=O)NR^{10}R^{11}$, —$(CR^{12}R^{13})_{v1}OR^{10}$, and —$NR^{10}(CR^{12}R^{13})_{v1}B(OR^{15})_2$. In some embodiments of a compound of Formula (I), (Ia), or (Ia-1), Y is pyrrolidinyl, piperidinyl, piperazinyl, or morpholinyl, each optionally substituted with one, two, or three substituents each independently selected from the group consisting of $C_1$-$C_6$ alkyl, $C_1$-$C_6$ haloalkyl, halogen, —$S(=O)_2R^{14}$, —$NR^{10}R^{11}$, —$(CR^{12}R^{13})_{v1}NR^{10}R^{11}$, —$C(=NR^{10})NR^{10}R^{11}$, —$C(=NR^{10})R^{10}$, —$C(=O)NR^{10}R^{11}$, —$C(=O)(CR^{12}R^{13})_{v1}NR^{10}R^{11}$, —$(CR^{12}R^{13})_{v1}C(=O)NR^{10}R^{11}$, and —$(CR^{12}R^{13})_{v1}OR^{10}$.

In some embodiments of a compound of Formula (I), (Ia), or (Ia-1), Y is pyrrolidinyl, piperidinyl, or piperazinyl, each optionally substituted with one, two, or three substituents each independently selected from the group consisting of $C_1$-$C_6$ alkyl, $C_1$-$C_6$ haloalkyl, halogen, —$S(=O)_2R^{14}$, —$NR^{10}R^{11}$, —$(CR^{12}R^{13})_{v1}NR^{10}R^{11}$, —$C(=NR^{10})NR^{10}R^{11}$, —$C(=NR^{10})R^{10}$, —$C(=O)NR^{10}R^{11}$, —$C(=O)(CR^{12}R^{13})_{v1}NR^{10}R^{11}$, —$(CR^{12}R^{13})_{v1}C(=O)NR^{10}R^{11}$, —$(CR^{12}R^{13})_{v1}OR^{10}$, and —$NR^{10}(CR^{12}R^{13})_{v1}B(OR^{15})_2$.

In some embodiments of a compound of Formula (I), (Ia), or (Ia-1), Y is pyrrolidinyl, piperidinyl, or piperazinyl, each optionally substituted with one, two, or three substituents each independently selected from the group consisting of $C_1$-$C_6$ alkyl, $C_1$-$C_6$ haloalkyl, halogen, —$S(=O)_2R^{14}$, —$NR^{10}R^{11}$, —$(CR^{12}R^{13})_{v1}NR^{10}R^{11}$, —$C(=NR^{10})NR^{10}R^{11}$, —$C(=NR^{10})R^{10}$, —$C(=O)NR^{10}R^{11}$, —$C(=O)(CR^{12}R^{13})_{v1}NR^{10}R^{11}$, —$(CR^{12}R^{13})_{v1}C(=O)NR^{10}R^{11}$, and —$(CR^{12}R^{13})_{v1}OR^{10}$.

In some embodiments of a compound of Formula (I), (Ia), or (Ia-1), Y is pyrrolidinyl, piperidinyl, or piperazinyl, each optionally substituted with one, two, or three substituents each independently selected from the group consisting of $C_1$-$C_6$ alkyl, $C_1$-$C_6$ haloalkyl, halogen, —$S(=O)_2R^{14}$, —$NR^{10}R^{11}$, —$(CR^{12}R^{13})_{v1}NR^{10}R^{11}$, —$C(=NR^{10})NR^{10}R^{11}$, and —$NR^{10}(CR^{12}R^{13})_{v1}B(OR^{15})_2$.

In some embodiments of a compound of Formula (I), (Ia), or (Ia-1), Y is pyrrolidinyl or piperidinyl, each optionally substituted with one, two, or three substituents each independently selected from the group consisting of $C_1$-$C_6$ alkyl, $C_1$-$C_6$ haloalkyl, halogen, —$S(=O)_2R^{14}$, —$NR^{10}R^{11}$, —$(CR^{12}R^{13})_{v1}NR^{10}R^{11}$, —$C(=NR^{10})NR^{10}R^{11}$, and —$(CR^{12}R^{13})_{v1}OR^{10}$.

In some embodiments of a compound of Formula (I), (Ia), or (Ia-1), Y is pyrrolidinyl or piperidinyl, each optionally substituted with one, two, or three substituents each independently selected from the group consisting of $C_1$-$C_6$ alkyl, $C_1$-$C_6$ haloalkyl, halogen, —$S(=O)_2R^{14}$, —$NR^{10}R^{11}$, —$(CR^{12}R^{13})_{v1}NR^{10}R^{11}$, —$C(=NR^{10})NR^{10}R^{11}$, —$C(=NR^{10})R^{10}$, —$C(=O)NR^{10}R^{11}$, —$C(=O)(CR^{12}R^{13})_{v1}NR^{10}R^{11}$, —$(CR^{12}R^{13})_{v1}C(=O)NR^{10}R^{11}$, and —$(CR^{12}R^{13})_{v1}OR^{10}$.

In some embodiments of a compound of Formula (I), (Ia), or (Ia-1), Y is pyrrolidinyl or piperidinyl, each optionally substituted with one, two, or three substituents each independently selected from the group consisting of $C_1$-$C_6$ alkyl, $C_1$-$C_6$ haloalkyl, halogen, —S(=O)$_2$R$^{14}$, —NR$^{10}$R$^{11}$, —(CR$^{12}$R$^{13}$)$_{v1}$NR$^{10}$R$^{11}$, —C(=NR$^{10}$)NR$^{10}$R$^{11}$, and —NR$^{10}$(CR$^{12}$R$^{13}$)$_{v1}$B(OR$^{15}$)$_2$.

In some embodiments of a compound of Formula (I), (Ia), or (Ia-1), Y is pyrrolidinyl or piperidinyl, each optionally substituted with one, two, or three substituents each independently selected from the group consisting of $C_1$-$C_6$ alkyl, $C_1$-$C_6$ haloalkyl, halogen, —S(=O)$_2$R$^{14}$, —NR$^{10}$R$^{11}$, —(CR$^{12}$R$^{13}$)$_{v1}$NR$^{10}$R$^{11}$, —C(=NR$^{10}$)NR$^{10}$R$^{11}$, and —(CR$^{12}$R$^{13}$)$_{v1}$OR$^{10}$.

In some embodiments of a compound of Formula (I), (Ia), or (Ia-1), Y is unsubstituted piperidinyl, unsubstituted pyrrolidinyl, unsubstituted piperazinyl, or unsubstituted morpholinyl. In some embodiments of a compound of Formula (I), (Ia), or (Ia-1), Y is unsubstituted piperidinyl. In some embodiments of a compound of Formula (I), (Ia), or (Ia-1), Y is unsubstituted pyrrolidinyl. In some embodiments of a compound of Formula (I), (Ia), or (Ia-1), Y is unsubstituted piperazinyl. In some embodiments of a compound of Formula (I), (Ia), or (Ia-1), Y is unsubstituted morpholinyl.

In some embodiments of a compound of Formula (I), (Ia), or (Ia-1), Y is heteroaryl selected from the group consisting of pyridyl, pyrimidinyl, pyridazinyl, and pyrazinyl each optionally substituted with one, two, or three substituents each independently selected from the group consisting of optionally substituted $C_1$-$C_6$ alkyl, optionally substituted $C_2$-$C_6$ alkenyl, optionally substituted $C_2$-$C_6$ alkynyl, —OR$^{20}$, —(CR$^{22}$R$^{23}$)$_{v2}$OR$^{20}$, —CN, —NO$_2$, halogen, —S(=O)$_2$R$^{24}$, —(CR$^{22}$R$^{23}$)$_{v2}$S(=O)$_2$R$^{24}$, —S(=O)$_2$NR$^{20}$R$^{21}$, —(CR$^{22}$R$^{23}$)$_{v2}$S(=O)$_2$NR$^{20}$R$^{21}$, —C(=O)OR$^{20}$, —(CR$^{22}$R$^{23}$)$_{v2}$C(=O)OR$^{20}$, —C(=O)NR$^{20}$R$^{21}$, —C(=O)(CR$^{22}$R$^{23}$)$_{v2}$NR$^{20}$R$^{21}$, —(CR$^{22}$R$^{23}$)$_{v2}$C(=O)NR$^{20}$R$^{21}$, —NR$^{20}$R$^{21}$, —NR$^{20}$(CR$^{22}$R$^{23}$)$_{w2}$NR$^{20}$R$^{21}$, —NR$^{20}$C(=NR$^{21}$)NR$^{20}$R$^{21}$, —C(=NR$^{20}$)NR$^{20}$R$^{21}$, —C(=NR$^{20}$)R$^{20}$, —N(R$^{20}$)C(=NR$^{21}$)R$^{20}$, —(CR$^{22}$R$^{23}$)$_{v2}$NR$^{20}$R$^{21}$, —(CR$^{22}$R$^{23}$)$_{v2}$N(R$^{20}$)C(=NR$^{21}$)NR$^{20}$R$^{21}$, —(CR$^{22}$R$^{23}$)$_{v2}$NR$^{20}$(CR$^{22}$R$^{23}$)$_{w2}$NR$^{20}$R$^{21}$, —NR$^{21}$C(=NR$^{21}$)NR$^{20}$(CR$^{22}$R$^{23}$)$_{w2}$NR$^{20}$R$^{21}$, —NR$^{20}$(CR$^{22}$R$^{23}$)$_{w2}$N(R$^{20}$)C(=NR$^{21}$)NR$^{20}$R$^{21}$, —(CR$^{22}$R$^{23}$)$_{v2}$C(=NR$^{21}$)NR$^{20}$R$^{21}$, —NR$^{20}$(CR$^{22}$R$^{23}$)$_{v2}$B(OR$^{25}$)$_2$, and —(CR$^{22}$R$^{23}$)$_{v2}$NR$^{20}$(CR$^{22}$R$^{23}$)$_{v2}$B(OR$^{25}$)$_2$; provided that at least one of the optional substituent is not —O($C_3$ alkenyl) when R$^4$ is $C_3$ alkenyl.

In some embodiments of a compound of Formula (I), (Ia), or (Ia-1), Y is optionally substituted heteroaryl selected from the group consisting of pyridyl, pyrimidinyl, pyridazinyl, and pyrazinyl.

In some embodiments of a compound of Formula (I), (Ia), or (Ia-1), Y is unsubstituted pyridyl. In some embodiments of a compound of Formula (I), (Ia), or (Ia-1), Y is unsubstituted pyrimidinyl. In some embodiments of a compound of Formula (I), (Ia), or (Ia-1), Y is unsubstituted pyridazinyl. In some embodiments of a compound of Formula (I), (Ia), or (Ia-1), Y is unsubstituted pyrazinyl.

In some embodiments of a compound of Formula (I), (Ia), or (Ia-1), Y is optionally substituted pyridyl. In some embodiments of a compound of Formula (I), (Ia), or (Ia-1), Y is pyridyl, pyrimidinyl, pyridazinyl, and pyrazinyl, each optionally substituted with one, two, or three substituents each independently selected from the group consisting of $C_1$-$C_6$ alkyl, $C_1$-$C_6$ haloalkyl, halogen, —S(=O)$_2$R$^{24}$, —NR$^{20}$R$^{21}$, —(CR$^{22}$R$^{23}$)$_{v2}$NR$^{20}$R$^{21}$, —C(=NR$^{20}$)NR$^{20}$R$^{21}$, —C(=NR$^{20}$)R$^{20}$, —C(=O)NR$^{20}$R$^{21}$, —C(=O)(CR$^{22}$R$^{23}$)$_{v1}$NR$^{20}$R$^{21}$, —(CR$^{22}$R$^{23}$)$_{v2}$C(=O)NR$^{20}$R$^{21}$, —(CR$^{22}$R$^{23}$)$_{v2}$OR$^{20}$, and —NR$^{20}$(CR$^{22}$R$^{23}$)$_{v2}$B(OR$^{25}$)$_2$.

In some embodiments of a compound of Formula (I), (Ia), or (Ia-1), Y is pyridyl optionally substituted with one, two, or three substituents each independently selected from the group consisting of $C_1$-$C_6$ alkyl, $C_1$-$C_6$ haloalkyl, halogen, —S(=O)$_2$R$^{24}$, —NR$^{20}$R$^{21}$, —(CR$^{22}$R$^{23}$)$_{v2}$NR$^{20}$R$^{21}$, —C(=NR$^{20}$)NR$^{20}$R$^{21}$, —C(=NR$^{20}$)R$^{20}$, —C(=O)NR$^{20}$R$^{21}$, —C(=O)(CR$^{22}$R$^{23}$)$_{v2}$NR$^{20}$R$^{21}$, —(CR$^{22}$R$^{23}$)$_{v2}$C(=O)NR$^{20}$R$^{21}$, —(CR$^{22}$R$^{23}$)$_{v2}$OR$^{20}$, and —NR$^{20}$(CR$^{22}$R$^{23}$)$_{v2}$B(OR$^{25}$)$_2$.

In some embodiments of a compound of Formula (I), (Ia), or (Ia-1), Y is pyridyl optionally substituted with one, two, or three substituents each independently selected from the group consisting of $C_1$-$C_6$ alkyl, $C_1$-$C_6$ haloalkyl, halogen, —NR$^{20}$R$^{21}$, —(CR$^{22}$R$^{23}$)$_{v2}$NR$^{20}$R$^{21}$, and —C(=NR$^{20}$)NR$^{20}$R$^{21}$.

In some embodiments of a compound of Formula (I), (Ia), or (Ia-1), Y is —NR$^{30}$R$^{31}$, —NR$^{30}$(CR$^{32}$R$^{33}$)$_{w3}$NR$^{30}$R$^{31}$, —NR$^{30}$C(=NR$^{31}$)NR$^{30}$R$^{31}$, —C(=NR$^{30}$)NR$^{30}$R$^{31}$, —C(=NR$^{30}$)R$^{30}$, —N(R$^{30}$)C(=NR$^{31}$)R$^{30}$, —(CR$^{32}$R$^{33}$)$_{v3}$NR$^{30}$R$^{31}$, —NR$^{31}$C(=NR$^{31}$)NR$^{30}$(CR$^{32}$R$^{33}$)$_{w3}$NR$^{30}$R$^{31}$, —NR$^{30}$(CR$^{32}$R$^{33}$)$_{w3}$N(R$^{30}$)C(=NR$^{31}$)NR$^{30}$R$^{31}$, or —NR$^{30}$(CR$^{32}$R$^{33}$)$_{v3}$B(OR$^{35}$)$_2$; provided that z is not 0.

In some embodiments of a compound of Formula (I), (Ia), or (Ia-1), Y is —NR$^{30}$R$^{31}$. In some embodiments of a compound of Formula (I), (Ia), or (Ia-1), Y is —NR$^{30}$C(=NR$^{31}$)NR$^{30}$R$^{31}$, —C(=NR$^{30}$)NR$^{30}$R$^{31}$, or —N(R$^{30}$)C(=NR$^{31}$)R$^{30}$. In some embodiments of a compound of Formula (I), (Ia), or (Ia-1), Y is —NR$^{30}$(CR$^{32}$R$^{33}$)$_{w3}$NR$^{30}$R$^{31}$, —(CR$^{32}$R$^{33}$)$_{v3}$NR$^{30}$R$^{31}$, —NR$^{31}$C(=NR$^{31}$)NR$^{30}$(CR$^{32}$R$^{33}$)$_{w3}$NR$^{30}$R$^{31}$, or —NR$^{30}$(CR$^{32}$R$^{33}$)$_{w3}$N(R$^{30}$)C(=NR$^{31}$)NR$^{30}$R$^{31}$. In some embodiments of a compound of Formula (I), (Ia), or (Ia-1), Y is —NR$^{30}$(CR$^{32}$R$^{33}$)$_{v3}$B(OR$^{35}$)$_2$.

In some embodiments of a compound of Formula (I), (Ia), or (Ia-1), R$^{10}$, R$^{11}$, R$^{20}$, R$^{21}$, R$^{30}$, R$^{31}$, R$^{40}$, and R$^{41}$ are independently selected from the group consisting of hydrogen, optionally substituted $C_1$-$C_6$ alkyl, optionally substituted $C_3$-$C_8$ cycloalkyl, or $C_2$-$C_8$ optionally substituted heterocycloalkyl. In some embodiments of a compound of Formula (I), (Ia), or (Ia-1), R$^{10}$, R$^{11}$, R$^{20}$, R$^{21}$, R$^{30}$, R$^{31}$, R$^{40}$, and R$^{41}$ are independently selected from the group consisting of hydrogen or optionally substituted $C_1$-$C_6$ alkyl. In some embodiments of a compound of Formula (I), (Ia), or (Ia-1), R$^{10}$, R$^{11}$, R$^{20}$, R$^{21}$, R$^{30}$, R$^{31}$, R$^{40}$, and R$^{41}$ are hydrogen. In some embodiments of a compound of Formula (I), (Ia), or (Ia-1), R$^{10}$ and R$^{11}$, or R$^{20}$ and R$^{21}$, or R$^{30}$ and R$^{31}$, or R$^{40}$ and R$^{41}$ are taken together with the nitrogen to which they are attached to form an optionally substituted $C_2$-$C_8$ heterocycloalkyl. In some embodiments of a compound of Formula (I), (Ia), or (Ia-1), R$^{10}$ and R$^{11}$, or R$^{20}$ and R$^{21}$, or R$^{30}$ and R$^{31}$, or R$^{40}$ and R$^{41}$ are taken together with the nitrogen to which they are attached to form an optionally substituted aziridine, azetidine, pyrrolidine, piperidine, morpholine, or piperazine. In some embodiments of a compound of Formula (I), (Ia), or (Ia-1), R$^{10}$ and R$^{11}$, or R$^{20}$ and R$^{21}$, or R$^{30}$ and R$^{31}$, or R$^{40}$ and R$^{41}$ are taken together with the nitrogen to which they are attached to form a pyrrolidine, piperidine, morpholine, or piperazine.

In some embodiments of a compound of Formula (I), (Ia), or (Ia-1), each R$^{12}$, R$^{13}$, R$^{22}$, R$^{23}$, R$^{32}$, R$^{33}$, R$^{42}$, and R$^{43}$ is independently selected from the group consisting of hydrogen, halogen, —CN, —OR$^a$, —NR$^a$R$^b$, or optionally substituted $C_1$-$C_6$ alkyl. In some embodiments of a compound of Formula (I), (Ia), or (Ia-1), each R$^{12}$, R$^{13}$, R$^{22}$, R$^{23}$, R$^{32}$, R$^{33}$, R$^{42}$, and R$^{43}$ is independently selected from the group consisting of hydrogen, halogen, —NR$^a$R$^b$, or $C_1$-$C_6$ alkyl. In some embodiments of a compound of Formula (I), (Ia), or (Ia-1), each $R^{12}$, $R^{13}$, $R^{22}$, $R^{23}$, $R^{32}$, $R^{33}$, $R^{42}$, and $R^{43}$ is hydrogen or $C_1$-$C_6$ alkyl. In some embodiments of a compound of Formula (I), (Ia), or (Ia-1), each $R^{12}$, $R^{13}$, $R^{22}$, $R^{23}$, $R^{32}$, $R^{33}$, $R^{42}$, and $R^{43}$ is hydrogen or halogen. In some embodiments of a compound of Formula (I), (Ia), or (Ia-1), each $R^{12}$, $R^{13}$, $R^{22}$, $R^{23}$, $R^{32}$, $R^{33}$, $R^{42}$, and $R^{43}$ is hydrogen or —$NR^aR^b$.

In some embodiments of a compound of Formula (I), (Ia), or (Ia-1), $R^{14}$, $R^{24}$, and $R^{44}$ are independently optionally substituted $C_1$-$C_6$ alkyl. In some embodiments of a compound of Formula (I), (Ia), or (Ia-1), $R^{14}$, $R^{24}$, and $R^{44}$ are independently $C_1$-$C_6$ alkyl. In some embodiments of a compound of Formula (I), (Ia), or (Ia-1), $R^{14}$, $R^{24}$, and $R^{44}$ are methyl.

In some embodiments of a compound of Formula (I), (Ia), or (Ia-1), each $R^{15}$, $R^{25}$, $R^{35}$, and $R^{45}$ is independently hydrogen or $C_1$-$C_6$ alkyl. In some embodiments of a compound of Formula (I), (Ia), or (Ia-1), each $R^{15}$, $R^{25}$, $R^{35}$, and $R^{45}$ is hydrogen. In some embodiments of a compound of Formula (I), (Ia), or (Ia-1), each $R^{15}$, $R^{25}$, $R^{35}$, and $R^{45}$ is $C_1$-$C_6$ alkyl. In some embodiments of a compound of Formula (I), (Ia), or (Ia-1), two $R^{15}$, or two $R^{25}$, or two $R^{35}$, or two $R^{45}$ are taken together with the atoms to which there are attached to form a cyclic boronate ester.

In some embodiments of a compound of Formula (I), (Ia), or (Ia-1), v1, v2, v3, and v4 are independently 1. In some embodiments of a compound of Formula (I), (Ia), or (Ia-1), v1, v2, v3, and v4 are independently 2. In some embodiments of a compound of Formula (I), (Ia), or (Ia-1), v1, v2, v3, and v4 are independently 3. In some embodiments of a compound of Formula (I), (Ia), or (Ia-1), v1, v2, v3, and v4 are independently 4.

In some embodiments of a compound of Formula (I), (Ia), or (Ia-1), w1, w2, w3, and w4 are independently 2. In some embodiments of a compound of Formula (I), (Ia), or (Ia-1), w1, w2, w3, and w4 are independently 3. In some embodiments of a compound of Formula (I), (Ia), or (Ia-1), w1, w2, w3, and w4 are independently 4.

In some embodiments of a compound of Formula (I), (Ia), or (Ia-1), $R^a$ and $R^b$ are independently hydrogen or optionally substituted $C_1$-$C_6$ alkyl. In some embodiments of a compound of Formula (I), (Ia), or (Ia-1), $R^a$ and $R^b$ are independently hydrogen or $C_1$-$C_6$ alkyl. In some embodiments of a compound of Formula (I), (Ia), or (Ia-1), $R^a$ and $R^b$ are hydrogen.

In some embodiments of a compound of Formula (I), (Ia), or (Ia-1), $R^a$ and $R^b$ are taken together with the nitrogen to which they are attached to form an optionally substituted $C_2$-$C_8$ heterocycloalkyl. In some embodiments of a compound of Formula (I), (Ia), or (Ia-1), $R^a$ and $R^b$ are taken together with the nitrogen to which they are attached to form an optionally substituted aziridine, azetidine, pyrrolidine, piperidine, morpholine, or piperazine. In some embodiments of a compound of Formula (I), (Ia), or (Ia-1), $R^a$ and $R^b$ are taken together with the nitrogen to which they are attached to form a pyrrolidine, piperidine, morpholine, or piperazine.

In some embodiments of a compound of Formula (I), (Ia), or (Ia-1), each $R^c$ is independently optionally substituted $C_1$-$C_6$ alkyl. In some embodiments of a compound of Formula (I), (Ia), or (Ia-1), each $R^c$ is independently $C_1$-$C_6$ alkyl.

Also described herein are compounds of Formula (II), or a pharmaceutically acceptable salt, solvate, or stereoisomer thereof:

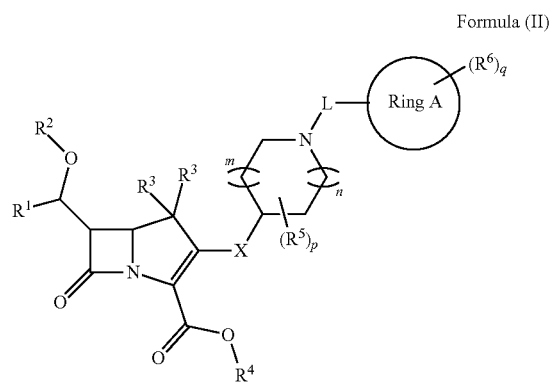

Formula (II)

wherein

Ring A is aryl, heteroaryl, cycloalkyl, or heterocycloalkyl; each optionally substituted with one, two, or three substituents each independently selected from the group consisting of oxo (when Ring A is cycloalkyl or heterocycloalkyl), optionally substituted $C_1$-$C_6$ alkyl, optionally substituted $C_2$-$C_6$ alkenyl, optionally substituted $C_2$-$C_6$ alkynyl, —$OR^{50}$, —$(CR^{52}R^{53})_{v5}OR^{50}$, —CN, —$NO_2$, halogen, —$S(=O)_2R^{54}$, —$(CR^{52}R^{53})_{v5}S(=O)_2R^{54}$, —$S(=O)_2NR^{50}R^{51}$, —$(CR^{52}R^{53})_{v5}S(=O)_2NR^{50}R^{51}$, —$C(=O)OR^{50}$, —$(CR^{52}R^{53})_{v5}C(=O)OR^{10}$, —$C(=O)NR^{50}R^{51}$, and —$(CR^{52}R^{53})_{v5}C(=O)NR^{50}R^{51}$;

X is —O—, —S—, —S(=O)—, —$S(=O)_2$—, or —$NR^7$—;

L is —$(CR^8R^9)_z$— or —$(CR^{18}R^{19})_yC(=O)$—;

$R^1$ is optionally substituted $C_1$-$C_6$ alkyl, optionally substituted $C_2$-$C_6$ alkenyl, or optionally substituted $C_2$-$C_6$ alkynyl;

$R^2$ is hydrogen, optionally substituted $C_1$-$C_6$ alkyl, optionally substituted $C_2$-$C_6$ alkenyl, optionally substituted $C_2$-$C_6$ alkynyl, or —$Si(R^c)_3$;

each $R^3$ is independently hydrogen, optionally substituted $C_1$-$C_6$ alkyl, optionally substituted $C_2$-$C_6$ alkenyl, optionally substituted $C_2$-$C_6$ alkynyl, or —$OR^a$;

$R^4$ is hydrogen, optionally substituted $C_1$-$C_6$ alkyl, optionally substituted $C_2$-$C_6$ alkenyl, optionally substituted $C_2$-$C_6$ alkynyl, optionally substituted aryl, optionally substituted heteroaryl, optionally substituted $C_3$-$C_8$ cycloalkyl, optionally substituted $C_2$-$C_8$ heterocycloalkyl, optionally substituted —$(C_1$-$C_6$ alkyl)$(C_3$-$C_8$ cycloalkyl), optionally substituted —$(C_1$-$C_6$ alkyl)$(C_2$-$C_8$ heterocycloalkyl), optionally substituted —$(C_1$-$C_6$ alkyl)(aryl), or optionally substituted —$(C_1$-$C_6$ alkyl)(heteroaryl);

each $R^5$ is independently hydrogen, halogen, optionally substituted $C_1$-$C_6$ alkyl, optionally substituted $C_2$-$C_6$ alkenyl, optionally substituted $C_2$-$C_6$ alkynyl, —$OR^{40}$, —$(CR^{42}R^{43})_{v4}OR^{40}$, —CN, —$NO_2$, —$S(=O)_2R^{44}$, —$(CR^{42}R^{43})_{v4}S(=O)_2R^{44}$, —$S(=O)_2NR^{40}R^{41}$, —$(CR^{42}R^{43})_{v4}S(=O)_2NR^{40}R^{41}$, —$C(=O)OR^{40}$, —$(CR^{42}R^{43})_{v4}C(=O)OR^{40}$, —$(CR^{42}R^{43})_{v4}C(=O)NR^{40}R^{41}$, —$NR^{40}R^{41}$, —$NR^{40}(CR^{42}R^{43})_{w4}NR^{40}R^{41}$, —$NR^{40}C(=NR^{41})NR^{40}R^{41}$, —$C(=NR^{40})NR^{40}R^{41}$, —$C(=NR^{40})R^{40}$, —$N(R^{40})C(=NR^{41})R^{40}$, —$(CR^{42}R^{43})_{v4}NR^{40}R^{41}$, —$(CR^{42}R^{43})_{v4}OR^{40}$, —$(CR^{42}R^{43})_{v4}N(R^{40})C(=NR^{41})NR^{40}R^{41}$, —$(CR^{42}R^{43})_{v4}NR^{40}(CR^{42}R^{43})_{w4}NR^{40}R^{41}$, —$NR^{41}C(=NR^{41})NR^{40}(CR^{42}R^{43})_{w4}NR^{40}R^{41}$, —$NR^{40}(CR^{42}R^{43})_{w4}N(R^{40})C(=NR^{41})NR^{40}R^{41}$, —(CR$^{42}$R$^{43}$)$_{v4}$C(=NR$^{41}$)NR$^{40}$R$^{41}$, —NR$^{40}$(CR$^{42}$R$^{43}$)$_{v4}$B(OR$^{45}$)$_2$, or —(CR$^{42}$R$^{43}$)$_{v4}$NR$^{40}$(CR$^{42}$R$^{43}$)$_{v4}$B(OR$^{45}$)$_2$;

each R$^6$ is independently a basic substituent;

R$^7$ is hydrogen, optionally substituted C$_1$-C$_6$ alkyl, —S(=O)$_2$R$^c$, or —S(=O)$_2$NR$^a$R$^b$;

each R$^8$ and R$^9$ is independently hydrogen, halogen, —CN, optionally substituted C$_1$-C$_6$ alkyl, optionally substituted C$_2$-C$_6$ alkenyl, optionally substituted C$_2$-C$_6$ alkynyl, —OR$^a$, —NR$^a$R$^b$, —C(=O)OR$^a$, —C(=O)NR$^a$R$^b$, —S(=O)$_2$R$^c$, or —S(=O)$_2$NR$^a$R$^b$;

each R$^{18}$ and R$^{19}$ is independently hydrogen, halogen, —CN, optionally substituted C$_1$-C$_6$ alkyl, optionally substituted C$_2$-C$_6$ alkenyl, optionally substituted C$_2$-C$_6$ alkynyl, —OR$^a$, —NR$^a$R$^b$, —C(=O)OR$^a$, —C(=O)NR$^a$R$^b$, —S(=O)$_2$R$^c$, or —S(=O)$_2$NR$^a$R$^b$;

each R$^{40}$, R$^{41}$, R$^{50}$, and R$^{51}$ is independently selected from the group consisting of hydrogen, optionally substituted C$_1$-C$_6$ alkyl, optionally substituted C$_2$-C$_6$ alkenyl, optionally substituted C$_2$-C$_6$ alkynyl, optionally substituted C$_3$-C$_8$ cycloalkyl, C$_2$-C$_8$ optionally substituted heterocycloalkyl, optionally substituted aryl, optionally substituted heteroaryl, optionally substituted —(C$_1$-C$_6$ alkyl)(C$_3$-C$_8$ cycloalkyl), optionally substituted —(C$_1$-C$_6$ alkyl)(C$_2$-C$_8$ heterocycloalkyl), optionally substituted —(C$_1$-C$_6$ alkyl)(aryl), and optionally substituted —(C$_1$-C$_6$ alkyl)(heteroaryl);

or R$^{40}$ and R$^{41}$, or R$^{50}$ and R$^{51}$ are taken together with the nitrogen to which they are attached to form an optionally substituted C$_2$-C$_8$ heterocycloalkyl;

each R$^{42}$, R$^{43}$, R$^{52}$, and R$^{53}$ is independently selected from the group consisting of hydrogen, halogen, —CN, —OR$^a$, —NR$^a$R$^b$, optionally substituted C$_1$-C$_6$ alkyl, optionally substituted C$_2$-C$_6$ alkenyl, optionally substituted C$_2$-C$_6$ alkynyl, optionally substituted C$_3$-C$_8$ cycloalkyl, optionally substituted C$_2$-C$_8$ heterocycloalkyl, optionally substituted aryl, and optionally substituted heteroaryl;

each R$^{44}$ and R$^{54}$ is independently optionally substituted C$_1$-C$_6$ alkyl, optionally substituted C$_2$-C$_6$ alkenyl, optionally substituted C$_2$-C$_6$ alkynyl, optionally substituted aryl, optionally substituted heteroaryl, optionally substituted C$_3$-C$_8$ cycloalkyl, optionally substituted C$_2$-C$_8$ heterocycloalkyl, optionally substituted —(C$_1$-C$_6$ alkyl)(C$_3$-C$_8$ cycloalkyl), optionally substituted —(C$_1$-C$_6$ alkyl)(C$_2$-C$_8$ heterocycloalkyl), optionally substituted —(C$_1$-C$_6$ alkyl)(aryl), or optionally substituted —(C$_1$-C$_6$ alkyl)(heteroaryl);

each R$^{45}$ is independently hydrogen or optionally substituted C$_1$-C$_6$ alkyl;

or two R$^{45}$ are taken together with the atoms to which there are attached to form a cyclic boronate ester;

R$^a$ and R$^b$ are independently hydrogen or optionally substituted C$_1$-C$_6$ alkyl;

or R$^a$ and R$^b$ are taken together with the nitrogen to which they are attached to form an optionally substituted C$_2$-C$_8$ heterocycloalkyl;

each R$^c$ is independently optionally substituted C$_1$-C$_6$ alkyl, optionally substituted C$_2$-C$_6$ alkenyl, or optionally substituted C$_2$-C$_6$ alkynyl;

n is 1-2;
m is 0-2;
p is 0-4;
q is 1-4;
v4 and v5 are independently 1-4;
w4 is 2-4;
y is 1-4; and
z is 0-5.

In some embodiments of a compound of Formula (II), X is —S—. In some embodiments of a compound of Formula (II), X is —O—. In some embodiments of a compound of Formula (II), X is —S(=O)—. In some embodiments of a compound of Formula (II), X is —S(=O)$_2$—. In some embodiments of a compound of Formula (II), X is —NR$^7$—. In some embodiments of a compound of Formula (II), X is —NR$^7$— and R$^7$ is hydrogen.

In some embodiments of a compound of Formula (II), R$^1$ is C$_1$-C$_6$ alkyl. In some embodiments of a compound of Formula (II), R$^1$ is methyl. In some embodiments of a compound of Formula (II), R$^1$ is C$_2$-C$_6$ alkenyl. In some embodiments of a compound of Formula (II), R$^1$ is C$_2$-C$_6$ alkynyl.

In some embodiments of a compound of Formula (II) R$^2$ is hydrogen. In some embodiments of a compound of Formula (II), R$^2$ is C$_1$-C$_6$ alkyl. In some embodiments of a compound of Formula (II), R$^2$ is methyl. In some embodiments of a compound of Formula (II), R$^2$ is C$_2$-C$_6$ alkenyl. In some embodiments of a compound of Formula (II), R$^2$ is C$_2$-C$_6$ alkynyl. In some embodiments of a compound of Formula (II), R$^2$ is —Si(R$^c$)$_3$.

In some embodiments of a compound of Formula (II), each R$^3$ is hydrogen. In some embodiments of a compound of Formula (II), each R$^3$ is independently hydrogen or C$_1$-C$_6$ alkyl. In some embodiments of a compound of Formula (II), each R$^3$ is independently hydrogen, C$_1$-C$_6$ alkyl, or OR$^a$. In some embodiments of a compound of Formula (II), each R$^3$ is independently hydrogen, C$_1$-C$_6$ alkyl, or OH. In some embodiments of a compound of Formula (II), each R$^3$ is independently C$_1$-C$_6$ alkyl. In some embodiments of a compound of Formula (II), one R$^3$ is methyl and the other R$^3$ is hydrogen. In some embodiments of a compound of Formula (II), each R$^3$ is independently hydrogen or C$_2$-C$_6$ alkenyl. In some embodiments of a compound of Formula (II), each R$^3$ is independently hydrogen or C$_2$-C$_6$ alkynyl.

In some embodiments of a compound of Formula (II), R$^4$ is hydrogen. In some embodiments of a compound of Formula (II), R$^4$ is C$_1$-C$_6$ alkyl. In some embodiments of a compound of Formula (II), R$^4$ is C$_2$-C$_6$ alkenyl. In some embodiments of a compound of Formula (II), R$^4$ is C$_2$-C$_6$ alkynyl. In some embodiments of a compound of Formula (II), R$^4$ is optionally substituted —(C$_1$-C$_6$ alkyl)(aryl). In some embodiments of a compound of Formula (II), R$^4$ is —(C$_1$-C$_6$ alkyl)(aryl) substituted with alkyl or —NO$_2$.

In some embodiments, a compound of Formula (II), or a pharmaceutically acceptable salt, solvate, or stereoisomer thereof, is of Formula (IIa), or a pharmaceutically acceptable salt, solvate, or stereoisomer thereof:

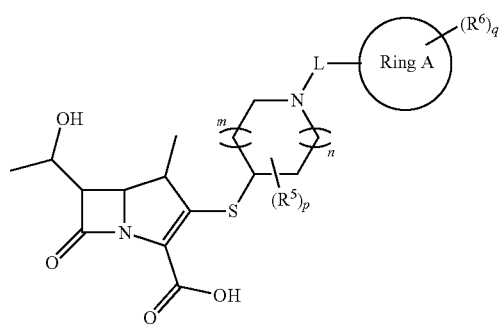

Formula (IIa)

wherein

Ring A is aryl, heteroaryl, cycloalkyl, or heterocycloalkyl; each optionally substituted with one, two, or three substituents each independently selected from the group consisting of oxo (when Ring A is cycloalkyl or heterocycloalkyl), optionally substituted $C_1$-$C_6$ alkyl, optionally substituted $C_2$-$C_6$ alkenyl, optionally substituted $C_2$-$C_6$ alkynyl, —$OR^{50}$, —$(CR^{52}R^{53})_{v5}OR^{50}$, —CN, —$NO_2$, halogen, —$S(=O)_2R^{54}$, —$(CR^{52}R^{53})_{v5}S(=O)_2R^{54}$, —$S(=O)_2NR^{50}R^{51}$, —$(CR^{52}R^{53})_{v5}S(=O)_2NR^{50}R^{51}$, —$C(=O)OR^{50}$, —$(CR^{52}R^{53})_{v5}C(=O)OR^{50}$, —$C(=O)NR^{50}R^{51}$, and —$(CR^{52}R^{53})_{v5}C(=O)NR^{50}R^{51}$;

L is —$(CR^8R^9)_z$— or —$(CR^{18}R^{19})_yC(=O)$—;

each $R^5$ is independently hydrogen, halogen, optionally substituted $C_1$-$C_6$ alkyl, optionally substituted $C_2$-$C_6$ alkenyl, optionally substituted $C_2$-$C_6$ alkynyl, —$OR^{40}$, —$(CR^{42}R^{43})_{v4}OR^{40}$, —CN, —$NO_2$, —$S(=O)_2R^{44}$, —$(CR^{42}R^{43})_{v4}S(=O)_2R^{44}$, —$S(=O)_2NR^{40}R^{41}$, —$(CR^{42}R^{43})_{v4}S(=O)_2NR^{40}R^{41}$, —$C(=O)OR^{40}$, —$(CR^{42}R^{43})_{v4}C(=O)OR^{40}$, —$(CR^{42}R^{43})_{v4}C(=O)NR^{40}R^{41}$, —$NR^{40}R^{41}$, —$NR^{40}(CR^{42}R^{43})_{w4}NR^{40}R^{41}$, —$NR^{40}C(=NR^{41})NR^{40}R^{41}$, —$C(=NR^{40})NR^{40}R^{41}$, —$C(=NR^{40})R^{40}$, —$N(R^{40})C(=NR^{41})R^{40}$, —$(CR^{42}R^{43})_{v4}NR^{40}R^{41}$, —$(CR^{42}R^{43})_{v4}OR^{40}$, —$(CR^{42}R^{43})_{v4}N(R^{40})C(=NR^{41})NR^{40}R^{41}$, —$(CR^{42}R^{43})_{v4}NR^{40}(CR^{42}R^{43})_{w4}NR^{40}R^{41}$, —$NR^{41}C(=NR^{41})NR^{40}(CR^{42}R^{43})_{w4}NR^{40}R^{41}$, —$NR^{40}(CR^{42}R^{43})_{w4}N(R^{40})C(=NR^{41})NR^{40}R^{41}$, —$(CR^{42}R^{43})_{w4}C(=NR^{41})NR^{40}R^{41}$, —$NR^{40}(CR^{42}R^{43})_{v4}B(OR^{45})_2$, or —$(CR^{42}R^{43})_{v4}NR^{40}(CR^{42}R^{43})_{v4}B(OR^{45})_2$;

each $R^6$ is independently a basic substituent;

each $R^8$ and $R^9$ is independently hydrogen, halogen, —CN, optionally substituted $C_1$-$C_6$ alkyl, optionally substituted $C_2$-$C_6$ alkenyl, optionally substituted $C_2$-$C_6$ alkynyl, —$OR^a$, —$NR^aR^b$, —$C(=O)OR^a$, —$C(=O)NR^aR^b$, —$S(=O)_2R^c$, or —$S(=O)_2NR^aR^b$;

each $R^{18}$ and $R^{19}$ is independently hydrogen, halogen, —CN, optionally substituted $C_1$-$C_6$ alkyl, optionally substituted $C_2$-$C_6$ alkenyl, optionally substituted $C_2$-$C_6$ alkynyl, —$OR^a$, —$NR^aR^b$, —$C(=O)OR^a$, —$C(=O)NR^aR^b$, —$S(=O)_2R^c$, or —$S(=O)_2NR^aR^b$;

each $R^{40}$, $R^{41}$, $R^{50}$, and $R^{51}$ is independently selected from the group consisting of hydrogen, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, $C_2$-$C_8$ optionally substituted heterocycloalkyl, optionally substituted aryl, optionally substituted heteroaryl, optionally substituted —($C_1$-$C_6$ alkyl)($C_3$-$C_8$ cycloalkyl), optionally substituted —($C_1$-$C_6$ alkyl)($C_2$-$C_8$ heterocycloalkyl), optionally substituted —($C_1$-$C_6$ alkyl)(aryl), and optionally substituted —($C_1$-$C_6$ alkyl)(heteroaryl);

or $R^{40}$ and $R^{41}$, or $R^{50}$ and $R^{51}$ are taken together with the nitrogen to which they are attached to form an optionally substituted $C_2$-$C_8$ heterocycloalkyl;

each $R^{42}$, $R^{43}$, $R^{52}$, and $R^{53}$ is independently selected from the group consisting of hydrogen, halogen, —CN, —$OR^a$, —$NR^aR^b$, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, optionally substituted $C_2$-$C_8$ heterocycloalkyl, optionally substituted aryl, and optionally substituted heteroaryl;

each $R^{44}$ and $R^{54}$ is independently optionally substituted $C_1$-$C_6$ alkyl, optionally substituted $C_2$-$C_6$ alkenyl, optionally substituted $C_2$-$C_6$ alkynyl, optionally substituted aryl, optionally substituted heteroaryl, optionally substituted $C_3$-$C_8$ cycloalkyl, optionally substituted $C_2$-$C_8$ heterocycloalkyl, optionally substituted —($C_1$-$C_6$ alkyl)($C_3$-$C_8$ cycloalkyl), optionally substituted —($C_1$-$C_6$ alkyl)($C_2$-$C_8$ heterocycloalkyl), optionally substituted —($C_1$-$C_6$ alkyl)(aryl), or optionally substituted —($C_1$-$C_6$ alkyl)(heteroaryl);

each $R^{45}$ is independently hydrogen or optionally substituted $C_1$-$C_6$ alkyl;

or two $R^{45}$ are taken together with the atoms to which there are attached to form a cyclic boronate ester;

$R^a$ and $R^b$ are independently hydrogen or optionally substituted $C_1$-$C_6$ alkyl;

or $R^a$ and $R^b$ are taken together with the nitrogen to which they are attached to form an optionally substituted $C_2$-$C_8$ heterocycloalkyl;

each $R^c$ is independently optionally substituted $C_1$-$C_6$ alkyl, optionally substituted $C_2$-$C_6$ alkenyl, or optionally substituted $C_2$-$C_6$ alkynyl;

n is 1-2;

m is 0-2;

p is 0-4;

q is 1-4;

v4 and v5 are independently 1-4;

w4 is 2-4;

y is 1-4; and z is 0-5.

In some embodiments, a compound of Formula (II) or (IIa), or a pharmaceutically acceptable salt, solvate, or stereoisomer thereof, is of Formula (IIa-1), or a pharmaceutically acceptable salt, solvate, or stereoisomer thereof:

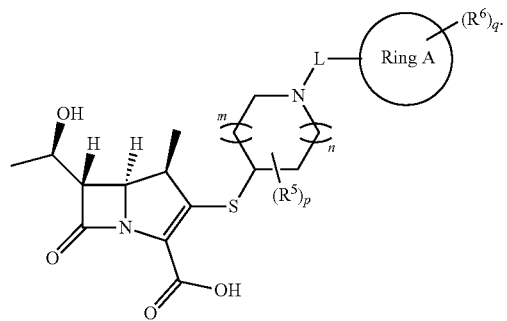

Formula (IIa-1)

In some embodiments of a compound of Formula (II), (IIa), or (IIa-1), Ring A is optionally substituted phenyl, optionally substituted cyclohexyl, optionally substituted piperidinyl, optionally substituted morpholinyl, or optionally substituted pyridyl. In some embodiments of a compound of Formula (II), (IIa), or (IIa-1), Ring A is phenyl, cyclohexyl, piperidinyl, morpholinyl, or pyridyl, each optionally substituted with one, two, or three halogen, —CN, —OH, $C_1$-$C_6$ alkyl, $C_1$-$C_6$ haloalkyl, $C_1$-$C_6$ alkoxy, or —$NO_2$. In some embodiments of a compound of Formula (II), (IIa), or (IIa-1), Ring A is phenyl, cyclohexyl, piperidinyl, morpholinyl, or pyridyl. In some embodiments of a compound of Formula (II), (IIa), or (IIa-1), Ring A is phenyl. In some embodiments of a compound of Formula (II), (IIa), or (IIa-1), Ring A is cyclohexyl.

In some embodiments of a compound of Formula (II), (IIa), or (IIa-1), $R^{50}$ and $R^{51}$ are independently selected from the group consisting of hydrogen, optionally substituted $C_1$-$C_6$ alkyl, optionally substituted $C_3$-$C_8$ cycloalkyl, or $C_2$-$C_8$ optionally substituted heterocycloalkyl. In some embodiments of a compound of Formula (II), (IIa), or (IIa-1), $R^{50}$ and $R^{51}$ are independently selected from the group consisting of hydrogen and optionally substituted $C_1$-$C_6$ alkyl.

In some embodiments of a compound of Formula (II), (IIa), or (IIa-1), $R^{52}$ and $R^{53}$ are independently selected from the group consisting of hydrogen, halogen, —CN, —$OR^a$, —$NR^aR^b$, or optionally substituted $C_1$-$C_6$ alkyl. In some embodiments of a compound of Formula (II), (IIa), or (IIa-1), $R^{52}$ and $R^{53}$ are independently selected from the group consisting of hydrogen, halogen, or optionally substituted $C_1$-$C_6$ alkyl.

In some embodiments of a compound of Formula (II), (IIa), or (IIa-1), $R^{54}$ is optionally substituted $C_1$-$C_6$ alkyl, optionally substituted $C_3$-$C_8$ cycloalkyl, or $C_2$-$C_8$ optionally substituted heterocycloalkyl. In some embodiments of a compound of Formula (II), (IIa), or (IIa-1), $R^{54}$ is optionally substituted $C_1$-$C_6$ alkyl.

In some embodiments of a compound of Formula (I), (Ia), or (Ia-1), n is 1 and m is 0 or 1.

In some embodiments of a compound of Formula (II), (IIa), or (IIa-1), n is 1 and m is 0. In some embodiments of a compound of Formula (II), (IIa), or (IIa-1) n is 1 and m is 1. In some embodiments of a compound of Formula (II), (IIa), or (IIa-1), n is 1 and m is 2.

In some embodiments of a compound of Formula (II), (IIa), or (IIa-1), n is 2 and m is 0. In some embodiments of a compound of Formula (II), (IIa), or (IIa-1) n is 2 and m is 1. In some embodiments of a compound of Formula (II), (IIa), or (IIa-1) n is 2 and m is 2.

In some embodiments of a compound of Formula (II), (IIa), or (IIa-1), L is —$(CR^8R^9)_z$—. In some embodiments of a compound of Formula (II), (IIa), or (IIa-1), z is 0. In some embodiments of a compound of Formula (II), (IIa), or (IIa-1), z is not 0. In some embodiments of a compound of Formula (II), (IIa), or (IIa-1), z is 1. In some embodiments of a compound of Formula (II), (IIa), or (IIa-1), z is 2. In some embodiments of a compound of Formula (II), (IIa), or (IIa-1), z is 3. In some embodiments of a compound of Formula (II), (IIa), or (IIa-1), z is 4. In some embodiments of a compound of Formula (II), (IIa), or (IIa-1), z is 5. In some embodiments of a compound of Formula (II), (IIa), or (IIa-1), z is 0-5. In some embodiments of a compound of Formula (II), (IIa), or (IIa-1), z is 0-4. In some embodiments of a compound of Formula (II), (IIa), or (IIa-1), z is 0-3. In some embodiments of a compound of Formula (II), (IIa), or (IIa-1), z is 0-2. In some embodiments of a compound of Formula (II), (IIa), or (IIa-1), z is 0 or 1. In some embodiments of a compound of Formula (II), (IIa), or (IIa-1), z is 1 or 2. In some embodiments of a compound of Formula (II), (IIa), or (IIa-1), z is 1-3. In some embodiments of a compound of Formula (II), (IIa), or (IIa-1), each $R^8$ and $R^9$ is independently hydrogen, halogen, —CN, optionally substituted $C_1$-$C_6$ alkyl, —$OR^a$, or —$NR^aR^b$. In some embodiments of a compound of Formula (II), (IIa), or (IIa-1), each $R^8$ and $R^9$ is independently hydrogen, halogen, —CN, $C_1$-$C_6$ alkyl, $C_1$-$C_6$ haloalkyl, —$OR^a$, or —$NR^aR^b$. In some embodiments of a compound of Formula (II), (IIa), or (IIa-1), each $R^8$ and $R^9$ is independently hydrogen, halogen, $C_1$-$C_6$ alkyl, or $C_1$-$C_6$ haloalkyl. In some embodiments of a compound of Formula (II), (IIa), or (IIa-1), each $R^8$ and $R^9$ are independently hydrogen, halogen, or $C_1$-$C_6$ alkyl. In some embodiments of a compound of Formula (II), (IIa), or (IIa-1), each $R^8$ and $R^9$ is independently hydrogen or $C_1$-$C_6$ alkyl. In some embodiments of a compound of Formula (II), (IIa), or (IIa-1), each $R^8$ and $R^9$ is independently hydrogen or methyl. In some embodiments of a compound of Formula (II), (IIa), or (IIa-1), each $R^8$ and $R^9$ is independently hydrogen or halogen. In some embodiments of a compound of Formula (II), (IIa), or (IIa-1), each $R^8$ and $R^9$ is hydrogen.

In some embodiments of a compound of Formula (II), (IIa), or (IIa-1), L is —$(CR^{18}R^{19})_yC(=O)$—. In some embodiments of a compound of Formula (II), (IIa), or (IIa-1), y is 1-3. In some embodiments of a compound of Formula (II), (IIa), or (IIa-1), y is 1 or 2. In some embodiments of a compound of Formula (II), (IIa), or (IIa-1), y is 1. In some embodiments of a compound of Formula (II), (IIa), or (IIa-1), y is 2. In some embodiments of a compound of Formula (II), (IIa), or (IIa-1), y is 3. In some embodiments of a compound of Formula (II), (IIa), or (IIa-1), y is 4. In some embodiments of a compound of Formula (II), (IIa), or (IIa-1), each $R^{18}$ and $R^{19}$ is independently hydrogen, halogen, —CN, optionally substituted $C_1$-$C_6$ alkyl, —$OR^a$, or —$NR^aR^b$. In some embodiments of a compound of Formula (II), (IIa), or (IIa-1), each $R^{18}$ and $R^{19}$ is independently hydrogen, halogen, or $C_1$-$C_6$ alkyl. In some embodiments of a compound of Formula (II), (IIa), or (IIa-1), each $R^{18}$ and $R^{19}$ is independently hydrogen or $C_1$-$C_6$ alkyl. In some embodiments of a compound of Formula (II), (IIa), or (IIa-1), each $R^{18}$ and $R^{19}$ is independently hydrogen or methyl. In some embodiments of a compound of Formula (II), (IIa), or (IIa-1), each $R^{18}$ and $R^{19}$ is independently hydrogen or halogen. In some embodiments of a compound of Formula (II), (IIa), or (IIa-1), each $R^{18}$ and $R^{19}$ is hydrogen.

In some embodiments of a compound of Formula (II), (IIa), or (IIa-1), p is 0. In some embodiments of a compound of Formula (II), (IIa), or (IIa-1), p is 1. In some embodiments of a compound of Formula (II), (IIa), or (IIa-1), p is 2. In some embodiments of a compound of Formula (II), (IIa), or (IIa-1), p is 3. In some embodiments of a compound of Formula (II), (IIa), or (IIa-1), p is 4.

In some embodiments of a compound of Formula (II), (IIa), or (IIa-1), each $R^5$ is independently hydrogen, halogen, optionally substituted $C_1$-$C_6$ alkyl, —$OR^{40}$, —$(CR^{42}R^{43})_{1-4}OR^{40}$, —CN, —$NO_2$, or —$NR^{40}R^{41}$. In some embodiments of a compound of Formula (II), (IIa), or (IIa-1), each $R^5$ is independently hydrogen or halogen. In some embodiments of a compound of Formula (II), (IIa), or (IIa-1), each $R^5$ is hydrogen. In some embodiments of a compound of Formula (II), (IIa), or (IIa-1), each $R^5$ is independently halogen or optionally substituted $C_1$-$C_6$ alkyl. In some embodiments of a compound of Formula (II), (IIa), or (IIa-1), each $R^5$ is independently optionally substituted $C_1$-$C_6$ alkyl. In some embodiments of a compound of Formula (II), (IIa), or (IIa-1), each $R^5$ is independently optionally substituted methyl. In some embodiments of a compound of Formula (II), (IIa), or (IIa-1), each $R^5$ is independently $C_1$-$C_6$ alkyl or $C_1$-$C_6$ hydroxyalkyl. In some embodiments of a compound of Formula (II), (IIa), or (IIa-1), each $R^5$ is independently methyl or —$CH_2OH$.

In some embodiments of a compound of Formula (II), (IIa), or (IIa-1), each $R^{40}$, $R^{41}$, $R^{50}$, and $R^{51}$ is independently selected from the group consisting of hydrogen, optionally substituted $C_1$-$C_6$ alkyl, optionally substituted $C_3$-$C_8$ cycloalkyl, or $C_2$-$C_8$ optionally substituted heterocycloalkyl. In some embodiments of a compound of Formula (II), (IIa), or (IIa-1), each $R^{40}$, $R^{41}$, $R^{50}$, and $R^{51}$ is independently selected from the group consisting of hydrogen or optionally substituted $C_1$-$C_6$ alkyl. In some embodiments of a compound of Formula (II), (IIa), or (IIa-1), each $R^{40}$, $R^{41}$, $R^{50}$, and $R^{51}$ is hydrogen.

In some embodiments of a compound of Formula (II), (IIa), or (IIa-1), $R^{40}$ and $R^{41}$, or $R^{50}$ and $R^{51}$ are taken together with the nitrogen to which they are attached to form an optionally substituted $C_2$-$C_8$ heterocycloalkyl. In some embodiments of a compound of Formula (II), (IIa), or (IIa-1), $R^{40}$ and $R^{41}$, or $R^{50}$ and $R^{51}$ are taken together with the nitrogen to which they are attached to form an optionally substituted aziridine, azetidine, pyrrolidine, piperidine, morpholine, or piperazine. In some embodiments of a compound of Formula (II), (IIa), or (IIa-1), $R^{40}$ and $R^{41}$, or $R^{50}$ and $R^{51}$ are taken together with the nitrogen to which they are attached to form a pyrrolidine, piperidine, morpholine, or piperazine.

In some embodiments of a compound of Formula (II), (IIa), or (IIa-1), each $R^{42}$, $R^{43}$, $R^{52}$, and $R^{53}$ is independently selected from the group consisting of hydrogen, halogen, —CN, —OR$^a$, —NR$^a$R$^b$, or optionally substituted $C_1$-$C_6$ alkyl. In some embodiments of a compound of Formula (II), (IIa), or (IIa-1), each $R^{42}$, $R^{43}$, $R^{52}$, and $R^{53}$ is independently selected from the group consisting of hydrogen, halogen, —NR$^a$R$^b$, or $C_1$-$C_6$ alkyl. In some embodiments of a compound of Formula (II), (IIa), or (IIa-1), each $R^{42}$, $R^{43}$, $R^{52}$, and $R^{53}$ is hydrogen or $C_1$-$C_6$ alkyl. In some embodiments of a compound of Formula (II), (IIa), or (IIa-1), each $R^{42}$, $R^{43}$, $R^{52}$, and $R^{53}$ is hydrogen or halogen. In some embodiments of a compound of Formula (II), (IIa), or (IIa-1), each $R^{42}$, $R^{43}$, $R^{52}$, and $R^{53}$ is hydrogen or —NR$^a$R$^b$.

In some embodiments of a compound of Formula (II), (IIa), or (IIa-1), $R^{44}$ and $R^{54}$ are independently optionally substituted $C_1$-$C_6$ alkyl. In some embodiments of a compound of Formula (II), (IIa), or (IIa-1), $R^{44}$ and $R^{54}$ are methyl.

In some embodiments of a compound of Formula (II), (IIa), or (IIa-1), $R^{45}$ is hydrogen or $C_1$-$C_6$ alkyl. In some embodiments of a compound of Formula (II), (IIa), or (IIa-1), $R^{45}$ is hydrogen. In some embodiments of a compound of Formula (II), (IIa), or (IIa-1), $R^{45}$ is $C_1$-$C_6$ alkyl.

In some embodiments of a compound of Formula (II), (IIa), or (IIa-1), two $R^{45}$ are taken together with the atoms to which there are attached to form a cyclic boronate ester.

In some embodiments of a compound of Formula (II), (IIa), or (IIa-1), q is 1. In some embodiments of a compound of Formula (II), (IIa), or (IIa-1), q is 2. In some embodiments of a compound of Formula (II), (IIa), or (IIa-1), q is 3. In some embodiments of a compound of Formula (II), (IIa), or (IIa-1), q is 4.

In some embodiments of a compound of Formula (II), (IIa), or (IIa-1), each $R^6$ is a basic substituent comprising at least one basic nitrogen. In some embodiments of a compound of Formula (II), (IIa), or (IIa-1), each $R^6$ is a basic substituent comprising one basic nitrogen. In some embodiments of a compound of Formula (II), (IIa), or (IIa-1), each $R^6$ is a basic substituent comprising two basic nitrogens.

In some embodiments of a compound of Formula (II), (IIa), or (IIa-1), each $R^6$ is independently —NR$^{60}$R$^{61}$, —NR$^{60}$(CR$^{62}$R$^{63}$)$_{w6}$NR$^{60}$R$^{61}$, —NR$^{60}$C(=NR$^{61}$)NR$^{60}$R$^{61}$, —C(=NR$^{60}$)NR$^{60}$R$^{61}$, —C(=NR$^{60}$)R$^{60}$, —N(R$^{60}$)C(=NR$^{61}$)R$^{60}$, —(CR$^{62}$R$^{63}$)$_{v6}$NR$^{60}$R$^{61}$, —C(=O)NR$^{60}$R$^{61}$, —C(=O)(CR$^{62}$R$^{63}$)$_{v6}$NR$^{60}$R$^{61}$, —(CR$^{62}$R$^{63}$)$_{v6}$C(=O)NR$^{60}$R$^{61}$, —(CR$^{62}$R$^{63}$)$_{v6}$N(R$^{60}$)C(=NR$^{61}$)NR$^{60}$R$^{61}$, —(CR$^{62}$R$^{63}$)$_{v6}$NR$^{60}$(CR$^{62}$R$^{63}$)$_{w6}$NR$^{60}$R$^{61}$, —NR$^{61}$C(=NR$^{61}$)NR$^{60}$(CR$^{62}$R$^{63}$)$_{w6}$NR$^{60}$R$^{61}$, —NR$^{60}$(CR$^{62}$R$^{63}$)$_{w6}$N(R$^{60}$)C(=NR$^{61}$)NR$^{60}$R$^{61}$, —(CR$^{62}$R$^{63}$)$_{v6}$C(=NR$^{61}$)NR$^{60}$R$^{61}$, —NR$^{60}$(CR$^{62}$R$^{63}$)$_{v6}$B(OR$^{65}$)$_2$, or —(CR$^{62}$R$^{63}$)$_{v6}$NR$^{60}$(CR$^{62}$R$^{63}$)$_{v6}$B(OR$^{65}$)$_2$.

In some embodiments of a compound of Formula (II), (IIa), or (IIa-1), each $R^6$ is independently —NR$^{60}$R$^{61}$, —NR$^{60}$(CR$^{62}$R$^{63}$)$_{w6}$NR$^{60}$R$^{61}$, —NR$^{60}$C(=NR$^{61}$)NR$^{60}$R$^{61}$, —C(=NR$^{60}$)NR$^{60}$R$^{61}$, —N(R$^{60}$)C(=NR$^{61}$)R$^{60}$, —(CR$^{62}$R$^{63}$)$_{v6}$NR$^{60}$R$^{61}$, —(CR$^{62}$R$^{63}$)$_{v6}$N(R$^{60}$)C(=NR$^{61}$) NR$^{60}$R$^{61}$, —(CR$^{62}$R$^{63}$)$_{v6}$NR$^{60}$(CR$^{62}$R$^{63}$)$_{w6}$NR$^{60}$R$^{61}$, —NR$^{60}$(CR$^{62}$R$^{63}$)$_{w6}$NR$^{60}$R$^{61}$, —NR$^{60}$C(=NR$^{61}$)NR$^{60}$R$^{61}$, —(CR$^{62}$R$^{63}$)$_{v6}$NR$^{60}$(CR$^{62}$R$^{63}$)$_{v6}$B(OR$^{65}$)$_2$, or —(CR$^{62}$R$^{63}$)$_{v6}$NR$^{60}$(CR$^{62}$R$^{63}$)$_{v6}$B(OR$^{65}$)$_2$.

In some embodiments of a compound of Formula (II), (IIa), or (IIa-1), each $R^6$ is independently —NR$^{60}$R$^{61}$, —NR$^{60}$(CR$^{62}$R$^{63}$)$_{w6}$NR$^{60}$R$^{61}$, —NR$^{60}$C(=NR$^{61}$)NR$^{60}$R$^{61}$, —C(=NR$^{60}$)NR$^{60}$R$^{61}$, —N(R$^{60}$)C(=NR$^{61}$)R$^{60}$, —(CR$^{62}$R$^{63}$)$_{v6}$NR$^{60}$R$^{61}$, —(CR$^{62}$R$^{63}$)$_{v6}$N(R$^{60}$)C(=NR$^{61}$) NR$^{60}$R$^{61}$, —(CR$^{62}$R$^{63}$)$_{v6}$NR$^{60}$(CR$^{62}$R$^{63}$)$_{w6}$NR$^{60}$R$^{61}$, —NR$^{61}$C(=NR$^{61}$)NR$^{60}$(CR$^{62}$R$^{63}$)$_{w6}$NR$^{60}$R$^{61}$, —NR$^{60}$(CR$^{62}$R$^{63}$)$_{w6}$N(R$^{60}$)C(=NR$^{61}$)NR$^{60}$R$^{61}$, or —(CR$^{62}$R$^{63}$)$_{v6}$C(=NR$^{61}$)NR$^{60}$R$^{61}$.

In some embodiments of a compound of Formula (II), (IIa), or (IIa-1), each $R^6$ is independently —NR$^{60}$R$^{61}$, —NR$^{60}$(CR$^{62}$R$^{63}$)$_{w6}$NR$^{60}$R$^{61}$, —NR$^{60}$C(=NR$^{61}$)NR$^{60}$R$^{61}$, —C(=NR$^{60}$)NR$^{60}$R$^{61}$, —N(R$^{60}$)C(=NR$^{61}$)R$^{60}$, or —(CR$^{62}$R$^{63}$)$_{v6}$NR$^{60}$R$^{61}$.

In some embodiments of a compound of Formula (II), (IIa), or (IIa-1), each $R^6$ is independently —NR$^{60}$R$^{61}$, —C(=NR$^{60}$)NR$^{60}$R$^{61}$, —(CR$^{62}$R$^{63}$)$_{v6}$NR$^{60}$R$^{61}$, or —NR$^{60}$(CR$^{62}$R$^{63}$)$_{v6}$B(OR$^{65}$)$_2$.

In some embodiments of a compound of Formula (II), (IIa), or (IIa-1), $R^6$ is —NR$^{60}$R$^{61}$.

In some embodiments of a compound of Formula (II), (IIa), or (IIa-1), $R^6$ is —(CR$^{62}$R$^{63}$)$_{v6}$NR$^{60}$R$^{61}$.

In some embodiments of a compound of Formula (II), (IIa), or (IIa-1), $R^6$ is —C(=NR$^{60}$)NR$^{60}$R$^{61}$.

In some embodiments of a compound of Formula (II), (IIa), or (IIa-1), $R^6$ is —NR$^{60}$(CR$^{62}$R$^{63}$)$_{v6}$B(OR$^{65}$)$_2$.

In some embodiments of a compound of Formula (II), (IIa), or (IIa-1), $R^6$ is as defined above and each $R^{60}$ and $R^{61}$ is independently selected from the group consisting of hydrogen, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, $C_2$-$C_8$ optionally substituted heterocycloalkyl, optionally substituted aryl, optionally substituted heteroaryl, optionally substituted —(C$_1$-C$_6$ alkyl)(C$_3$-C$_8$ cycloalkyl), optionally substituted —(C$_1$-C$_6$ alkyl)(C$_2$-C$_8$ heterocycloalkyl), optionally substituted —(C$_1$-C$_6$ alkyl)(aryl), and optionally substituted —(C$_1$-C$_6$ alkyl)(heteroaryl); or $R^{60}$ and $R^{61}$ are taken together with the nitrogen to which they are attached to form an optionally substituted $C_2$-$C_8$ heterocycloalkyl. In some embodiments of a compound of Formula (II), (IIa), or (IIa-1), $R^6$ is as defined above and each $R^{60}$ and $R^{61}$ is independently selected from the group consisting of hydrogen, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, $C_2$-$C_8$ optionally substituted heterocycloalkyl, optionally substituted aryl, optionally substituted heteroaryl, optionally substituted —(C$_1$-C$_6$ alkyl)(C$_3$-C$_8$ cycloalkyl), optionally substituted —(C$_1$-C$_6$ alkyl)(C$_2$-C$_8$ heterocycloalkyl), optionally substituted —(C$_1$-C$_6$ alkyl)(aryl), and optionally substituted —(C$_1$-C$_6$ alkyl)(heteroaryl). In some embodiments of a compound of Formula (II), (IIa), or (IIa-1), $R^6$ is as defined above and each $R^{60}$ and $R^{61}$ is independently selected from the group consisting of hydrogen, optionally substituted $C_1$-$C_6$ alkyl, optionally substituted $C_3$-$C_8$ cycloalkyl, or $C_2$-$C_8$ optionally substituted heterocycloalkyl. In some embodiments of a compound of Formula (II), (IIa), or (IIa-1), $R^6$ is as defined above and each $R^{60}$ and $R^{61}$ is independently selected from the group consisting of hydrogen and optionally substituted $C_1$-$C_6$ alkyl. In some embodiments of a compound of Formula (II), (IIa), or (IIa-1), $R^6$ is as defined above and each $R^{60}$ and $R^{61}$ is independently selected from the group consisting of hydrogen and $C_1$-$C_6$ alkyl. In some embodiments of a compound of Formula (II), (IIa), or (IIa-1), $R^6$ is as defined above and each $R^{60}$ and $R^{61}$ is hydrogen.

In some embodiments of a compound of Formula (II), (IIa), or (IIa-1), $R^6$ is as defined above and $R^{60}$ and $R^{61}$ are taken together with the nitrogen to which they are attached to form an optionally substituted $C_2$-$C_8$ heterocycloalkyl. In some embodiments of a compound of Formula (II), (IIa), or (IIa-1), $R^6$ is as defined above and $R^{60}$ and $R^{61}$ are taken together with the nitrogen to which they are attached to form an optionally substituted aziridine, azetidine, pyrrolidine, piperidine, morpholine, or piperazine. In some embodiments of a compound of Formula (II), (IIa), or (IIa-1), $R^6$ is as defined above and $R^{60}$ and $R^{61}$ are taken together with the nitrogen to which they are attached to form a pyrrolidine, piperidine, morpholine, or piperazine.

In some embodiments of a compound of Formula (II), (IIa), or (IIa-1), $R^6$ is as defined above and each $R^{62}$ and $R^{63}$ is independently selected from the group consisting of hydrogen, halogen, —CN, —OR$^a$, —NR$^a$R$^b$, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, optionally substituted $C_2$-$C_8$ heterocycloalkyl, optionally substituted aryl, and optionally substituted heteroaryl. In some embodiments of a compound of Formula (II), (IIa), or (IIa-1), $R^6$ is as defined above and each $R^{62}$ and $R^{63}$ is independently selected from the group consisting of hydrogen, halogen, —CN, —OR$^a$, —NR$^a$R$^b$, or optionally substituted $C_1$-$C_6$ alkyl. In some embodiments of a compound of Formula (II), (IIa), or (IIa-1), $R^6$ is as defined above and each $R^{62}$ and $R^{63}$ is independently selected from the group consisting of hydrogen, halogen, —NR$^a$R$^b$, or $C_1$-$C_6$ alkyl. In some embodiments of a compound of Formula (II), (IIa), or (IIa-1), $R^6$ is as defined above and each $R^{62}$ and $R^{63}$ is independently selected from the group consisting of hydrogen and halogen. In some embodiments of a compound of Formula (II), (IIa), or (IIa-1), $R^6$ is as defined above and each $R^{62}$ and $R^{63}$ is independently selected from the group consisting of hydrogen and —NR$^a$R$^b$. In some embodiments of a compound of Formula (II), (IIa), or (IIa-1), $R^6$ is as defined above and each $R^{62}$ and $R^{63}$ is independently selected from the group consisting of hydrogen and $C_1$-$C_6$ alkyl. In some embodiments of a compound of Formula (II), (IIa), or (IIa-1), $R^6$ is as defined above and each $R^{62}$ and $R^{63}$ is hydrogen.

In some embodiments of a compound of Formula (II), (IIa), or (IIa-1), $R^6$ is as defined above and each $R^{65}$ is independently hydrogen or optionally substituted $C_1$-$C_6$ alkyl; or two $R^{65}$ are taken together with the atoms to which there are attached to form a cyclic boronate ester. In some embodiments of a compound of Formula (II), (IIa), or (IIa-1), $R^6$ is as defined above and each $R^{65}$ is independently hydrogen or optionally substituted $C_1$-$C_6$ alkyl. In some embodiments of a compound of Formula (II), (IIa), or (IIa-1), $R^6$ is as defined above and each $R^{65}$ is hydrogen.

In some embodiments of a compound of Formula (II), (IIa), or (IIa-1), $R^6$ is as defined above and two $R^{65}$ are taken together with the atoms to which there are attached to form a cyclic boronate ester.

In some embodiments of a compound of Formula (II), (IIa), or (IIa-1), $R^6$ is as defined above and v6 is 1-4. In some embodiments of a compound of Formula (II), (IIa), or (IIa-1), $R^6$ is as defined above and v6 is 1. In some embodiments of a compound of Formula (II), (IIa), or (IIa-1), $R^6$ is as defined above and v6 is 2. In some embodiments of a compound of Formula (II), (IIa), or (IIa-1), $R^6$ is as defined above and v6 is 3. In some embodiments of a compound of Formula (II), (IIa), or (IIa-1), $R^6$ is as defined above and v6 is 4.

In some embodiments of a compound of Formula (II), (IIa), or (IIa-1), $R^6$ is as defined above and w6 is 2-4. In some embodiments of a compound of Formula (II), (IIa), or (IIa-1), $R^6$ is as defined above and w6 is 2. In some embodiments of a compound of Formula (II), (IIa), or (IIa-1), $R^6$ is as defined above and w6 is 3. In some embodiments of a compound of Formula (II), (IIa), or (IIa-1), $R^6$ is as defined above and w6 is 4.

In some embodiments of a compound of Formula (II), (IIa), or (IIa-1), $R^a$ and $R^b$ are independently hydrogen or optionally substituted $C_1$-$C_6$ alkyl. In some embodiments of a compound of Formula (II), (IIa), or (IIa-1), $R^a$ and $R^b$ are independently hydrogen or $C_1$-$C_6$ alkyl. In some embodiments of a compound of Formula (II), (IIa), or (IIa-1), $R^a$ and $R^b$ are hydrogen.

In some embodiments of a compound of Formula (II), (IIa), or (IIa-1), $R^a$ and $R^b$ are taken together with the nitrogen to which they are attached to form an optionally substituted $C_2$-$C_8$ heterocycloalkyl. In some embodiments of a compound of Formula (II), (IIa), or (IIa-1), $R^a$ and $R^b$ are taken together with the nitrogen to which they are attached to form an optionally substituted aziridine, azetidine, pyrrolidine, piperidine, morpholine, or piperazine. In some embodiments of a compound of Formula (II), (IIa), or (IIa-1), $R^a$ and $R^b$ are taken together with the nitrogen to which they are attached to form a pyrrolidine, piperidine, morpholine, or piperazine.

In some embodiments of a compound of Formula (II), (IIa), or (IIa-1), each $R^c$ is independently optionally substituted $C_1$-$C_6$ alkyl. In some embodiments of a compound of Formula (II), (IIa), or (IIa-1), each $R^c$ is independently $C_1$-$C_6$ alkyl.

Also described herein are compounds of Formula (III), or a pharmaceutically acceptable salt, solvate, or stereoisomer thereof:

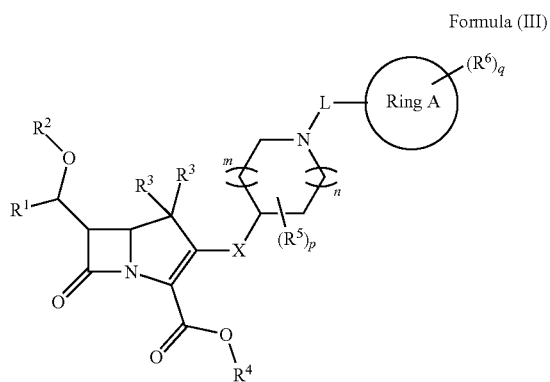

Formula (III)

wherein

Ring A is aryl, heteroaryl, cycloalkyl, or heterocycloalkyl; each optionally substituted with one, two, or three substituents each independently selected from the group consisting of oxo (when Ring A is cycloalkyl or heterocycloalkyl), optionally substituted $C_1$-$C_6$ alkyl, optionally substituted $C_2$-$C_6$ alkenyl, optionally substituted $C_2$-$C_6$ alkynyl, —$OR^{50}$, —$(CR^{52}R^{53})_{v5}OR^{50}$, —CN, —$NO_2$, halogen, —$S(=O)_2R^{54}$, —$(CR^{52}R^{53})_{v5}S(=O)_2R^{54}$, —$S(=O)_2NR^{50}R^{51}$, —$(CR^{52}R^{53})_{v5}S(=O)_2NR^{50}R^{51}$, —$C(=O)OR^{50}$, —$(CR^{52}R^{53})_{v5}C(=O)OR^{10}$, —$C(=O)NR^{50}R^{51}$, and —$(CR^{52}R^{53})_{v5}C(=O)NR^{50}R^{51}$;

X is —O—, —S—, —S(=O)—, —$S(=O)_2$—, or —$NR^7$—;

L is —$(CR^8R^9)_z$— or —$(CR^{18}R^{19})_yC(=O)$—;

$R^1$ is optionally substituted $C_1$-$C_6$ alkyl, optionally substituted $C_2$-$C_6$ alkenyl, or optionally substituted $C_2$-$C_6$ alkynyl;

$R^2$ is hydrogen, optionally substituted $C_1$-$C_6$ alkyl, optionally substituted $C_2$-$C_6$ alkenyl, optionally substituted $C_2$-$C_6$ alkynyl, or —$Si(R^c)_3$;

each $R^3$ is independently hydrogen, optionally substituted $C_1$-$C_6$ alkyl, optionally substituted $C_2$-$C_6$ alkenyl, optionally substituted $C_2$-$C_6$ alkynyl, or —$OR^a$;

$R^4$ is hydrogen, optionally substituted $C_1$-$C_6$ alkyl, optionally substituted $C_2$-$C_6$ alkenyl, optionally substituted $C_2$-$C_6$ alkynyl, optionally substituted aryl, optionally substituted heteroaryl, optionally substituted $C_3$-$C_8$ cycloalkyl, optionally substituted $C_2$-$C_8$ heterocycloalkyl, optionally substituted —($C_1$-$C_6$ alkyl)($C_3$-$C_8$ cycloalkyl), optionally substituted —($C_1$-$C_6$ alkyl)($C_2$-$C_8$ heterocycloalkyl), optionally substituted —($C_1$-$C_6$ alkyl)(aryl), or optionally substituted —($C_1$-$C_6$ alkyl)(heteroaryl);

each $R^5$ is independently hydrogen, halogen, optionally substituted $C_1$-$C_6$ alkyl, optionally substituted $C_2$-$C_6$ alkenyl, optionally substituted $C_2$-$C_6$ alkynyl, —$OR^{40}$, —$(CR^{42}R^{43})_{v4}OR^{40}$, —CN, —$NO_2$, —$S(=O)_2R^{44}$, —$(CR^{42}R^{43})_{v4}S(=O)_2R^{44}$, —$S(=O)_2NR^{40}R^{41}$, —$(CR^{42}R^{43})_{v4}S(=O)_2NR^{40}R^{41}$, —$C(=O)OR^{40}$, —$(CR^{42}R^{43})_{v4}C(=O)OR^{40}$, —$(CR^{42}R^{43})_{v4}C(=O)NR^{40}R^{41}$, —$NR^{40}R^{41}$, —$NR^{40}(CR^{42}R^{43})_{w4}NR^{40}R^{41}$, —$NR^{40}C(=NR^{41})NR^{40}R^{41}$, —$C(=NR^{40})NR^{40}R^{41}$, —$C(=NR^{40})R^{40}$, —$N(R^{40})C(=NR^{41})R^{40}$, —$(CR^{42}R^{43})_{v4}NR^{40}R^{41}$, —$(CR^{42}R^{43})_{v4}OR^{40}$, —$(CR^{42}R^{43})_{v4}N(R^{40})C(=NR^{41})NR^{40}R^{41}$, —$(CR^{42}R^{43})_{v4}NR^{40}(CR^{42}R^{43})_{w4}NR^{40}R^{41}$, —$NR^{41}C(=NR^{41})NR^{40}(CR^{42}R^{43})_{w4}NR^{40}R^{41}$, —$NR^{40}(CR^{42}R^{43})_{w4}N(R^{40})C(=NR^{41})NR^{40}R^{41}$, —$(CR^{42}R^{43})_{v4}C(=NR^{41})NR^{40}R^{41}$, —$NR^{40}(CR^{42}R^{43})_{v4}B(OR^{45})_2$, or —$(CR^{42}R^{43})_{v4}NR^{40}(CR^{42}R^{43})_{v4}B(OR^{45})_2$;

each $R^6$ is independently a basic substituent;

$R^7$ is hydrogen, optionally substituted $C_1$-$C_6$ alkyl, —$S(=O)_2R^c$, or —$S(=O)_2NR^aR^b$;

each $R^8$ and $R^9$ is independently hydrogen, halogen, —CN, optionally substituted $C_1$-$C_6$ alkyl, optionally substituted $C_2$-$C_6$ alkenyl, optionally substituted $C_2$-$C_6$ alkynyl, —$OR^a$, —$NR^aR^b$, —$C(=O)OR^a$, —$C(=O)NR^aR^b$, —$S(=O)_2R^c$, or —$S(=O)_2NR^aR^b$;

each $R^{18}$ and $R^{19}$ is independently hydrogen, halogen, —CN, optionally substituted $C_1$-$C_6$ alkyl, optionally substituted $C_2$-$C_6$ alkenyl, optionally substituted $C_2$-$C_6$ alkynyl, —$OR^a$, —$NR^aR^b$, —$C(=O)OR^a$, —$C(=O)NR^aR^b$, —$S(=O)_2R^c$, or —$S(=O)_2NR^aR^b$;

each $R^{40}$, $R^{41}$, $R^{50}$, and $R^{51}$ is independently selected from the group consisting of hydrogen, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, $C_2$-$C_8$ optionally substituted heterocycloalkyl, optionally substituted aryl, optionally substituted heteroaryl, optionally substituted —($C_1$-$C_6$ alkyl)($C_3$-$C_8$ cycloalkyl), optionally substituted —($C_1$-$C_6$ alkyl)($C_2$-$C_8$ heterocycloalkyl), optionally substituted —($C_1$-$C_6$ alkyl)(aryl), and optionally substituted —($C_1$-$C_6$ alkyl)(heteroaryl);

or $R^{40}$ and $R^{41}$, or $R^{50}$ and $R^{51}$ are taken together with the nitrogen to which they are attached to form an optionally substituted $C_2$-$C_8$ heterocycloalkyl;

each $R^{42}$, $R^{43}$, $R^{52}$, and $R^{53}$ is independently selected from the group consisting of hydrogen, halogen, —CN, —$OR^a$, —$NR^aR^b$, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, optionally substituted $C_2$-$C_8$ heterocycloalkyl, optionally substituted aryl, and optionally substituted heteroaryl;

each $R^{44}$ and $R^{54}$ is independently optionally substituted $C_1$-$C_6$ alkyl, optionally substituted $C_2$-$C_6$ alkenyl, optionally substituted $C_2$-$C_6$ alkynyl, optionally substituted aryl, optionally substituted heteroaryl, optionally substituted $C_3$-$C_8$ cycloalkyl, optionally substituted $C_2$-$C_8$ heterocycloalkyl, optionally substituted —($C_1$-$C_6$ alkyl)($C_3$-$C_8$ cycloalkyl), optionally substituted —($C_1$-$C_6$ alkyl)($C_2$-$C_8$ heterocycloalkyl), optionally substituted —($C_1$-$C_6$ alkyl)(aryl), or optionally substituted —($C_1$-$C_6$ alkyl)(heteroaryl);

each $R^{45}$ is independently hydrogen or optionally substituted $C_1$-$C_6$ alkyl;

or two $R^{45}$ are taken together with the atoms to which there are attached to form a cyclic boronate ester;

$R^a$ and $R^b$ are independently hydrogen or optionally substituted $C_1$-$C_6$ alkyl;

or $R^a$ and $R^b$ are taken together with the nitrogen to which they are attached to form an optionally substituted $C_2$-$C_8$ heterocycloalkyl;

each $R^c$ is independently optionally substituted $C_1$-$C_6$ alkyl, optionally substituted $C_2$-$C_6$ alkenyl, or optionally substituted $C_2$-$C_6$ alkynyl;

n is 0-2;

m is 0-2;

p is 0-4;

q is 1-4;

v4 and v5 are independently 1-4;

w4 is 2-4;

y is 1-4; and z is 1-5.

In some embodiments of a compound of Formula (III), X is —S—. In some embodiments of a compound of Formula (III), X is —O—. In some embodiments of a compound of Formula (III), X is —S(=O)—. In some embodiments of a compound of Formula (III), X is —$S(=O)_2$—. In some embodiments of a compound of Formula (III), X is —$NR^7$—. In some embodiments of a compound of Formula (III), X is —$NR^7$— and $R^7$ is hydrogen.

In some embodiments of a compound of Formula (III), $R^1$ is $C_1$-$C_6$ alkyl. In some embodiments of a compound of Formula (III), $R^1$ is methyl. In some embodiments of a compound of Formula (III), $R^1$ is $C_2$-$C_6$ alkenyl. In some embodiments of a compound of Formula (III), $R^1$ is $C_2$-$C_6$ alkynyl.

In some embodiments of a compound of Formula (III) $R^2$ is hydrogen. In some embodiments of a compound of Formula (III), $R^2$ is $C_1$-$C_6$ alkyl. In some embodiments of a compound of Formula (III), $R^2$ is methyl. In some embodiments of a compound of Formula (III), $R^2$ is $C_2$-$C_6$ alkenyl. In some embodiments of a compound of Formula (III), $R^2$ is $C_2$-$C_6$ alkynyl. In some embodiments of a compound of Formula (III), $R^2$ is —$Si(R^c)_3$.

In some embodiments of a compound of Formula (III), each $R^3$ is hydrogen. In some embodiments of a compound of Formula (III), each $R^3$ is independently hydrogen or $C_1$-$C_6$ alkyl. In some embodiments of a compound of Formula (III), each $R^3$ is independently hydrogen, $C_1$-$C_6$ alkyl, or $OR^a$. In some embodiments of a compound of Formula (III), each $R^3$ is independently hydrogen, $C_1$-$C_6$ alkyl, or OH. In some embodiments of a compound of Formula (III), each $R^3$ is independently $C_1$-$C_6$ alkyl. In some embodiments of a compound of Formula (III), one $R^3$ is methyl and the other $R^3$ is hydrogen. In some embodiments of a compound of Formula (III), each $R^3$ is independently hydrogen or $C_2$-$C_6$ alkenyl. In some embodiments of a compound of Formula (III), each $R^3$ is independently hydrogen or $C_2$-$C_6$ alkynyl.

In some embodiments of a compound of Formula (III), $R^4$ is hydrogen. In some embodiments of a compound of Formula (III), $R^4$ is $C_1$-$C_6$ alkyl. In some embodiments of a compound of Formula (III), $R^4$ is $C_2$-$C_6$ alkenyl. In some embodiments of a compound of Formula (III), $R^4$ is $C_2$-$C_6$ alkynyl. In some embodiments of a compound of Formula (III), $R^4$ is optionally substituted —($C_1$-$C_6$ alkyl)(aryl). In some embodiments of a compound of Formula (III), $R^4$ is —($C_1$-$C_6$ alkyl)(aryl) substituted with alkyl or —$NO_2$.

In some embodiments, a compound of Formula (III) or a pharmaceutically acceptable salt, solvate, or stereoisomer thereof is of Formula (IIIa) or a pharmaceutically acceptable salt, solvate, or stereoisomer thereof:

Formula (IIIa)

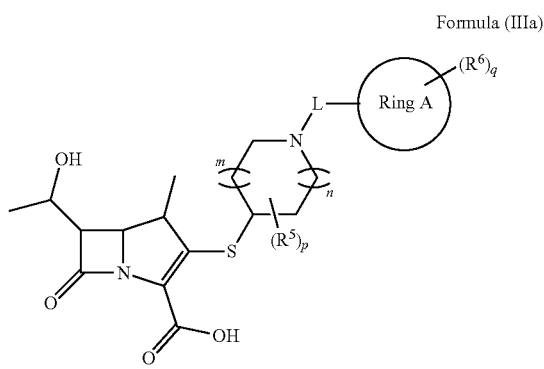

wherein

Ring A is aryl, heteroaryl, cycloalkyl, or heterocycloalkyl; each optionally substituted with one, two, or three substituents each independently selected from the group consisting of oxo (when Ring A is cycloalkyl or heterocycloalkyl), optionally substituted $C_1$-$C_6$ alkyl, optionally substituted $C_2$-$C_6$ alkenyl, optionally substituted $C_2$-$C_6$ alkynyl, —$OR^{50}$, —$(CR^{52}R^{53})_{v5}OR^{50}$, —CN, —$NO_2$, halogen, —$S(=O)_2R^{54}$, —$(CR^{52}R^{53})_{v5}S(=O)_2R^{54}$, —$S(=O)_2NR^{50}R^{51}$, —$(CR^{52}R^{53})_{v5}S(=O)_2NR^{50}R^{51}$, —$C(=O)OR^{50}$, —$(CR^{52}R^{53})_{v5}C(=O)OR^{50}$, —$C(=O)NR^{50}R^{51}$, and —$(CR^{52}R^{53})_{v5}C(=O)NR^{50}R^{51}$;

L is —$(CR^8R^9)_z$— or —$(CR^{18}R^{19})_yC(=O)$—;

each $R^5$ is independently hydrogen, halogen, optionally substituted $C_1$-$C_6$ alkyl, optionally substituted $C_2$-$C_6$ alkenyl, optionally substituted $C_2$-$C_6$ alkynyl, —$OR^{40}$, —$(CR^{42}R^{43})_{v4}OR^{40}$, —CN, —$NO_2$, —$S(=O)_2R^{44}$, —$(CR^{42}R^{43})_{v4}S(=O)_2R^{44}$, —$S(=O)_2NR^{40}R^{41}$, —$(CR^{42}R^{43})_{v4}S(=O)_2NR^{40}R^{41}$, —$C(=O)OR^{40}$, —$(CR^{42}R^{43})_{v4}C(=O)OR^{40}$, —$(CR^{42}R^{43})_{v4}C(=O)NR^{40}R^{41}$, —$NR^{40}R^{41}$, —$NR^{40}(CR^{42}R^{43})_{v4}NR^{40}R^{41}$, —$NR^{40}C(=NR^{41})NR^{40}R^{41}$, —$C(=NR^{40})NR^{40}R^{41}$, —$N(R^{40})C(=NR^{41})R^{40}$, —$(CR^{42}R^{43})_{v4}NR^{40}R^{41}$, —$(CR^{42}R^{43})_{v4}OR^{40}$, —$(CR^{42}R^{43})_{v4}N(R^{40})C(=NR^{41})NR^{40}R^{41}$, —$(CR^{42}R^{43})_{v4}NR^{40}(CR^{42}R^{43})_{v4}NR^{40}R^{41}$, —$NR^{41}C(=NR^{41})NR^{40}(CR^{42}R^{43})_{v4}NR^{40}R^{41}$, —$NR^{40}(CR^{42}R^{43})_{v4}N(R^{40})C(=NR^{41})NR^{40}R^{41}$, —$(CR^{42}R^{43})_{v4}C(=NR^{41})NR^{40}R^{41}$, —$NR^{40}(CR^{42}R^{43})_{v4}B(OR^{45})_2$, or —$(CR^{42}R^{43})_{v4}NR^{40}(CR^{42}R^{43})_{v4}B(OR^{45})_2$;

each $R^6$ is independently a basic substituent;

each $R^8$ and $R^9$ is independently hydrogen, halogen, —CN, optionally substituted $C_1$-$C_6$ alkyl, optionally substituted $C_2$-$C_6$ alkenyl, optionally substituted $C_2$-$C_6$ alkynyl, —$OR^a$, —$NR^aR^b$, —$C(=O)OR^a$, —$C(=O)NR^aR^b$, —$S(=O)_2R^c$, or —$S(=O)_2NR^aR^b$;

each $R^{18}$ and $R^{19}$ is independently hydrogen, halogen, —CN, optionally substituted $C_1$-$C_6$ alkyl, optionally substituted $C_2$-$C_6$ alkenyl, optionally substituted $C_2$-$C_6$ alkynyl, —$OR^a$, —$NR^aR^b$, —$C(=O)OR^a$, —$C(=O)NR^aR^b$, —$S(=O)_2R^c$, or —$S(=O)_2NR^aR^b$;

each $R^{40}$, $R^{41}$, $R^{50}$, and $R^{51}$ is independently selected from the group consisting of hydrogen, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, $C_2$-$C_8$ optionally substituted heterocycloalkyl, optionally substituted aryl, optionally substituted heteroaryl, optionally substituted —($C_1$-$C_6$ alkyl)($C_3$-$C_8$ cycloalkyl), optionally substituted —($C_1$-$C_6$ alkyl)($C_2$-$C_8$ heterocycloalkyl), optionally substituted —($C_1$-$C_6$ alkyl)(aryl), and optionally substituted —($C_1$-$C_6$ alkyl)(heteroaryl);

or $R^{40}$ and $R^{41}$, or $R^{50}$ and $R^{51}$ are taken together with the nitrogen to which they are attached to form an optionally substituted $C_2$-$C_8$ heterocycloalkyl;

each $R^{42}$, $R^{43}$, $R^{52}$, and $R^{53}$ is independently selected from the group consisting of hydrogen, halogen, —CN, —$OR^a$, —$NR^aR^b$, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, optionally substituted $C_2$-$C_8$ heterocycloalkyl, optionally substituted aryl, and optionally substituted heteroaryl;

each $R^{44}$ and $R^{54}$ is independently optionally substituted $C_1$-$C_6$ alkyl, optionally substituted $C_2$-$C_6$ alkenyl, optionally substituted $C_2$-$C_6$ alkynyl, optionally substituted aryl, optionally substituted heteroaryl, optionally substituted $C_3$-$C_8$ cycloalkyl, optionally substituted $C_2$-$C_8$ heterocycloalkyl, optionally substituted —($C_1$-$C_6$ alkyl)($C_3$-$C_8$ cycloalkyl), optionally substituted —($C_1$-$C_6$ alkyl)($C_2$-$C_8$ heterocycloalkyl), optionally substituted —($C_1$-$C_6$ alkyl)(aryl), or optionally substituted —($C_1$-$C_6$ alkyl)(heteroaryl);

each $R^{45}$ is independently hydrogen or optionally substituted $C_1$-$C_6$ alkyl;

or two $R^{45}$ are taken together with the atoms to which there are attached to form a cyclic boronate ester;

$R^a$ and $R^b$ are independently hydrogen or optionally substituted $C_1$-$C_6$ alkyl;

or $R^a$ and $R^b$ are taken together with the nitrogen to which they are attached to form an optionally substituted $C_2$-$C_8$ heterocycloalkyl;

each $R^c$ is independently optionally substituted $C_1$-$C_6$ alkyl, optionally substituted $C_2$-$C_6$ alkenyl, or optionally substituted $C_2$-$C_6$ alkynyl;

n is 0-2;

m is 0-2;

p is 0-4;

q is 1-4;
v4 and v5 are independently 1-4;
w4 is 2-4;
y is 1-4; and
z is 1-5.

In some embodiments, a compound of Formula (III) or (IIIa), or a pharmaceutically acceptable salt, solvate, or stereoisomer thereof is of Formula (IIIa-1) or a pharmaceutically acceptable salt, solvate, or stereoisomer thereof:

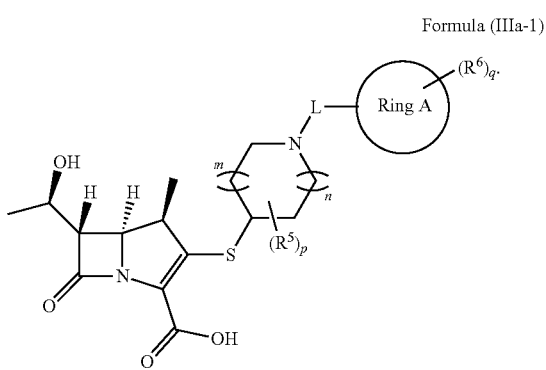

Formula (IIIa-1)

In some embodiments of a compound of Formula (III), (IIIa), or (IIIa-1), Ring A is optionally substituted phenyl, optionally substituted cyclohexyl, optionally substituted piperidinyl, optionally substituted morpholinyl, or optionally substituted pyridyl. In some embodiments of a compound of Formula (III), (IIIa), or (IIIa-1), Ring A is phenyl, cyclohexyl, piperidinyl, morpholinyl, or pyridyl, each optionally substituted with one, two, or three halogen, —CN, —OH, $C_1$-$C_6$ alkyl, $C_1$-$C_6$ haloalkyl, $C_1$-$C_6$ alkoxy, or —$NO_2$. In some embodiments of a compound of Formula (III), (IIIa), or (IIIa-1), Ring A is phenyl, cyclohexyl, piperidinyl, morpholinyl, or pyridyl. In some embodiments of a compound of Formula (III), (IIIa), or (IIIa-1), Ring A is phenyl. In some embodiments of a compound of Formula (III), (IIIa), or (IIIa-1), Ring A is cyclohexyl.

In some embodiments of a compound of Formula (III), (IIIa), or (IIIa-1), $R^{50}$ and $R^{51}$ are independently selected from the group consisting of hydrogen, optionally substituted $C_1$-$C_6$ alkyl, optionally substituted $C_3$-$C_8$ cycloalkyl, or $C_2$-$C_8$ optionally substituted heterocycloalkyl. In some embodiments of a compound of Formula (III), (IIIa), or (IIIa-1), $R^{50}$ and $R^{51}$ are independently selected from the group consisting of hydrogen and optionally substituted $C_1$-$C_6$ alkyl.

In some embodiments of a compound of Formula (III), (IIIa), or (IIIa-1), $R^{52}$ and $R^{53}$ are independently selected from the group consisting of hydrogen, halogen, —CN, —$OR^a$, —$NR^aR^b$, or optionally substituted $C_1$-$C_6$ alkyl. In some embodiments of a compound of Formula (III), (IIIa), or (IIIa-1), $R^{52}$ and $R^{53}$ are independently selected from the group consisting of hydrogen, halogen, or optionally substituted $C_1$-$C_6$ alkyl.

In some embodiments of a compound of Formula (III), (IIIa), or (IIIa-1), $R^{54}$ is optionally substituted $C_1$-$C_6$ alkyl, optionally substituted $C_3$-$C_8$ cycloalkyl, or $C_2$-$C_8$ optionally substituted heterocycloalkyl. In some embodiments of a compound of Formula (III), (IIIa), or (IIIa-1), $R^{54}$ is optionally substituted $C_1$-$C_6$ alkyl.

In some embodiments of a compound of Formula (I), (Ia), or (Ia-1), n is 0 or 1 and m is 0 or 1. In some embodiments of a compound of Formula (I), (Ia), or (Ia-1), n is 1 and m is 0 or 1.

In some embodiments of a compound of Formula (III), (IIIa), or (IIIa-1), n is 0 and m is 0. In some embodiments of a compound of Formula (III), (IIIa), or (IIIa-1) n is 0 and m is 1. In some embodiments of a compound of Formula (III), (IIIa), or (IIIa-1), n is 0 and m is 2.

In some embodiments of a compound of Formula (III), (IIIa), or (IIIa-1), n is 1 and m is 0. In some embodiments of a compound of Formula (III), (IIIa), or (IIIa-1) n is 1 and m is 1. In some embodiments of a compound of Formula (III), (IIIa), or (IIIa-1), n is 1 and m is 2.

In some embodiments of a compound of Formula (III), (IIIa), or (IIIa-1), n is 2 and m is 0. In some embodiments of a compound of Formula (III), (IIIa), or (IIIa-1) n is 2 and m is 1. In some embodiments of a compound of Formula (III), (IIIa), or (IIIa-1) n is 2 and m is 2.

In some embodiments of a compound of Formula (III), (IIIa), or (IIIa-1), L is —$(CR^8R^9)_z$—. In some embodiments of a compound of Formula (III), (IIIa), or (IIIa-1), z is 1. In some embodiments of a compound of Formula (III), (IIIa), or (IIIa-1), z is 2. In some embodiments of a compound of Formula (III), (IIIa), or (IIIa-1), z is 3. In some embodiments of a compound of Formula (III), (IIIa), or (IIIa-1), z is 4. In some embodiments of a compound of Formula (III), (IIIa), or (IIIa-1), z is 5. In some embodiments of a compound of Formula (III), (IIIa), or (IIIa-1), z is 1-5. In some embodiments of a compound of Formula (III), (IIIa), or (IIIa-1), z is 1-4. In some embodiments of a compound of Formula (III), (IIIa), or (IIIa-1), z is 1-3. In some embodiments of a compound of Formula (III), (IIIa), or (IIIa-1), z is 1 or 2. In some embodiments of a compound of Formula (III), (IIIa), or (IIIa-1), each $R^8$ and $R^9$ is independently hydrogen, halogen, —CN, optionally substituted $C_1$-$C_6$ alkyl, —$OR^a$, or —$NR^aR^b$. In some embodiments of a compound of Formula (III), (IIIa), or (IIIa-1), each $R^8$ and $R^9$ is independently hydrogen, halogen, —CN, $C_1$-$C_6$ alkyl, $C_1$-$C_6$ haloalkyl, —$OR^a$, or —$NR^aR^b$. In some embodiments of a compound of Formula (III), (IIIa), or (IIIa-1), each $R^8$ and $R^9$ is independently hydrogen, halogen, $C_1$-$C_6$ alkyl, or $C_1$-$C_6$ haloalkyl. In some embodiments of a compound of Formula (III), (IIIa), or (IIIa-1), each $R^8$ and $R^9$ is independently hydrogen, halogen, or $C_1$-$C_6$ alkyl. In some embodiments of a compound of Formula (III), (IIIa), or (IIIa-1), each $R^8$ and $R^9$ are independently hydrogen or $C_1$-$C_6$ alkyl. In some embodiments of a compound of Formula (III), (IIIa), or (IIIa-1), each $R^8$ and $R^9$ is independently hydrogen or methyl. In some embodiments of a compound of Formula (III), (IIIa), or (IIIa-1), each $R^8$ and $R^9$ is independently hydrogen or halogen. In some embodiments of a compound of Formula (III), (IIIa), or (IIIa-1), each $R^8$ and $R^9$ is hydrogen.

In some embodiments of a compound of Formula (III), (IIIa), or (IIIa-1), L is —$(CR^{18}R^{19})_yC(=O)$—. In some embodiments of a compound of Formula (III), (IIIa), or (IIIa-1), y is 1-3. In some embodiments of a compound of Formula (III), (IIIa), or (IIIa-1), y is 1 or 2. In some embodiments of a compound of Formula (III), (IIIa), or (IIIa-1), y is 1. In some embodiments of a compound of Formula (III), (IIIa), or (IIIa-1), y is 2. In some embodiments of a compound of Formula (III), (IIIa), or (IIIa-1), y is 3. In some embodiments of a compound of Formula (III), (IIIa), or (IIIa-1), y is 4. In some embodiments of a compound of Formula (III), (IIIa), or (IIIa-1), each $R^{18}$ and $R^{19}$ is independently hydrogen, halogen, —CN, optionally substituted $C_1$-$C_6$ alkyl, —$OR^a$, or —$NR^aR^b$. In some embodiments of a compound of Formula (III), (IIIa), or (IIIa-1), each $R^{18}$ and $R^{11}$ is independently hydrogen, halogen, or $C_1$-$C_6$ alkyl. In some embodiments of a compound of Formula (III), (IIIa), or (IIIa-1), each $R^{18}$ and $R^{19}$ is independently hydrogen or $C_1$-$C_6$ alkyl. In some embodiments of a compound of Formula (III), (IIIa), or (IIIa-1), each $R^{18}$ and $R^{19}$ is independently hydrogen or methyl. In some embodiments of a compound of Formula (III), (IIIa), or (IIIa-1), each $R^{18}$ and $R^{19}$ is independently hydrogen or halogen. In some embodiments of a compound of Formula (III), (IIIa), or (IIIa-1), each $R^{18}$ and $R^{19}$ is hydrogen.

In some embodiments of a compound of Formula (III), (IIIa), or (IIIa-1), p is 0. In some embodiments of a compound of Formula (III), (IIIa), or (IIIa-1), p is 1. In some embodiments of a compound of Formula (III), (IIIa), or (IIIa-1), p is 2. In some embodiments of a compound of Formula (III), (IIIa), or (IIIa-1), p is 3. In some embodiments of a compound of Formula (III), (IIIa), or (IIIa-1), p is 4. In some embodiments of a compound of Formula (III), (IIIa), or (IIIa-1), each $R^5$ is independently hydrogen, halogen, optionally substituted $C_1$-$C_6$ alkyl, —$OR^{40}$, —$(CR^{42}R^{43})_{v4}OR^{40}$, —CN, —$NO_2$, or —$NR^{40}R^{41}$. In some embodiments of a compound of Formula (III), (IIIa), or (IIIa-1), each $R^5$ is independently hydrogen or halogen. In some embodiments of a compound of Formula (III), (IIIa), or (IIIa-1), each $R^5$ is hydrogen. In some embodiments of a compound of Formula (III), (IIIa), or (IIIa-1), each $R^5$ is independently halogen or optionally substituted $C_1$-$C_6$ alkyl. In some embodiments of a compound of Formula (III), (IIIa), or (IIIa-1), each $R^5$ is independently optionally substituted $C_1$-$C_6$ alkyl. In some embodiments of a compound of Formula (III), (IIIa), or (IIIa-1), each $R^5$ is independently optionally substituted methyl. In some embodiments of a compound of Formula (III), (IIIa), or (IIIa-1), each $R^5$ is independently $C_1$-$C_6$ alkyl or $C_1$-$C_6$ hydroxyalkyl. In some embodiments of a compound of Formula (III), (IIIa), or (IIIa-1), each $R^5$ is independently methyl or —$CH_2OH$.

In some embodiments of a compound of Formula (III), (IIIa), or (IIIa-1), each $R^{40}$, $R^{41}$, $R^{50}$, and $R^{51}$ is independently selected from the group consisting of hydrogen, optionally substituted $C_1$-$C_6$ alkyl, optionally substituted $C_3$-$C_8$ cycloalkyl, or $C_2$-$C_8$ optionally substituted heterocycloalkyl. In some embodiments of a compound of Formula (III), (IIIa), or (IIIa-1), each $R^{40}$, $R^{41}$, $R^{50}$, and $R^{51}$ is independently selected from the group consisting of hydrogen or optionally substituted $C_1$-$C_6$ alkyl. In some embodiments of a compound of Formula (III), (IIIa), or (IIIa-1), each $R^{40}$, $R^{41}$, $R^{50}$, and $R^{51}$ is hydrogen.

In some embodiments of a compound of Formula (III), (IIIa), or (IIIa-1), $R^{40}$ and $R^{41}$, or $R^{50}$ and $R^{51}$ are taken together with the nitrogen to which they are attached to form an optionally substituted $C_2$-$C_8$ heterocycloalkyl. In some embodiments of a compound of Formula (III), (IIIa), or (IIIa-1), $R^{40}$ and $R^{41}$, or $R^{50}$ and $R^{51}$ are taken together with the nitrogen to which they are attached to form an optionally substituted aziridine, azetidine, pyrrolidine, piperidine, morpholine, or piperazine. In some embodiments of a compound of Formula (III), (IIIa), or (IIIa-1), $R^{40}$ and $R^{41}$, or $R^{50}$ and $R^{51}$ are taken together with the nitrogen to which they are attached to form a pyrrolidine, piperidine, morpholine, or piperazine.

In some embodiments of a compound of Formula (III), (IIIa), or (IIIa-1), each $R^{42}$, $R^{43}$, $R^{52}$, and $R^{53}$ is independently selected from the group consisting of hydrogen, halogen, —CN, —$OR^a$, —$NR^aR^b$, or optionally substituted $C_1$-$C_6$ alkyl. In some embodiments of a compound of Formula (III), (IIIa), or (IIIa-1), each $R^{42}$, $R^{43}$, $R^{52}$, and $R^{53}$ is independently selected from the group consisting of hydrogen, halogen, —$NR^aR^b$, or $C_1$-$C_6$ alkyl. In some embodiments of a compound of Formula (III), (IIIa), or (IIIa-1), each $R^{42}$, $R^{43}$, $R^{52}$, and $R^{53}$ is hydrogen or $C_1$-$C_6$ alkyl. In some embodiments of a compound of Formula (III), (IIIa), or (IIIa-1), each $R^{42}$, $R^{43}$, $R^{52}$, and $R^{53}$ is hydrogen or halogen. In some embodiments of a compound of Formula (III), (IIIa), or (IIIa-1), each $R^{42}$, $R^{43}$, $R^{52}$, and $R^{53}$ is hydrogen or —$NR^aR^b$.

In some embodiments of a compound of Formula (III), (IIIa), or (IIIa-1), $R^{44}$ and $R^{54}$ are independently optionally substituted $C_1$-$C_6$ alkyl. In some embodiments of a compound of Formula (III), (IIIa), or (IIIa-1), $R^{44}$ and $R^{54}$ are methyl.

In some embodiments of a compound of Formula (III), (IIIa), or (IIIa-1), $R^{45}$ is hydrogen or $C_1$-$C_6$ alkyl. In some embodiments of a compound of Formula (III), (IIIa), or (IIIa-1), $R^{45}$ is hydrogen. In some embodiments of a compound of Formula (III), (IIIa), or (IIIa-1), $R^{45}$ is $C_1$-$C_6$ alkyl.

In some embodiments of a compound of Formula (III), (IIIa), or (IIIa-1), two $R^{45}$ are taken together with the atoms to which there are attached to form a cyclic boronate ester.

In some embodiments of a compound of Formula (III), (IIIa), or (IIIa-1), q is 1. In some embodiments of a compound of Formula (III), (IIIa), or (IIIa-1), q is 2. In some embodiments of a compound of Formula (III), (IIIa), or (IIIa-1), q is 3. In some embodiments of a compound of Formula (III), (IIIa), or (IIIa-1), q is 4.

In some embodiments of a compound of Formula (III), (IIIa), or (IIIa-1), each $R^6$ is a basic substituent comprising at least one basic nitrogen. In some embodiments of a compound of Formula (III), (IIIa), or (IIIa-1), each $R^6$ is a basic substituent comprising one basic nitrogen. In some embodiments of a compound of Formula (III), (IIIa), or (IIIa-1), each $R^6$ is a basic substituent comprising two basic nitrogens.

In some embodiments of a compound of Formula (III), (IIIa), or (IIIa-1), each $R^6$ is independently —$NR^{60}R^{61}$, —$NR^{60}(CR^{62}R^{63})_{w6}NR^{60}R^{61}$, —$NR^{60}C(=NR^{61})NR^{60}R^{61}$, —$C(=NR^{60})NR^{60}R^{61}$, —$C(=NR^{60})R^{60}$, —$N(R^{60})C(=NR^{61})R^{60}$, —$(CR^{62}R^{63})_{v6}NR^{60}R^{61}$, —$C(=O)NR^{60}R^{61}$, —$C(=O)(CR^{62}R^{63})_{v6}NR^{60}R^{61}$, —$(CR^{62}R^{63})_{v6}C(=O)NR^{60}R^{61}$, —$(CR^{62}R^{63})_{v6}N(R^{60})C(=NR^{61})NR^{60}R^{61}$, —$(CR^{62}R^{63})_{v6}NR^{60}(CR^{62}R^{63})_{w6}NR^{60}R^{61}$, —$NR^{61}C(=NR^{61})NR^{60}(CR^{62}R^{63})_{w6}NR^{60}R^{61}$, —$NR^{60}(CR^{62}R^{63})_{w6}N(R^{60})C(=NR^{61})NR^{60}R^{61}$, —$(CR^{62}R^{63})_{v6}C(=NR^{61})NR^{60}R^{61}$, —$NR^{60}(CR^{62}R^{63})_{v6}B(OR^{65})_2$, or —$(CR^{62}R^{63})_{v6}NR^{60}(CR^{62}R^{63})_{v6}B(OR^{65})_2$.

In some embodiments of a compound of Formula (III), (IIIa), or (IIIa-1), each $R^6$ is independently —$NR^{60}R^{61}$, —$NR^{60}(CR^{62}R^{63})_{w6}NR^{60}R^{61}$, —$NR^{60}C(=NR^{61})NR^{60}R^{61}$, —$C(=NR^{60})NR^{60}R^{61}$, —$N(R^{60})C(=NR^{61})R^{60}$, —$(CR^{62}R^{63})_{v6}NR^{60}R^{61}$, —$(CR^{62}R^{63})_{v6}N(R^{60})C(=NR^{61})NR^{60}R^{61}$, —$(CR^{62}R^{63})_{v6}NR^{60}(CR^{62}R^{63})_{w6}NR^{60}R^{61}$, —$NR^{61}C(=NR^{61})NR^{60}(CR^{62}R^{63})_{w6}NR^{60}R^{61}$, —$NR^{60}(CR^{62}R^{63})_{w6}N(R^{60})C(=NR^{61})NR^{60}R^{61}$, —$(CR^{62}R^{63})_{v6}C(=NR^{61})NR^{60}R^{61}$, —$NR^{60}(CR^{62}R^{63})_{v6}B(OR^{65})_2$, or —$(CR^{62}R^{63})_{v6}NR^{60}(CR^{62}R^{63})_{v6}B(OR^{65})_2$.

In some embodiments of a compound of Formula (III), (IIIa), or (IIIa-1), each $R^6$ is independently —$NR^{60}R^{61}$, —$NR^{60}(CR^{62}R^{63})_{w6}NR^{60}R^{61}$, —$NR^{60}C(=NR^{61})NR^{60}R^{61}$, —$C(=NR^{60})NR^{60}R^{61}$, —$N(R^{60})C(=NR^{61})R^{60}$, —$(CR^{62}R^{63})_{v6}NR^{60}R^{61}$, —$(CR^{62}R^{63})_{v6}N(R^{60})C(=NR^{61})NR^{60}R^{61}$, —$(CR^{62}R^{63})_{v6}NR^{60}(CR^{62}R^{63})_{w6}NR^{60}R^{61}$, —$NR^{61}C(=NR^{61})NR^{60}(CR^{62}R^{63})_{w6}NR^{60}R^{61}$, —$NR^{60}(CR^{62}R^{63})_{w6}N(R^{60})C(=NR^{61})NR^{60}R^{61}$, or —$(CR^{62}R^{63})_{v6}C(=NR^{61})NR^{60}R^{61}$; v6 is 1-4; and w6 is 2-4.

In some embodiments of a compound of Formula (III), (IIIa), or (IIIa-1), each $R^6$ is independently —$NR^{60}R^{61}$, —NR$^{60}$(CR$^{62}$R$^{63}$)$_{w6}$NR$^{60}$R$^{61}$, —NR$^{60}$C(=NR$^{61}$)NR$^{60}$R$^{61}$, —C(=NR$^{60}$)NR$^{60}$R$^{61}$, —N(R$^{60}$)C(=NR$^{61}$)R$^{60}$, or —(CR$^{62}$R$^{63}$)$_{v6}$NR$^{60}$R$^{61}$.

In some embodiments of a compound of Formula (III), (IIIa), or (IIIa-1), each R$^6$ is independently —NR$^{60}$R$^{61}$, —C(=NR$^{60}$)NR$^{60}$R$^{61}$, —(CR$^{62}$R$^{63}$)$_{v6}$NR$^{60}$R$^{61}$, or —NR$^{60}$(CR$^{62}$R$^{63}$)$_{v6}$B(OR$^{65}$)$_2$.

In some embodiments of a compound of Formula (III), (IIIa), or (IIIa-1), R$^6$ is —NR$^{60}$R$^{61}$.

In some embodiments of a compound of Formula (III), (IIIa), or (IIIa-1), R$^6$ is —(CR$^{62}$R$^{63}$)$_{v6}$NR$^{60}$R$^{61}$.

In some embodiments of a compound of Formula (III), (IIIa), or (IIIa-1), R$^6$ is —C(=NR$^{60}$)NR$^{60}$R$^{61}$.

In some embodiments of a compound of Formula (III), (IIIa), or (IIIa-1), R$^6$ is —NR$^{60}$(CR$^{62}$R$^{63}$)$_{v6}$B(OR$^{65}$)$_2$.

In some embodiments of a compound of Formula (III), (IIIa), or (IIIa-1), R$^6$ is as defined above and each R$^{60}$ and R$^{61}$ is independently selected from the group consisting of hydrogen, optionally substituted C$_1$-C$_6$ alkyl, optionally substituted C$_2$-C$_6$ alkenyl, optionally substituted C$_2$-C$_6$ alkynyl, optionally substituted C$_3$-C$_8$ cycloalkyl, C$_2$-C$_8$ optionally substituted heterocycloalkyl, optionally substituted aryl, optionally substituted heteroaryl, optionally substituted —(C$_1$-C$_6$ alkyl)(C$_3$-C$_8$ cycloalkyl), optionally substituted —(C$_1$-C$_6$ alkyl)(C$_2$-C$_8$ heterocycloalkyl), optionally substituted —(C$_1$-C$_6$ alkyl)(aryl), and optionally substituted —(C$_1$-C$_6$ alkyl)(heteroaryl); or R$^{60}$ and R$^{61}$ are taken together with the nitrogen to which they are attached to form an optionally substituted C$_2$-C$_8$ heterocycloalkyl. In some embodiments of a compound of Formula (III), (IIIa), or (IIIa-1), R$^6$ is as defined above and each R$^{60}$ and R$^{61}$ is independently selected from the group consisting of hydrogen, optionally substituted C$_1$-C$_6$ alkyl, optionally substituted C$_2$-C$_6$ alkenyl, optionally substituted C$_2$-C$_6$ alkynyl, optionally substituted C$_3$-C$_8$ cycloalkyl, C$_2$-C$_8$ optionally substituted heterocycloalkyl, optionally substituted aryl, optionally substituted heteroaryl, optionally substituted —(C$_1$-C$_6$ alkyl)(C$_3$-C$_8$ cycloalkyl), optionally substituted —(C$_1$-C$_6$ alkyl)(C$_2$-C$_8$ heterocycloalkyl), optionally substituted —(C$_1$-C$_6$ alkyl)(aryl), and optionally substituted —(C$_1$-C$_6$ alkyl)(heteroaryl). In some embodiments of a compound of Formula (III), (IIIa), or (IIIa-1), R$^6$ is as defined above and each R$^{60}$ and R$^{61}$ is independently selected from the group consisting of hydrogen, optionally substituted C$_1$-C$_6$ alkyl, optionally substituted C$_3$-C$_8$ cycloalkyl, or C$_2$-C$_8$ optionally substituted heterocycloalkyl. In some embodiments of a compound of Formula (III), (IIIa), or (IIIa-1), R$^6$ is as defined above and each R$^{60}$ and R$^{61}$ is independently selected from the group consisting of hydrogen and optionally substituted C$_1$-C$_6$ alkyl. In some embodiments of a compound of Formula (III), (IIIa), or (IIIa-1), R$^6$ is as defined above and each R$^{60}$ and R$^{61}$ is independently selected from the group consisting of hydrogen and C$_1$-C$_6$ alkyl. In some embodiments of a compound of Formula (III), (IIIa), or (IIIa-1), R$^6$ is as defined above and each R$^{60}$ and R$^{61}$ is hydrogen.

In some embodiments of a compound of Formula (III), (IIIa), or (IIIa-1), R$^6$ is as defined above and R$^{60}$ and R$^{61}$ are taken together with the nitrogen to which they are attached to form an optionally substituted C$_2$-C$_8$ heterocycloalkyl. In some embodiments of a compound of Formula (III), (IIIa), or (IIIa-1), R$^6$ is as defined above and R$^{60}$ and R$^{61}$ are taken together with the nitrogen to which they are attached to form an optionally substituted aziridine, azetidine, pyrrolidine, piperidine, morpholine, or piperazine. In some embodiments of a compound of Formula (III), (IIIa), or (IIIa-1), R$^6$ is as defined above and R$^{60}$ and R$^{61}$ are taken together with the nitrogen to which they are attached to form a pyrrolidine, piperidine, morpholine, or piperazine.

In some embodiments of a compound of Formula (II), (IIa), or (IIa-1), R$^6$ is as defined above and each R$^{62}$ and R$^{63}$ is independently selected from the group consisting of hydrogen, halogen, —CN, —OR$^a$, —NR$^a$R$^b$, optionally substituted C$_1$-C$_6$ alkyl, optionally substituted C$_2$-C$_6$ alkenyl, optionally substituted C$_2$-C$_6$ alkynyl, optionally substituted C$_3$-C$_8$ cycloalkyl, optionally substituted C$_2$-C$_8$ heterocycloalkyl, optionally substituted aryl, and optionally substituted heteroaryl. In some embodiments of a compound of Formula (III), (IIIa), or (IIIa-1), R$^6$ is as defined above and each R$^{62}$ and R$^{63}$ is independently selected from the group consisting of hydrogen, halogen, —CN, —OR$^a$, —NR$^a$R$^b$, or optionally substituted C$_1$-C$_6$ alkyl. In some embodiments of a compound of Formula (III), (IIIa), or (IIIa-1), R$^6$ is as defined above and each R$^{62}$ and R$^{63}$ is independently selected from the group consisting of hydrogen, halogen, —NR$^a$R$^b$, or C$_1$-C$_6$ alkyl. In some embodiments of a compound of Formula (III), (IIIa), or (IIIa-1), R$^6$ is as defined above and each R$^{62}$ and R$^{63}$ is independently selected from the group consisting of hydrogen and halogen. In some embodiments of a compound of Formula (III), (IIIa), or (IIIa-1), R$^6$ is as defined above and each R$^{62}$ and R$^{63}$ is independently selected from the group consisting of hydrogen and —NR$^a$R$^b$. In some embodiments of a compound of Formula (III), (IIIa), or (IIIa-1), R$^6$ is as defined above and each R$^{62}$ and R$^{63}$ is independently selected from the group consisting of hydrogen and C$_1$-C$_6$ alkyl. In some embodiments of a compound of Formula (III), (IIIa), or (IIIa-1), R$^6$ is as defined above and each R$^{62}$ and R$^{63}$ is hydrogen.

In some embodiments of a compound of Formula (III), (IIIa), or (IIIa-1), R$^6$ is as defined above and each R$^{65}$ is independently hydrogen or optionally substituted C$_1$-C$_6$ alkyl; or two R$^{65}$ are taken together with the atoms to which there are attached to form a cyclic boronate ester.

In some embodiments of a compound of Formula (III), (IIIa), or (IIIa-1), R$^6$ is as defined above and each R$^{65}$ is independently hydrogen or optionally substituted C$_1$-C$_6$ alkyl. In some embodiments of a compound of Formula (III), (IIIa), or (IIIa-1), R$^6$ is as defined above and each R$^{65}$ is hydrogen.

In some embodiments of a compound of Formula (III), (IIIa), or (IIIa-1), R$^6$ is as defined above and two R$^{65}$ are taken together with the atoms to which there are attached to form a cyclic boronate ester.

In some embodiments of a compound of Formula (III), (IIIa), or (IIIa-1), R$^6$ is as defined above and v6 is 1-4. In some embodiments of a compound of Formula (III), (IIIa), or (IIIa-1), R$^6$ is as defined above and v6 is 1. In some embodiments of a compound of Formula (III), (IIIa), or (IIIa-1), R$^6$ is as defined above and v6 is 2. In some embodiments of a compound of Formula (III), (IIIa), or (IIIa-1), R$^6$ is as defined above and v6 is 3. In some embodiments of a compound of Formula (III), (IIIa), or (IIIa-1), R$^6$ is as defined above and v6 is 4.

In some embodiments of a compound of Formula (III), (IIIa), or (IIIa-1), R$^6$ is as defined above and w6 is 2-4. In some embodiments of a compound of Formula (III), (IIIa), or (IIIa-1), R$^6$ is as defined above and w6 is 2. In some embodiments of a compound of Formula (III), (IIIa), or (IIIa-1), R$^6$ is as defined above and w6 is 3. In some embodiments of a compound of Formula (III), (IIIa), or (IIIa-1), R$^6$ is as defined above and w6 is 4.

In some embodiments of a compound of Formula (III), (IIIa), or (IIIa-1), R$^a$ and R$^b$ are independently hydrogen or optionally substituted C$_1$-C$_6$ alkyl. In some embodiments of a compound of Formula (III), (IIIa), or (IIIa-1), $R^a$ and $R^b$ are independently hydrogen or $C_1$-$C_6$ alkyl. In some embodiments of a compound of Formula (III), (IIIa), or (IIIa-1), $R^a$ and $R^b$ are hydrogen.

In some embodiments of a compound of Formula (III), (IIIa), or (IIIa-1), $R^a$ and $R^b$ are taken together with the nitrogen to which they are attached to form an optionally substituted $C_2$-$C_8$ heterocycloalkyl. In some embodiments of a compound of Formula (III), (IIIa), or (IIIa-1), $R^a$ and $R^b$ are taken together with the nitrogen to which they are attached to form an optionally substituted aziridine, azetidine, pyrrolidine, piperidine, morpholine, or piperazine. In some embodiments of a compound of Formula (III), (IIIa), or (IIIa-1), $R^a$ and $R^b$ are taken together with the nitrogen to which they are attached to form a pyrrolidine, piperidine, morpholine, or piperazine.

In some embodiments of a compound of Formula (III), (IIIa), or (IIIa-1), each $R^c$ is independently optionally substituted $C_1$-$C_6$ alkyl. In some embodiments of a compound of Formula (III), (IIIa), or (IIIa-1), each $R^c$ is independently $C_1$-$C_6$ alkyl.

Also described herein are compounds of Formula (IV), or a pharmaceutically acceptable salt, solvate, or stereoisomer thereof:

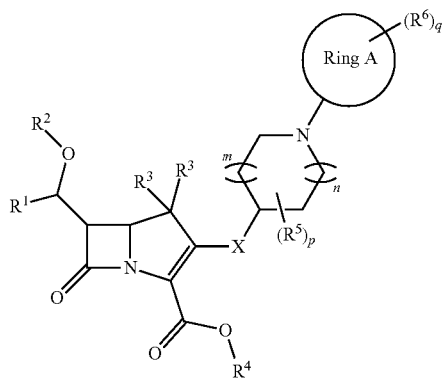

Formula (IV)

wherein
Ring A is cycloalkyl or heterocycloalkyl; each optionally substituted with one, two, or three substituents each independently selected from the group consisting of oxo, optionally substituted $C_1$-$C_6$ alkyl, optionally substituted $C_2$-$C_6$ alkenyl, optionally substituted $C_2$-$C_6$ alkynyl, —$OR^{50}$, —$(CR^{52}R^{53})_{\nu 5}OR^{50}$, —CN, —$NO_2$, halogen, —$S(=O)_2R^{54}$, —$(CR^{52}R^{53})_{\nu 5}S(=O)_2R^{54}$, —$S(=O)_2NR^{50}R^{51}$, —$(CR^{52}R^{53})_{\nu 5}S(=O)_2NR^{50}R^{51}$, —$C(=O)OR^{50}$, —$(CR^{52}R^{53})_{\nu 5}C(=O)OR^{10}$, —$C(=O)NR^{50}R^{51}$, and —$(CR^{52}R^{53})_{\nu 5}C(=O)NR^{50}R^{51}$;

X is —O—, —S—, —S(=O)—, —$S(=O)_2$—, or —$NR^7$—;

$R^1$ is optionally substituted $C_1$-$C_6$ alkyl, optionally substituted $C_2$-$C_6$ alkenyl, or optionally substituted $C_2$-$C_6$ alkynyl;

$R^2$ is hydrogen, optionally substituted $C_1$-$C_6$ alkyl, optionally substituted $C_2$-$C_6$ alkenyl, optionally substituted $C_2$-$C_6$ alkynyl, or —$Si(R^c)_3$;

each $R^3$ is independently hydrogen, optionally substituted $C_1$-$C_6$ alkyl, optionally substituted $C_2$-$C_6$ alkenyl, optionally substituted $C_2$-$C_6$ alkynyl, or —$OR^a$;

$R^4$ is hydrogen, optionally substituted $C_1$-$C_6$ alkyl, optionally substituted $C_2$-$C_6$ alkenyl, optionally substituted $C_2$-$C_6$ alkynyl, optionally substituted aryl, optionally substituted heteroaryl, optionally substituted $C_3$-$C_8$ cycloalkyl, optionally substituted $C_2$-$C_8$ heterocycloalkyl, optionally substituted —($C_1$-$C_6$ alkyl)($C_3$-$C_8$ cycloalkyl), optionally substituted —($C_1$-$C_6$ alkyl)($C_2$-$C_8$ heterocycloalkyl), optionally substituted —($C_1$-$C_6$ alkyl)(aryl), or optionally substituted —($C_1$-$C_6$ alkyl)(heteroaryl);

each $R^5$ is independently hydrogen, halogen, optionally substituted $C_1$-$C_6$ alkyl, optionally substituted $C_2$-$C_6$ alkenyl, optionally substituted $C_2$-$C_6$ alkynyl, —$OR^{40}$, —$(CR^{42}R^{43})_{\nu 4}OR^{40}$, —CN, —$NO_2$, —$S(=O)_2R^{44}$, —$(CR^{42}R^{43})_{\nu 4}S(=O)_2R^{44}$, —$S(=O)_2NR^{40}R^{41}$, —$(CR^{42}R^{43})_{\nu 4}S(=O)_2NR^{40}R^{41}$, —$C(=O)OR^{40}$, —$(CR^{42}R^{43})_{\nu 4}C(=O)OR^{40}$, —$(CR^{42}R^{43})_{\nu 4}C(=O)NR^{40}R^{41}$, —$NR^{40}R^{41}$, —$NR^{40}(CR^{42}R^{43})_{\nu 4}NR^{40}R^{41}$, —$NR^{40}C(=NR^{41})NR^{40}R^{41}$, —$C(=NR^{40})NR^{40}R^{41}$, —$C(=NR^{40})R^{40}$, —$N(R^{40})C(=NR^{41})R^{40}$, —$(CR^{42}R^{43})_{\nu 4}NR^{40}R^{41}$, —$(CR^{42}R^{43})_{\nu 4}OR^{40}$, —$(CR^{42}R^{43})_{\nu 4}N(R^{40})C(=NR^{41})NR^{40}R^{41}$, —$(CR^{42}R^{43})_{\nu 4}NR^{40}(CR^{42}R^{43})_{\nu 4}NR^{40}R^{41}$, —$NR^{41}C(=NR^{41})NR^{40}(CR^{42}R^{43})_{\nu 4}NR^{40}R^{41}$, —$NR^{40}(CR^{42}R^{43})_{\nu 4}N(R^{40})C(=NR^{41})NR^{40}R^{41}$, —$(CR^{42}R^{43})_{\nu 4}C(=NR^{41})NR^{40}R^{41}$, —$NR^{40}(CR^{42}R^{43})_{\nu 4}B(OR^{45})_2$, or —$(CR^{42}R^{43})_{\nu 4}NR^{40}(CR^{42}R^{43})_{\nu 4}B(OR^{45})_2$;

each $R^6$ is independently a basic substituent;

$R^7$ is hydrogen, optionally substituted $C_1$-$C_6$ alkyl, —$S(=O)_2R^c$, or —$S(=O)_2NR^aR^b$;

each $R^{40}$, $R^{41}$, $R^{50}$, and $R^{51}$ is independently selected from the group consisting of hydrogen, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, $C_2$-$C_8$ optionally substituted heterocycloalkyl, optionally substituted aryl, optionally substituted heteroaryl, optionally substituted —($C_1$-$C_6$ alkyl)($C_3$-$C_8$ cycloalkyl), optionally substituted —($C_1$-$C_6$ alkyl)($C_2$-$C_8$ heterocycloalkyl), optionally substituted —($C_1$-$C_6$ alkyl)(aryl), and optionally substituted —($C_1$-$C_6$ alkyl)(heteroaryl);

or $R^{40}$ and $R^{41}$, or $R^{50}$ and $R^{51}$ are taken together with the nitrogen to which they are attached to form an optionally substituted $C_2$-$C_8$ heterocycloalkyl;

each $R^{42}$, $R^{43}$, $R^{52}$, and $R^{53}$ is independently selected from the group consisting of hydrogen, halogen, —CN, —$OR^a$, —$NR^aR^b$, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, optionally substituted $C_2$-$C_8$ heterocycloalkyl, optionally substituted aryl, and optionally substituted heteroaryl;

each $R^{44}$ and $R^{54}$ is independently optionally substituted $C_1$-$C_6$ alkyl, optionally substituted $C_2$-$C_6$ alkenyl, optionally substituted $C_2$-$C_6$ alkynyl, optionally substituted aryl, optionally substituted heteroaryl, optionally substituted $C_3$-$C_8$ cycloalkyl, optionally substituted $C_2$-$C_8$ heterocycloalkyl, optionally substituted —($C_1$-$C_6$ alkyl)($C_3$-$C_8$ cycloalkyl), optionally substituted —($C_1$-$C_6$ alkyl)($C_2$-$C_8$ heterocycloalkyl), optionally substituted —($C_1$-$C_6$ alkyl)(aryl), or optionally substituted —($C_1$-$C_6$ alkyl)(heteroaryl);

each $R^{45}$ is independently hydrogen or optionally substituted $C_1$-$C_6$ alkyl;

or two $R^{45}$ are taken together with the atoms to which there are attached to form a cyclic boronate ester;

$R^a$ and $R^b$ are independently hydrogen or optionally substituted $C_1$-$C_6$ alkyl;

or $R^a$ and $R^b$ are taken together with the nitrogen to which they are attached to form an optionally substituted $C_2$-$C_8$ heterocycloalkyl;

each $R^c$ is independently optionally substituted $C_1$-$C_6$ alkyl, optionally substituted $C_2$-$C_6$ alkenyl, or optionally substituted $C_2$-$C_6$ alkynyl;

n is 0-2;

m is 0-2;

p is 0-4;

q is 1-4;

v4 and v5 are independently 1-4; and w4 is 2-4.

In some embodiments of a compound of Formula (IV), X is —S—. In some embodiments of a compound of Formula (IV), X is —O—. In some embodiments of Formula (IV), X is —S(═O)—. In some embodiments of a compound of Formula (IV), X is —S(═O)$_2$—. In some embodiments of a compound of Formula (IV), X is —NR$^7$—. In some embodiments of a compound of Formula (IV), X is —NR$^7$— and $R^7$ is hydrogen.

In some embodiments of a compound of Formula (IV), $R^1$ is $C_1$-$C_6$ alkyl. In some embodiments of a compound of Formula (IV), $R^1$ is methyl. In some embodiments of a compound of Formula (IV), $R^1$ is $C_2$-$C_6$ alkenyl. In some embodiments of a compound of Formula (IV), $R^1$ is $C_2$-$C_6$ alkynyl.

In some embodiments of a compound of Formula (IV) $R^2$ is hydrogen. In some embodiments of a compound of Formula (IV), $R^2$ is $C_1$-$C_6$ alkyl. In some embodiments of a compound of Formula (IV), $R^2$ is methyl. In some embodiments of a compound of Formula (IV), $R^2$ is $C_2$-$C_6$ alkenyl. In some embodiments of a compound of Formula (IV), $R^2$ is $C_2$-$C_6$ alkynyl. In some embodiments of a compound of Formula (IV), $R^2$ is —Si(R$^c$)$_3$.

In some embodiments of a compound of Formula (IV), each $R^3$ is hydrogen. In some embodiments of a compound of Formula (IV), each $R^3$ is independently hydrogen or $C_1$-$C_6$ alkyl. In some embodiments of a compound of Formula (IV), each $R^3$ is independently hydrogen, $C_1$-$C_6$ alkyl, or OR$^a$. In some embodiments of a compound of Formula (IV), each $R^3$ is independently hydrogen, $C_1$-$C_6$ alkyl, or OH. In some embodiments of a compound of Formula (IV), each $R^3$ is independently $C_1$-$C_6$ alkyl. In some embodiments of a compound of Formula (IV), one $R^3$ is methyl and the other $R^3$ is hydrogen. In some embodiments of a compound of Formula (IV), each $R^3$ is independently hydrogen or $C_2$-$C_6$ alkenyl. In some embodiments of a compound of Formula (IV), each $R^3$ is independently hydrogen or $C_2$-$C_6$ alkynyl.

In some embodiments of a compound of Formula (IV), $R^4$ is hydrogen. In some embodiments of a compound of Formula (IV), $R^4$ is $C_1$-$C_6$ alkyl. In some embodiments of a compound of Formula (IV), $R^4$ is $C_2$-$C_6$ alkenyl. In some embodiments of a compound of Formula (IV), $R^4$ is $C_2$-$C_6$ alkynyl. In some embodiments of a compound of Formula (IV), $R^4$ is optionally substituted —(C$_1$-C$_6$ alkyl)(aryl). In some embodiments of a compound of Formula (IV), $R^4$ is —(C$_1$-C$_6$ alkyl)(aryl) substituted with alkyl or —NO$_2$.

In some embodiments, a compound of Formula (IV) or a pharmaceutically acceptable salt, solvate, or stereoisomer thereof is of Formula (IVa) or a pharmaceutically acceptable salt, solvate, or stereoisomer thereof:

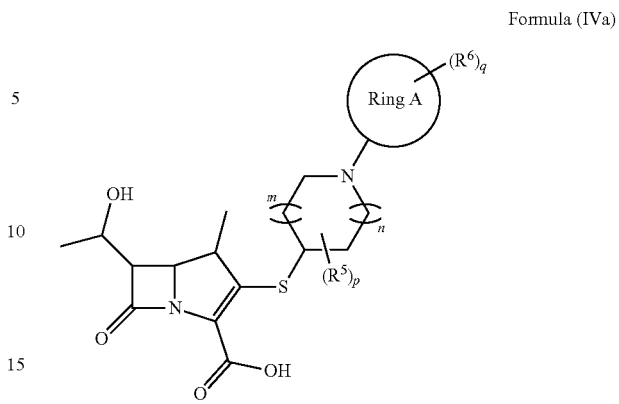

Formula (IVa)

wherein

Ring A is cycloalkyl or heterocycloalkyl; each optionally substituted with one, two, or three substituents each independently selected from the group consisting of oxo optionally substituted $C_1$-$C_6$ alkyl, optionally substituted $C_2$-$C_6$ alkenyl, optionally substituted $C_2$-$C_6$ alkynyl, —OR$^{50}$, —(CR$^{52}$R$^{53}$)$_{v5}$OR$^{50}$, —CN, —NO$_2$, halogen, —S(═O)$_2$R$^{54}$, —(CR$^{52}$R$^{53}$)$_{v5}$S(═O)$_2$R$^{54}$, —S(═O)$_2$NR$^{50}$R$^{51}$, —(CR$^{52}$R$^{53}$)$_{v5}$S(═O)$_2$NR$^{50}$R$^{51}$, —C(═O)OR$^{50}$, —(CR$^{52}$R$^{53}$)$_{v5}$C(═O)OR$^{50}$, —C(═O)NR$^{50}$R$^{51}$, and —(CR$^{52}$R$^{53}$)$_{v5}$C(═O)NR$^{50}$R$^{51}$;

each $R^5$ is independently hydrogen, halogen, optionally substituted $C_1$-$C_6$ alkyl, optionally substituted $C_2$-$C_6$ alkenyl, optionally substituted $C_2$-$C_6$ alkynyl, —OR$^{40}$, —(CR$^{42}$R$^{43}$)$_{v4}$OR$^{40}$, —CN, —NO$_2$, —S(═O)$_2$R$^{44}$, —(CR$^{42}$R$^{43}$)$_{v4}$S(═O)$_2$R$^{44}$, —S(═O)$_2$NR$^{40}$R$^{41}$, —(CR$^{42}$R$^{43}$)$_{v4}$S(═O)$_2$NR$^{40}$R$^{41}$, —C(═O)OR$^{40}$, —(CR$^{42}$R$^{43}$)$_{v4}$C(═O)OR$^{40}$, —(CR$^{42}$R$^{43}$)$_{v4}$C(═O)NR$^{40}$R$^{41}$, —NR$^{40}$R$^{41}$, —NR$^{40}$(CR$^{42}$R$^{43}$)$_{w4}$NR$^{40}$R$^{41}$, —NR$^{40}$C(═NR$^{41}$)NR$^{40}$R$^{41}$, —C(═NR$^{40}$)NR$^{40}$R$^{41}$, —N(R$^{40}$)C(═NR$^{41}$)R$^{40}$, —(CR$^{42}$R$^{43}$)$_{v4}$NR$^{40}$R$^{41}$, —(CR$^{42}$R$^{43}$)$_{v4}$OR$^{40}$, —(CR$^{42}$R$^{43}$)$_{v4}$N(R$^{40}$)C(═NR$^{41}$)NR$^{40}$R$^{41}$, —(CR$^{42}$R$^{43}$)$_{v4}$NR$^{40}$(CR$^{42}$R$^{43}$)$_{w4}$NR$^{40}$R$^{41}$, —NR$^{41}$C(═NR$^{41}$)NR$^{40}$(CR$^{42}$R$^{43}$)$_{w4}$NR$^{40}$R$^{41}$, —NR$^{40}$(CR$^{42}$R$^{43}$)$_{w4}$N(R$^{40}$)C(═NR$^{41}$)NR$^{40}$R$^{41}$, —(CR$^{42}$R$^{43}$)$_{v4}$C(═NR$^{41}$)NR$^{40}$R$^{41}$, —NR$^{40}$(CR$^{42}$R$^{43}$)$_{v4}$B(OR$^{45}$)$_2$, or —(CR$^{42}$R$^{43}$)$_{v4}$NR$^{40}$(CR$^{42}$R$^{43}$)$_{v4}$B(OR$^{45}$)$_2$;

each $R^6$ is independently a basic substituent;

each $R^{40}$, $R^{41}$, $R^{50}$, and $R^{51}$ is independently selected from the group consisting of hydrogen, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, $C_2$-$C_8$ optionally substituted heterocycloalkyl, optionally substituted aryl, optionally substituted heteroaryl, optionally substituted —(C$_1$-C$_6$ alkyl)(C$_3$-C$_8$ cycloalkyl), optionally substituted —(C$_1$-C$_6$ alkyl)(C$_2$-C$_8$ heterocycloalkyl), optionally substituted —(C$_1$-C$_6$ alkyl)(aryl), and optionally substituted —(C$_1$-C$_6$ alkyl)(heteroaryl);

or $R^{40}$ and $R^{41}$, or $R^{50}$ and $R^{51}$ are taken together with the nitrogen to which they are attached to form an optionally substituted $C_2$-$C_8$ heterocycloalkyl;

each $R^{42}$, $R^{43}$, $R^{52}$, and $R^{53}$ is independently selected from the group consisting of hydrogen, halogen, —CN, —OR$^a$, —NR$^a$R$^b$, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, optionally substituted C$_2$-C$_8$ heterocycloalkyl, optionally substituted aryl, and optionally substituted heteroaryl;

each R$^{44}$ and R$^{54}$ is independently optionally substituted C$_1$-C$_6$ alkyl, optionally substituted C$_2$-C$_6$ alkenyl, optionally substituted C$_2$-C$_6$ alkynyl, optionally substituted aryl, optionally substituted heteroaryl, optionally substituted C$_3$-C$_8$ cycloalkyl, optionally substituted C$_2$-C$_8$ heterocycloalkyl, optionally substituted —(C$_1$-C$_6$ alkyl)(C$_3$-C$_8$ cycloalkyl), optionally substituted —(C$_1$-C$_6$ alkyl)(C$_2$-C$_8$ heterocycloalkyl), optionally substituted —(C$_1$-C$_6$ alkyl)(aryl), or optionally substituted —(C$_1$-C$_6$ alkyl)(heteroaryl);

each R$^{45}$ is independently hydrogen or optionally substituted C$_1$-C$_6$ alkyl;

or two R$^{45}$ are taken together with the atoms to which there are attached to form a cyclic boronate ester;

R$^a$ and R$^b$ are independently hydrogen or optionally substituted C$_1$-C$_6$ alkyl;

or R$^a$ and R$^b$ are taken together with the nitrogen to which they are attached to form an optionally substituted C$_2$-C$_8$ heterocycloalkyl;

each R$^c$ is independently optionally substituted C$_1$-C$_6$ alkyl, optionally substituted C$_2$-C$_6$ alkenyl, or optionally substituted C$_2$-C$_6$ alkynyl;

n is 0-2;
m is 0-2;
p is 0-4;
q is 1-4;
v4 and v5 are independently 1-4; and
w4 is 2-4.

In some embodiments, a compound of Formula (IV) or (IVa), or a pharmaceutically acceptable salt, solvate, or stereoisomer thereof is of Formula (IVa-1) or a pharmaceutically acceptable salt, solvate, or stereoisomer thereof:

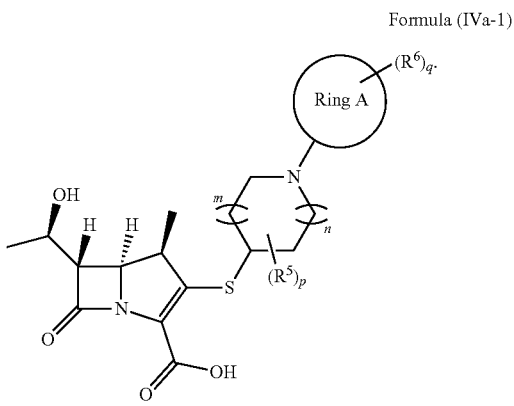

Formula (IVa-1)

In some embodiments of a compound of Formula (IV), (IVa), or (IVa-1), Ring A is optionally substituted cyclohexyl, optionally substituted piperidinyl, or optionally substituted morpholinyl. In some embodiments of a compound of Formula (IV), (IVa), or (IVa-1), Ring A is cyclohexyl, piperidinyl, or morpholinyl, each optionally substituted with one, two, or three halogen, —CN, —OH, C$_1$-C$_6$ alkyl, C$_1$-C$_6$ haloalkyl, C$_1$-C$_6$ alkoxy, or —NO$_2$. In some embodiments of a compound of Formula (IV), (IVa), or (IVa-1), Ring A is cyclohexyl, piperidinyl, or morpholinyl. In some embodiments of a compound of Formula (IV), (IVa), or (IVa-1), Ring A is cyclohexyl.

In some embodiments of a compound of Formula (IV), (IVa), or (IVa-1), R$^{50}$ and R$^{51}$ are independently selected from the group consisting of hydrogen, optionally substituted C$_1$-C$_6$ alkyl, optionally substituted C$_3$-C$_8$ cycloalkyl, or C$_2$-C$_8$ optionally substituted heterocycloalkyl. In some embodiments of a compound of Formula (IV), (IVa), or (IVa-1), R$^{50}$ and R$^{51}$ are independently selected from the group consisting of hydrogen and optionally substituted C$_1$-C$_6$ alkyl.

In some embodiments of a compound of Formula (IV), (IVa), or (IVa-1), R$^{52}$ and R$^{53}$ are independently selected from the group consisting of hydrogen, halogen, —CN, —OR$^a$, —NR$^a$R$^b$, or optionally substituted C$_1$-C$_6$ alkyl. In some embodiments of a compound of Formula (IV), (IVa), or (IVa-1), R$^{52}$ and R$^{53}$ are independently selected from the group consisting of hydrogen, halogen, or optionally substituted C$_1$-C$_6$ alkyl.

In some embodiments of a compound of Formula (IV), (IVa), or (IVa-1), R$^{54}$ is optionally substituted C$_1$-C$_6$ alkyl, optionally substituted C$_3$-C$_8$ cycloalkyl, or C$_2$-C$_8$ optionally substituted heterocycloalkyl. In some embodiments of a compound of Formula (IV), (IVa), or (IVa-1), R$^{54}$ is optionally substituted C$_1$-C$_6$ alkyl.

In some embodiments of a compound of Formula (I), (Ia), or (Ia-1), n is 0 or 1 and m is 0 or 1. In some embodiments of a compound of Formula (I), (Ia), or (Ia-1), n is 1 and m is 0 or 1.

In some embodiments of a compound of Formula (IV), (IVa), or (IVa-1), n is 0 and m is 0. In some embodiments of a compound of Formula (IV), (IVa), or (IVa-1) n is 0 and m is 1. In some embodiments of a compound of Formula (IV), (IVa), or (IVa-1), n is 0 and m is 2.

In some embodiments of a compound of Formula (IV), (IVa), or (IVa-1), n is 1 and m is 0. In some embodiments of a compound of Formula (IV), (IVa), or (IVa-1) n is 1 and m is 1. In some embodiments of a compound of Formula (IV), (IVa), or (IVa-1), n is 1 and m is 2.

In some embodiments of a compound of Formula (IV), (IVa), or (IVa-1), n is 2 and m is 0. In some embodiments of a compound of Formula (IV), (IVa), or (IVa-1) n is 2 and m is 1. In some embodiments of a compound of Formula (IV), (IVa), or (IVa-1) n is 2 and m is 2.

In some embodiments of a compound of Formula (IV), (IVa), or (IVa-1), p is 0. In some embodiments of a compound of Formula (IV), (IVa), or (IVa-1), p is 1. In some embodiments of a compound of Formula (IV), (IVa), or (IVa-1), p is 2. In some embodiments of a compound of Formula (IV), (IVa), or (IVa-1), p is 3. In some embodiments of a compound of Formula (IV), (IVa), or (IVa-1), p is 4. In some embodiments of a compound of Formula (IV), (IVa), or (IVa-1), each R$^5$ is independently hydrogen, halogen, optionally substituted C$_1$-C$_6$ alkyl, —OR$^{40}$, —(CR$^{42}$R$^{43}$)$_{v4}$OR$^{40}$, —CN, —NO$_2$, or —NR$^{40}$R$^{41}$. In some embodiments of a compound of Formula (IV), (IVa), or (IVa-1), each R$^5$ is independently hydrogen or halogen. In some embodiments of a compound of Formula (IV), (IVa), or (IVa-1), each R$^5$ is hydrogen. In some embodiments of a compound of Formula (IV), (IVa), or (IVa-1), each R$^5$ is independently halogen or optionally substituted C$_1$-C$_6$ alkyl. In some embodiments of a compound of Formula (IV), (IVa), or (IVa-1), each R$^5$ is independently optionally substituted C$_1$-C$_6$ alkyl. In some embodiments of a compound of Formula (IV), (IVa), or (IVa-1), each R$^5$ is independently optionally substituted methyl. In some embodiments of a compound of Formula (IV), (IVa), or (IVa-1), each R$^5$ is independently C$_1$-C$_6$ alkyl or C$_1$-C$_6$ hydroxyalkyl. In some embodiments of a compound of Formula (IV), (IVa), or (IVa-1), each $R^5$ is independently methyl or —$CH_2OH$.

In some embodiments of a compound of Formula (IV), (IVa), or (IVa-1), each $R^{40}$, $R^{41}$, $R^{50}$, and $R^{51}$ is independently selected from the group consisting of hydrogen, optionally substituted $C_1$-$C_6$ alkyl, optionally substituted $C_3$-$C_8$ cycloalkyl, or $C_2$-$C_8$ optionally substituted heterocycloalkyl. In some embodiments of a compound of Formula (IV), (IVa), or (IVa-1), each $R^{40}$, $R^{41}$, $R^{50}$, and $R^{51}$ is independently selected from the group consisting of hydrogen or optionally substituted $C_1$-$C_6$ alkyl. In some embodiments of a compound of Formula (IV), (IVa), or (IVa-1), each $R^{40}$, $R^{41}$, $R^{50}$, and $R^{51}$ is hydrogen.

In some embodiments of a compound of Formula (IV), (IVa), or (IVa-1), $R^{40}$ and $R^{41}$, or $R^{50}$ and $R^{51}$ are taken together with the nitrogen to which they are attached to form an optionally substituted $C_2$-$C_8$ heterocycloalkyl. In some embodiments of a compound of Formula (IV), (IVa), or (IVa-1), $R^{40}$ and $R^{41}$, or $R^{50}$ and $R^{51}$ are taken together with the nitrogen to which they are attached to form an optionally substituted aziridine, azetidine, pyrrolidine, piperidine, morpholine, or piperazine. In some embodiments of a compound of Formula (IV), (IVa), or (IVa-1), $R^{40}$ and $R^{41}$, or $R^{50}$ and $R^{51}$ are taken together with the nitrogen to which they are attached to form a pyrrolidine, piperidine, morpholine, or piperazine.

In some embodiments of a compound of Formula (IV), (IVa), or (IVa-1), each $R^{42}$, $R^{43}$, $R^{52}$, and $R^{53}$ is independently selected from the group consisting of hydrogen, halogen, —CN, —$OR^a$, —$NR^aR^b$, or optionally substituted $C_1$-$C_6$ alkyl. In some embodiments of a compound of Formula (IV), (IVa), or (IVa-1), each $R^{42}$, $R^{43}$, $R^{52}$, and $R^{53}$ is independently selected from the group consisting of hydrogen, halogen, —$NR^aR^b$, or $C_1$-$C_6$ alkyl. In some embodiments of a compound of Formula (IV), (IVa), or (IVa-1), each $R^{42}$, $R^{43}$, $R^{52}$, and $R^{53}$ is hydrogen or $C_1$-$C_6$ alkyl. In some embodiments of a compound of Formula (IV), (IVa), or (IVa-1), each $R^{42}$, $R^{43}$, $R^{52}$, and $R^{53}$ is hydrogen or halogen. In some embodiments of a compound of Formula (IV), (IVa), or (IVa-1), each $R^{42}$, $R^{43}$, $R^{52}$, and $R^{53}$ is hydrogen or —$NR^aR^b$.

In some embodiments of a compound of Formula (IV), (IVa), or (IVa-1), $R^{44}$ and $R^{54}$ are independently optionally substituted $C_1$-$C_6$ alkyl. In some embodiments of a compound of Formula (IV), (IVa), or (IVa-1), $R^{44}$ and $R^{54}$ are methyl.

In some embodiments of a compound of Formula (IV), (IVa), or (IVa-1), $R^{45}$ is hydrogen or $C_1$-$C_6$ alkyl. In some embodiments of a compound of Formula (IV), (IVa), or (IVa-1), $R^{45}$ is hydrogen. In some embodiments of a compound of Formula (IV), (IVa), or (IVa-1), $R^{45}$ is $C_1$-$C_6$ alkyl.

In some embodiments of a compound of Formula (IV), (IVa), or (IVa-1), two $R^{45}$ are taken together with the atoms to which there are attached to form a cyclic boronate ester.

In some embodiments of a compound of Formula (IV), (IVa), or (IVa-1), q is 1. In some embodiments of a compound of Formula (IV), (IVa), or (IVa-1), q is 2. In some embodiments of a compound of Formula (IV), (IVa), or (IVa-1), q is 3. In some embodiments of a compound of Formula (IV), (IVa), or (IVa-1), q is 4.

In some embodiments of a compound of Formula (IV), (IVa), or (IVa-1), each $R^6$ is a basic substituent comprising at least one basic nitrogen. In some embodiments of a compound of Formula (IV), (IVa), or (IVa-1), each $R^6$ is a basic substituent comprising one basic nitrogen. In some embodiments of a compound of Formula (IV), (IVa), or (IVa-1), each $R^6$ is a basic substituent comprising two basic nitrogens.

In some embodiments of a compound of Formula (IV), (IVa), or (IVa-1), each $R^6$ is independently —$NR^{60}R^{61}$, —$NR^{60}(CR^{62}R^{63})_{w6}NR^{60}R^{61}$, —$NR^{60}C(=NR^{61})NR^{60}R^{61}$, —$C(=NR^{60})NR^{60}R^{61}$, —$C(=NR^{60})R^{60}$, —$N(R^{60})C(=NR^{61})R^{60}$, —$(CR^{62}R^{63})_{v6}NR^{60}R^{61}$, —$C(=O)NR^{60}R^{61}$, —$C(=O)(CR^{62}R^{63})_{v6}NR^{60}R^{61}$, —$(CR^{62}R^{63})_{v6}C(=O)NR^{60}R^{61}$, —$(CR^{62}R^{63})_{v6}N(R^{60})C(=NR^{61})NR^{60}R^{61}$, —$(CR^{62}R^{63})_{v6}NR^{60}(CR^{62}R^{63})_{w6}NR^{60}R^{61}$, —$NR^{61}C(=NR^{61})NR^{60}(CR^{62}R^{63})_{w6}NR^{60}R^{61}$, —$NR^{60}(CR^{62}R^{63})_{w6}N(R^{60})C(=NR^{61})NR^{60}R^{61}$, —$(CR^{62}R^{63})_{v6}C(=NR^{61})NR^{60}R^{61}$, —$NR^{60}(CR^{62}R^{63})_{v6}B(OR^{65})_2$, or —$(CR^{62}R^{63})_{v6}NR^{60}(CR^{62}R^{63})_{v6}B(OR^{65})_2$.

In some embodiments of a compound of Formula (IV), (IVa), or (IVa-1), each $R^6$ is independently —$NR^{60}R^{61}$, —$NR^{60}(CR^{62}R^{63})_{w6}NR^{60}R^{61}$, —$NR^{60}C(=NR^{61})NR^{60}R^{61}$, —$C(=NR^{60})NR^{60}R^{61}$, —$N(R^{60})C(=NR^{61})R^{60}$, —$(CR^{62}R^{63})_{v6}NR^{60}R^{61}$, —$(CR^{62}R^{63})_{v6}N(R^{60})C(=NR^{61})NR^{60}R^{61}$, —$(CR^{62}R^{63})_{v6}NR^{60}(CR^{62}R^{63})_{w6}NR^{60}R^{61}$, —$NR^{61}C(=NR^{61})NR^{60}(CR^{62}R^{63})_{w6}NR^{60}R^{61}$, —$NR^{60}(CR^{62}R^{63})_{w6}N(R^{60})C(=NR^{61})NR^{60}R^{61}$, —$(CR^{62}R^{63})_{v6}C(=NR^{61})NR^{60}R^{61}$, —$NR^{60}(CR^{62}R^{63})_{v6}B(OR^{65})_2$, or —$(CR^{62}R^{63})_{v6}NR^{60}(CR^{62}R^{63})_{v6}B(OR^{65})_2$.

In some embodiments of a compound of Formula (IV), (IVa), or (IVa-1), each $R^6$ is independently —$NR^{60}R^{61}$, —$NR^{60}(CR^{62}R^{63})_{w6}NR^{60}R^{61}$, —$NR^{60}C(=NR^{61})NR^{60}R^{61}$, —$C(=NR^{60})NR^{60}R^{61}$, —$N(R^{60})C(=NR^{61})R^{60}$, —$(CR^{62}R^{63})_{v6}NR^{60}R^{61}$, —$(CR^{62}R^{63})_{v6}N(R^{60})C(=NR^{61})NR^{60}R^{61}$, —$(CR^{62}R^{63})_{v6}NR^{60}(CR^{62}R^{63})_{w6}NR^{60}R^{61}$, —$NR^{61}C(=NR^{61})NR^{60}(CR^{62}R^{63})_{w6}NR^{60}R^{61}$, —$NR^{60}(CR^{62}R^{63})_{w6}N(R^{60})C(=NR^{61})NR^{60}R^{61}$, or —$(CR^{62}R^{63})_{v6}C(=NR^{61})NR^{60}R^{61}$.

In some embodiments of a compound of Formula (IV), (IVa), or (IVa-1), each $R^6$ is independently —$NR^{60}R^{61}$, —$NR^{60}(CR^{62}R^{63})_{w6}NR^{60}R^{61}$, —$NR^{60}C(=NR^{61})NR^{60}R^{61}$, —$C(=NR^{60})NR^{60}R^{61}$, —$N(R^{60})C(=NR^{61})R^{60}$, or —$(CR^{62}R^{63})_{v6}NR^{60}R^{61}$.

In some embodiments of a compound of Formula (IV), (IVa), or (IVa-1), each $R^6$ is independently —$NR^{60}R^{61}$, —$C(=NR^{60})NR^{60}R^{61}$, —$(CR^{62}R^{63})_{v6}NR^{60}R^{61}$, or —$NR^{60}(CR^{62}R^{63})_{v6}B(OR^{65})_2$.

In some embodiments of a compound of Formula (IV), (IVa), or (IVa-1), $R^6$ is —$NR^{60}R^{61}$.

In some embodiments of a compound of Formula (IV), (IVa), or (IVa-1), $R^6$ is —$(CR^{62}R^{63})_{v6}NR^{60}R^{61}$.

In some embodiments of a compound of Formula (IV), (IVa), or (IVa-1), $R^6$ is —$C(=NR^{60})NR^{60}R^{61}$.

In some embodiments of a compound of Formula (IV), (IVa), or (IVa-1), $R^6$ is —$NR^{60}(CR^{62}R^{63})_{v6}B(OR^{65})_2$.

In some embodiments of a compound of Formula (IV), (IVa), or (IVa-1), $R^6$ is as defined above and each $R^{60}$ and $R^{61}$ is independently selected from the group consisting of hydrogen, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, $C_2$-$C_8$ optionally substituted heterocycloalkyl, optionally substituted aryl, optionally substituted heteroaryl, optionally substituted —($C_1$-$C_6$ alkyl)($C_3$-$C_8$ cycloalkyl), optionally substituted —($C_1$-$C_6$ alkyl)($C_2$-$C_8$ heterocycloalkyl), optionally substituted —($C_1$-$C_6$ alkyl)(aryl), and optionally substituted —($C_1$-$C_6$ alkyl)(heteroaryl); or $R^{60}$ and $R^{61}$ are taken together with the nitrogen to which they are attached to form an optionally substituted $C_2$-$C_8$ heterocycloalkyl. In some embodiments of a compound of Formula (IV), (IVa), or (IVa-1), $R^6$ is as defined above and each $R^{60}$ and $R^{61}$ is independently selected from the group consisting of hydrogen, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, $C_2$-$C_8$ optionally substituted heterocycloalkyl, optionally substituted aryl, optionally substituted heteroaryl, optionally substituted —($C_1$-$C_6$ alkyl)($C_3$-$C_8$ cycloalkyl), optionally substituted —($C_1$-$C_6$ alkyl)($C_2$-$C_8$ heterocycloalkyl), optionally substituted —($C_1$-$C_6$ alkyl)(aryl), and optionally substituted —($C_1$-$C_6$ alkyl)(heteroaryl). In some embodiments of a compound of Formula (IV), (IVa), or (IVa-1), $R^6$ is as defined above and each $R^{60}$ and $R^{61}$ is independently selected from the group consisting of hydrogen, optionally substituted $C_1$-$C_6$ alkyl, optionally substituted $C_3$-$C_8$ cycloalkyl, or $C_2$-$C_8$ optionally substituted heterocycloalkyl. In some embodiments of a compound of Formula (IV), (IVa), or (IVa-1), $R^6$ is as defined above and each $R^{60}$ and $R^{61}$ is independently selected from the group consisting of hydrogen and optionally substituted $C_1$-$C_6$ alkyl. In some embodiments of a compound of Formula (IV), (IVa), or (IVa-1), each $R^6$ is as defined above and each $R^{60}$ and $R^{61}$ is independently selected from the group consisting of hydrogen and $C_1$-$C_6$ alkyl. In some embodiments of a compound of Formula (IV), (IVa), or (IVa-1), $R^6$ is as defined above and each $R^{60}$ and $R^{61}$ is hydrogen.

In some embodiments of a compound of Formula (IV), (IVa), or (IVa-1), $R^6$ is as defined above and $R^{60}$ and $R^{61}$ are taken together with the nitrogen to which they are attached to form an optionally substituted $C_2$-$C_8$ heterocycloalkyl. In some embodiments of a compound of Formula (IV), (IVa), or (IVa-1), $R^6$ is as defined above and $R^{60}$ and $R^{61}$ are taken together with the nitrogen to which they are attached to form an optionally substituted aziridine, azetidine, pyrrolidine, piperidine, morpholine, or piperazine. In some embodiments of a compound of Formula (IV), (IVa), or (IVa-1), $R^6$ is as defined above and $R^{60}$ and $R^{61}$ are taken together with the nitrogen to which they are attached to form a pyrrolidine, piperidine, morpholine, or piperazine.

In some embodiments of a compound of Formula (IV), (IVa), or (IVa-1), $R^6$ is as defined above and each $R^{62}$ and $R^{63}$ is independently selected from the group consisting of hydrogen, halogen, —CN, —$OR^a$, —$NR^aR^b$, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, optionally substituted $C_2$-$C_8$ heterocycloalkyl, optionally substituted aryl, and optionally substituted heteroaryl. In some embodiments of a compound of Formula (IV), (IVa), or (IVa-1), $R^6$ is as defined above and each $R^{62}$ and $R^{63}$ is independently selected from the group consisting of hydrogen, halogen, —CN, —$OR^a$, —$NR^aR^b$, or optionally substituted $C_1$-$C_6$ alkyl. In some embodiments of a compound of Formula (IV), (IVa), or (IVa-1), $R^6$ is as defined above and each $R^{62}$ and $R^{63}$ is independently selected from the group consisting of hydrogen, halogen, —$NR^aR^b$, or $C_1$-$C_6$ alkyl. In some embodiments of a compound of Formula (IV), (IVa), or (IVa-1), $R^6$ is as defined above and each $R^{62}$ and $R^{63}$ is independently selected from the group consisting of hydrogen and halogen. In some embodiments of a compound of Formula (IV), (IVa), or (IVa-1), $R^6$ is as defined above and each $R^{62}$ and $R^{63}$ is independently selected from the group consisting of hydrogen and —$NR^aR^b$. In some embodiments of a compound of Formula (IV), (IVa), or (IVa-1), $R^6$ is as defined above and each $R^{62}$ and $R^{63}$ is independently selected from the group consisting of hydrogen and $C_1$-$C_6$ alkyl. In some embodiments of a compound of Formula (IV), (IVa), or (IVa-1), $R^6$ is as defined above and each $R^{62}$ and $R^{63}$ is hydrogen.

In some embodiments of a compound of Formula (IV), (IVa), or (IVa-1), $R^6$ is as defined above and each $R^{65}$ is independently hydrogen or optionally substituted $C_1$-$C_6$ alkyl. In some embodiments of a compound of Formula (IV), (IVa), or (IVa-1), $R^6$ is as defined above and each $R^{65}$ is hydrogen.

In some embodiments of a compound of Formula (IV), (IVa), or (IVa-1), $R^6$ is as defined above and each $R^{65}$ is independently hydrogen or optionally substituted $C_1$-$C_6$ alkyl; or two $R^{65}$ are taken together with the atoms to which there are attached to form a cyclic boronate ester.

In some embodiments of a compound of Formula (IV), (IVa), or (IVa-1), $R^6$ is as defined above and two $R^{65}$ are taken together with the atoms to which there are attached to form a cyclic boronate ester.

In some embodiments of a compound of Formula (IV), (IVa), or (IVa-1), $R^6$ is as defined above and v6 is 1-4. In some embodiments of a compound of Formula (IV), (IVa), or (IVa-1), $R^6$ is as defined above and v6 is 1. In some embodiments of a compound of Formula (IV), (IVa), or (IVa-1), $R^6$ is as defined above and v6 is 2. In some embodiments of a compound of Formula (IV), (IVa), or (IVa-1), $R^6$ is as defined above and v6 is 3. In some embodiments of a compound of Formula (IV), (IVa), or (IVa-1), $R^6$ is as defined above and v6 is 4.

In some embodiments of a compound of Formula (IV), (IVa), or (IVa-1), $R^6$ is as defined above and w6 is 2-4. In some embodiments of a compound of Formula (IV), (IVa), or (IVa-1), $R^6$ is as defined above and w6 is 2. In some embodiments of a compound of Formula (IV), (IVa), or (IVa-1), $R^6$ is as defined above and w6 is 3. In some embodiments of a compound of Formula (IV), (IVa), or (IVa-1), $R^6$ is as defined above and w6 is 4.

In some embodiments of a compound of Formula (IV), (IVa), or (IVa-1), $R^a$ and $R^b$ are independently hydrogen or optionally substituted $C_1$-$C_6$ alkyl. In some embodiments of a compound of Formula (IV), (IVa), or (IVa-1), $R^a$ and $R^b$ are independently hydrogen or $C_1$-$C_6$ alkyl. In some embodiments of a compound of Formula (IV), (IVa), or (IVa-1), $R^a$ and $R^b$ are hydrogen.

In some embodiments of a compound of Formula (IV), (IVa), or (IVa-1), $R^a$ and $R^b$ are taken together with the nitrogen to which they are attached to form an optionally substituted $C_2$-$C_8$ heterocycloalkyl. In some embodiments of a compound of Formula (IV), (IVa), or (IVa-1), $R^a$ and $R^b$ are taken together with the nitrogen to which they are attached to form an optionally substituted aziridine, azetidine, pyrrolidine, piperidine, morpholine, or piperazine. In some embodiments of a compound of Formula (IV), (IVa), or (IVa-1), $R^a$ and $R^b$ are taken together with the nitrogen to which they are attached to form a pyrrolidine, piperidine, morpholine, or piperazine.

In some embodiments of a compound of Formula (IV), (IVa), or (IVa-1), each $R^c$ is independently optionally substituted $C_1$-$C_6$ alkyl. In some embodiments of a compound of Formula (IV), (IVa), or (IVa-1), each $R^c$ is independently $C_1$-$C_6$ alkyl.

Described herein are compounds, or a pharmaceutically acceptable salt, solvate, or stereoisomer thereof, selected from the group consisting of:

| Ex. | Structure | MW | ESI-MS (m/z) for [MH]+ |
|---|---|---|---|
| 1 | 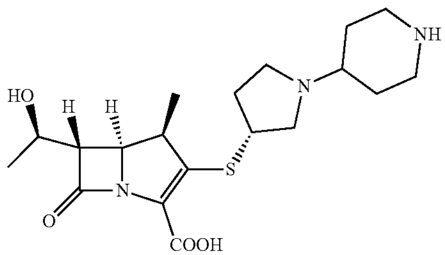 [SMILES: C[C@@H](O)[C@H]1C(=O)N2C(C(=O)O)=C(S[C@@H]3CCN(C4CCNCC4)C3)[C@H](C)[C@H]12] | 395.518 | 396 |
| 2 | 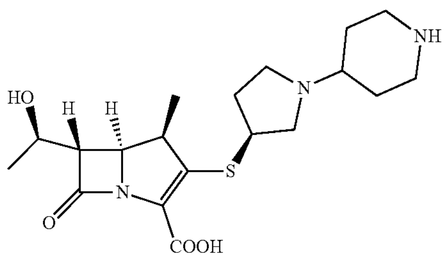 [SMILES: C[C@@H](O)[C@H]1C(=O)N2C(C(=O)O)=C(S[C@H]3CCN(C4CCNCC4)C3)[C@H](C)[C@H]12] | 395.518 | 396 |
| 3 | 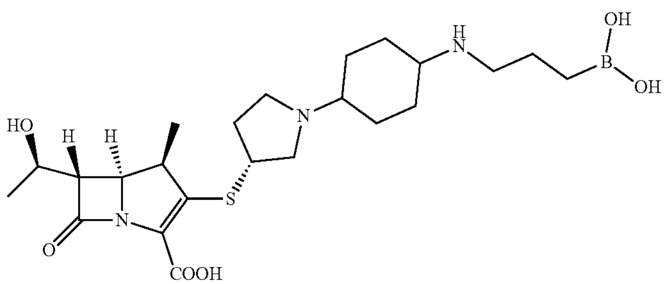 [SMILES: C[C@@H](O)[C@H]1C(=O)N2C(C(=O)O)=C(S[C@@H]3CCN(C4CCC(NCCCB(O)O)CC4)C3)[C@H](C)[C@H]12] | 495.442 | 496 |
| 4 | 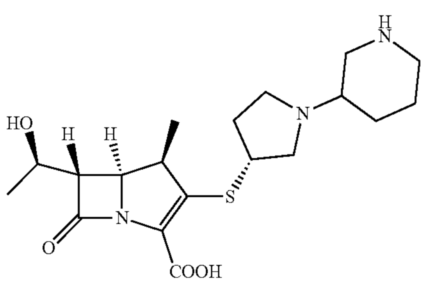 [SMILES: C[C@@H](O)[C@H]1C(=O)N2C(C(=O)O)=C(S[C@@H]3CCN(C4CCCNC4)C3)[C@H](C)[C@H]12] | 395.518 | 396 |
| 5 | 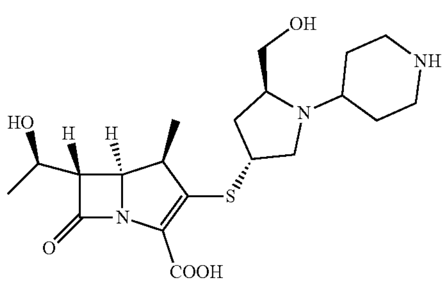 [SMILES: C[C@@H](O)[C@H]1C(=O)N2C(C(=O)O)=C(S[C@@H]3C[C@@H](CO)N(C4CCNCC4)C3)[C@H](C)[C@H]12] | 425.544 | 426 |
| 6 | 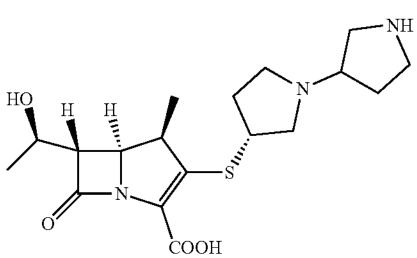 [SMILES: C[C@@H](O)[C@H]1C(=O)N2C(C(=O)O)=C(S[C@@H]3CCN(C4CCNC4)C3)[C@H](C)[C@H]12] | 381.491 | 382 |

| Ex. | Structure | MW | ESI-MS (m/z) for [MH]+ |
|---|---|---|---|
| 7 | 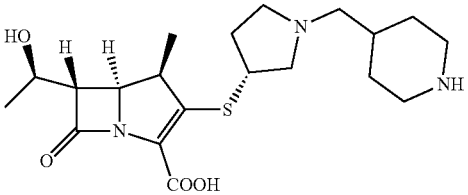 [SMILES: C[C@@H](O)[C@H]1C(=O)N2C(C(=O)O)=C(S[C@@H]3CCN(CC4CCNCC4)C3)[C@H](C)[C@H]12] | 409.545 | 410 |
| 8 | 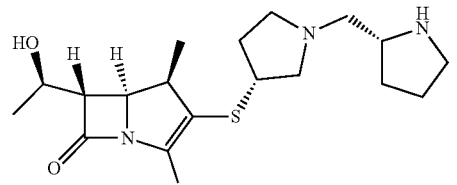 | 395.518 | 396 |
| 9 | 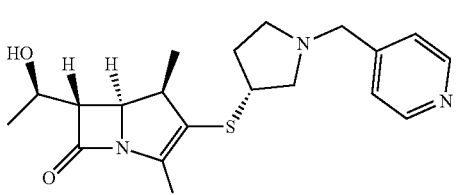 | 403.497 | 404 |
| 10 | 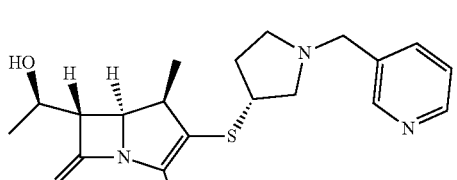 | 403.497 | 404 |
| 11 | 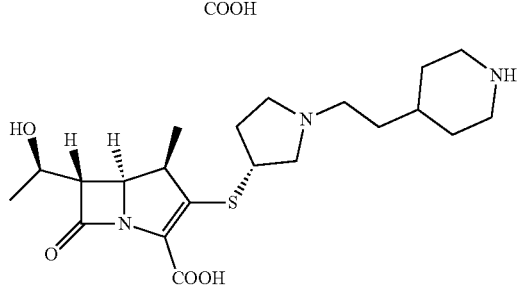 | 423.572 | 424 |
| 12 | 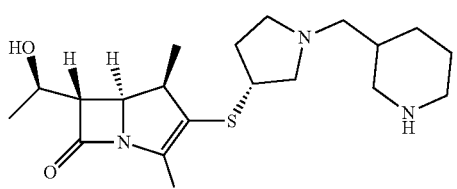 | 409.545 | 410 |
| 13 | 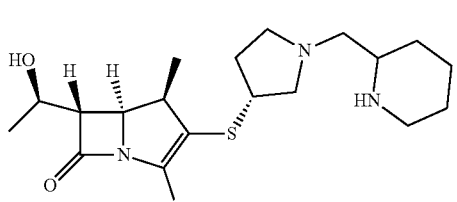 | 409.545 | 410 |

-continued
| Ex. | Structure | MW | ESI-MS (m/z) for [MH]+ |
|---|---|---|---|
| 14 | 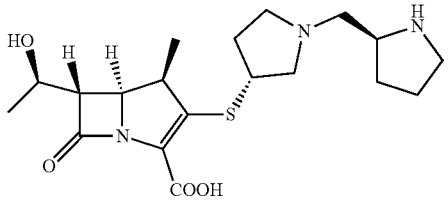 [SMILES: C[C@@H](O)[C@H]1C(=O)N2C(C(=O)O)=C(S[C@@H]3CCN(C[C@@H]4CCCN4)C3)[C@H](C)[C@H]12] | 395.518 | 396 |
| 15 | 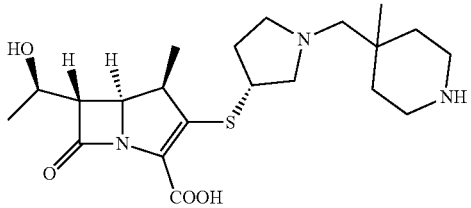 [SMILES: C[C@@H](O)[C@H]1C(=O)N2C(C(=O)O)=C(S[C@@H]3CCN(CC4(C)CCNCC4)C3)[C@H](C)[C@H]12] | 423.572 | 424 |
| 16 | 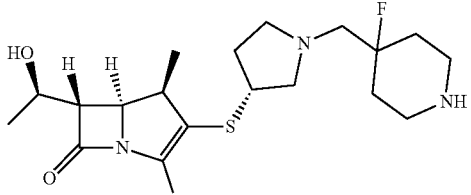 | 427.535 | 428 |
| 17 | 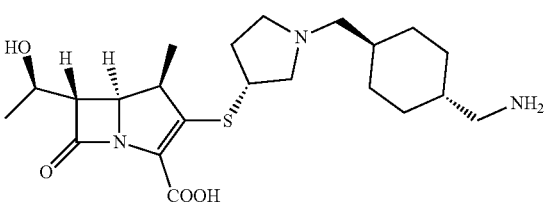 [SMILES: C[C@@H](O)[C@H]1C(=O)N2C(C(=O)O)=C(S[C@@H]3CCN(C[C@H]4CC[C@H](CN)CC4)C3)[C@H](C)[C@H]12] | 437.599 | 438 |
| 18 | 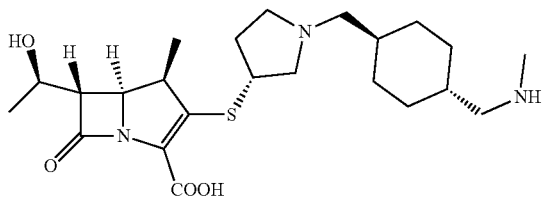 [SMILES: CNC[C@H]1CC[C@H](CN2CC[C@@H](SC3=C(C(=O)O)N4C(=O)[C@H]([C@@H](C)O)[C@H]4[C@H]3C)C2)CC1] | 451.626 | 452 |
| 19 | 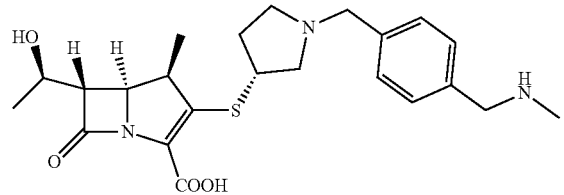 [SMILES: CNCc1ccc(CN2CC[C@@H](SC3=C(C(=O)O)N4C(=O)[C@H]([C@@H](C)O)[C@H]4[C@H]3C)C2)cc1] | 445.578 | 446 |

-continued

| Ex. | Structure | MW | ESI-MS (m/z) for [MH]+ |
|---|---|---|---|
| 20 | 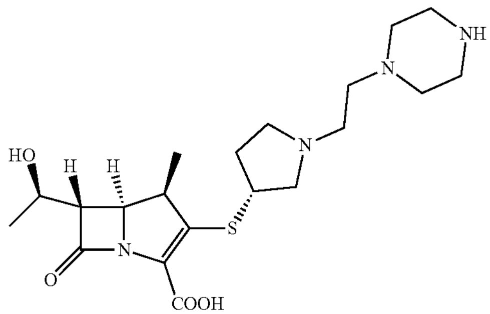 [SMILES: C[C@@H](O)[C@H]1C(=O)N2C(C(=O)O)=C(S[C@@H]3CCN(CCN4CCNCC4)C3)[C@H](C)[C@H]12] | 424.560 | 425 |
| 21 | 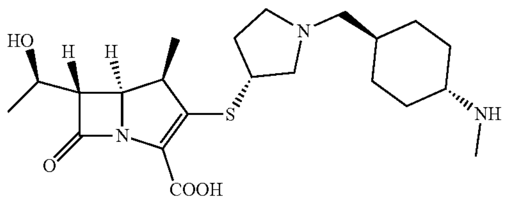 [SMILES: CN[C@H]1CC[C@H](CN2CC[C@@H](SC3=C(C(=O)O)N4C(=O)[C@H]([C@@H](C)O)[C@H]4[C@H]3C)C2)CC1] | 437.599 | 438 |
| 22 | 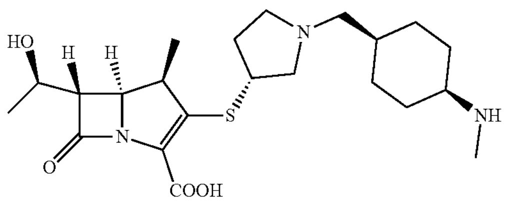 [SMILES: CN[C@H]1CC[C@@H](CN2CC[C@@H](SC3=C(C(=O)O)N4C(=O)[C@H]([C@@H](C)O)[C@H]4[C@H]3C)C2)CC1] | 437.599 | 438 |
| 23 | 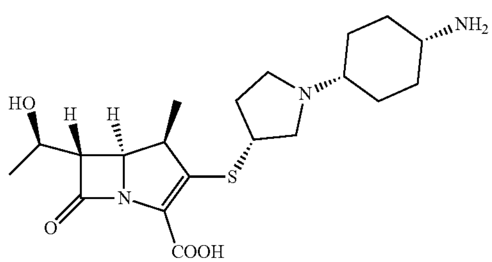 [SMILES: C[C@@H](O)[C@H]1C(=O)N2C(C(=O)O)=C(S[C@@H]3CCN([C@H]4CC[C@@H](N)CC4)C3)[C@H](C)[C@H]12] | 409.545 | 410 |
| 24 | 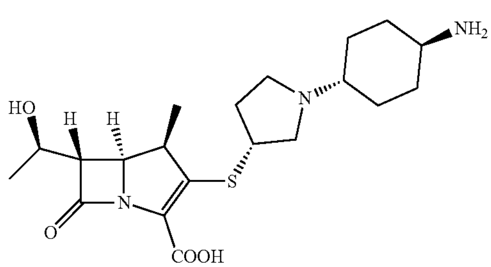 [SMILES: C[C@@H](O)[C@H]1C(=O)N2C(C(=O)O)=C(S[C@@H]3CCN([C@H]4CC[C@H](N)CC4)C3)[C@H](C)[C@H]12] | 409.545 | 410 |
| 25 | 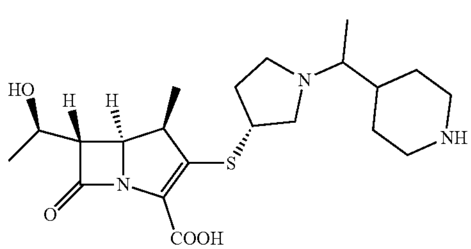 [SMILES: CC(C1CCNCC1)N1CC[C@@H](SC2=C(C(=O)O)N3C(=O)[C@H]([C@@H](C)O)[C@H]3[C@H]2C)C1] | 423.572 | 424 |

| Ex. | Structure | MW | ESI-MS (m/z) for [MH]+ |
|---|---|---|---|
| 26 | 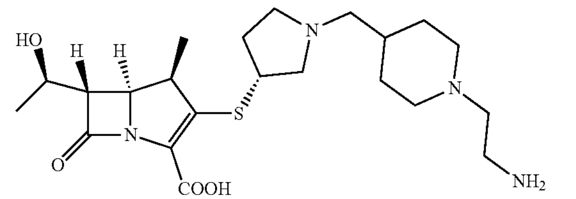 [SMILES: C[C@@H](O)[C@H]1C(=O)N2C(C(=O)O)=C(S[C@@H]3CCN(CC4CCN(CCN)CC4)C3)[C@H](C)[C@H]12] | 452.614 | 453 |
| 27 | 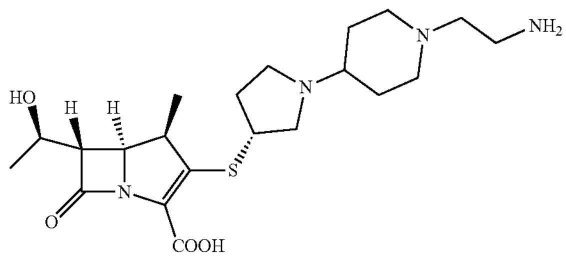 [SMILES: C[C@@H](O)[C@H]1C(=O)N2C(C(=O)O)=C(S[C@@H]3CCN(C4CCN(CCN)CC4)C3)[C@H](C)[C@H]12] | 438.587 | 439 |
| 28 | 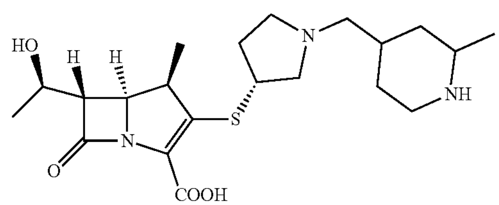 [SMILES: CC1CC(CN2CC[C@@H](SC3=C(C(=O)O)N4C(=O)[C@H]([C@@H](C)O)[C@H]4[C@H]3C)C2)CCN1] | 423.572 | 424 |
| 29 | 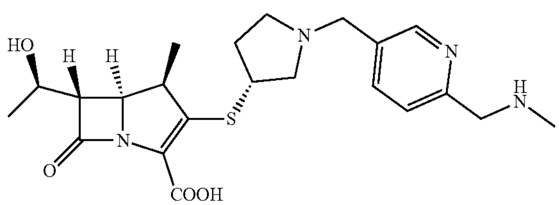 [SMILES: CNCc1ccc(CN2CC[C@@H](SC3=C(C(=O)O)N4C(=O)[C@H]([C@@H](C)O)[C@H]4[C@H]3C)C2)cn1] | 446.566 | 447 |
| 30 | 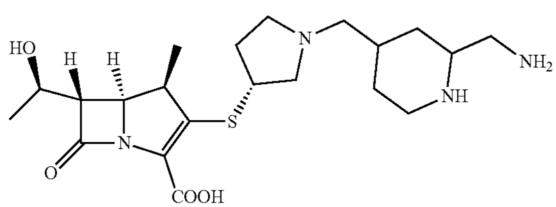 [SMILES: C[C@@H](O)[C@H]1C(=O)N2C(C(=O)O)=C(S[C@@H]3CCN(CC4CCNC(CN)C4)C3)[C@H](C)[C@H]12] | 438.587 | 439 |
| 31 | 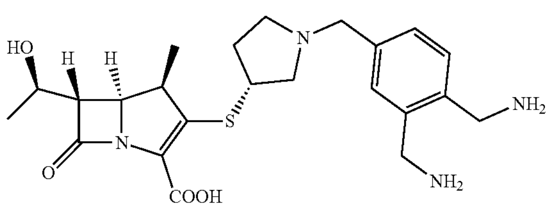 [SMILES: C[C@@H](O)[C@H]1C(=O)N2C(C(=O)O)=C(S[C@@H]3CCN(Cc4ccc(CN)c(CN)c4)C3)[C@H](C)[C@H]12] | 460.593 | 461 |
| 32 | 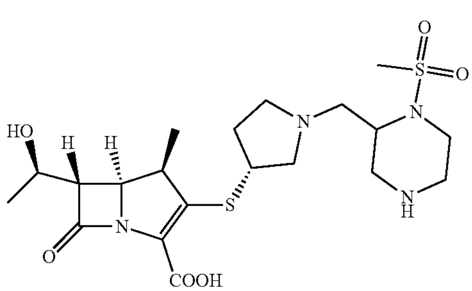 [SMILES: C[C@@H](O)[C@H]1C(=O)N2C(C(=O)O)=C(S[C@@H]3CCN(CC4CNCCN4S(C)(=O)=O)C3)[C@H](C)[C@H]12] | 488.618 | 489 |

-continued

| Ex. | Structure | MW | ESI-MS (m/z) for [MH]+ |
|---|---|---|---|
| 33 | 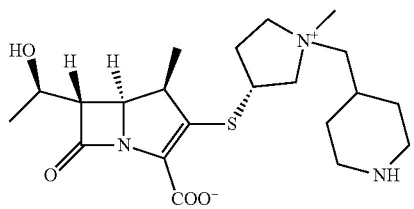 | 423.572 | 424 |
| 34 | 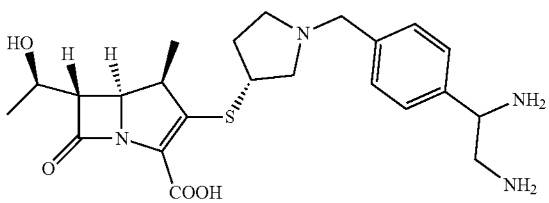 [SMILES: C[C@@H](O)[C@H]1C(=O)N2C(C(=O)O)=C(S[C@@H]3CCN(Cc4ccc(C(N)CN)cc4)C3)[C@H](C)[C@H]12] | 460.593 | 461 |
| 35 | 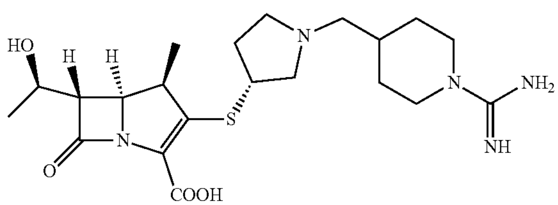 [SMILES: C[C@@H](O)[C@H]1C(=O)N2C(C(=O)O)=C(S[C@@H]3CCN(CC4CCN(C(=N)N)CC4)C3)[C@H](C)[C@H]12] | 451.586 | 451 |
| 36 | 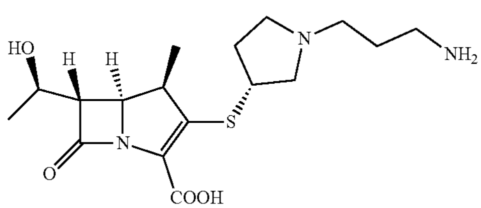 [SMILES: C[C@@H](O)[C@H]1C(=O)N2C(C(=O)O)=C(S[C@@H]3CCN(CCCN)C3)[C@H](C)[C@H]12] | 369.480 | 370 |
| 37 | 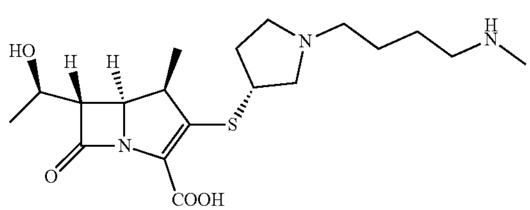 [SMILES: CNCCCCN1CC[C@@H](SC2=C(C(=O)O)N3C(=O)[C@H]([C@@H](C)O)[C@H]3[C@H]2C)C1] | 397.534 | 398 |
| 38 | 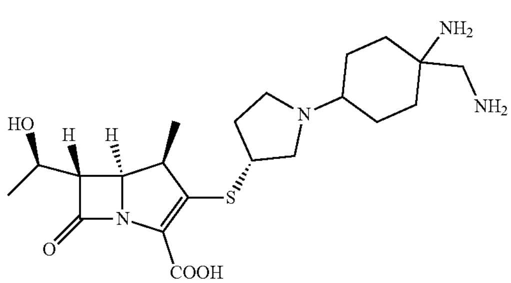 [SMILES: C[C@@H](O)[C@H]1C(=O)N2C(C(=O)O)=C(S[C@@H]3CCN(C4CCC(N)(CN)CC4)C3)[C@H](C)[C@H]12] | 438.587 | 439 |
| 39 | 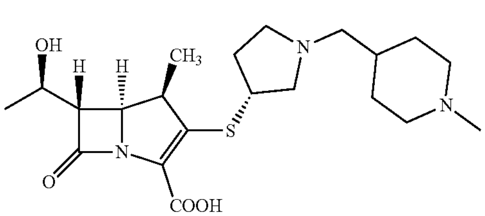 [SMILES: C[C@@H](O)[C@H]1C(=O)N2C(C(=O)O)=C(S[C@@H]3CCN(CC4CCN(C)CC4)C3)[C@H](C)[C@H]12] | 423.57 | 424 |

| Ex. | Structure | MW | ESI-MS (m/z) for [MH]+ |
|---|---|---|---|
| 40 | 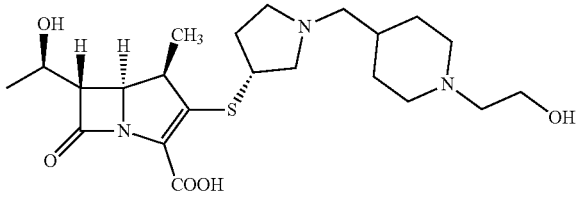 [SMILES: C[C@@H](O)[C@H]1C(=O)N2C(C(=O)O)=C(S[C@@H]3CCN(CC4CCN(CCO)CC4)C3)[C@H](C)[C@H]12] | 453.6 | 454 |
| 41 | 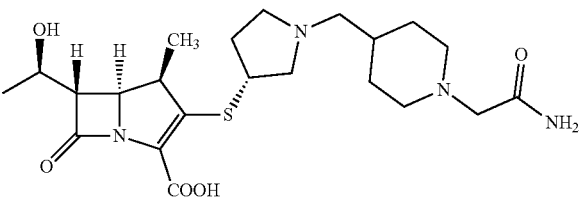 [SMILES: C[C@@H](O)[C@H]1C(=O)N2C(C(=O)O)=C(S[C@@H]3CCN(CC4CCN(CC(N)=O)CC4)C3)[C@H](C)[C@H]12] | 466.6 | 467 |
| 42 | 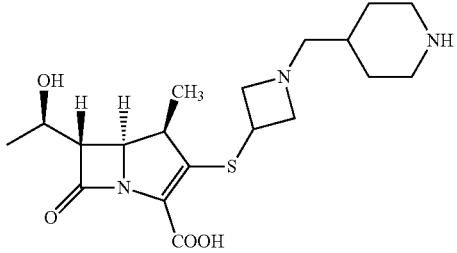 [SMILES: C[C@@H](O)[C@H]1C(=O)N2C(C(=O)O)=C(SC3CN(CC4CCNCC4)C3)[C@H](C)[C@H]12] | 395.518 | 396 |
| 43 | 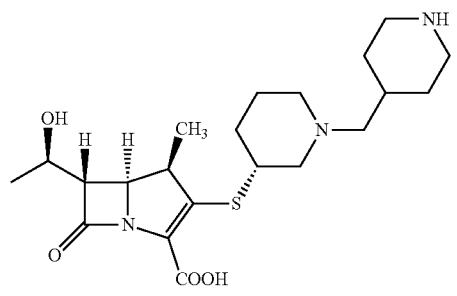 [SMILES: C[C@@H](O)[C@H]1C(=O)N2C(C(=O)O)=C(S[C@@H]3CCCN(CC4CCNCC4)C3)[C@H](C)[C@H]12] | 423.57 | 424 |
| 44 | 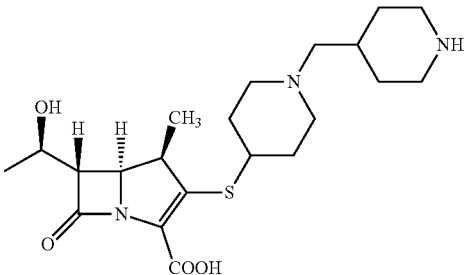 [SMILES: C[C@@H](O)[C@H]1C(=O)N2C(C(=O)O)=C(SC3CCN(CC4CCNCC4)CC3)[C@H](C)[C@H]12] | 423.57 | 424 |
| 45 | 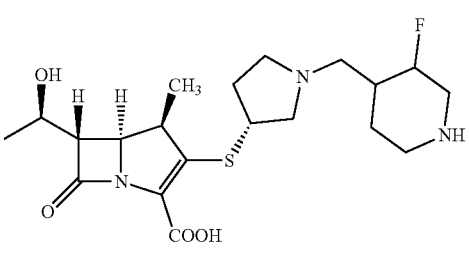 [SMILES: C[C@@H](O)[C@H]1C(=O)N2C(C(=O)O)=C(S[C@@H]3CCN(CC4CCNCC4F)C3)[C@H](C)[C@H]12] | 427.54 | 428 |

-continued

| Ex. | Structure | MW | ESI-MS (m/z) for [MH]+ |
|---|---|---|---|
| 46 | 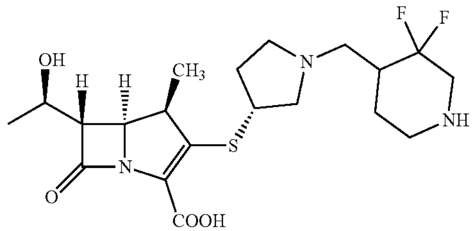 [SMILES: C[C@@H](O)[C@H]1C(=O)N2C(C(=O)O)=C(S[C@@H]3CCN(CC4CCNCC4(F)F)C3)[C@H](C)[C@H]12] | 445.53 | 446 |
| 47 | 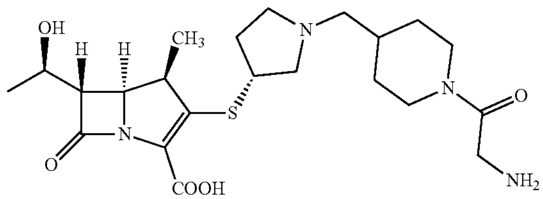 [SMILES: C[C@@H](O)[C@H]1C(=O)N2C(C(=O)O)=C(S[C@@H]3CCN(CC4CCN(C(=O)CN)CC4)C3)[C@H](C)[C@H]12] | 466.60 | 467 |
| 48 | 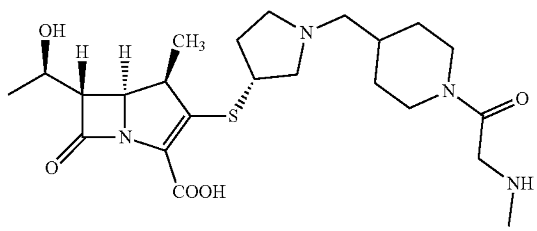 [SMILES: CNCC(=O)N1CCC(CN2CC[C@@H](SC3=C(C(=O)O)N4C(=O)[C@H]([C@@H](C)O)[C@H]4[C@H]3C)C2)CC1] | 480.62 | 481 |
| 49 | 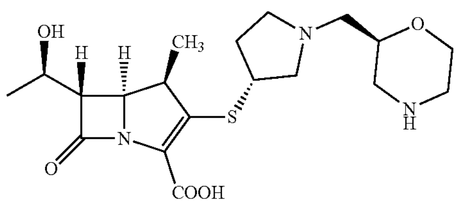 [SMILES: C[C@@H](O)[C@H]1C(=O)N2C(C(=O)O)=C(S[C@@H]3CCN(C[C@@H]4CNCCO4)C3)[C@H](C)[C@H]12] | 411.52 | 412.1 |
| 50 | 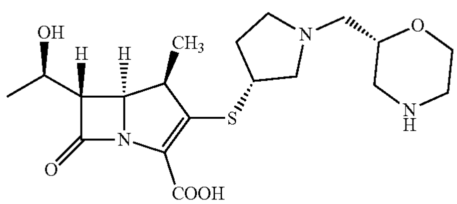 [SMILES: C[C@@H](O)[C@H]1C(=O)N2C(C(=O)O)=C(S[C@@H]3CCN(C[C@H]4CNCCO4)C3)[C@H](C)[C@H]12] | 411.52 | 412.1 |
| 51 | 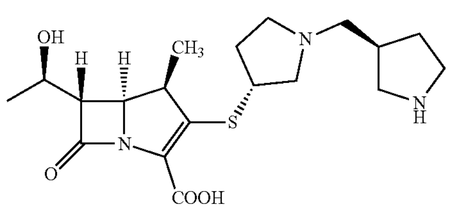 [SMILES: C[C@@H](O)[C@H]1C(=O)N2C(C(=O)O)=C(S[C@@H]3CCN(C[C@H]4CCNC4)C3)[C@H](C)[C@H]12] | 395.52 | 396 |
| 52 | 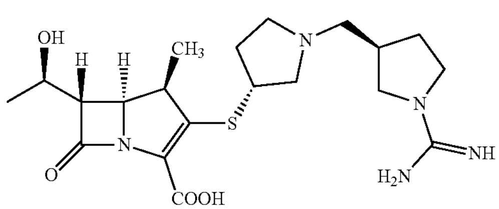 [SMILES: C[C@@H](O)[C@H]1C(=O)N2C(C(=O)O)=C(S[C@@H]3CCN(C[C@H]4CCN(C(=N)N)C4)C3)[C@H](C)[C@H]12] | 437.56 | 438 |

| Ex. | Structure | MW | ESI-MS (m/z) for [MH]+ |
|---|---|---|---|
| 53 | 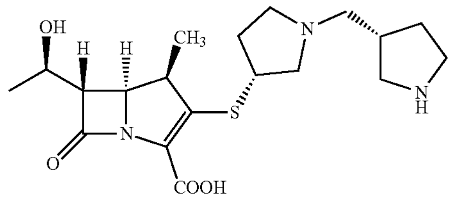 [SMILES: C[C@@H](O)[C@H]1C(=O)N2C(C(=O)O)=C(S[C@@H]3CCN(C[C@@H]4CCNC4)C3)[C@H](C)[C@H]12] | 395.52 | 396 |
| 54 | 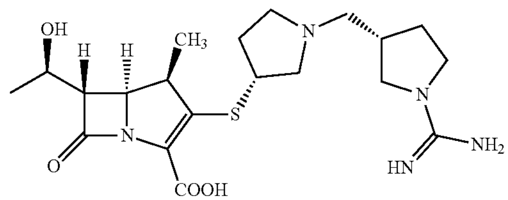 [SMILES: C[C@@H](O)[C@H]1C(=O)N2C(C(=O)O)=C(S[C@@H]3CCN(C[C@@H]4CCN(C(=N)N)C4)C3)[C@H](C)[C@H]12] | 437.56 | 438 |
| 55 | 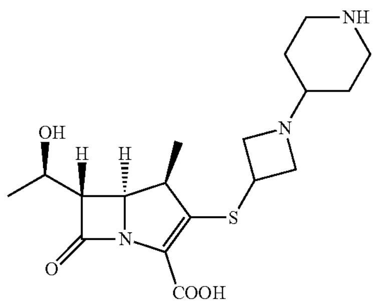 [SMILES: C[C@@H](O)[C@H]1C(=O)N2C(C(=O)O)=C(SC3CN(C4CCNCC4)C3)[C@H](C)[C@H]12] | 381.49 | 382 |
| 56 | 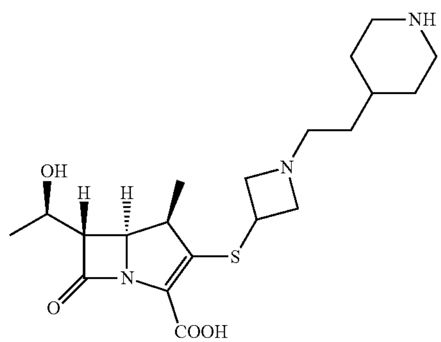 [SMILES: C[C@@H](O)[C@H]1C(=O)N2C(C(=O)O)=C(SC3CN(CCC4CCNCC4)C3)[C@H](C)[C@H]12] | 409.55 | 410 |
| 57 | 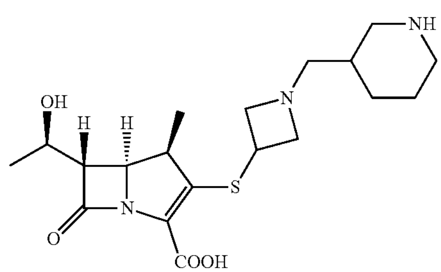 [SMILES: C[C@@H](O)[C@H]1C(=O)N2C(C(=O)O)=C(SC3CN(CC4CCCNC4)C3)[C@H](C)[C@H]12] | 395.52 | 396 |
| 58 | 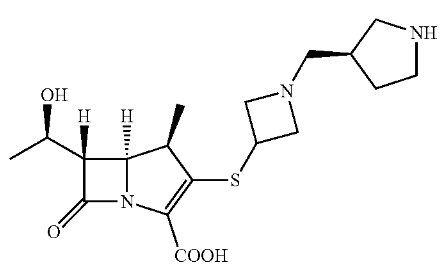 [SMILES: C[C@@H](O)[C@H]1C(=O)N2C(C(=O)O)=C(SC3CN(C[C@@H]4CCNC4)C3)[C@H](C)[C@H]12] | 381.49 | 382 |

-continued
| Ex. | Structure | MW | ESI-MS (m/z) for [MH]+ |
|---|---|---|---|
| 59 | 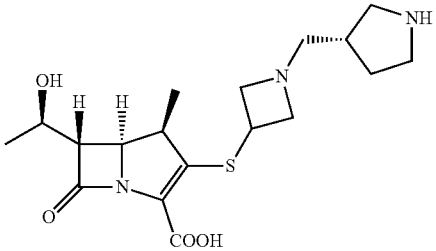 [SMILES: C[C@@H](O)[C@H]1C(=O)N2C(C(=O)O)=C(SC3CN(C[C@H]4CCNC4)C3)[C@H](C)[C@H]12] | 381.49 | 382 |
| 60 | 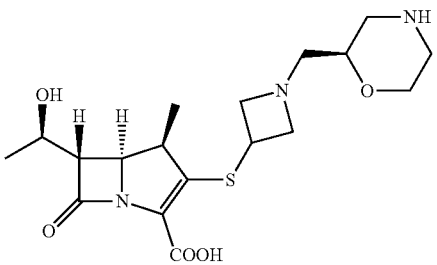 [SMILES: C[C@@H](O)[C@H]1C(=O)N2C(C(=O)O)=C(SC3CN(C[C@H]4CNCCO4)C3)[C@H](C)[C@H]12] | 397.49 | 398 |
| 61 | 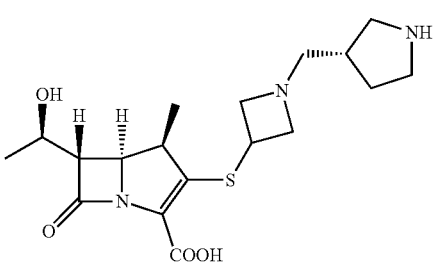 [SMILES: C[C@@H](O)[C@H]1C(=O)N2C(C(=O)O)=C(SC3CN(C[C@H]4CCNC4)C3)[C@H](C)[C@H]12] | 397.49 | 398 |
| 62 | 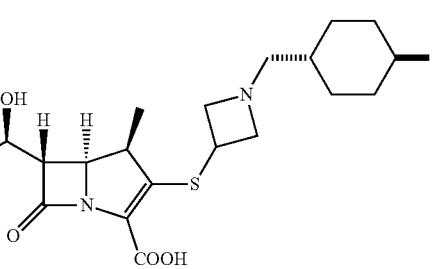 | 409.55 | 410 |
| 63 | 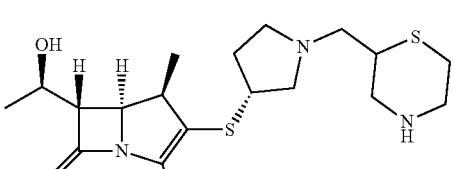 | 427.58 | 428 |
| 64 | 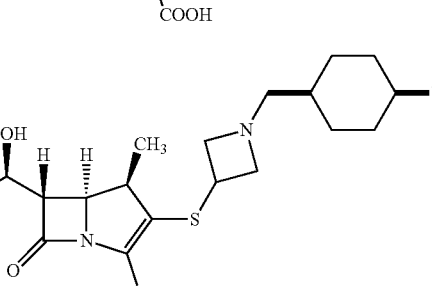 | 409.55 | 410 |

-continued
| Ex. | Structure | MW | ESI-MS (m/z) for [MH]+ |
|---|---|---|---|
| 65 | 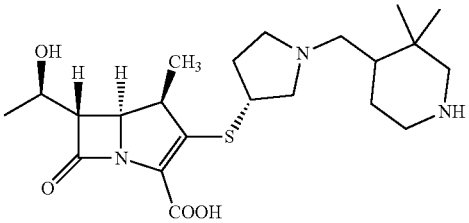 [SMILES: C[C@@H](O)[C@H]1C(=O)N2C(C(=O)O)=C(S[C@@H]3CCN(CC4CCNCC4(C)C)C3)[C@H](C)[C@H]12] | 437.60 | 438 |
| 66 | 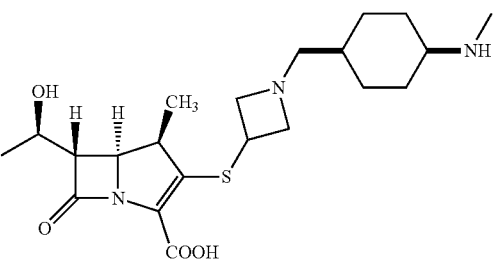 | 423.57 | 424 |
| 67 | 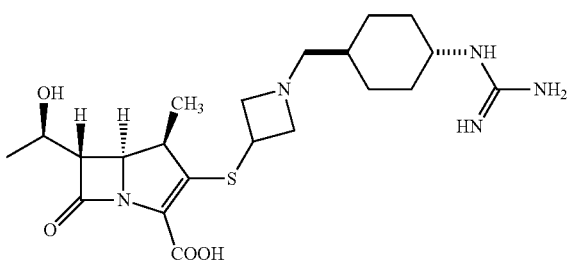 | 451.59 | 452 |
| 68 | 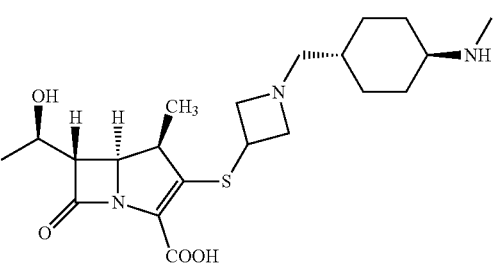 [SMILES: CN[C@H]1CC[C@H](CN2CC(SC3=C(C(=O)O)N4C(=O)[C@H]([C@@H](C)O)[C@H]4[C@H]3C)C2)CC1] | 423.57 | 424 |
| 69 | 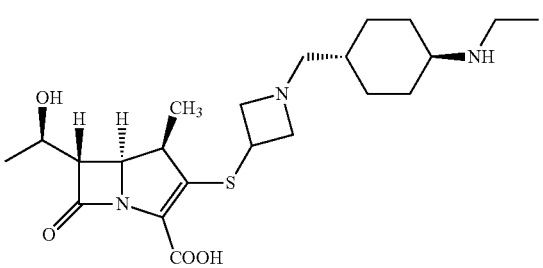 [SMILES: CCN[C@H]1CC[C@H](CN2CC(SC3=C(C(=O)O)N4C(=O)[C@H]([C@@H](C)O)[C@H]4[C@H]3C)C2)CC1] | 437.60 | 438 |
| 70 | 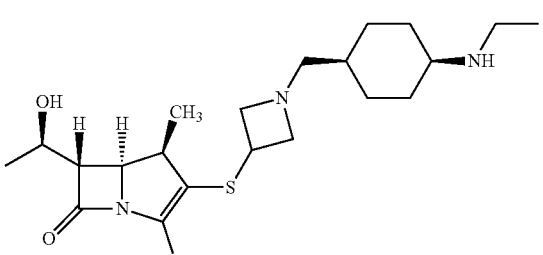 | 437.60 | 438 |

-continued

| Ex. | Structure | MW | ESI-MS (m/z) for [MH]+ |
|---|---|---|---|
| 71 | 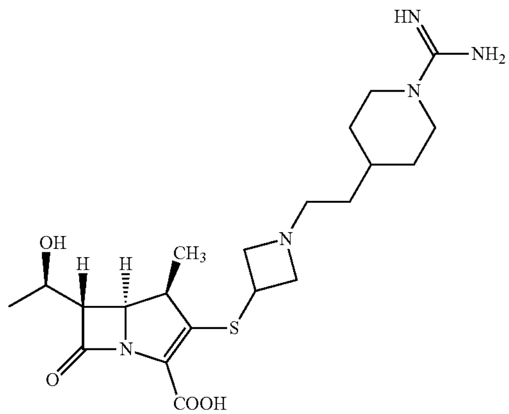 [SMILES: C[C@@H](O)[C@H]1C(=O)N2C(C(=O)O)=C(SC3CN(CCC4CCN(C(=N)N)CC4)C3)[C@H](C)[C@H]12] | 451.59 | 452 |
| 72 | 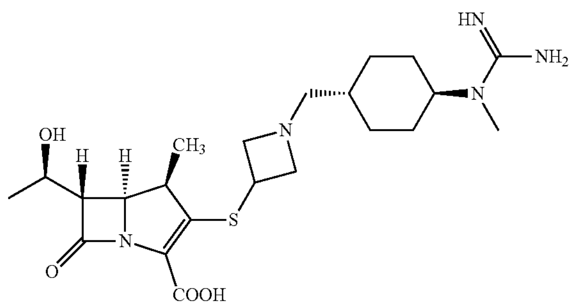 [SMILES: C[C@@H](O)[C@H]1C(=O)N2C(C(=O)O)=C(SC3CN(C[C@H]4CC[C@H](N(C)C(=N)N)CC4)C3)[C@H](C)[C@H]12] | 465.61 | 466 |
| 73 | 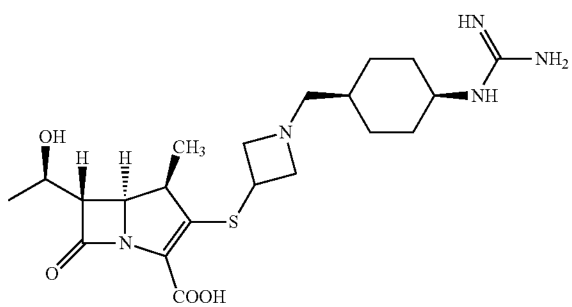 [SMILES: C[C@@H](O)[C@H]1C(=O)N2C(C(=O)O)=C(SC3CN(C[C@H]4CC[C@@H](NC(=N)N)CC4)C3)[C@H](C)[C@H]12] | 451.59 | 452 |
| 74 | 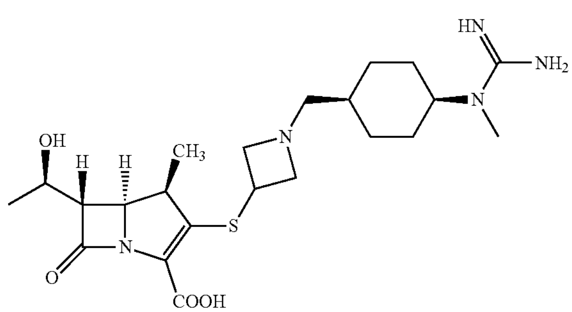 [SMILES: C[C@@H](O)[C@H]1C(=O)N2C(C(=O)O)=C(SC3CN(C[C@H]4CC[C@@H](N(C)C(=N)N)CC4)C3)[C@H](C)[C@H]12] | 465.61 | 466 |

Described herein are compounds, or a pharmaceutically acceptable salt, solvate, or stereoisomer thereof, selected from the group consisting of:
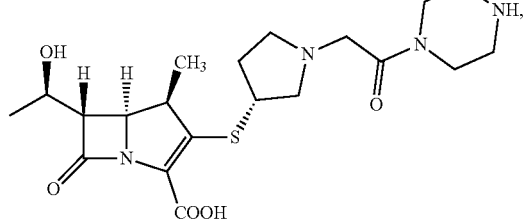
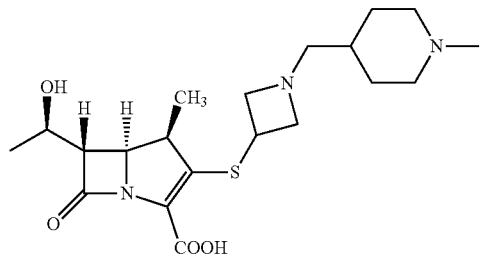
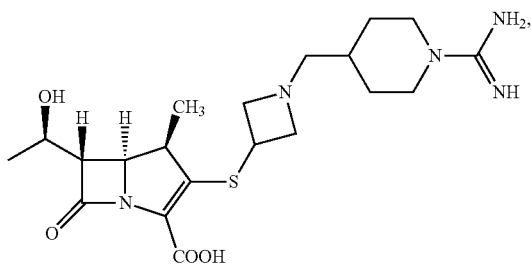
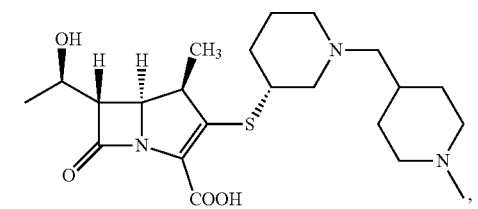
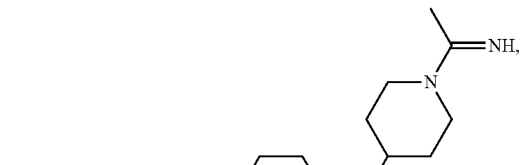
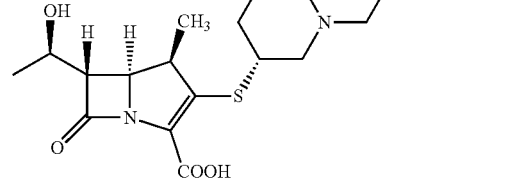
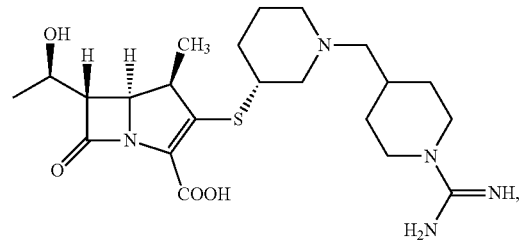
-continued
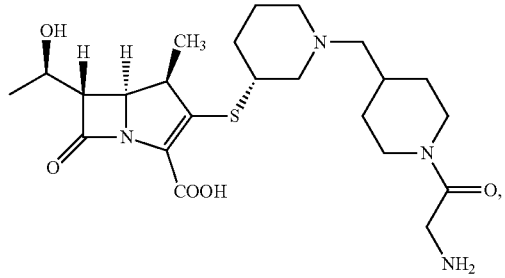
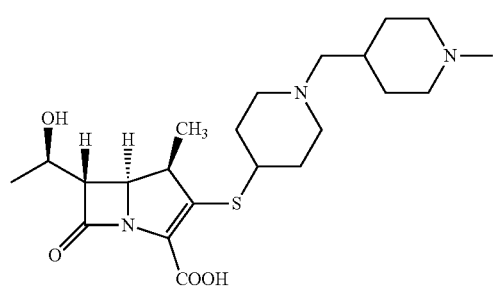
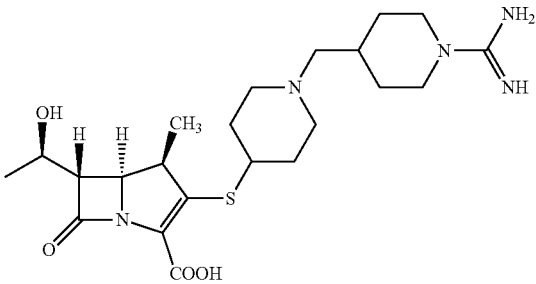
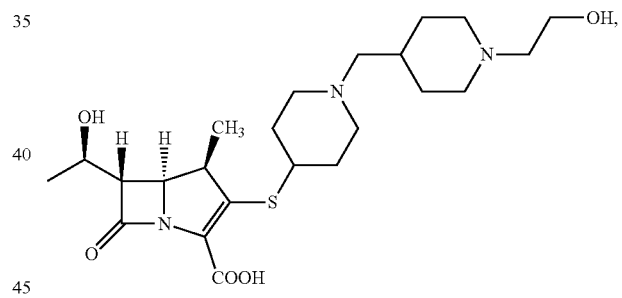
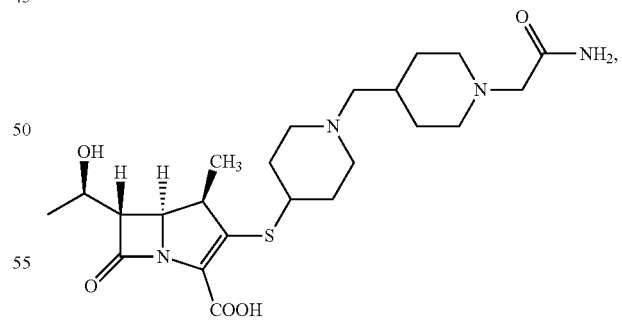
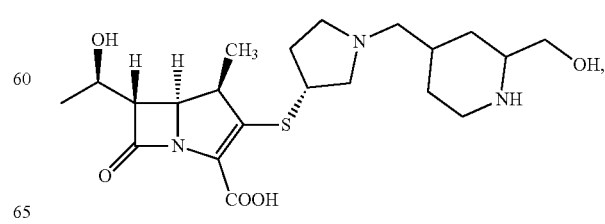

83
-continued
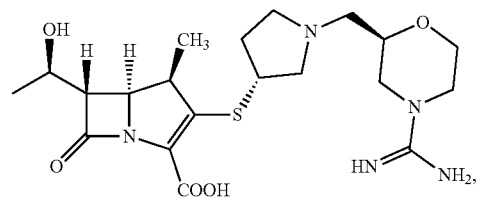
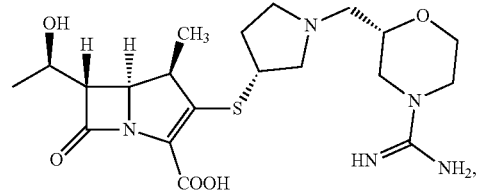
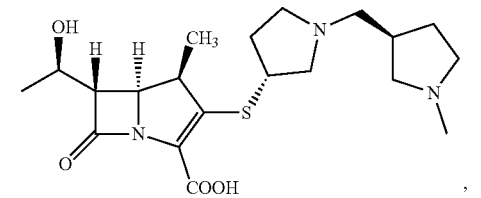
,
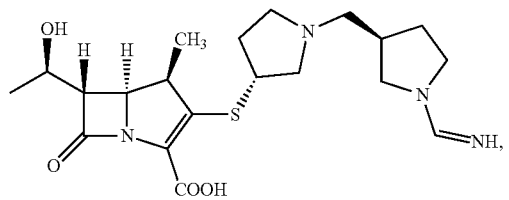
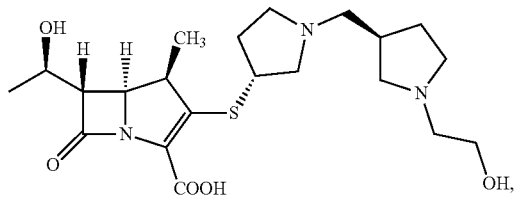
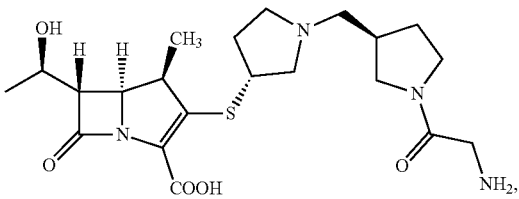
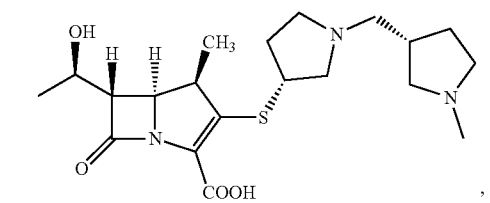
,
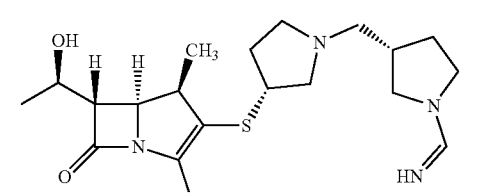
,
84
-continued
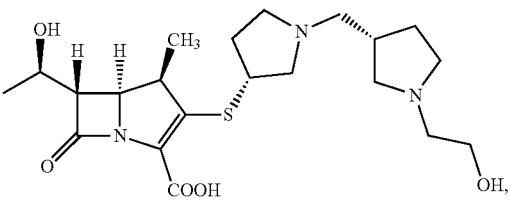
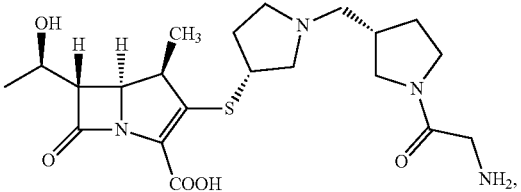
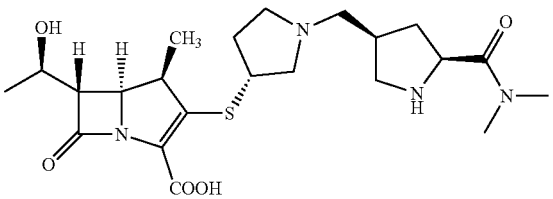
,
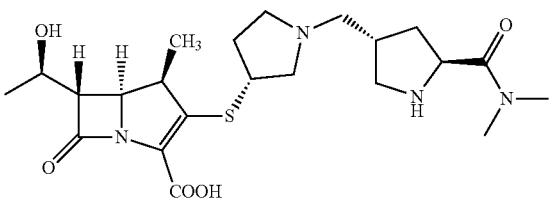
,
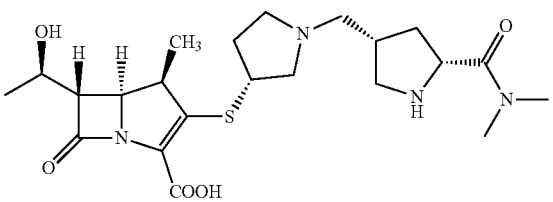
,
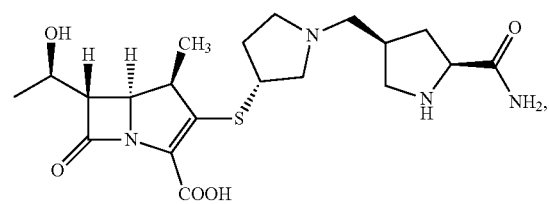
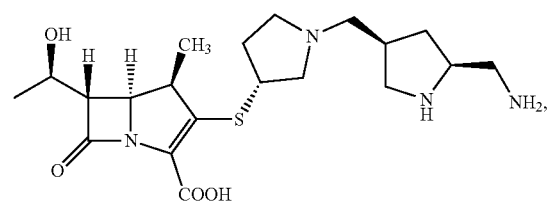
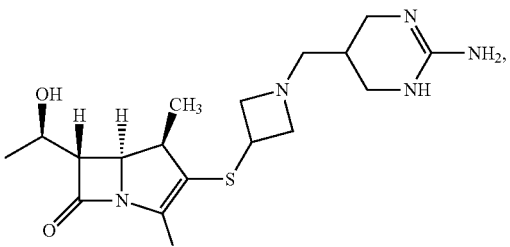

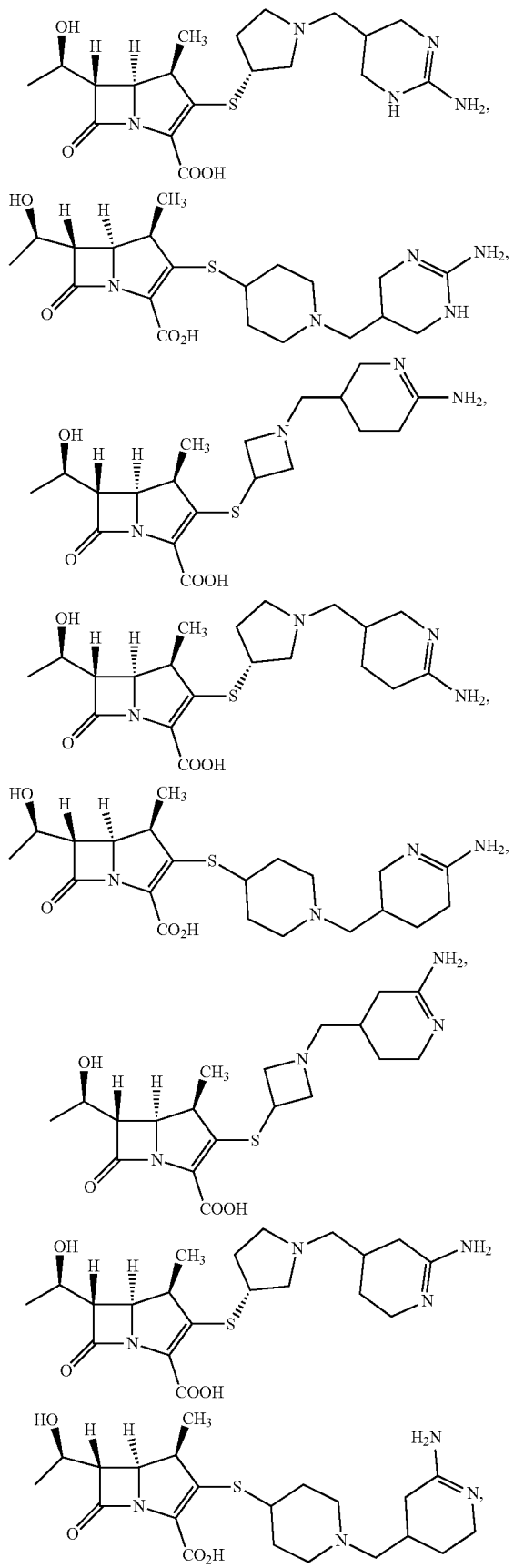
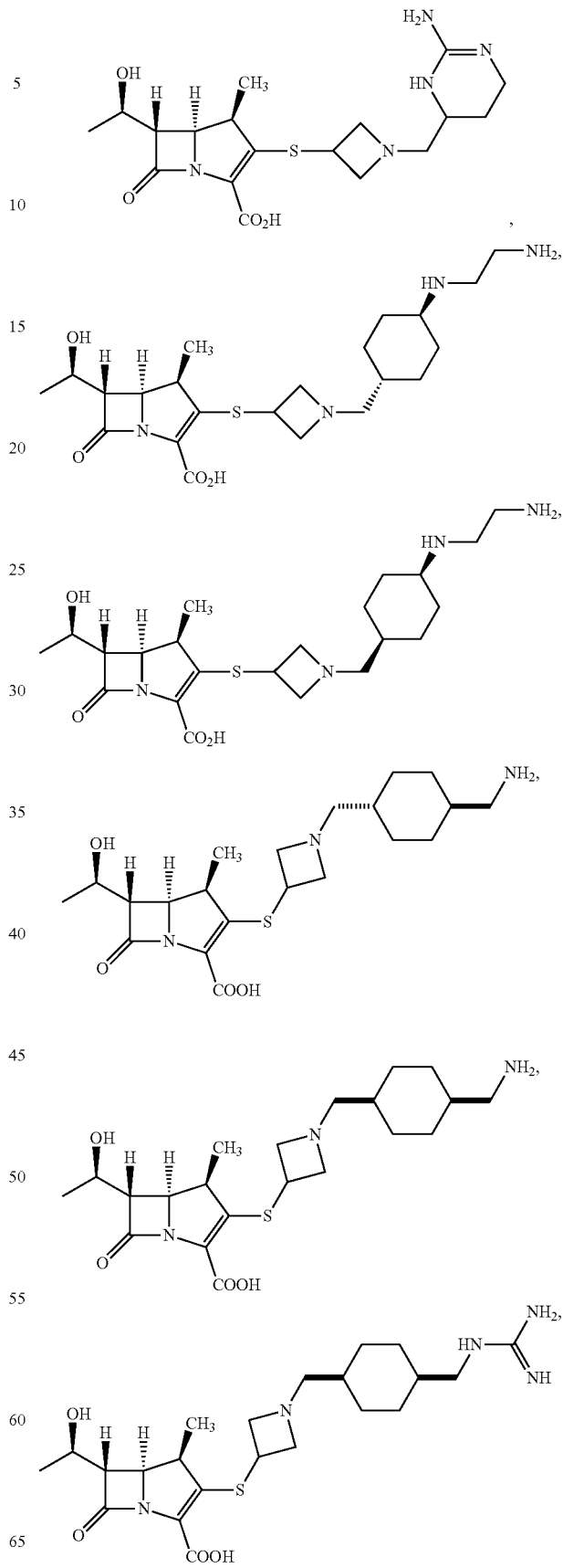

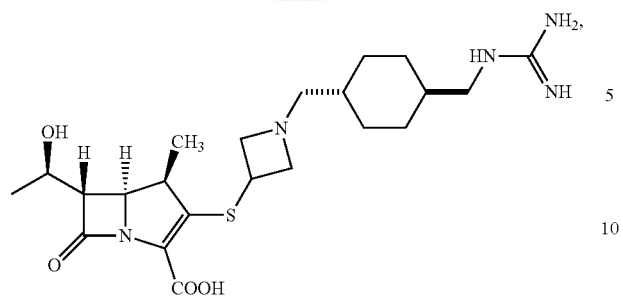
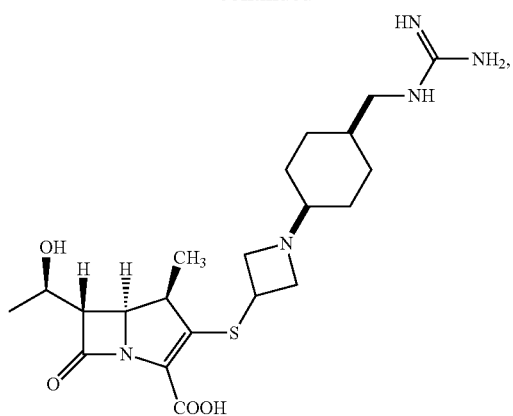
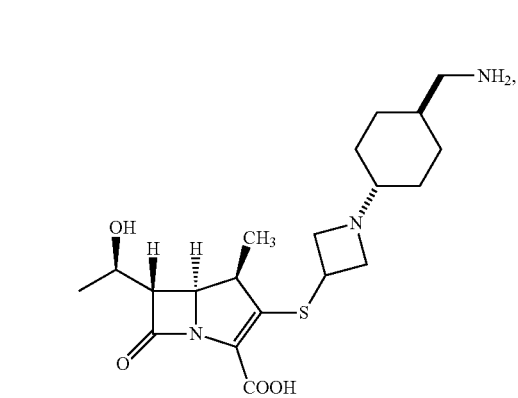
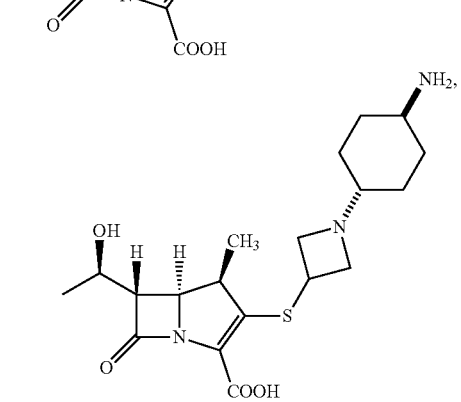
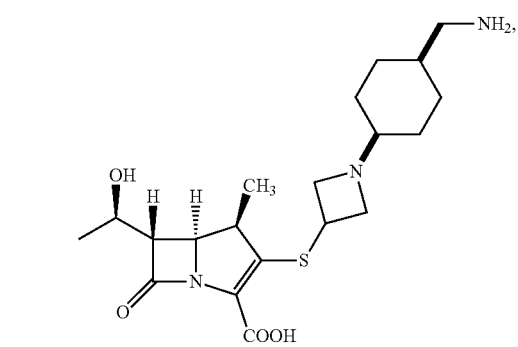
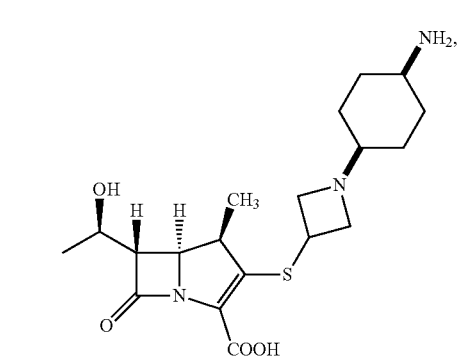
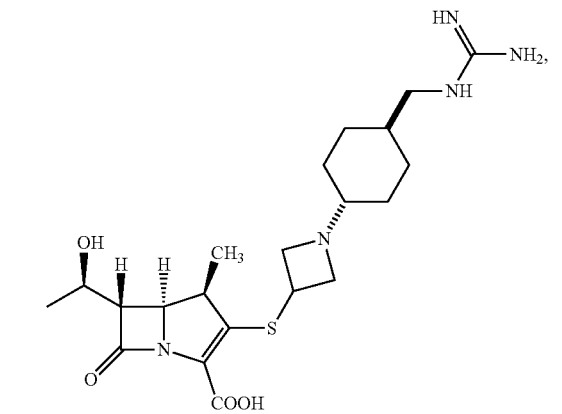
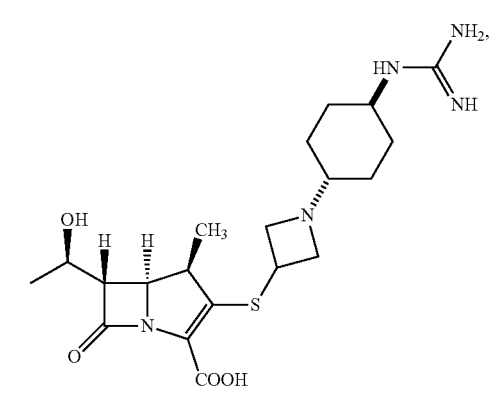

-continued

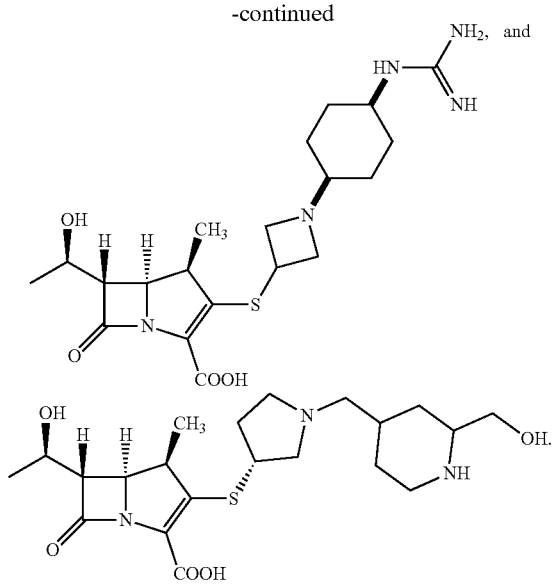

Further Forms of Compounds Disclosed Herein
Isomers/Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds of Formula (I), Formula (Ia), Formula (Ia-1), Formula (II), Formula (IIa), Formula (IIa-1), Formula (III), Formula (IIIa), Formula (IIIa-1), or a solvate, or stereoisomer thereof, include isotopes of hydrogen, carbon, nitrogen, oxygen, phosphorous, sulfur, fluorine and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the metabolites, pharmaceutically acceptable salts, esters, prodrugs, solvate, hydrates or derivatives thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i.e., $^{3}H$ and carbon-14, i.e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compounds, pharmaceutically acceptable salt, ester, prodrug, solvate, hydrate, or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of Formula (I), Formula (Ia), Formula (Ia-1), Formula (II), Formula (IIa), Formula (IIa-1), Formula (III), Formula (IIIa), Formula (IIIa-1), or a solvate, or stereoisomer thereof, or by separately reacting a purified compound in its free form with a suitable acid or base, and isolating the salt thus formed.

Examples of pharmaceutically acceptable salts include those salts prepared by reaction of the compounds described herein with a mineral, organic acid, or inorganic base, such salts including, acetate, acrylate, adipate, alginate, aspartate, benzoate, benzene sulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylateundeconate, and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methane sulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylen-ebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds of Formula (I), Formula (Ia), Formula (Ia-1), Formula (II), Formula (IIa), Formula (IIa-1), Formula (III), Formula (IIIa), Formula (IIIa-1), solvate, or stereoisomer thereof and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4}$ alkyl$)_4$, and the like.

Representative organic amines useful for the formation of base addition salts include ethylamine, diethylamine, ethylenediamine, ethanolamine, diethanolamine, piperazine, and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Preparation of Compounds

Described herein are compounds, or a pharmaceutically acceptable salt, solvate, or stereoisomer thereof useful in the treatment of bacterial infections and processes for their preparation. In some embodiments, compounds described herein, or a pharmaceutically acceptable salt, solvate, or stereoisomer thereof are synthesized using standard synthetic reactions known to those of skill in the art or using methods known in the art. The reactions can be employed in a linear sequence to provide the compounds or they may be used to synthesize fragments which are subsequently joined by the methods known in the art. In some embodiments, the starting material used for the synthesis of the compounds described herein are synthesized or are obtained from commercial sources, such as, but not limited to, Aldrich Chemical Co. (Milwaukee, Wisconsin), Bachem (Torrance, California), or Sigma Chemical Co. (St. Louis, Mo.). In some embodiments, the compounds described herein, and other related compounds having different substituents are synthesized using techniques and materials known to those of skill in the art, such as described, for example, in March, ADVANCED ORGANIC CHEMISTRY $4^{th}$ Ed., (Wiley 1992); Carey and Sundberg, ADVANCED ORGANIC CHEMISTRY $4^{th}$ Ed., Vols. A and B (Plenum 2000, 2001); Green and Wuts, PROTECTIVE GROUPS IN ORGANIC SYNTHESIS $3^{rd}$ Ed., (Wiley 1999); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989), all of which are incorporated by reference for such disclosures. In some embodiments, general methods for the preparation of compound as disclosed herein are derived from known reactions in the field, and the reactions are modified by the use of appropriate reagents and conditions, as would be recognized by the skilled person, for the introduction of the various moieties found in the formulae as provided herein.

In some embodiments, the products of the reactions are isolated and purified, if desired, using conventional techniques, including, but not limited to, filtration, distillation, crystallization, chromatography, and the like. In some embodiments, such materials are characterized using conventional means, including physical constants and spectral data.

Pharmaceutical Compositions/Formulations

In another aspect, provided herein are pharmaceutical compositions comprising a compound describe herein, or a pharmaceutically acceptable salt, solvate, or stereoisomer thereof, and at least one pharmaceutically acceptable excipient. Pharmaceutical compositions are formulated in a conventional manner using one or more pharmaceutically acceptable excipients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the pharmaceutically acceptable excipient is selected from carriers, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, and any combinations thereof.

The pharmaceutical compositions described herein are administered to a subject by appropriate administration routes, including, but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, liquids, gels, syrups, elixirs, slurries, suspensions, self-emulsifying dispersions, solid solutions, liposomal dispersions, aerosols, solid oral dosage forms, powders, immediate release formulations, controlled release formulations, fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Pharmaceutical compositions including compounds described herein, or a pharmaceutically acceptable salt, solvate, or stereoisomer thereof are manufactured in a conventional manner, such as, by way of example only, by means of conventional mixing, dissolving, granulating, dragee-making, levigating, emulsifying, encapsulating, entrapping, or compression processes.

Pharmaceutical compositions for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active compound doses.

Pharmaceutical compositions that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In soft capsules, the active compounds are dissolved or suspended in suitable liquids, such as fatty oils, liquid paraffin, or liquid polyethylene glycols. In some embodiments, stabilizers are added.

Pharmaceutical compositions for parental use are formulated as infusions or injections. In some embodiments, the pharmaceutical composition suitable for injection or infusion includes sterile aqueous solutions, or dispersions, or sterile powders comprising a compound described herein, or a pharmaceutically acceptable salt, solvate, or stereoisomer thereof. In some embodiments, the pharmaceutical composition comprises a liquid carrier. In some embodiments, the liquid carrier is a solvent or liquid dispersion medium comprising, for example, water, saline, ethanol, a polyol (for example, glycerol, propylene glycol, liquid polyethylene glycols, and the like), vegetable oils, nontoxic glyceryl esters, and any combinations thereof thereof. In some embodiments, the pharmaceutical compositions further comprise a preservative to prevent growth of microorganisms.

Combination Treatment

Disclosed herein are combinations of compounds described herein, or a pharmaceutically acceptable salt, solvate, or stereoisomer thereof with one or more antibiotics for the treatment of bacterial infections. In some embodiments, the antibiotic is administered by a route and in an amount commonly used, therefore, contemporaneously or sequentially with a compound described herein, or a pharmaceutically acceptable salt, solvate, or stereoisomer thereof. When a compound described herein, or a pharmaceutically acceptable salt, solvate, or stereoisomer thereof is used contemporaneously with one or more antibiotics, a pharmaceutical composition in unit dosage form containing such other drugs and the compound of the present disclosure is optionally used. In some embodiments, the combination therapy also includes therapies in which the compound described herein, or a pharmaceutically acceptable salt, solvate, or stereoisomer thereof and one or more antibiotic are administered on different overlapping schedules. In some embodiments, when used in combination with one or more antibiotics, the compound described herein, or a pharmaceutically acceptable salt, solvate, or stereoisomer thereof is used in lower doses than when each is used singly.

In some embodiments, the one or more antibiotics are beta-lactam antibiotics. In certain embodiments, the beta-lactam antibiotic is a penicillin, a penem, a carbapenem, a cephalosporin, a cephamycin, a monobactam, or combinations thereof. Penicillins include, but are not limited to, amoxicillin, ampicillin, azidocillin, azlocillin, bacampicillin, benzathinebenzylpenicillin, benzathinephenoxymethylpenicillin, benzylpenicillin (G), carbenicillin, carindacillin, clometocillin, cloxacillin, dicloxacillin, epicillin, flucloxacillin, hetacillin, mecillinam, metampicillin, meticillin, mezlocillin, nafcillin, oxacillin, penamecillin, pheneticillin, phenoxymethylpenicillin (V), piperacillin, pivampicillin, pivmecillinam, procaine benzylpenicillin, propicillin, sulbenicillin, talampicillin, temocillin, ticarcillin, or any combinations thereof. Penems include, but are not limited to, faropenem. Carbapenems include, but are not limited to, biapenem, ertapenem, doripenem, imipenem, meropenem, panipenem, or any combinations thereof. Cephalosprins/cephamycins include, but are not limited to, cefacetrile, cefaclor, cefadroxil, cefalexin, cefaloglycin, cefalonium, cefaloridine, cefalotin, cefamandole, cefapirin, cefatrizine, cefazaflur, cefazedone, cefazolin, cefbuperazone, cefcapene, cefdaloxime, cefdinir, cefditoren, cefepime, cefetamet, cefixime, cefmenoxime, cefmetazole, cefminox, cefodizime, cefonicid, cefoperazone, ceforanide, cefotaxime, cefotetan, cefotiam, cefovecin, cefoxitin, cefozopran, cefpimizole, cefpiramide, cefpirome, cefpodoxime, cefprozil, cefquinome, cefquinome, cefradine, cefroxadine, cefsulodin, ceftarolinefosamil, ceftazidime, cefteram, ceftezole, ceftibuten, ceftiofur, ceftiolene, ceftizoxime, ceftobiprole, ceftriaxone, cefuroxime, cefuzonam, flomoxef, latamoxef, loracarbef, or any combinations thereof. Monobactams include, but are not limited to, aztreonam, carumonam, nocardicin A, tigemonam, or any combinations thereof.

Also disclosed herein, are combination of compounds described herein, or a pharmaceutically acceptable salt, solvate, or stereoisomer thereof with one or more beta-lactamase inhibitors for the treatment of bacterial infections. In some embodiments, the beta-lactamase inhibitor is VNRX-5133, clavulanic acid, sulbactam, tazobactam, or any combinations thereof. In some embodiments, the beta-lactamase inhibitor is VNRX-5133.

Also disclosed herein, are combination of compounds described herein, or a pharmaceutically acceptable salt, solvate, or stereoisomer thereof with one or more non beta-lactam beta-lactamase inhibitors for the treatment of bacterial infections. In some embodiments, the non beta-lactam beta-lactamase inhibitor is avibactam, relebactam, or any combinations thereof.

Administration of Pharmaceutical Composition

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In some embodiments, compounds described herein, or a pharmaceutically acceptable salt, solvate, or stereoisomer thereof and compositions thereof are administered in any suitable manner. The manner of administration can be chosen based on, for example, whether local or systemic treatment is desired, and on the area to be treated. For example, the compositions can be administered orally, parenterally (e.g., intravenous, subcutaneous, intraperitoneal, or intramuscular injection), by inhalation, extracorporeally, topically (including transdermally, ophthalmically, vaginally, rectally, intranasally) or the like.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained.

Assays for Antibacterial Activity

Assays for the inhibition of bacterial growth are well known in the art.

Methods

Disclosed herein are methods of treating a bacterial infection in a subject, comprising administering to the subject an effective amount of a compound described herein, or a pharmaceutically acceptable salt, solvate, or stereoisomer thereof. Also disclosed herein are methods of treating a bacterial infection in a subject, comprising administering to the subject a pharmaceutical composition comprising an effective amount of a compound described herein, or a pharmaceutically acceptable salt, solvate, or stereoisomer thereof. In some embodiments, the bacterial infection is caused by gram-negative bacteria. In some embodiments, the bacterial infection is caused by multidrug-resistant (MDR) bacteria. In some embodiments, the bacterial infection is caused by carbapenem resistant Enterobacteriaceae (CRE). In some embodiments, the bacterial infection is caused by an aerobic bacteria. In some embodiments, the bacterial infection is caused by an anaerobic bacteria. In some embodiments, the bacterial infection is an upper or lower respiratory tract infection, a urinary tract infection, an intra-abdominal infection, a skin infection, or septicemia.

In some embodiments, the bacterial infection is caused by a bacteria that include *Pseudomonas aeruginosa, Pseudomonas fluorescens, Pseudomonas acidovorans, Pseudomonas alcaligenes, Pseudomonas putida, Stenotrophomonasmaltophilia, Burkholderiacepacia, Aeromonashydrophilia, Escherichia coli, Citrobacterfreundii, Salmonella typhimurium, Salmonella typhi, Salmonella paratyphi, Salmonella enteritidis, Shigelladysenteriae, Shigellaflexneri, Shigellasonnei, Enterobacter cloacae, Enterobacter aerogenes, Klebsiella pneumoniae, Klebsiellaoxytoca, Serratiamarcescens, Francisellatularensis, Morganellamorganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilusinfluenzae, Haemophilusparainfluenzae, Haemophilushaemolyticus, Haemophilusparahaemolyticus, Haemophilusducreyi, Pasteurellamultocida, Pasteurellahaemolytica, Branhamellacatarrhalis, Helicobacter pylori, Campylobacter fetus, Campylobacter jejuni, Campylobacter coli, Borreliaburgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroidesfragilis, Bacteroidesdistasonis, Bacteroides 3452A homology group, Bacteroidesvulgatus, Bacteroidesovalus, Bacteroidesthetaiotaomicron, Bacteroidesuniformis, Bacteroideseggerthii, Bacteroidessplanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus* intermedius, Staphylococcus hyicus subsp. hyicus, Staphylococcus haemolyticus, Staphylococcus hominis, or Staphylococcus saccharolyticus.

In some embodiments, the infection that is treated is caused by a bacteria that includes Pseudomonas aeruginosa, Pseudomonas fluorescens, Stenotrophomonasmaltophilia, Escherichia coli, Citrobacterfreundii, Salmonella typhimurium, Salmonella typhi, Salmonella paratyphi, Salmonella enteritidis, Shigelladysenteriae, Shigellaflexneri, Shigellasonnei, Enterobacter cloacae, Enterobacter aerogenes, Klebsiella pneumoniae, Klebsiellaoxytoca, Serratiamarcescens, Acinetobacter calcoaceticus, Acinetobacter haemolyticus, Yersinia enterocolitica, Yersinia pestis, Yersinia pseudotuberculosis, Yersinia intermedia, Haemophilusinfluenzae, Haemophilusparainfluenzae, Haemophilushaemolyticus, Haemophilusparahaemolyticus, Helicobacter pylori, Campylobacter fetus, Campylobacter jejuni, Campylobacter coli, Vibrio cholerae, Vibrio parahaemolyticus, Legionella pneumophila, Listeria monocytogenes, Neisseria gonorrhoeae, Neisseria meningitidis, Moraxella, Bacteroidesfragilis, Bacteroidesvulgatus, Bacteroidesovalus, Bacteroidesthetaiotaomicron, Bacteroidesuniformis, Bacteroideseggerthii, or Bacteroidessplanchnicus.

Also disclosed herein are methods for inhibiting bacterial growth, such methods comprising contacting a bacterial cell culture, or a bacterially infected cell culture, tissue, or organism, with a carbapenem derivative described herein. Preferably, the bacteria to be inhibited by administration of a compound described herein, or a pharmaceutically acceptable salt, solvate, or stereoisomer thereof are bacteria that are resistant to beta-lactam antibiotics. The term "resistant" is well-understood by those of ordinary skill in the art (see, e g Payne et al., *Antimicrobial Agents and Chemotherapy* 38 767-772 (1994), Hanaki et al., *Antimicrobial Agents and Chemotherapy* 30 1120-1126 (1995)).

These methods are useful for inhibiting bacterial growth in a variety of contexts. In certain embodiments, a compound described herein, or a pharmaceutically acceptable salt, solvate, or stereoisomer thereof is administered to an experimental cell culture in vitro to prevent the growth of beta-lactam resistant bacteria. In certain some embodiments, a compound described herein, or a pharmaceutically acceptable salt, solvate, or stereoisomer thereof is administered to a mammal, including a human to prevent the growth of beta-lactam resistant bacteria in vivo. The method according to this embodiment comprises administering a therapeutically effective amount of a compound described herein, or a pharmaceutically acceptable salt, solvate, or stereoisomer thereof for a therapeutically effective period of time to a mammal, including a human.

EXAMPLES

General Examples for the Preparation of Compounds

The starting materials and intermediates for the compounds of this invention may be prepared by the application or adaptation of the methods described below, their obvious chemical equivalents, or, for example, as described in literature such as The Science of Synthesis, Volumes 1-8. Editors E. M. Carreira et al. Thieme publishers (2001-2008). The use of protective groups may be as described in methodology compendia such as *Greene's Protective Groups in Organic Synthesis*, Fourth Edition. John Wiley & Sons, Inc. 2006.

Certain compounds described herein, or a pharmaceutically acceptable salt, solvate, or stereoisomer thereof (SCHEME 1) are prepared from the corresponding functional-group-protected beta-lactams II by hydrogenation in the presence of a catalyst such as platinum on carbon, at a temperature between 0° C. and 10° C., followed by purification of the crude products by flash chromatography on MCI GEL CHP20P.

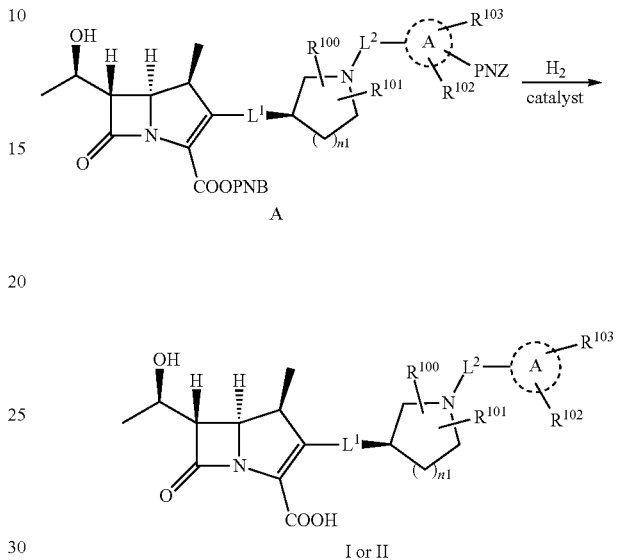

The functional-group-protected intermediates A may be prepared according to the route outlined in SCHEME 2. Pyrrolidine-thiols B were coupled with the carbonyl compounds C in the presence of a reducing reagent such as sodium triacetoxyborohydride to give the thiols D, which were condensed with the known and commercially available enol phosphate E in the presence of a base such as Hünig's base (DIEA, diisopropylethylamine). Pyrrolidine-thiols B, and the carbonyl compounds C may be obtained from commercial sources, prepared according to known methods in the literature, or prepared by a number of different reaction sequences.

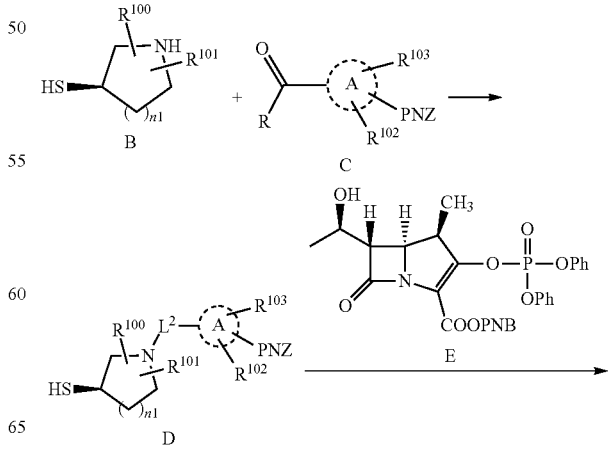

-continued

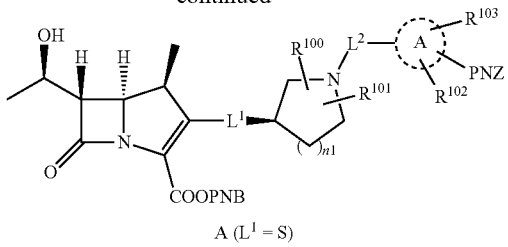

A (L¹ = S)

Synthetic Examples

The following preparations of compounds described herein, or a pharmaceutically acceptable salt, solvate, or stereoisomer thereof and intermediates are given to enable those of skill in the art to more clearly understand and to practice the present invention. They should not be considered as limiting the scope of the invention, but merely as illustrative and representative thereof.

Example 1: (4R,5S,6S)-6-((R)-1-hydroxyethyl)-4-methyl-7-oxo-3-(((R)-1-(piperidin-4-yl)pyrrolidin-3-yl)thio)-1-azabicyclo[3.2.0]hept-2-ene-2-carboxylic acid

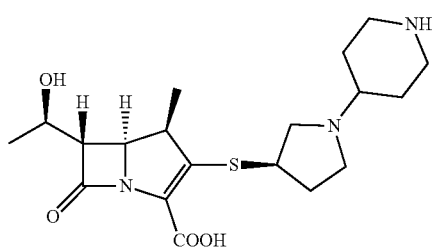 [SMILES: C[C@@H](O)[C@H]1C(=O)N2C(C(=O)O)=C(S[C@@H]3CCN(C4CCNCC4)C3)[C@H](C)[C@H]12]

Step 1: Synthesis of tert-butyl (S)-3-((methylsulfonyl)oxy)pyrrolidine-1-carboxylate

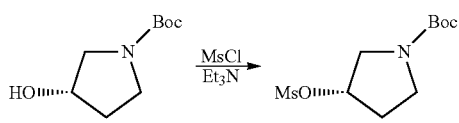 [SMILES: "Et3N" ; "MsCl" ; CC(C)(C)OC(=O)N1CC[C@H](O)C1 ; CC(C)(C)OC(=O)N1CC[C@H](OS(C)(=O)=O)C1]

To a solution of (S)-Boc-3-pyrrolidinol (8.42 g, 45 mmol) in DCM (150 mL) at 0° C. was added triethylamine (9.5 mL, 68.2 mmol) followed by methanesulfonyl chloride (4 mL, 50.8 mmol). The reaction mixture was stirred at 0° C. for 30 min, then warmed to rt for 30 min, washed with saturated aqueous NaHCO₃, dried over Na₂SO₄, concentrated in vacuo, yielding the crude product, which was used directly for the next step without further purification.

Step 2: Synthesis of tert-butyl (R)-3-(acetylthio)pyrrolidine-1-carboxylate

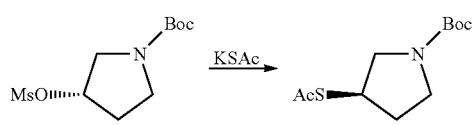

To a solution of the crude methylate in acetone (380 mL) was added potassium thioacetate (7.8 g, 68.3 mmol). The reaction mixture was refluxed for 20 h, cooled to rt, filtered, and the filtrate was concentrated. To the residue was added diethyl ether, washed with water, brine, dried over Na₂SO₄, concentrated in vacuo, and purified by flash chromatography on silica gel (hexane-EtOAc, 20:1-2:1) to afford the product, 9 g.

Step 3: Synthesis of tert-butyl (R)-3-mercaptopyrrolidine-1-carboxylate

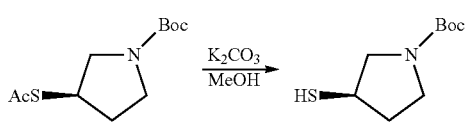

To a solution of the above product (9 g, 36.7 mmol) in methanol (60 mL) was added potassium carbonate (10.2 g, 73.9 mmol). The reaction mixture was stirred at 50° C. under Argon for 2 h, then cooled in ice-bath, acidified with 1 N HCl to pH 4-5, extracted with diethyl ether. The organic extracts were combined, washed with water, brine, dried over Na₂SO₄, and concentrated in vacuo to give the crude thiol, which was used directly for the next step without further purification.

Step 4: Synthesis of (R)-pyrrolidine-3-thiol

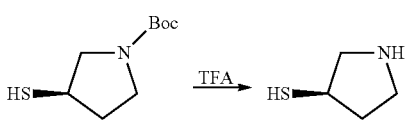 [SMILES: CC(C)(C)OC(=O)N1CC[C@@H](S)C1 ; S[C@@H]1CCNC1 ; "TFA"]

The above crude product was dissolved in DCM (70 mL), treated with TFA (70 mL) at 0° C. for 1 h, and then concentrated in vacuo to give the crude product as a TFA salt, which was used directly for the next step without further purification.

Step 5: Synthesis of 4-nitrobenzyl 4-oxopiperidine-1-carboxylate

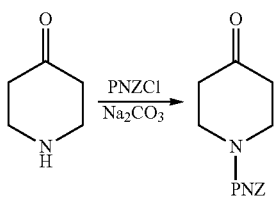

To a solution of 4-piperidinone hydrochloride hydrate (4.59 g, 30 mmol) in dioxane (50 mL) and water (25 mL) was added sodium carbonate (6.36 g, 60 mmol) followed by 4-nitrobenzyl chloroformate (7.12 g, 33 mmol) at 0° C. The reaction mixture was stirred in ice-bath for 2 h, diluted with water, extracted with EtOAc. The organic extracts were combined, dried over Na₂SO₄, concentrated in vacuo. To the crude product was added hexane, then filtered, the solid was collected, washed with hexane, dried in vacuo to afford the product, 7.1 g. ESI-MS m/z 279 (MH)⁺.

Step 6: Synthesis of 4-nitrobenzyl (R)-4-(3-mercaptopyrrolidin-1-yl)piperidine-1-carboxylate

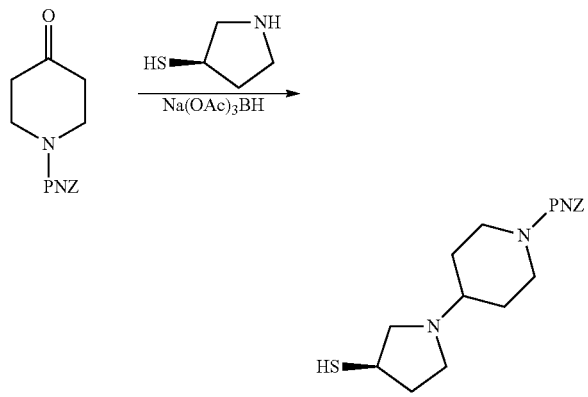

To a solution of the above product (1.2 g, 4.29 mmol), (R)-pyrrolidine-3-thiol from Step 4 (crude, 5.3 mmol) in 1,2-dichloroethane (30 mL) was added sodium triacetoxyborohydride (1.37 g, 6.43 mmol). The reaction mixture was stirred at rt overnight, washed with saturated aqueous NaHCO$_3$, dried over Na$_2$SO$_4$, concentrated in vacuo. The residue was purified twice by flash chromatography on silica gel (DCM-MeOH, 30:1-5:1) to afford the pure product, 400 mg. ESI-MS m/z 366 (MH)$^+$.

Step 7: Synthesis of 4-nitrobenzyl (R)-4-(3-mercaptopyrrolidin-1-yl)piperidine-1-carboxylate 4-nitrobenzyl (4R,5S,6S)-6-((R)-1-hydroxyethyl)-4-methyl-3-(((R)-1-(1-(((4-nitrobenzyl)oxy)carbonyl)piperidin-4-yl)pyrrolidin-3-yl)thio)-7-oxo-1-azabicyclo[3.2.0]hept-2-ene-2-carboxylate

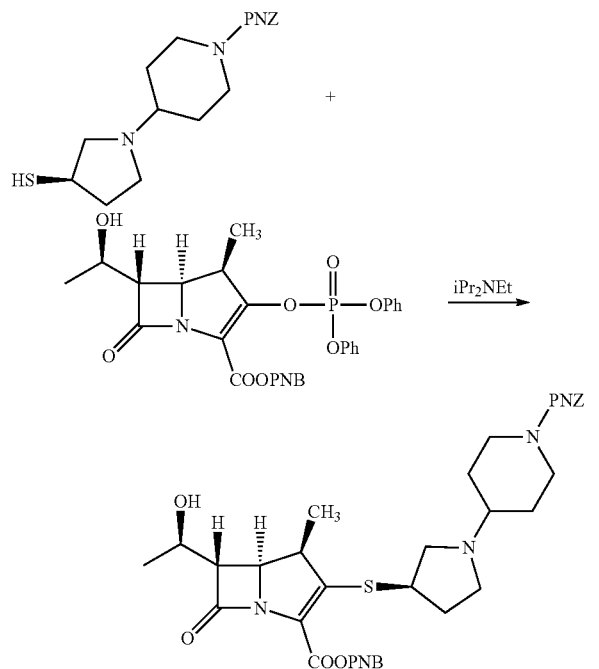

To the above product (183 mg, 0.5 mmol), and 4-nitrobenzyl (4R,5R,6S)-3-((diphenoxyphosphoryl)oxy)-6-((R)-1-hydroxyethyl)-4-methyl-7-oxo-1-azabicyclo[3.2.0]hept-2-ene-2-carboxylate (327 mg, 0.55 mmol) was add dry acetonitrile (15 mL) under Argon at 0° C., followed by diisopropylethylamine (0.12 mL, 0.66 mmol). The reaction mixture was stirred in ice-bath for 8 h, kept in the refrigerator for 20 h, then concentrated. The residue was purified twice by flash chromatography on silica gel (EtOAc, then hexane-acetone, 1:1-0:100) to yield the product, 220 mg. ESI-MS m/z 710 (MH)$^+$.

Step 8: Synthesis of (4R,5S,6S)-6-((R)-1-hydroxyethyl)-4-methyl-7-oxo-3-(((R)-1-(piperidin-4-yl)pyrrolidin-3-yl)thio)-1-azabicyclo[3.2.0]hept-2-ene-2-carboxylic acid

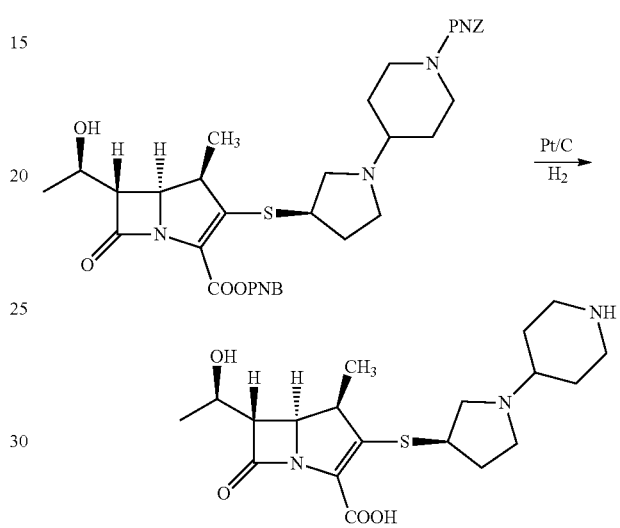

The above product (210 mg, 0.3 mmol) in THF (5 mL), iPrOH (5 mL), and phosphate buffer (pH 7, 10 mL) was hydrogenated in the presence of 5% Pt/C (130 mg) in ice-bath for 6 h. The reaction mixture was filtered through a pad of celite, washed with small amount of water and EtOAc. The aqueous layer was separated, washed with EtOAc, then purified by flash chromatography on MCI GEL CHP20P (0-10% aqueous THF) followed by lyophilized to yield the product, 40 mg. ESI-MS m/z 396 (MH)$^+$.

Example 2: (4R,5S,6S)-6-((R)-1-hydroxyethyl)-4-methyl-7-oxo-3-(((S)-1-(piperidin-4-yl)pyrrolidin-3-yl)thio)-1-azabicyclo[3.2.0]hept-2-ene-2-carboxylic acid

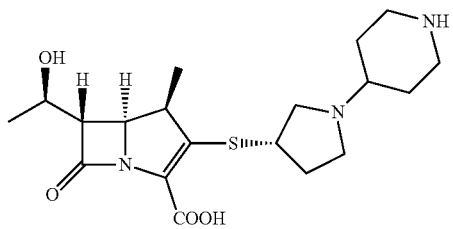 [SMILES: C[C@@H](O)[C@H]1C(=O)N2C(C(=O)O)=C(S[C@H]3CCN(C4CCNCC4)C3)[C@H](C)[C@H]12]

By following the same reaction procedures as described in Example 1, except in Step 1 using (R)-Boc-3-pyrrolidinol instead of (S)-Boc-3-pyrrolidinol as starting material, the target compound was prepared. ESI-MS m/z 396 (MH)$^+$.

Example 3: (4R,5S,6S)-3-(((R)-1-(4-((3-boronopropyl)amino)cyclohexyl)pyrrolidin-3-yl)thio)-6-((R)-1-hydroxyethyl)-4-methyl-7-oxo-1-azabicyclo[3.2.0]hept-2-ene-2-carboxylic acid

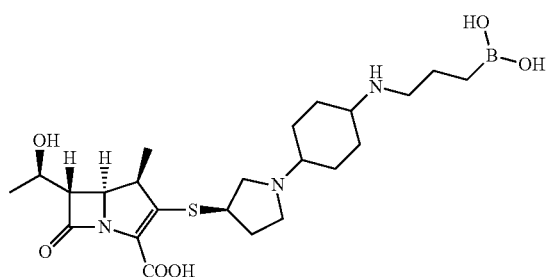 [SMILES: C[C@@H](O)[C@H]1C(=O)N2C(C(=O)O)=C(S[C@@H]3CCN(C4CCC(NCCCB(O)O)CC4)C3)[C@H](C)[C@H]12]

Step 1: Synthesis of 4-nitrobenzyl (4-oxocyclohexyl)(3-(4,4,5,5-tetramethyl-1,3,2-dioxaborolan-2-yl)propyl) carbamate

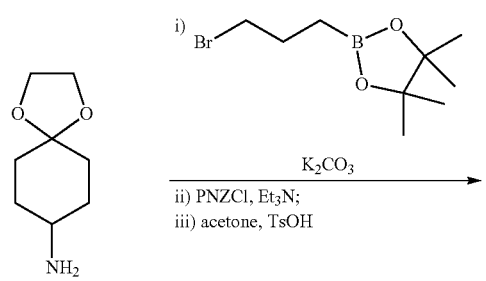

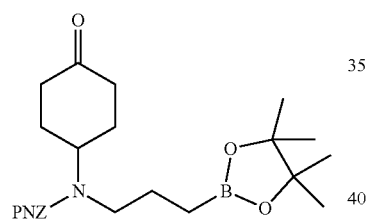

Part i). 8-Amino-1,4-dioxaspiro[4.5]decane (2.1 g, 13.4 mmol) was reacted with 3-bromopropylboronic acid pinacol ester (2.3 g, 9.24 mmol) in acetonitrile (50 mL) in the presence of K₂CO₃ (2.07 g, 15 mmol) at reflux for 4 h, then cooled to rt, filtered, and the filtrate was concentrated in vacuo to afford the crude product, which was used directly for the next step without further purification.

Part ii). The crude product from Part i) was dissolved in DCM (100 mL), triethylamine (2.98 mL, 20.7 mmol) was added, followed by 4-nitrobenzyl chloroformate (3.19 g, 14.8 mmol). The reaction mixture was stirred at rt overnight, washed with saturated aqueous NaHCO₃, dried over Na₂SO₄, concentrated in vacuo. The residue was purified by flash chromatography on silica gel (hexane-EtOAc, 20:1-1:1) to afford the product, 1.45 g. ESI-MS m/z 505 (MH)+.

Part iii). The product from Part ii) (1.4 g, 2.78 mmol) was dissolved in acetone (60 mL), toluenesulfonic acid monohydrate (133 mg, 0.7 mmol) was added. The reaction mixture was stirred at rt for 60 h, concentrated in vacuo. The residue was dissolved in DCM, washed with saturated aqueous NaHCO₃, dried over Na₂SO₄, concentrated in vacuo to give the crude product, which was used directly for the next step without further purification. ESI-MS m/z 461 (MH)+.

Step 2: Synthesis of (4R,5S,6S)-3-(((R)-1-(4-((3-boronopropyl)amino)cyclohexyl)pyrrolidin-3-yl)thio)-6-((R)-1-hydroxyethyl)-4-methyl-7-oxo-1-azabicyclo[3.2.0]hept-2-ene-2-carboxylic acid

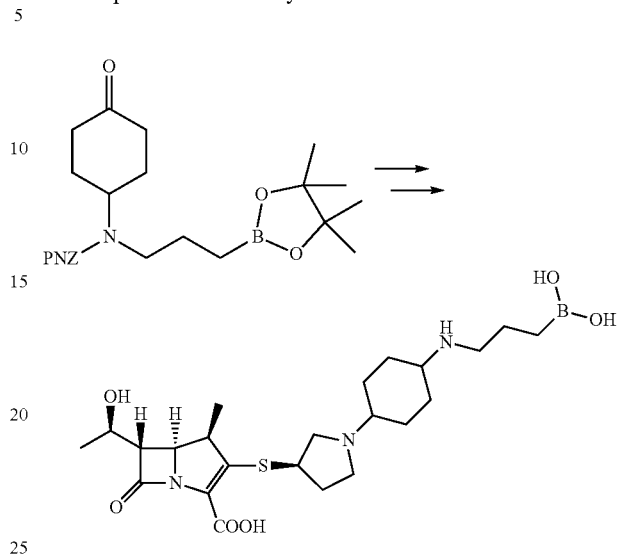

By following the same reaction procedures as described in Steps 6, 7 and 8 of Example 1, the above ketone was converted to the target compound. ESI-MS m/z 496 (MH)+.

Example 4: (4R,5S,6S)-6-((R)-1-hydroxyethyl)-4-methyl-7-oxo-3-(((3R)-1-(piperidin-3-yl)pyrrolidin-3-yl)thio)-1-azabicyclo[3.2.0]hept-2-ene-2-carboxylic acid

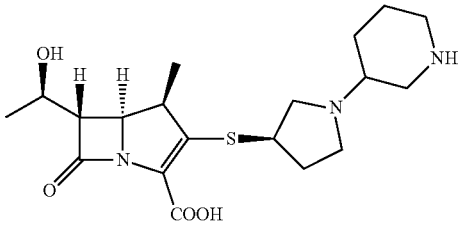 [SMILES: C[C@@H](O)[C@H]1C(=O)N2C(C(=O)O)=C(S[C@@H]3CCN(C4CCCNC4)C3)[C@H](C)[C@H]12]

By following the same reaction procedures as described in Example 1, except in Step 5 using 3-piperidinone hydrochloride hydrate instead of 4-piperidinone hydrochloride hydrate as starting material, the target compound was prepared. ESI-MS m/z 396 (MH)+.

Example 5: (4R,5S,6S)-6-((R)-1-hydroxyethyl)-3-(((3R,5S)-5-(hydroxymethyl)-1-(piperidin-4-yl)pyrrolidin-3-yl)thio)-4-methyl-7-oxo-1-azabicyclo[3.2.0]hept-2-ene-2-carboxylic acid

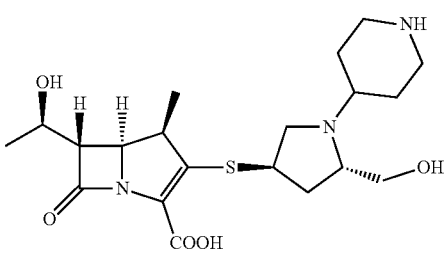 [SMILES: C[C@@H](O)[C@H]1C(=O)N2C(C(=O)O)=C(S[C@@H]3C[C@@H](CO)N(C4CCNCC4)C3)[C@H](C)[C@H]12]

Step 1: Synthesis of 1-(tert-butyl) 2-methyl (2S,4R)-4-(acetylthio)pyrrolidine-1,2-dicarboxylate

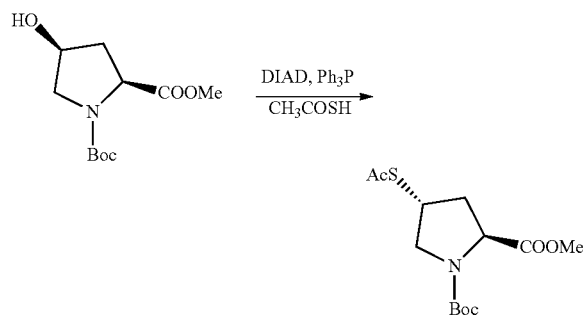

To a solution of Boc-cis-L-4-hydroxyproline methyl ester (2.45 g, 10 mmol) in THF (80 mL) was added triphenylphosphine (3.67 g, 14 mmol) followed by DIAD (2.7 mL, 14 mmol) at 0° C. under Argon. After 30 min, thioacetic acid (1.29 mL, 18 mmol) was added, and the reaction mixture was stirred between 0-10° C. for 3 h, then concentrated in vacuo. The residue was purified by flash chromatography on silica gel (hexane-EtOAc, 30:1-2:1) to afford the product, 3.02 g.

Step 2: Synthesis of tert-butyl (2S,4R)-2-(hydroxymethyl)-4-mercaptopyrrolidine-1-carboxylate

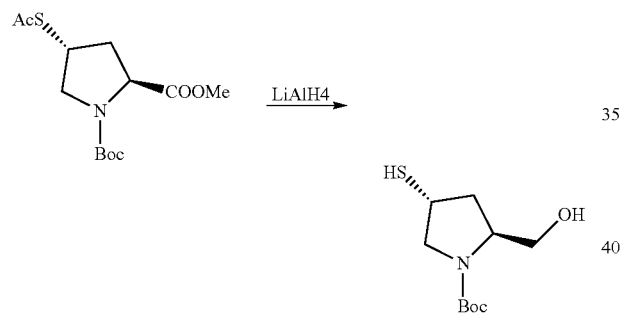

To a solution of the above product (3.02 g, 10 mmol) in THF (100 mL) at −30° C. under Argon was added LiAlH$_4$ (950 mg, 25 mmol). The reaction mixture was stirred between −30-0° C. for 2 h, quenched by careful addition of water, and 1 N HCl to pH 3-4, extracted with EtOAc. The combined organic extracts were washed with brine, dried over Na$_2$SO$_4$, concentrated in vacuo, yielding the crude product, which was used directly for the next step without further purification.

Step 3: Synthesis of ((2S,4R)-4-mercaptopyrrolidin-2-yl)methanol

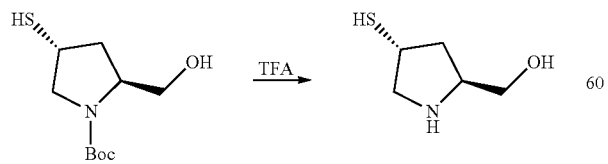

The above crude product (10 mmol) was dissolved in DCM (25 mL), and treated with TFA (25 mL) at 0° C. for 1 h, then concentrated and dried in vacuo, yielding the crude product as TFA salt, which was used directly for the next step without further purification.

Step 4: Synthesis of (4R,5S,6S)-6-((R)-1-hydroxyethyl)-3-(((3R,5S)-5-(hydroxymethyl)-1-(piperidin-4-yl)pyrrolidin-3-yl)thio)-4-methyl-7-oxo-1-azabicyclo[3.2.0]hept-2-ene-2-carboxylic acid

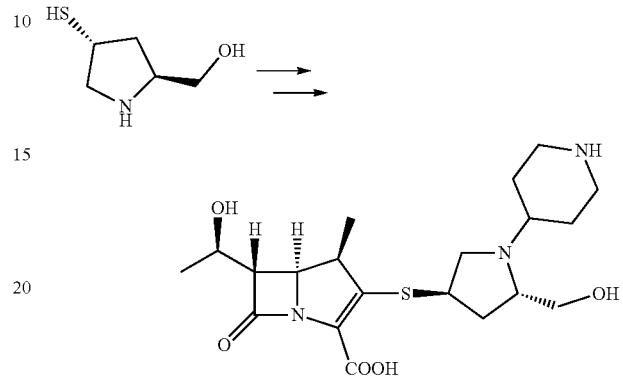

By using the same reaction procedures as described in Steps 6, 7 and 8 of Example 1, the above thiol was converted to the target compound. ESI-MS m/z 426 (MH)$^+$.

Example 6: (4R,5S,6S)-3-(((3R)-[1,3'-bipyrrolidin]-3-yl)thio)-6-((R)-1-hydroxyethyl)-4-methyl-7-oxo-1-azabicyclo[3.2.0]hept-2-ene-2-carboxylic acid

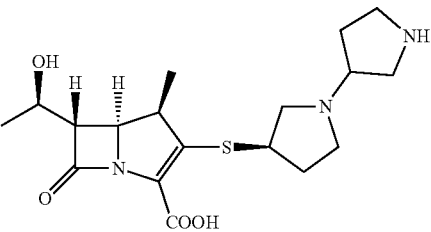 [SMILES: C[C@@H](O)[C@H]1C(=O)N2C(C(=O)O)=C(S[C@@H]3CCN(C4CCNC4)C3)[C@H](C)[C@H]12]

By following the same reaction procedures as described in Example 1, except in Step 5 using 3-pyrrolidinone hydrochloride instead of 4-piperidinone hydrochloride hydrate as starting material, the target compound was prepared. ESI-MS m/z 382 (MH)$^+$.

Example 7: (4R,5S,6S)-6-((R)-1-hydroxyethyl)-4-methyl-7-oxo-3-(((R)-1-(piperidin-4-ylmethyl)pyrrolidin-3-yl)thio)-1-azabicyclo[3.2.0]hept-2-ene-2-carboxylic acid

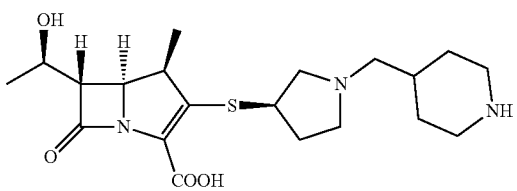 [SMILES: C[C@@H](O)[C@H]1C(=O)N2C(C(=O)O)=C(S[C@@H]3CCN(CC4CCNCC4)C3)[C@H](C)[C@H]12]

Step 1: Synthesis of 4-nitrobenzyl 4-formylpiperidine-1-carboxylate

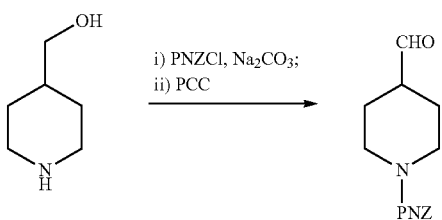

Part i). By using the same reaction procedures as described in Step 5 of Example 1, 4-piperidinemethanol (2.07 g, 18 mmol) was converted to the PNZ carbamate, 5.2 g. ESI-MS m/z 295 (MH)+

Part ii). The product from Part i) (1.77 g, 6 mmol) was oxidized with PCC (2.59 g, 12 mmol) in DCM (60 mL) at rt for 5 h, diluted with diethyl ether, filtered through a Florisil column, the filtrate was concentrated to yield the crude aldehyde product, which was used directly for the next step without further purification. ESI-MS m/z 293 (MH)+.

Step 2: Synthesis of (4R,5S,6S)-6-((R)-1-hydroxyethyl)-4-methyl-7-oxo-3-(((R)-1-(piperidin-4-ylmethyl)pyrrolidin-3-yl)thio)-1-azabicyclo[3.2.0]hept-2-ene-2-carboxylic acid

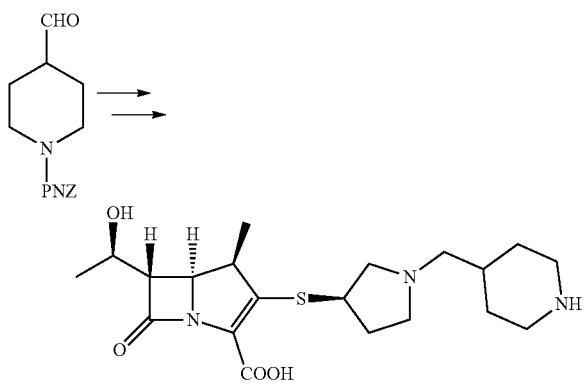

By using the same reaction procedures as described in Steps 6, 7 and 8 of Example 1, the above aldehyde was converted to the target compound. ESI-MS m/z 410 (MH)+.

Example 8: (4R,5S,6S)-6-((R)-1-hydroxyethyl)-4-methyl-7-oxo-3-(((R)-1-(((R)-pyrrolidin-2-yl)methyl)pyrrolidin-3-yl)thio)-1-azabicyclo[3.2.0]hept-2-ene-2-carboxylic acid

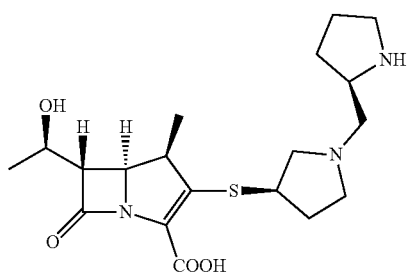 [SMILES: C[C@@H](O)[C@H]1C(=O)N2C(C(=O)O)=C(S[C@@H]3CCN(C[C@H]4CCCN4)C3)[C@H](C)[C@H]12]

By using the same reaction procedures as described in above Example 7, except in Step 1 using (R)-prolinol instead of 4-piperidinemethanol as starting material, the target compound was prepared. ESI-MS m/z 396 (MH)+.

Example 9: (4R,5S,6S)-6-((R)-1-hydroxyethyl)-4-methyl-7-oxo-3-(((R)-1-(pyridin-4-ylmethyl)pyrrolidin-3-yl)thio)-1-azabicyclo[3.2.0]hept-2-ene-2-carboxylic acid

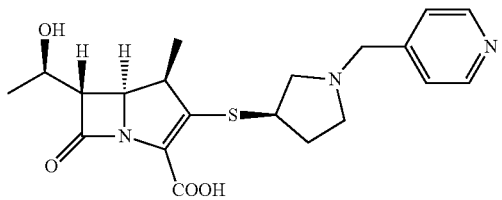 [SMILES: C[C@@H](O)[C@H]1C(=O)N2C(C(=O)O)=C(S[C@@H]3CCN(Cc4ccncc4)C3)[C@H](C)[C@H]12]

By using the same reaction procedures as described in Steps 6, 7 and 8 of Example 1, 4-pyridinecarboxaldehyde was converted to the target compound. ESI-MS m/z 404 (MH)+.

Example 10: (4R,5S,6S)-6-((R)-1-hydroxyethyl)-4-methyl-7-oxo-3-(((R)-1-(pyridin-3-ylmethyl)pyrrolidin-3-yl)thio)-1-azabicyclo[3.2.0]hept-2-ene-2-carboxylic acid

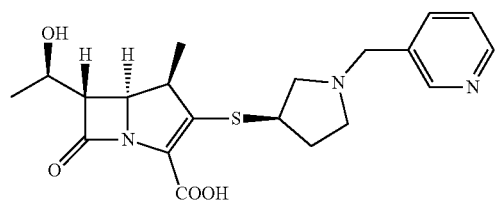 [SMILES: C[C@@H](O)[C@H]1C(=O)N2C(C(=O)O)=C(S[C@@H]3CCN(Cc4cccnc4)C3)[C@H](C)[C@H]12]

By using the same reaction procedures as described in Steps 6, 7 and 8 of Example 1,3-pyridinecarboxaldehyde was converted to the target compound. ESI-MS m/z 404 (MH)+.

Example 11: (4R,5S,6S)-6-((R)-1-hydroxyethyl)-4-methyl-7-oxo-3-(((R)-1-(2-(piperidin-4-yl)ethyl)pyrrolidin-3-yl)thio)-1-azabicyclo[3.2.0]hept-2-ene-2-carboxylic acid

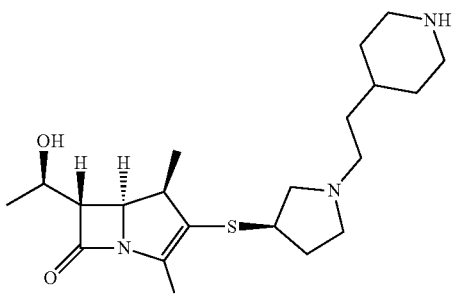

By using the same reaction procedures as described in above Example 7, except in Step 1 using 4-piperidineethanol instead of 4-piperidinemethanol as starting material, the target compound was prepared. ESI-MS m/z 424 (MH)+.

Example 12: (4R,5S,6S)-6-((R)-1-hydroxyethyl)-4-methyl-7-oxo-3-(((3R)-1-(piperidin-3-ylmethyl)pyrrolidin-3-yl)thio)-1-azabicyclo[3.2.0]hept-2-ene-2-carboxylic acid

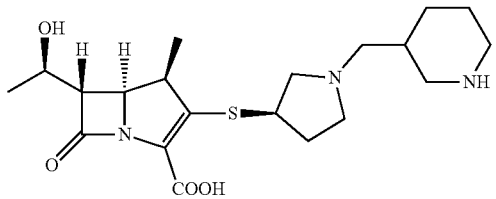 [SMILES: C[C@@H](O)[C@H]1C(=O)N2C(C(=O)O)=C(S[C@@H]3CCN(CC4CCCNC4)C3)[C@H](C)[C@H]12]

By using the same reaction procedures as described in above Example 7, except in Step 1 using 3-piperidinemethanol instead of 4-piperidinemethanol as starting material, the target compound was prepared. ESI-MS m/z 410 (MH)$^+$.

Example 13: (4R,5S,6S)-6-((R)-1-hydroxyethyl)-4-methyl-7-oxo-3-(((3R)-1-(piperidin-2-ylmethyl)pyrrolidin-3-yl)thio)-1-azabicyclo[3.2.0]hept-2-ene-2-carboxylic acid

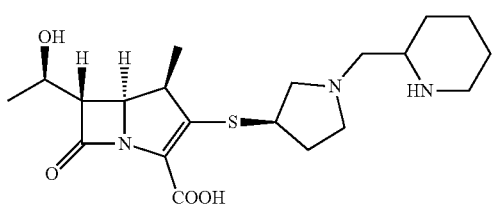 [SMILES: C[C@@H](O)[C@H]1C(=O)N2C(C(=O)O)=C(S[C@@H]3CCN(CC4CCCCN4)C3)[C@H](C)[C@H]12]

By using the same reaction procedures as described in above Example 7, except in Step 1 using 2-piperidinemethanol instead of 4-piperidinemethanol as starting material, the target compound was prepared. ESI-MS m/z 410 (MH)$^+$.

Example 14: (4R,5S,6S)-6-((R)-1-hydroxyethyl)-4-methyl-7-oxo-3-(((R)-1-(((S)-pyrrolidin-2-yl)methyl)pyrrolidin-3-yl)thio)-1-azabicyclo[3.2.0]hept-2-ene-2-carboxylic acid

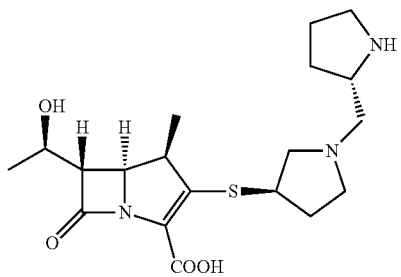 [SMILES: C[C@@H](O)[C@H]1C(=O)N2C(C(=O)O)=C(S[C@@H]3CCN(C[C@@H]4CCCN4)C3)[C@H](C)[C@H]12]

By using the same reaction procedures as described in above Example 7, except in Step 1 using (S)-prolinol instead of 4-piperidinemethanol as starting material, the target compound was prepared. ESI-MS m/z 396 (MH)$^+$.

Example 15: (4R,5S,6S)-6-((R)-1-hydroxyethyl)-4-methyl-3-(((R)-1-((4-methylpiperidin-4-yl)methyl)pyrrolidin-3-yl)thio)-7-oxo-1-azabicyclo[3.2.0]hept-2-ene-2-carboxylic acid

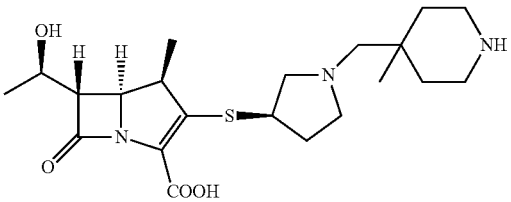 [SMILES: C[C@@H](O)[C@H]1C(=O)N2C(C(=O)O)=C(S[C@@H]3CCN(CC4(C)CCNCC4)C3)[C@H](C)[C@H]12]

Step 1: Synthesis of (4-methylpiperidin-4-yl)methanol

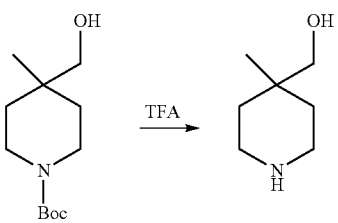

1-Boc-4-(hydroxymethyl)-4-methylpiperidine (2.29 g, 10 mmol) in DCM (25 mL) was treated with TFA (25 mL) in ice-bath for 1 h, then concentrated in vacuo to yield the crude product as TFA salt, which was used directly for the next step without further purification.

Step 2: Synthesis of (4R,5S,6S)-6-((R)-1-hydroxyethyl)-4-methyl-3-(((R)-1-((4-methylpiperidin-4-yl)methyl)pyrrolidin-3-yl)thio)-7-oxo-1-azabicyclo[3.2.0]hept-2-ene-2-carboxylic acid

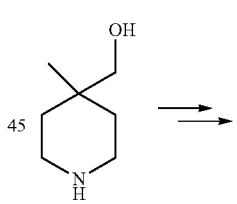

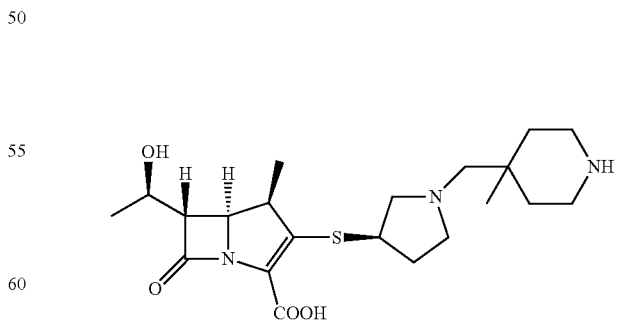

By using the same reaction procedures as described in Example 7, the above product (4-methylpiperidin-4-yl)methanol was converted to the target compound. ESI-MS m/z 424 (MH)$^+$.

Example 16: (4R,5S,6S)-3-(((R)-1-((4-fluoropiperidin-4-yl)methyl)pyrrolidin-3-yl)thio)-6-((R)-1-hydroxyethyl)-4-methyl-7-oxo-1-azabicyclo[3.2.0]hept-2-ene-2-carboxylic acid

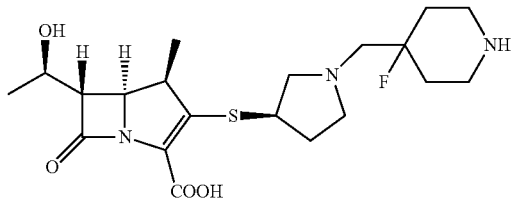 [SMILES: C[C@@H](O)[C@H]1C(=O)N2C(C(=O)O)=C(S[C@@H]3CCN(CC4(F)CCNCC4)C3)[C@H](C)[C@H]12]

Step 1: Synthesis of (4-fluoropiperidin-4-yl)methanol

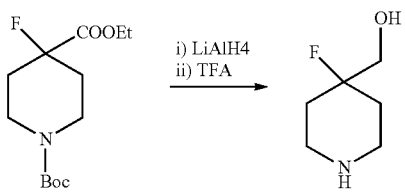 [SMILES: CCOC(=O)C1(F)CCN(C(=O)OC(C)(C)C)CC1 ; OCC1(F)CCNCC1]

To ethyl N-Boc-4-fluoropiperidine-4-carboxylate (2.75 g, 10 mmol) in THF (100 mL) at −30° C. under Argon was added LiAlH$_4$ (760 mg, 20 mmol). The reaction mixture was stirred between −30-0° C. for 2 h, quenched by careful addition of water, and 1 N HCl to pH 3-4, extracted with EtOAc. The organic extracts were combined, washed with brine, dried over Na$_2$SO$_4$, concentrated in vacuo, yielding the crude product, which was treated with TFA (35 mL) in DCM (35 mL) in a similar manner as described in Step 1 of Example 15 to afford the crude product as TFA salt, which was used directly for the next step without further purification.

Step 2: Synthesis of (4R,5S,6S)-3-(((R)-1-((4-fluoropiperidin-4-yl)methyl)pyrrolidin-3-yl)thio)-6-((R)-1-hydroxyethyl)-4-methyl-7-oxo-1-azabicyclo[3.2.0]hept-2-ene-2-carboxylic acid

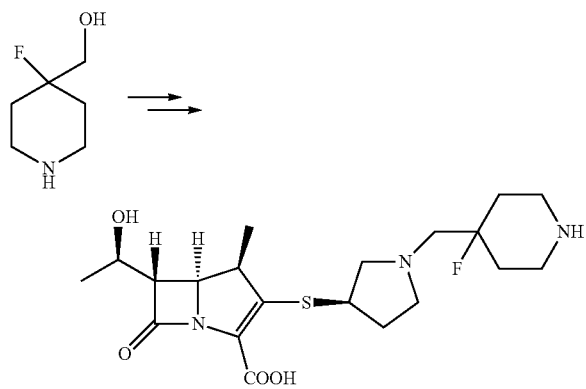

By using the same reaction procedures as described in Example 7, the above product (4-fluoropiperidin-4-yl)methanol was converted to the target compound. ESI-MS m/z 428 (MH)$^+$.

Example 17: (4R,5S,6S)-3-(((R)-1-(((1r,4R)-4-(aminomethyl)cyclohexyl)methyl)pyrrolidin-3-yl)thio)-6-((R)-1-hydroxyethyl)-4-methyl-7-oxo-1-azabicyclo[3.2.0]hept-2-ene-2-carboxylic acid

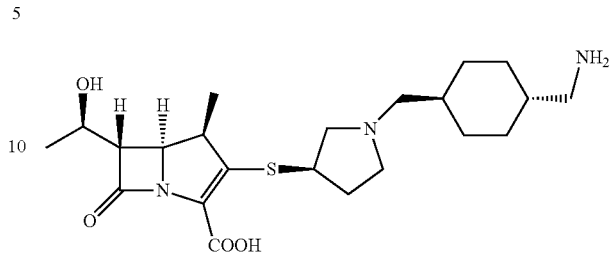

By using the same reaction procedures as described in above Example 7, except in Step 1 using trans-4-[aminoethyl(cyclohexyl)]methanol instead of 4-piperidinemethanol as starting material, the target compound was prepared. ESI-MS m/z 438 (MH)$^+$.

Example 18: (4R,5S,6S)-6-((R)-1-hydroxyethyl)-4-methyl-3-(((R)-1-(((1r,4R)-4-((methylamino)methyl)cyclohexyl)methyl)pyrrolidin-3-yl)thio)-7-oxo-1-azabicyclo[3.2.0]hept-2-ene-2-carboxylic acid

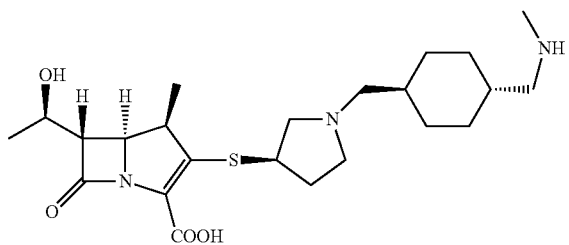 [SMILES: CNC[C@H]1CC[C@H](CN2CC[C@@H](SC3=C(C(=O)O)N4C(=O)[C@H]([C@@H](C)O)[C@H]4[C@H]3C)C2)CC1]

Step 1: Synthesis of ((1 r, 4r)-4-((methylamino)methyl)cyclohexyl)methanol

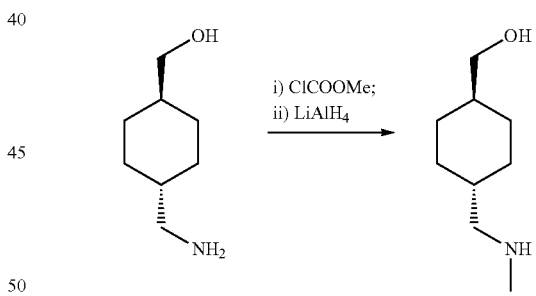

Part i). To trans-4-[aminomethyl(cyclohexyl)]methanol (715 mg, 5 mmol) in DCM (30 mL) at 0° C. was added triethylamine (1.05 mL, 7.5 mmol) followed by methyl chloroformate (0.45 mL, 5.8 mmol). The reaction mixture was stirred in ice-bath for 45 min, washed with saturated aqueous NaHCO$_3$, dried over Na$_2$SO$_4$, concentrated in vacuo to give the crude product.

Part ii). The product from Part i) was dissolved in THF (60 mL), added LiAlH$_4$ (684 mg, 18 mmol). The reaction mixture was stirred at 45° C. overnight, cooled in ice-bath, quenched with water (0.7 mL), 15% NaOH (0.7 mL), EtOAc (50 mL), and water (2 mL). The mixture was stirred at rt for 1 h, filtered through a pad of celite, the filtrate was concentrated, and dried in vacuo, yielding the crude product, which was used directly for the next step without further purification.

Step 2: Synthesis of (4R,5S,6S)-6-((R)-1-hydroxyethyl)-4-methyl-3-(((R)-1-(((1r,4R)-4-((methylamino)methyl)cyclohexyl)methyl)pyrrolidin-3-yl)thio)-7-oxo-1-azabicyclo[3.2.0]hept-2-ene-2-carboxylic acid

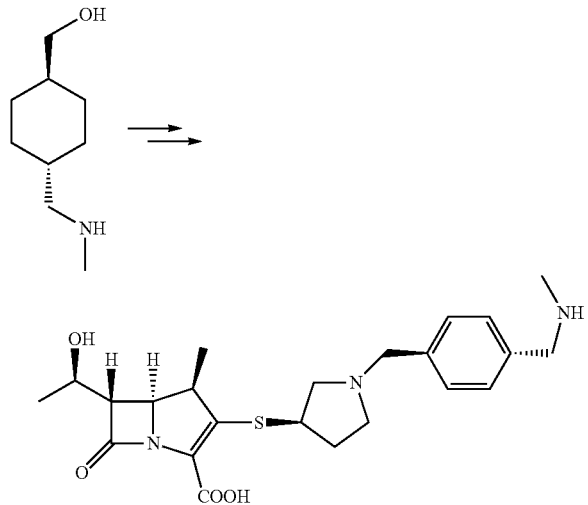

By using the same reaction procedures as described in Example 7, the above product ((1R,4R)-4-((methylamino)methyl)cyclohexyl)methanol was converted to the target compound. ESI-MS m/z 452 (MH)$^+$.

Example 19: (4R,5S,6S)-6-((R)-1-hydroxyethyl)-4-methyl-3-(((R)-1-(4-((methylamino)methyl)benzyl)pyrrolidin-3-yl)thio)-7-oxo-1-azabicyclo[3.2.0]hept-2-ene-2-carboxylic acid

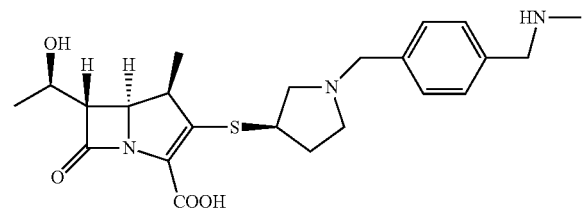 [SMILES: CNCc1ccc(CN2CC[C@@H](SC3=C(C(=O)O)N4C(=O)[C@H]([C@@H](C)O)[C@H]4[C@H]3C)C2)cc1]

By using the same reaction procedures as described in Example 18, except in Step 1 using 4-aminomethylbenzyl alcohol instead of trans-4-[aminomethyl(cyclohexyl)]methanol as starting material, the target compound was prepared. ESI-MS m/z 446 (MH)$^+$.

Example 20: (4R,5S,6S)-6-((R)-1-hydroxyethyl)-4-methyl-7-oxo-3-(((R)-1-(2-(piperazin-1-yl)ethyl)pyrrolidin-3-yl)thio)-1-azabicyclo[3.2.0]hept-2-ene-2-carboxylic acid

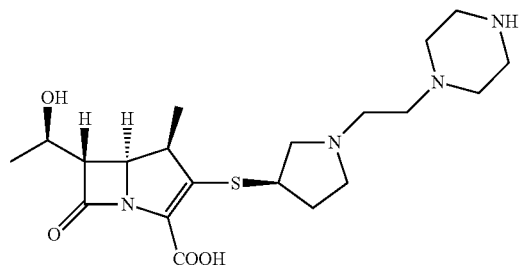 [SMILES: C[C@@H](O)[C@H]1C(=O)N2C(C(=O)O)=C(S[C@@H]3CCN(CCN4CCNCC4)C3)[C@H](C)[C@H]12]

Step 1: Synthesis of 4-nitrobenzyl 4-(2-oxoethyl)piperazine-1-carboxylate

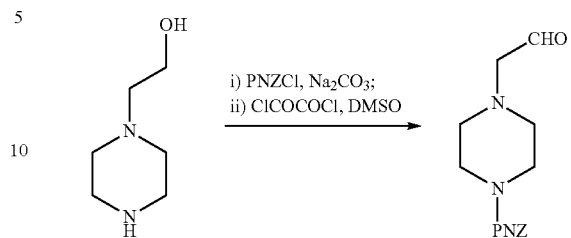

Part i). By using the same reaction procedures as described in Step 5 of Example 1, 1-piperazineethanol (1.3 g, 10 mmol) was converted to the PNZ carbamate, 3.06 g. ESI-MS m/z 310 (MH)$^+$.

Part ii). To oxalyl chloride (0.76 mL, 9 mmol) in DCM (20 mL) at −78° C. was added DMSO (1.28 mL, 18 mmol) under Argon. After 10 min, to the reaction mixture was added dropwise a solution of the product from Part i) (1.39 g, 4.5 mmol) in DCM (20 mL), and the reaction mixture was stirred for 1 h, then triethylamine (3.76 mL, 27 mmol) was added, the reaction was warmed to rt, quenched with water, extracted with DCM. The organic extracts were combined, washed with brine, dried over Na$_2$SO$_4$, concentrated in vacuo, yielding the crude product, which was used directly for the next step without further purification. ESI-MS m/z 308 (MH)$^+$ Step 2: Synthesis of (4R,5S,6S)-6-((R)-1-hydroxyethyl)-4-methyl-7-oxo-3-(((R)-1-(2-(piperazin-1-yl)ethyl)pyrrolidin-3-yl)thio)-1-azabicyclo[3.2.0]hept-2-ene-2-carboxylic acid

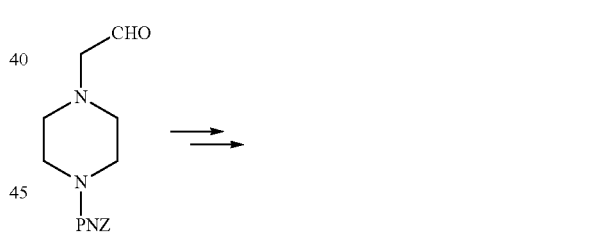

By following the same reaction procedures as described in Steps 6, 7 and 8 of Example 1, the above aldehyde was converted to the target compound. ESI-MS m/z 425 (MH)$^+$.

Example 21: Synthesis of (4R,5S,6S)-6-((R)-1-hydroxyethyl)-4-methyl-3-(((R)-1-(((1r,4R)-4-(methylamino)cyclohexyl)methyl)pyrrolidin-3-yl)thio)-7-oxo-1-azabicyclo[3.2.0]hept-2-ene-2-carboxylic acid

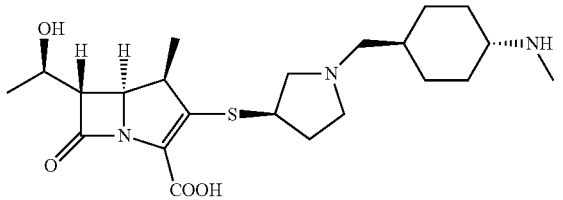 [SMILES: CN[C@H]1CC[C@H](CN2CC[C@@H](SC3=C(C(=O)O)N4C(=O)[C@H]([C@@H](C)O)[C@H]4[C@H]3C)C2)CC1]

By using the same reaction procedures as described in Example 18, except in Step 1 using methyl trans-4-aminocyclohexane-carboxylate hydrochloride instead of trans-4-[aminomethyl(cyclohexyl)]methanol as starting material, the target compound was prepared. ESI-MS m/z 438 (MH)+.

Example 22: (4R,5S,6S)-6-((R)-1-hydroxyethyl)-4-methyl-3-(((R)-1-(((1s,4S)-4-(methylamino)cyclohexyl)methyl)pyrrolidin-3-yl)thio)-7-oxo-1-azabicyclo[3.2.0]hept-2-ene-2-carboxylic acid

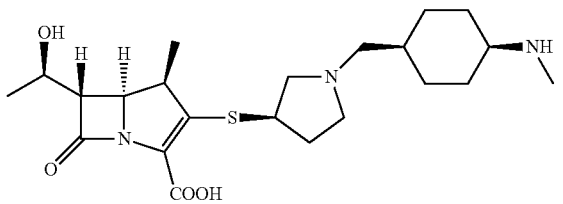 [SMILES: CN[C@H]1CC[C@@H](CN2CC[C@@H](SC3=C(C(=O)O)N4C(=O)[C@H]([C@@H](C)O)[C@H]4[C@H]3C)C2)CC1]

By following the same reaction procedures as described in Example 18, except in Step 1 using methyl cis-4-aminocyclohexane-carboxylate hydrochloride instead of trans-4-[aminomethyl(cyclohexyl)]methanol as starting material, the target compound was prepared. ESI-MS m/z 438 (MH)+.

Example 23: (4R,5S,6S)-3-(((R)-1-((1r,4R)-4-aminocyclohexyl)pyrrolidin-3-yl)thio)-6-((R)-1-hydroxyethyl)-4-methyl-7-oxo-1-azabicyclo[3.2.0]hept-2-ene-2-carboxylic acid

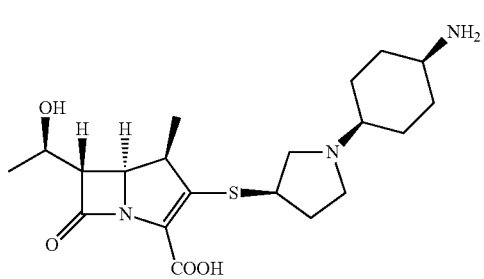 [SMILES: C[C@@H](O)[C@H]1C(=O)N2C(C(=O)O)=C(S[C@@H]3CCN([C@H]4CC[C@@H](N)CC4)C3)[C@H](C)[C@H]12]

Example 24: (4R,5S,6S)-3-(((R)-1-((1s,4S)-4-aminocyclohexyl)pyrrolidin-3-yl)thio)-6-((R)-1-hydroxyethyl)-4-methyl-7-oxo-1-azabicyclo[3.2.0]hept-2-ene-2-carboxylic acid

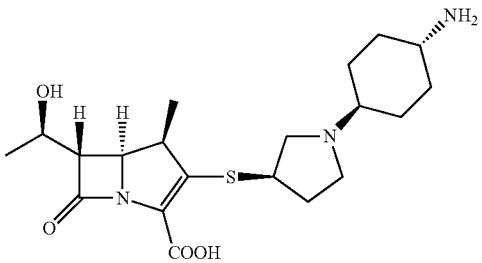 [SMILES: C[C@@H](O)[C@H]1C(=O)N2C(C(=O)O)=C(S[C@@H]3CCN([C@H]4CC[C@H](N)CC4)C3)[C@H](C)[C@H]12]

Step 1: Synthesis of 4-nitrobenzyl (4-oxocyclohexyl)carbamate

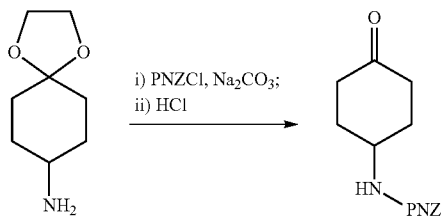

Part i). By using the same reaction procedures as described in Step 5 of Example 1, 1,4-dioxaspiro[4.5]decan-8-amine hydrochloride (965 mg, 5 mmol) was converted to the PNZ carbamate, 1.66 g. ESI-MS m/z 337 (MH)+.

Part ii). The product from Part i) (1.66 g, 4.94 mmol) was dissolved in THF (60 mL), treated with 2 N HCl (30 mL) at rt for overnight, extracted with DCM. The combined organic extracts were dried over Na₂SO₄, concentrated in vacuo to yield the crude ketone product, which was used directly for the next step without further purification. ESI-MS m/z 293 (MH)+.

Step 2: Synthesis of (4R,5S,6S)-3-(((R)-1-((1s,4S)-4-aminocyclohexyl)pyrrolidin-3-yl)thio)-6-((R)-1-hydroxyethyl)-4-methyl-7-oxo-1-azabicyclo[3.2.0]hept-2-ene-2-carboxylic acid, and (4R,5S,6S)-3-(((R)-1-((1r,4R)-4-aminocyclohexyl)pyrrolidin-3-yl)thio)-6-((R)-1-hydroxyethyl)-4-methyl-7-oxo-1-azabicyclo[3.2.0]hept-2-ene-2-carboxylic acid

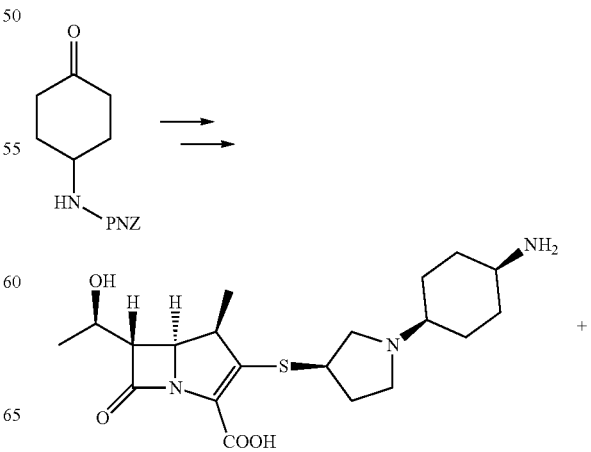

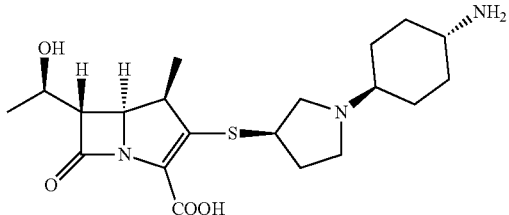

By using the same reaction procedures as described in Steps 6, 7 and 8 of Example 1, the above ketone was converted to the target compounds, Example 23 and Example 24. ESI-MS m/z 410 (MH)⁺.

Example 25: (4R,5S,6S)-6-((R)-1-hydroxyethyl)-4-methyl-7-oxo-3-(((3R)-1-(1-(piperidin-4-yl)ethyl)pyrrolidin-3-yl)thio)-1-azabicyclo[3.2.0]hept-2-ene-2-carboxylic acid

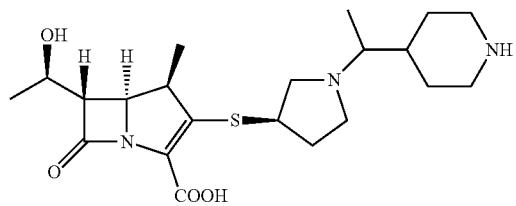 [SMILES: CC(C1CCNCC1)N1CC[C@@H](SC2=C(C(=O)O)N3C(=O)[C@H]([C@@H](C)O)[C@H]3[C@H]2C)C1]

By following the same reaction procedures as described in Example 1, except in Step 5 using 1-(piperidin-4-yl)ethanone hydrochloride instead of 4-piperidinone hydrochloride hydrate as starting material, the target compound was prepared. ESI-MS m/z 424 (MH)⁺.

Example 26: (4R,5S,6S)-3-(((R)-1-((1-(2-aminoethyl)piperidin-4-yl)methyl)pyrrolidin-3-yl)thio)-6-((R)-1-hydroxyethyl)-4-methyl-7-oxo-1-azabicyclo[3.2.0]hept-2-ene-2-carboxylic acid

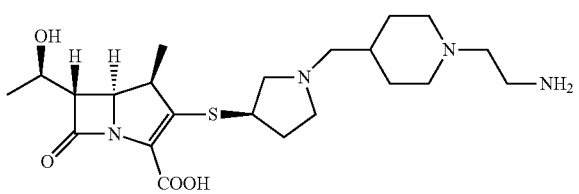 [SMILES: C[C@@H](O)[C@H]1C(=O)N2C(C(=O)O)=C(S[C@@H]3CCN(CC4CCN(CCN)CC4)C3)[C@H](C)[C@H]12]

By following the same reaction procedures as described in Example 20, except in Step 1 using (1-(2-aminoethyl)piperidin-4-yl)methanol instead of 1-piperazineethanol as starting material, the target compound was prepared. ESI-MS m/z 453 (MH)⁺.

Example 27: (4R,5S,6S)-3-(((R)-1-(1-(2-aminoethyl)piperidin-4-yl)pyrrolidin-3-yl)thio)-6-((R)-1-hydroxyethyl)-4-methyl-7-oxo-1-azabicyclo[3.2.0]hept-2-ene-2-carboxylic acid

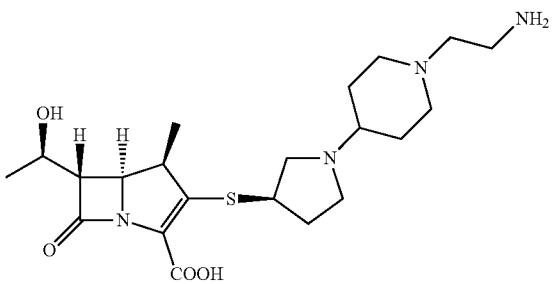 [SMILES: C[C@@H](O)[C@H]1C(=O)N2C(C(=O)O)=C(S[C@@H]3CCN(C4CCN(CCN)CC4)C3)[C@H](C)[C@H]12]

By following the same reaction procedures as described in Example 20, except in Step 1 using 1-(2-aminoethyl)piperidin-4-ol instead of 1-piperazineethanol as starting material, the target compound was prepared. ESI-MS m/z 439 (MH)⁺.

Example 28: (4R,5S,6S)-6-((R)-1-hydroxyethyl)-4-methyl-3-(((3R)-1-((2-methylpiperidin-4-yl)methyl)pyrrolidin-3-yl)thio)-7-oxo-1-azabicyclo[3.2.0]hept-2-ene-2-carboxylic acid

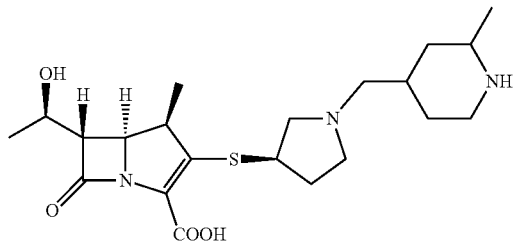 [SMILES: CC1CC(CN2CC[C@@H](SC3=C(C(=O)O)N4C(=O)[C@H]([C@@H](C)O)[C@H]4[C@H]3C)C2)CCN1]

Step 1: Synthesis of methy 2-methylpiperidine-4-carboxylate

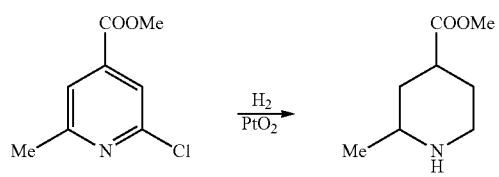

Methyl 2-chloro-6-methylisonicotinate (3.6 g, 19.5 mmol) in TFA (60 mL) was hydrogenated in the presence of platinum oxide hydrate (660 mg) at 60 psi at rt for 3 days. The reaction mixture was filtered, and the filtrate was concentrated to give the product as TFA salt, which was used directly for the next step without further purification.

Step 2: Synthesis of 1-(tert-butyl) 4-methyl 2-methylpiperidine-1,4-dicarboxylate

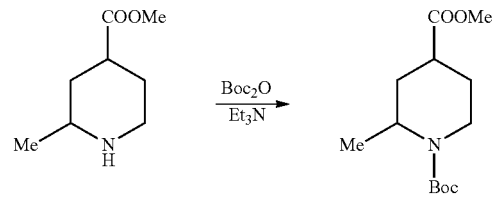 [SMILES: "Boc2O" ; "Et3N" ; COC(=O)C1CCNC(C)C1 ; COC(=O)C1CCN(C(=O)OC(C)(C)C)C(C)C1]

The above product (19.5 mmol) was dissolved in DCM (200 mL), triethylamine was added, followed by di-tert-dicarbonate (6.54 g, 30 mmol). The reaction mixture was stirred at rt overnight, washed with saturated aqueous NaHCO₃, dried over Na₂SO₄, concentrated in vacuo. The residue was purified by flash chromatography on silica gel (hexane-EtOAc, 50:1-2:1) to afford the pure product, 4.2 g.

Step 3: Synthesis of (4R,5S,6S)-6-((R)-1-hydroxyethyl)-4-methyl-3-(((3R)-1-((2-methylpiperidin-4-yl)methyl)pyrrolidin-3-yl)thio)-7-oxo-1-azabicyclo[3.2.0]hept-2-ene-2-carboxylic acid

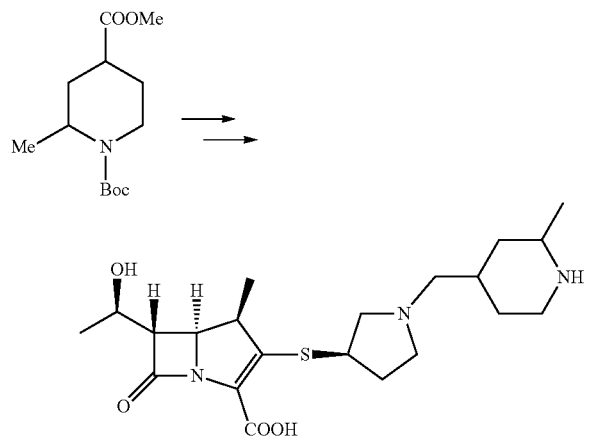

By following the same reaction procedures as described in Example 16, the above product was converted to the target compound. ESI-MS m/z 424 (MH)⁺.

Example 29: (4R,5S,6S)-6-((R)-1-hydroxyethyl)-4-methyl-3-(((R)-1-((6-((methylamino)methyl)pyridin-3-yl)methyl)pyrrolidin-3-yl)thio)-7-oxo-1-azabicyclo[3.2.0]hept-2-ene-2-carboxylic acid

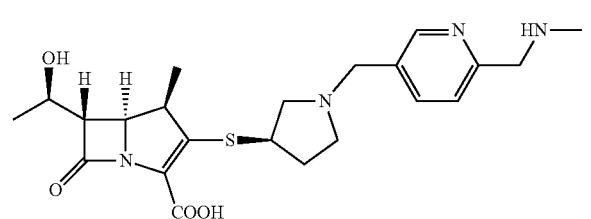 [SMILES: CNCc1ccc(CN2CC[C@@H](SC3=C(C(=O)O)N4C(=O)[C@H]([C@@H](C)O)[C@H]4[C@H]3C)C2)cn1]

Step 1: Synthesis of methyl 6-(bromomethyl)nicotinate

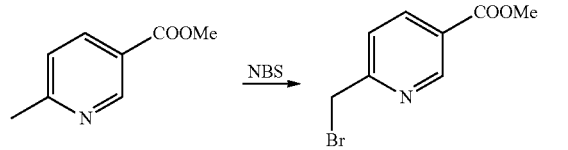

Methyl 6-methylpyridine-3-carboxylate (3.02 g, 20 mmol) was reacted with N-bromo succinimide in the presence of AIBN (494 mg, 3 mmol) under Argon at reflux for 3 h. The reaction mixture was filtered, and the filtrate was concentrated in vacuo. The residue was purified by flash chromatography on silica gel (hexane-EtOAc, 40:1-3:2) to yield the bromide product, 2.29 g. ESI-MS m/z 230/232 (MH/MH+2)⁺.

Step 2: Synthesis of (6-(bromoethyl)pyridin-3-yl)methanol

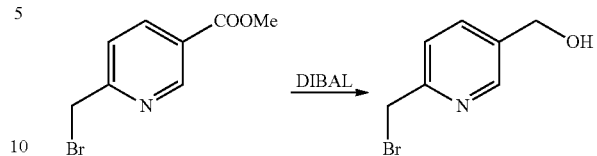

To a solution of DIBAL (16 mL, 1.0 M in toluene, 16 mmol) in toluene (8 mL) was added dropwise a solution of the above product (1.38 g, 6 mmol) in toluene (15 mL) under Argon at 0° C. The reaction mixture was stirred at 0° C. for 3 h, quenched with 1 N HCl to pH 6-7, extracted with DCM. The organic extracts were combined, dried over Na₂SO₄, concentrated in vacuo. The residue was purified twice by flash chromatography on silica gel (hexane-EtOAc, 2:1-0:100) to afford the alcohol product, which was immediately used for the next step. ESI-MS m/z 202/204 (MH/MH+2)⁺.

Step 3: Synthesis of (6-((methylamino)methyl)pyridin-3-yl)methanol

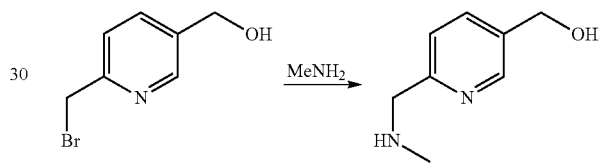

The above product was immediately treated with methylamine (30 mL, 2.0 M in THF, 60 mmol) dissolved in DCM (200 mL) in the presence of NaHCO₃ (504 mg, 6 mmol) at rt overnight, then concentrated in vacuo to give the crude amine product, which was used directly for the next step without further purification. ESI-MS m/z 153 (MH)⁺.

Step 4: Synthesis of (4R,5S,6S)-6-((R)-1-hydroxyethyl)-4-methyl-3-(((R)-1-((6-((methylamino)methyl)pyridin-3-yl)methyl)pyrrolidin-3-yl)thio)-7-oxo-1-azabicyclo[3.2.0]hept-2-ene-2-carboxylic acid

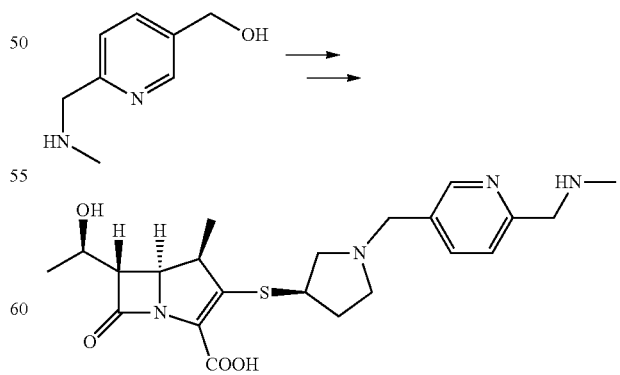

By following the same reaction procedures as described in Example 20, the above product was converted to the target compound. ESI-MS m/z 447 (MH)⁺.

Example 30: (4R,5S,6S)-3-(((3R)-1-((2-(aminomethyl)piperidin-4-yl)methyl)pyrrolidin-3-yl)thio)-6-((R)-1-hydroxyethyl)-4-methyl-7-oxo-1-azabicyclo[3.2.0]hept-2-ene-2-carboxylic acid

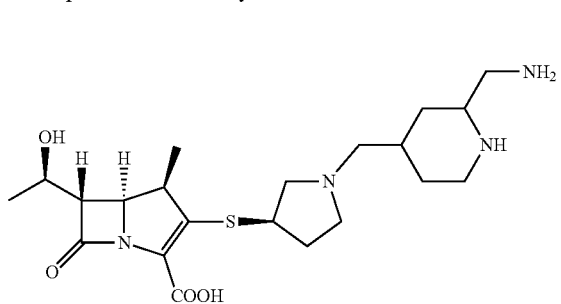

By following the same reaction procedures as described in Example 28, except in Step 1 using methyl 2-cyanoisonicotinate instead of methyl 2-chloro-6-methylisonicotinate as starting material, the target compound was prepared. ESI-MS m/z 439 (MH)⁺.

Example 31: (4R,5S,6S)-3-(((R)-1-(3,4-bis(aminomethyl)benzyl)pyrrolidin-3-yl)thio)-6-((R)-1-hydroxyethyl)-4-methyl-7-oxo-1-azabicyclo[3.2.0]hept-2-ene-2-carboxylic acid

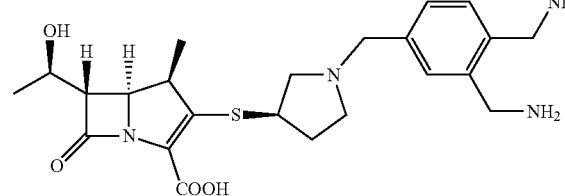

Step 1: Synthesis of (3,4-bis(azidomethyl)phenyl)methanol

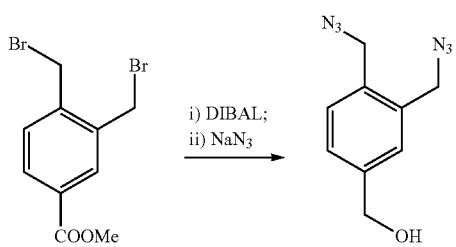 [SMILES: COC(=O)c1ccc(CBr)c(CBr)c1 ; [N-]=[N+]=NCc1ccc(CO)cc1CN=[N+]=[N-]]

Part i). By using the same reaction procedures as described in step 2 of Example 29, methyl 3,4-bis(bromomethyl)benzoate (1.94 g, 6 mmol) was converted to the crude alcohol, which was directly used for the next step without further purification. ESI-MS m/z 292/294 (MH/MH+2)⁺.

Part ii). The product from Part i) (6 mmol) was dissolved in DMF (60 mL), and treated with sodium azide (1.18 g, 18 mmol) at rt overnight, quenched with water, extracted with EtOAc-Et2O (1:1). The organic extracts were combined, washed with water, brine, dried over Na₂SO₄, concentrated in vacuo. The residue was purified by flash chromatography on silica gel (hexane-EtOAc, 4:1-1:1) to afford the azide product, 1.3 g. ESI-MS m/z 219 (MH)⁺.

Step 2: Synthesis of (3,4-bis(aminomethyl)phenyl)methanol

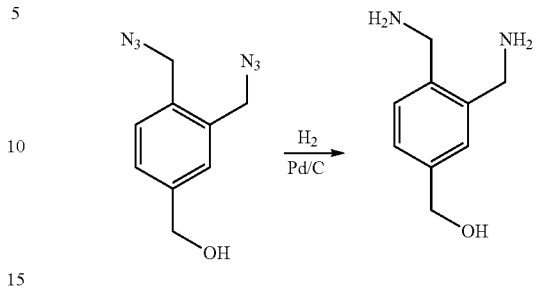

The above azide (1.3 g, 5.96 mmol) was dissolved in methanol (100 mL), and hydrogenated in the presence of 10% Pd/C (400 mg) at rt overnight, filtered through a pad of celite, and the filtrate was concentrated in vacuo to give the product, 990 mg. ESI-MS m/z 167 (MH)⁺.

Step 3: Synthesis of (4R,5S,6S)-3-(((R)-1-(3,4-bis(aminomethyl)benzyl)pyrrolidin-3-yl)thio)-6-((R)-1-hydroxyethyl)-4-methyl-7-oxo-1-azabicyclo[3.2.0]hept-2-ene-2-carboxylic acid

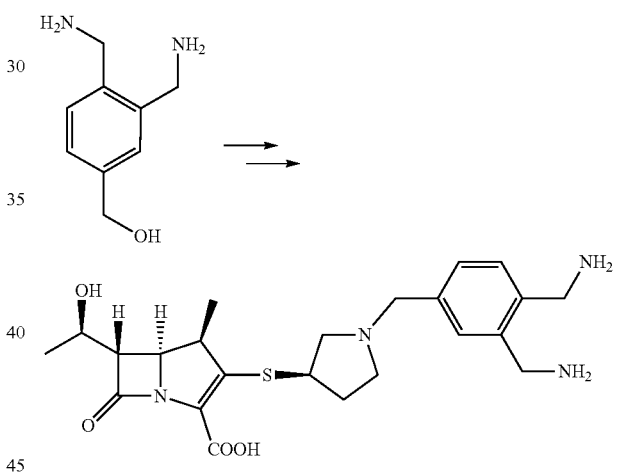

By following the same reaction procedures as described in Example 7, the above product (3,4-bis(aminomethyl)phenyl)methanol was converted to the target compound. ESI-MS m/z 461 (MH)⁺.

Example 32: (4R,5S,6S)-6-((R)-1-hydroxyethyl)-4-methyl-3-(((3R)-1-((1-(methylsulfonyl)piperazin-2-yl)methyl)pyrrolidin-3-yl)thio)-7-oxo-1-azabicyclo[3.2.0]hept-2-ene-2-carboxylic acid

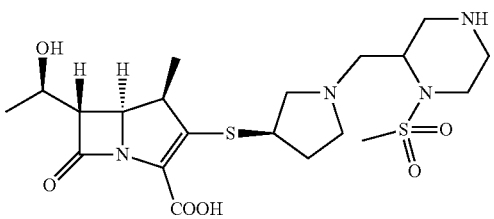 [SMILES: C[C@@H](O)[C@H]1C(=O)N2C(C(=O)O)=C(S[C@@H]3CCN(CC4CNCCN4S(C)(=O)=O)C3)[C@H](C)[C@H]12]

Step 1: Synthesis of tert-butyl 3-(hydroxymethyl)-4-(methylsulfonyl)piperazine-1-carboxylate

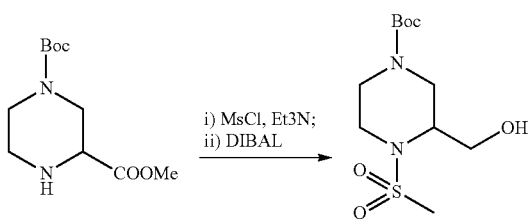 [SMILES: COC(=O)C1CN(C(=O)OC(C)(C)C)CCN1 ; CC(C)(C)OC(=O)N1CCN(S(C)(=O)=O)C(CO)C1]

Part i). To N-4-Boc-piperazine-2-carboxylic acid methyl ester hydrochloride (4.2 g, 15 mmol) in DCM (200 mL) was added triethylamine (5.29 mL, 38 mmol), followed by methanesulfonyl chloride (1.38 mL, 18 mmol). The reaction mixture was stirred at rt for 18 h, washed with saturated aqueous NaHCO₃, dried over Na₂SO₄, concentrated in vacuo to give the product.

Part ii). To the product from Part i) (15 mmol) in DCM (100 mL) at 0° C. under Argon was added dropwise DIBAL (45 mL, 1.0 M in DCM, 45 mmol). After 3 h, the reaction mixture was quenched with 2 N NaOH (50 mL), stirred for 30 min. The organic layer was separated, dried over Na₂SO₄, concentrated in vacuo. The residue was purified by flash chromatography on silica gel (hexane-EtOAc, 4:1-0:100) to afford the product, 2.53 g.

Step 2: Synthesis of 4-nitrobenzyl 3-(hydroxymethyl)-4-(methylsulfonyl)piperazine-1-carboxylate

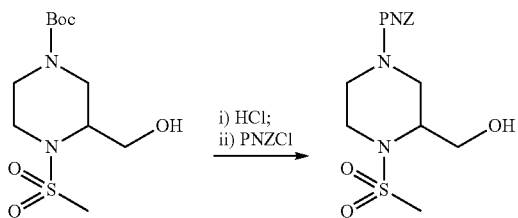

Part i). To a solution of the product from Step 1 (2.5 g, 8.5 mmol) in DCM (25 mL) and methanol (50 mL) was added 4.0 M HCl in dioxane (50 mL). The reaction mixture was stirred at rt for 2 h, then concentrated to give the crude product.

Part ii). By using the same reaction procedures as described in Step 5 of Example 1, this crude product was converted to the PNZ carbamate, 2.9 g. ESI-MS m/z 374 (MH)⁺.

Step 3: Synthesis of 4-nitrobenzyl 3-formyl-4-(methylsulfonyl)piperazine-1-carboxylate

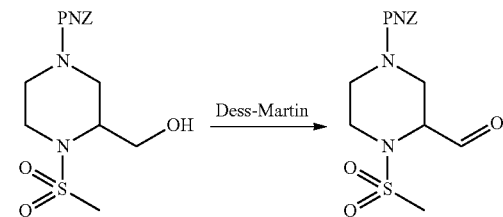

To a solution of the product from Step 2 (1.38 g, 3.7 mmol) in DCM (90 mL) was added NaHCO₃ (960 mg, 11.4 mmol) followed by Dess-Martin periodinane (1.8 g, 4.26 mmol). The reaction mixture was stirred at rt for 1 h, quenched with saturated aqueous NaHCO₃ and saturated aqueous Na₂S₂O₃, stirred for 30 min. The organic layer was separated, and the aqueous was extracted with DCM. The organic extracts were combined, dried over Na₂SO₄, concentrated in vacuo to yield the aldehyde, which was used directly for the next step without further purification. ESI-MS m/z 372 (MH)⁺;

Step 4: Synthesis of (4R,5S,6S)-6-((R)-1-hydroxyethyl)-4-methyl-3-(((3R)-1-((1-(methylsulfonyl)piperazin-2-yl)methyl)pyrrolidin-3-yl)thio)-7-oxo-1-azabicyclo[3.2.0]hept-2-ene-2-carboxylic acid

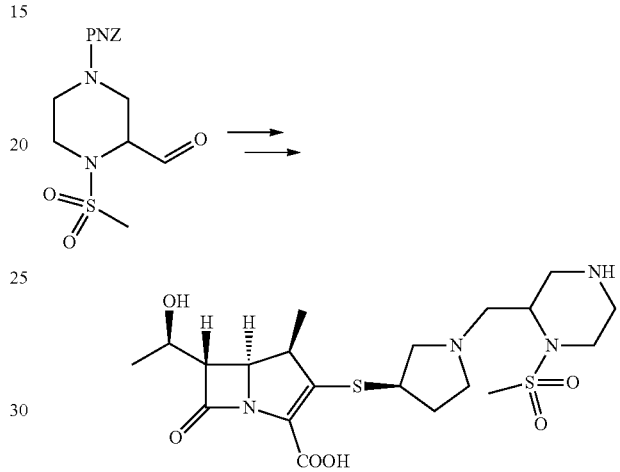

By using the same reaction procedures as described in Steps 6, 7 and 8 of Example 1, the above aldehyde was converted to the target compound. ESI-MS m/z 489 (MH)⁺.

Example 33: (4R,5S,6S)-6-((R)-1-hydroxyethyl)-4-methyl-3-(((3R)-1-methyl-1-(piperidin-4-ylmethyl)pyrrolidin-1-ium-3-yl)thio)-7-oxo-1-azabicyclo[3.2.0]hept-2-ene-2-carboxylate

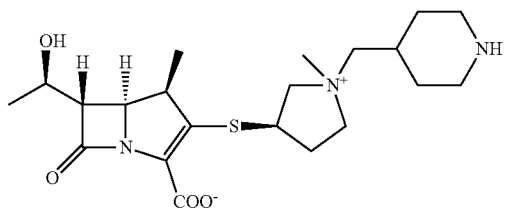

Step 1: Synthesis of (3R)-3-(((4R,5S,6S)-6-((R)-1-hydroxyethyl)-4-methyl-2-(((4-nitrobenzyl)oxy)carbonyl)-7-oxo-1-azabicyclo[3.2.0]hept-2-en-3-yl)thio)-1-methyl-1-((1-(((4-nitrobenzyl)oxy)carbonyl)piperidin-4-yl)methyl)pyrrolidin-1-ium iodide

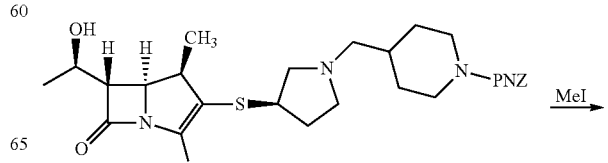

-continued

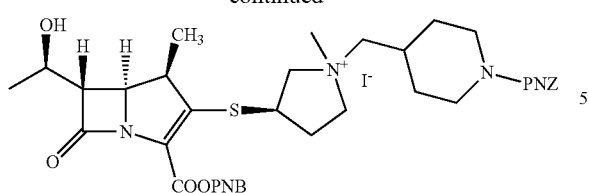

4-Nitrobenzyl (4R,5S,6S)-6-((R)-1-hydroxyethyl)-4-methyl-3-(((R)-1-((1-(((4-nitrobenzyl)oxy)carbonyl)piperidin-4-yl)methyl)pyrrolidin-3-yl)thio)-7-oxo-1-azabicyclo[3.2.0]hept-2-ene-2-carboxylate (362 mg, 0.5 mmol), which was prepared as an intermediate for the synthesis of Example 7, was dissolved in acetone (5 mL) was allowed to react with excess methyl iodide (0.5 mL, 8 mmol) at rt for 19 h, then concentrated in vacuo to afford the quaternary ammonium salt, which was used directly for the next step without further purification.

Step 2: Synthesis of (4R,5S,6S)-6-((R)-1-hydroxyethyl)-4-methyl-3-(((3R)-1-methyl-1-(piperidin-4-ylmethyl)pyrrolidin-1-ium-3-yl)thio)-7-oxo-1-azabicyclo[3.2.0]hept-2-ene-2-carboxylate

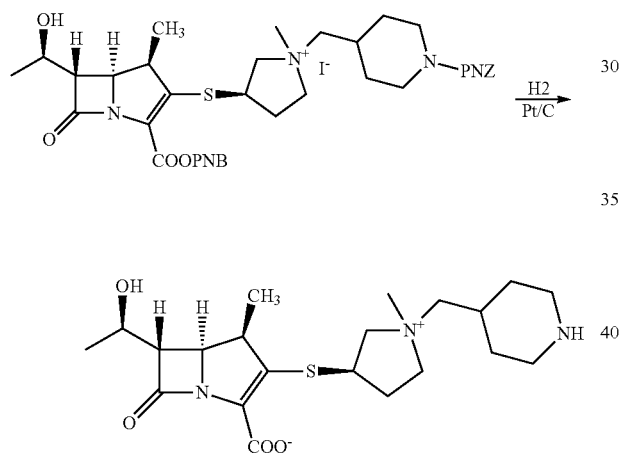

By using the same reaction procedures as described in Step 8 of Example 1, the above crude product was hydrogenated in the presence of 5% Pt/C to yield the target compound. ESI-MS m/z 424 (MH)$^+$.

Example 34: (4R,5S,6S)-3-(((3R)-1-(4-(1,2-diaminoethyl)benzyl)pyrrolidin-3-yl)thio)-6-((R)-1-hydroxyethyl)-4-methyl-7-oxo-1-azabicyclo[3.2.0]hept-2-ene-2-carboxylic acid

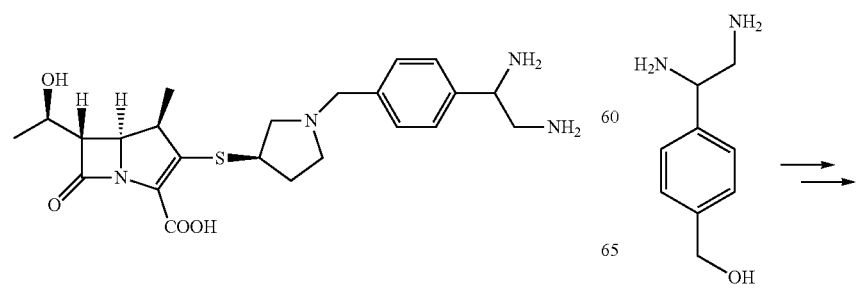

Step 1: Synthesis of methyl 4-(amino(cyano)methyl)benzoate

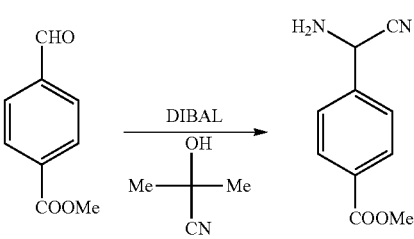 [SMILES: COC(=O)c1ccc(C=O)cc1 ; CC(C)(O)C#N ; COC(=O)c1ccc(C(N)C#N)cc1]

To a solution of methyl 4-formylbenzoate (3.28 g, 20 mmol) in THF (80 mL) was added LiHMDS (24 mL, 1.0 M in THF, 24 mmol) at −40° C. under Argon. The reaction mixture was stirred between −40° C.—rt for 4 h, then added acetone cyanohydrins (3.66 mL, 40 mmol). The reaction mixture was stirred at rt overnight, quenched with saturated aqueous NaHCO$_3$, extracted with EtOAc. The organic extracts were combined, dried over Na$_2$SO$_4$, concentrated in vacuo. The residue was purified by flash chromatography on silica gel (hexane-EtOAc, 2:1-1:4) to afford the product, 2.5 g. ESI-MS m/z 191 (MH)$^+$.

Step 2: Synthesis of (4-(1,2-diaminoethyl)phenyl)methanol

To a solution of the above cyanohydrin product (1.9 g, 10 mmol) in DCM (12 mL) at −10° C. under Argon was added dropwise DIBAL (70 mL, 1.0 M in DCM, 70 mmol). The reaction mixture was stirred between −10-0° C. for 3 h, quenched with 2 N NaOH (70 mL), more DCM (60 mL) was added. The resulting mixture was stirred at rt for 1 h, filtered, the filtrate was evaporated to remove DCM, yielding the crude product as an aqueous solution, which was used directly for the next step without further purification. ESI-MS m/z 167 (MH)$^+$.

Step 3: Synthesis of (4R,5S,6S)-3-(((3R)-1-(4-(1,2-diaminoethyl)benzyl)pyrrolidin-3-yl)thio)-6-((R)-1-hydroxyethyl)-4-methyl-7-oxo-1-azabicyclo[3.2.0]hept-2-ene-2-carboxylic acid

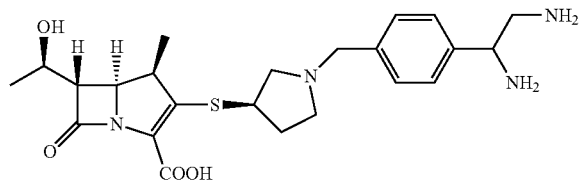

By following the same reaction procedures as described in Example 7, the above product (4-(1,2-diaminoethyl)phenyl)methanol was converted to the target compound. ESI-MS m/z 461 (MH)$^+$.

Example 35: (4R,5S,6S)-3-(((R)-1-((1-carbamimidoylpiperidin-4-yl)methyl)pyrrolidin-3-yl)thio)-6-((R)-1-hydroxyethyl)-4-methyl-7-oxo-1-azabicyclo[3.2.0]hept-2-ene-2-carboxylic acid

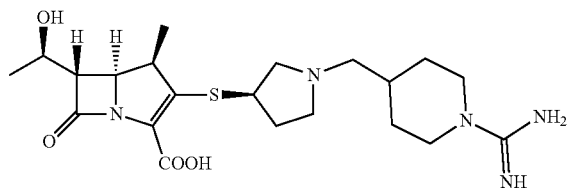 [SMILES: C[C@@H](O)[C@H]1C(=O)N2C(C(=O)O)=C(S[C@@H]3CCN(CC4CCN(C(=N)N)CC4)C3)[C@H](C)[C@H]12]

Step 1: Synthesis of tert-butyl (((tert-butoxycarbonyl)imino)(4-formylpiperidin-1-yl)methyl)carbamate

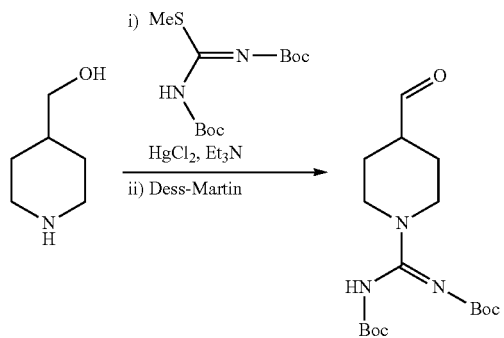 [SMILES: OCC1CCNCC1 ; CSC(=NC(=O)OC(C)(C)C)NC(=O)OC(C)(C)C ; CC(C)(C)OC(=O)N=C(NC(=O)OC(C)(C)C)N1CCC(C=O)CC1]

Part i). To a solution of 4-piperidinemethanol (2.07 g, 18 mmol) in DCM (150 mL) was added 1,3-bis(tert-butoxycarbonyl)-2-methyl-2-thiopseudourea (5.81 g, 20 mmol), thiethylamine (7.5 mL, 54 mmol), and HgCl$_2$ (5.43 g, 20 mmol). The reaction mixture was stirred at rt overnight, filtered, the filtrate was washed with saturated aqueous NH$_4$Cl, water and brine, dried over Na$_2$SO$_4$, concentrated in vacuo. The residue was purified by flash chromatography on silica gel (hexane-EtOAc, 10:1-2:1) to afford the product, 6.4 g.

Part ii). By using the same reaction procedures as described in Step 3 of Example 32, this alcohol was converted to the corresponding crude aldehyde, which was used directly for the next step without further purification.

Step 2: Synthesis of 4-nitrobenzyl (4R,5S,6S)-3-(((R)-1-((1-(N,N'-bis(tert-butoxycarbonyl)carbamimidoyl)piperidin-4-yl)methyl)pyrrolidin-3-yl)thio)-6-((R)-1-hydroxyethyl)-4-methyl-7-oxo-1-azabicyclo[3.2.0]hept-2-ene-2-carboxylate

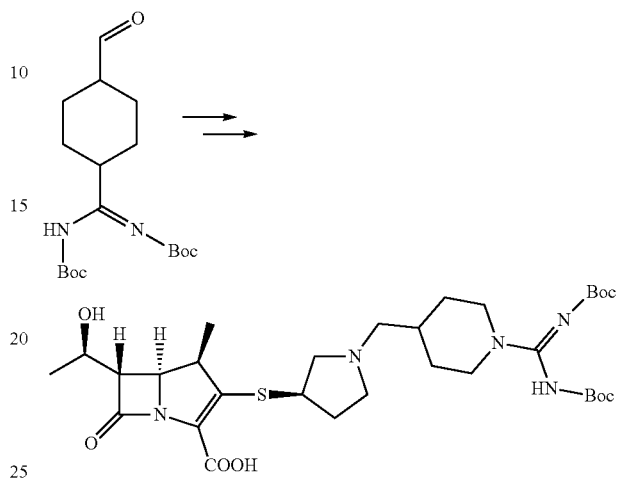

By following the same reaction procedures as described in Steps 6 and 7 of Example 1, the above aldehyde was converted to the target compound. ESI-MS m/z 787 (MH)$^+$.

Step 3: Synthesis of 4-nitrobenzyl (4R,5S,6S)-3-(((R)-1-((1-carbamimidoylpiperidin-4-yl)methyl)pyrrolidin-3-yl)thio)-6-((R)-1-hydroxyethyl)-4-methyl-7-oxo-1-azabicyclo[3.2.0]hept-2-ene-2-carboxylate

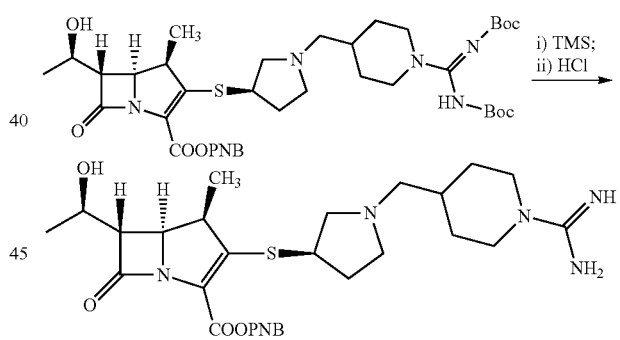

To a solution of the above product (472 mg, 0.6 mmol) in DCM (12 mL) was added triethylamine (1.0 mL, 7.2 mmol), followed by trimethylsilyl trifluoromethanesulfonate (0.66 mL, 3.6 mmol) at 0° C. under Argon. After 5 min, the reaction mixture was allowed to warm to rt, and stirred for 39 h, quenched with methanol (2 mL) and phosphate buffer solution (pH 7), extracted with DCM. The organic extracts were combined, washed with brine, dried over Na$_2$SO$_4$, concentrated in vacuo. The residue was then dissolved in THE (20 mL). To this solution at 0° C. was added water (5 mL), followed by a few drops of 1 N HCl to adjust the pH to 2. After 10 min, it was quenched with saturated aqueous NaHCO$_3$, extracted with EtOAc, and DCM. The organic extracts were combined, dried over Na$_2$SO$_4$, concentrated in vacuo, yielding the crude product, which was used directly for the next step without further purification. ESI-MS m/z 587 (MH)$^+$.

Step 4: Synthesis of (4R,5S,6S)-3-(((R)-1-((1-carbamimidoylpiperidin-4-yl)methyl)pyrrolidin-3-yl)thio)-6-((R)-1-hydroxyethyl)-4-methyl-7-oxo-1-azabicyclo[3.2.0]hept-2-ene-2-carboxylic acid

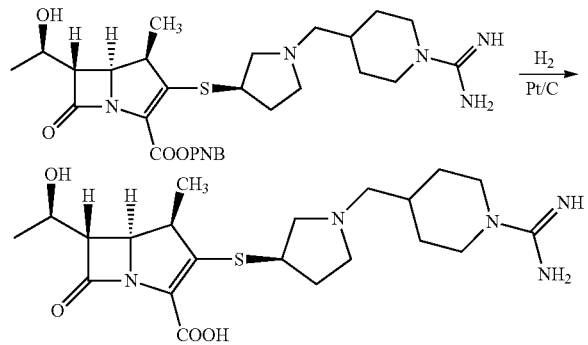

By following the same reaction procedures as described in Step 8 of Example 1, the above crude product was hydrogenated in the presence of 5% Pt/C to yield the target compound, 45 mg. ESI-MS m/z 452 (MH)$^+$.

Example 36: (4R,5S,6S)-3-(((R)-1-(3-aminopropyl)pyrrolidin-3-yl)thio)-6-((R)-1-hydroxyethyl)-4-methyl-7-oxo-1-azabicyclo[3.2.0]hept-2-ene-2-carboxylic acid

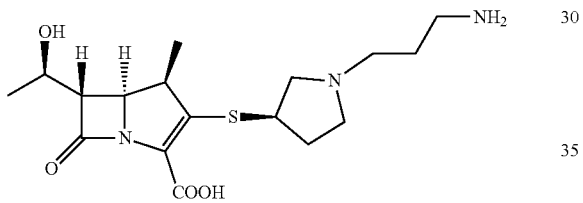

By using the same reaction procedures as described in Step 5 of Example 1, 3-amino-1-propanol was converted to the corresponding PNZ carbamate, which was further converted to target compound by following the same reaction procedures as described in Steps 3 and 4 of Example 32. ESI-MS m/z 370 (MH)$^+$.

Example 37: (4R,5S,6S)-6-((R)-1-hydroxyethyl)-4-methyl-3-(((R)-1-(4-(methylamino)butyl)pyrrolidin-3-yl)thio)-7-oxo-1-azabicyclo[3.2.0]hept-2-ene-2-carboxylic acid

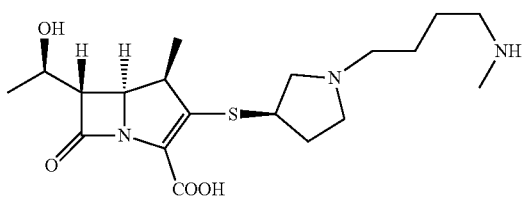 [SMILES: CNCCCCN1CC[C@@H](SC2=C(C(=O)O)N3C(=O)[C@H]([C@@H](C)O)[C@H]3[C@H]2C)C1]

Step 1: Synthesis of ((4,4-diethoxy-N-methylbutan-1-amine

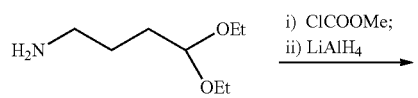

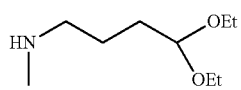

By following the same reaction procedures as described in Step 1 of Example 18, 4,4-diethoxybutylamine (2.42 g, 15 mmol) was converted to the crude target compound, which was used directly for the next step without further purification.

Step 2: Synthesis of 4-nitrobenzyl methyl(4-oxobutyl)carbamate

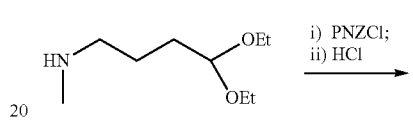

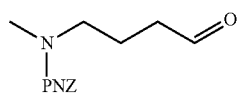

Part i). By using the same reaction procedures as described in Step 5 of Example 1, the above crude product was converted to the PNZ carbamate, 4 g. ESI-MS m/z 355 (MH)$^+$.

Part ii). The product from Part i) (2.62 g, 7.4 mmol) was dissolved in 1,4-dioxane (30 mL), treated with 6 N HCl (30 mL) at rt for 1 h, diluted with water, extracted with EtOAc. The combined organic extracts were washed with brine, dried over Na$_2$SO$_4$, concentrated in vacuo, yielding the crude product, which was used directly for the next step without further purification. ESI-MS m/z 281 (MH)$^+$.

Step 3: Synthesis of (4R,5S,6S)-6-((R)-1-hydroxyethyl)-4-methyl-3-(((R)-1-(4-(methylamino)butyl)pyrrolidin-3-yl)thio)-7-oxo-1-azabicyclo[3.2.0]hept-2-ene-2-carboxylic acid

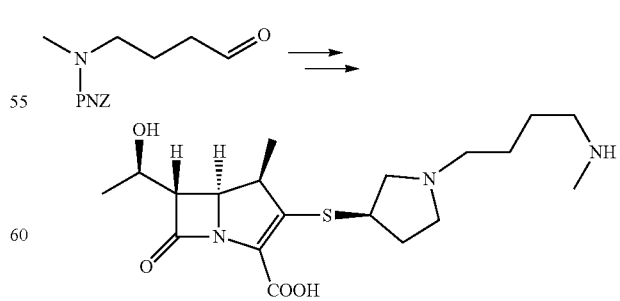

By following the same reaction procedures as described in Steps 6, 7 and 8 of Example 1, the above aldehyde was converted to the target compound. ESI-MS m/z 398 (MH)$^+$.

Example 38: (4R,5S,6S)-3-(((R)-1-(4-amino-4-(aminomethyl)cyclohexyl)pyrrolidin-3-yl)thio)-6-((R)-1-hydroxyethyl)-4-methyl-7-oxo-1-azabicyclo[3.2.0]hept-2-ene-2-carboxylic acid

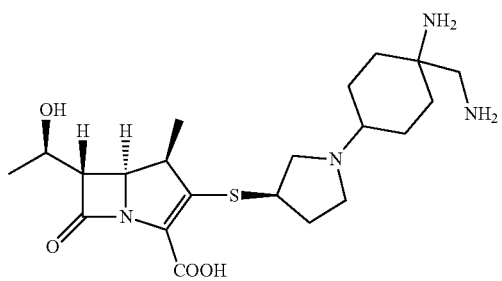 [SMILES: C[C@@H](O)[C@H]1C(=O)N2C(C(=O)O)=C(S[C@@H]3CCN(C4CCC(N)(CN)CC4)C3)[C@H](C)[C@H]12]

Step 1: Synthesis of 8-amino-1,4-dioxaspiro[4.5]decane-8-carbonitrile

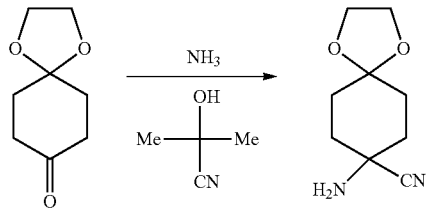

To 1,4-cyclohexandione monoethylene ketal (3.12 g, 20 mmol) in THF (40 mL) at −5° C. was added ammonia (7 N in MeOH, 11.5 mL, 80.5 mmol). The reaction mixture was stirred between −5-10° C. for 1.5 h, then acetone cyanohydrins (3.66 mL, 40 mmol) was added. The reaction mixture was stirred at rt overnight, concentrated in vacuo. The residue was purified by flash chromatography on silica gel (hexane-EtOAc, 4:1-0:100) to afford the product, 1.6 g.

Step 2: Synthesis of 4-nitrobenzyl ((8-amino-1,4-dioxaspiro[4.5]decan-8-yl)methyl)carbamate

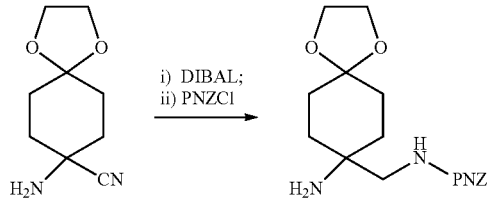

Part i). By following the same reaction procedures as described in Step 2 of Example 34, the above product (1.6 g, 8.8 mmol) was reduced with DIBAL to give the crude diamine.

Part ii). By using the same reaction procedures as described in Step 5 of Example 1, the crude diamine was reacted with 4-nitrobenzyl chloroformate to afford the mono-PNZ carbamate product, 2.5 g. ESI-MS m/z 366 (MH)⁺.

Step 3: Synthesis of 4-nitrobenzyl (1-(((((4-nitrobenzyl)oxy)carbonyl)amino)methyl)-4-oxocyclohexyl)carbamate

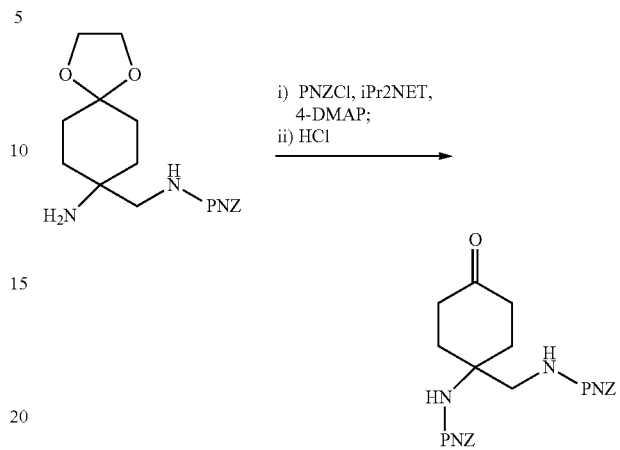

Part i). To a DCM (40 mL) solution of the above product (730 mg, 2 mmol) was added diisopropylethylamine (0.53 mL, 3 mmol) followed by 4-nitrobenzyl chloroformate (648 mg, 3 mmol) and DMAP (49 mg, 0.4 mmol). The reaction mixture was stirred at rt for 3 h, washed with saturated aqueous NaHCO₃, dried over Na₂SO₄, concentrated in vacuo. The residue was purified by flash chromatography on silica gel (hexane-EtOAc, 2:1-1:6) to afford the product, 1.08 g. ESI-MS m/z 545 (MH)⁺.

Part ii). The product from Part i) was dissolved in THF (40 mL), treated with 2 N HCl (20 mL) at rt overnight. The reaction mixture was extracted with DCM. The organic extracts were combined, dried over Na₂SO₄, concentrated in vacuo to afford the ketone, which was used directly for the next step without further purification. ESI-MS m/z 501 (MH)⁺.

Step 4: Synthesis of (4R,5S,6S)-3-(((R)-1-(4-amino-4-(aminomethyl)cyclohexyl)pyrrolidin-3-yl)thio)-6-((R)-1-hydroxyethyl)-4-methyl-7-oxo-1-azabicyclo[3.2.0]hept-2-ene-2-carboxylic acid

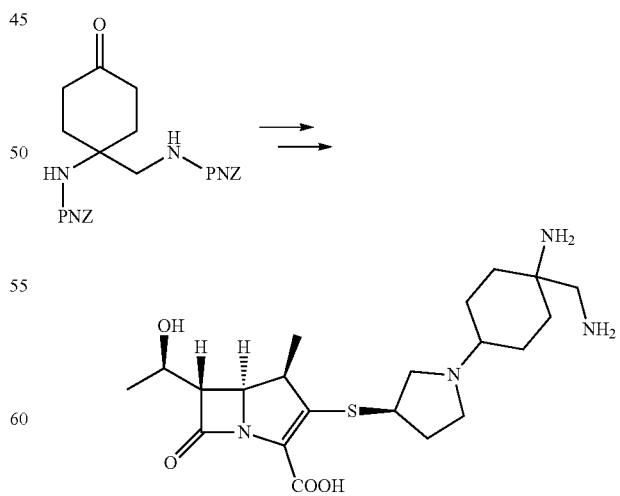

By using the same reaction procedures as described in step 6, 7 and 8 of Example 1, the above ketone was converted to the target compound. ESI-MS m/z 439 (MH)⁺.

Example 39: (4R,5S,6S)-6-((R)-1-hydroxyethyl)-4-methyl-3-(((R)-1-((1-methyl piperidin-4-yl) methyl) pyrrolidin-3-yl)thio)-7-oxo-1-azabicyclo[3.2.0]hept-2-ene-2-carboxylic acid

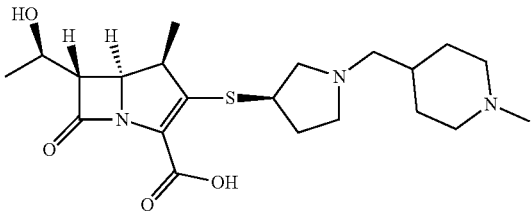 [SMILES: C[C@@H](O)[C@H]1C(=O)N2C(C(=O)O)=C(S[C@@H]3CCN(CC4CCN(C)CC4)C3)[C@H](C)[C@H]12]

Step 1: Synthesis of tert-butyl (R)-4-((3-mercaptopyrrolidin-1-yl)methyl)piperidine-1-carboxylate

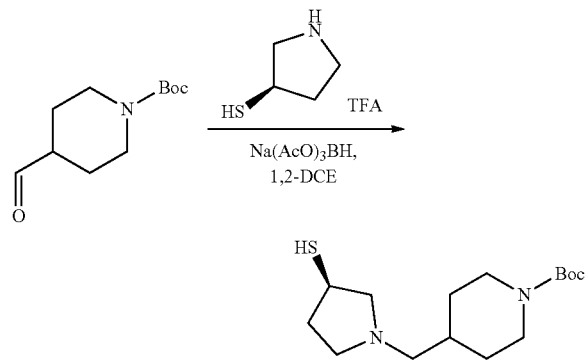

To a solution of tert-butyl 4-formylpiperidine-1-carboxylate (3.0 g, 14.1 mmol), (R)-pyrrolidine-3-thiol (crude, 14.1 mmol) in 1,2-dichloroethane (30 mL) was added sodium triacetoxyborohydride (5.98 g, 28.2 mmol). The reaction mixture was stirred at rt overnight, washed with saturated aqueous NaHCO₃, dried over Na₂SO₄, concentrated in vacuo. The residue was purified twice by flash chromatography on silica gel (DCM-MeOH, 30:1-10:1) to afford the pure product, 3.2 g. ESI-MS m/z 301 (MH)⁺.

Step 2: Synthesis of (4R,5S,6S)-3-(((R)-1-((1-(tert-butoxycarbonyl)piperidin-4-yl)methyl) pyrrolidin-3-yl)thio)-6-((R)-1-hydroxyethyl)-4-methyl-7-oxo-1-azabicyclo[3.2.0]hept-2-ene-2-carboxylic 4-nitrobenzoic anhydride

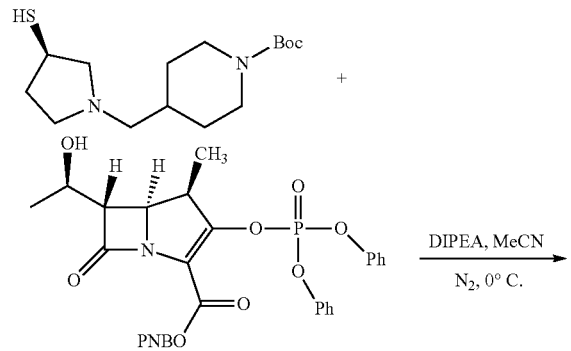

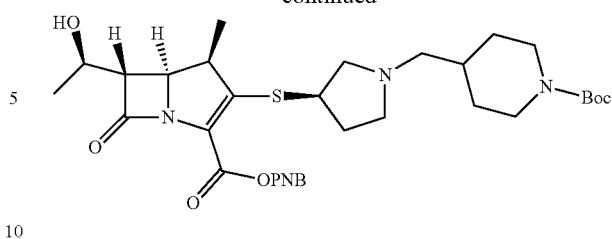

To the above product (2 g, 6.56 mmol), and 4-nitrobenzyl (4R,5R,6S)-3-((diphenoxy phosphoryl)oxy)-6-((R)-1-hydroxyethyl)-4-methyl-7-oxo-1-azabicyclo[3.2.0]hept-2-ene-2-carboxylate (2.6 g, 4.37 mmol) was add dry acetonitrile (50 mL) under Argon at 0° C., followed by diisopropylethylamine (1.08 g, 8.74 mmol). The reaction mixture was stirred in ice-water bath for 12 h, then concentrated. The residue was purified twice by flash chromatography on silica gel (EtOAc/MeOH=, 100:1-10:1) to yield the product, 3 g. ESI-MS m/z 645 (MH)⁺.

Step 3: Synthesis of (4R,5S,6S)-6-((R)-1-hydroxyethyl)-4-methyl-7-oxo-3-(((R)-1-(piperidin-4-ylmethyl)pyrrolidin-3-yl)thio)-1-azabicyclo[3.2.0]hept-2-ene-2-carboxylic 4-nitrobenzoic anhydride

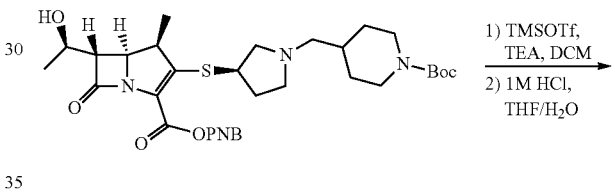

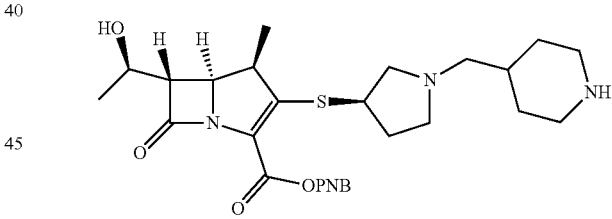

To a solution of the above product (3 g, 4.65 mmol) in DCM (100 mL) was added triethylamine (7.5 mL, 55.8 mmol), followed by trimethylsilyl trifluoromethanesulfonate (5.1 mL, 27.9 mmol) at 0° C. under Argon. After 5 min, the reaction mixture was allowed to warm to rt, and stirred for 19 h, quenched with methanol (4 mL) and phosphate buffer solution (pH 7), extracted with DCM. The organic extracts were combined, washed with brine, dried over Na₂SO₄, concentrated in vacuo. The residue was then dissolved in THF (80 mL). To this solution at 0° C. was added water (20 mL), followed by a few drops of 1 N HCl to adjust to pH 2. After 10 min, it was quenched with saturated aqueous NaHCO₃, extracted with EtOAc, and DCM. The organic extracts were combined, dried over Na₂SO₄, concentrated in vacuo, yielding the crude product, which was used directly for the next step without further purification. ESI-MS m/z 545 (MH)⁺.

Step 4: Synthesis of (4R,5S,6S)-6-((R)-1-hydroxyethyl)-4-methyl-3-(((R)-1-((1-methylpiperidin-4-yl)methyl) pyrrolidin-3-yl)thio)-7-oxo-1-azabicyclo[3.2.0]hept-2-ene-2-carboxylic 4-nitrobenzoic anhydride

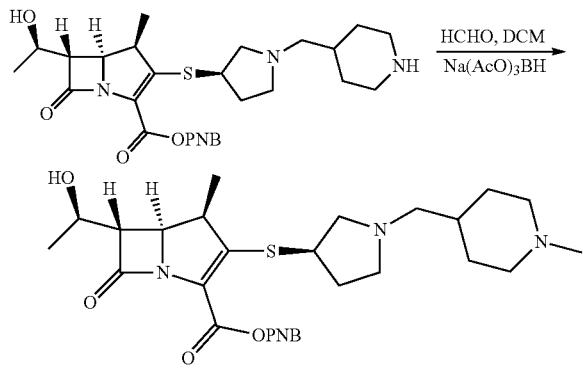

To a solution of (4R,5S,6S)-6-((R)-1-hydroxyethyl)-4-methyl-7-oxo-3-(((R)-1-(piperidin-4-ylmethyl)pyrrolidin-3-yl)thio)-1-azabicyclo[3.2.0]hept-2-ene-2-carboxylic 4-nitrobenzoic anhydride (1.0 g, 1.83 mmol), HCHO (148 mg, 2.0 mmol, 37% aqueous solution) was added sodium triacetoxyborohydride (780 mg, 3.6 mmol). The reaction mixture was stirred at rt overnight, washed with saturated aqueous NaHCO3, dried over Na2SO4, concentrated in vacuo. The residue was purified by flash chromatography on MCI-GEL (H2O-THL, 100:1-2:1) to afford the pure product, 140 mg. ESI-MS m/z 559 (MH)$^+$.

Step 5: Synthesis of (4R,5S,6S)-6-((R)-1-hydroxyethyl)-4-methyl-3-(((R)-1-((1-methylpiperidin-4-yl)methyl) pyrrolidin-3-yl)thio)-7-oxo-1-azabicyclo[3.2.0]hept-2-ene-2-carboxylic acid

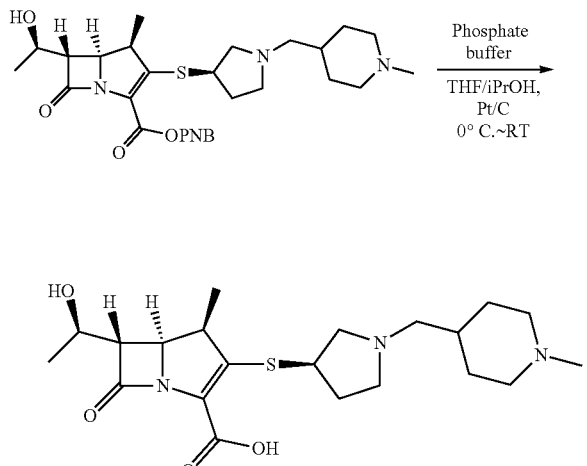

By following the same reaction procedures as described in Step 8 of Example 1, the above crude product was hydrogenated in the presence of 5% Pt/C to yield the target compound, 25 mg. ESI-MS m/z 424 (MH)$^+$.

Example 40: (4R,5S,6S)-6-((R)-1-hydroxyethyl)-3-(((R)-1-((1-(2-hydroxyethyl) piperidin-4-yl)methyl)pyrrolidin-3-yl)thio)-4-methyl-7-oxo-1-azabicyclo[3.2.0]hept-2-ene-2-carboxylic acid

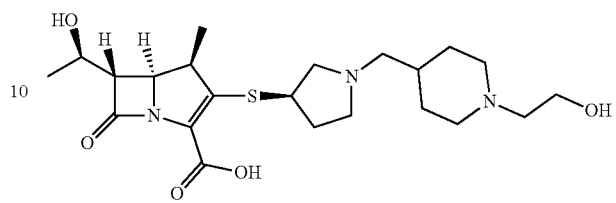

Step 1: Synthesis of tert-butyl (R)-4-((3-(acetylthio)pyrrolidin-1-yl)methyl)piperidine-1-carboxylate

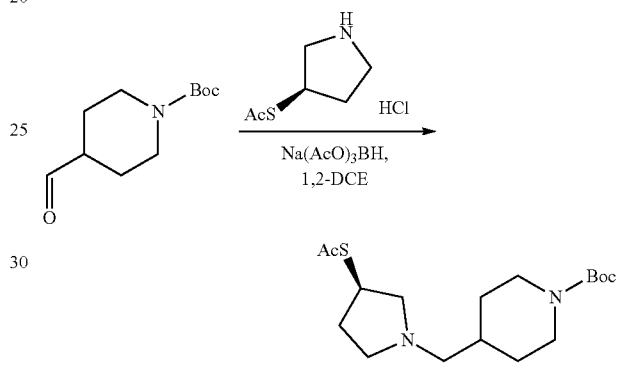

To a solution of tert-butyl 4-formylpiperidine-1-carboxylate (3.0 g, 14.1 mmol), (R)—S-(pyrrolidin-3-yl) ethanethioate hydrochloride (crude, 14.1 mmol) in 1,2-dichloroethane (30 mL) was added sodium triacetoxyborohydride (5.98 g, 28.2 mmol). The reaction mixture was stirred at rt overnight, washed with saturated aqueous NaHCO$_3$, dried over Na$_2$SO$_4$, concentrated in vacuo. The residue was purified twice by flash chromatography on silica gel (DCM-MeOH, 30:1-10:1) to afford the pure product, 3.5 g. ESI-MS m/z 343 (MH)$^+$.

Step 2: Synthesis of (R)—S-(1-(piperidin-4-ylmethyl) pyrrolidin-3-yl) ethanethioate hydrochloride

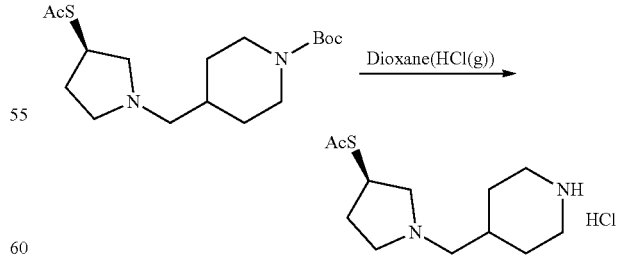

The above crude product was dissolved in dioxane saturated with HCl(g) (35 mL) at 0° C., and was stirred for 1 h at rt, and then concentrated in vacuo to give the crude product as a HCl salt, which was used directly for the next step without further purification.

Step 3: Synthesis of (R)—S-(1-((1-(2-hydroxyethyl)piperidin-4-yl)methyl)pyrrolidin-3-yl) ethanethioate

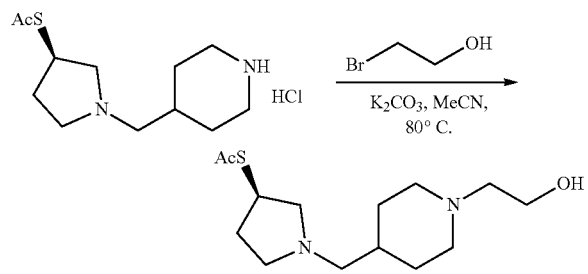

To a solution of the above product (3 g, 10.7 mmol) in MeCN (60 mL) was added K₂CO₃ (2.95 g, 21.4 mmol), followed by 2-bromoethan-1-ol (2.67 g, 21.4 mmol) at rt. The reaction mixture was allowed to warm to 80° C., and stirred for 12 h, filtered through a pad of celite. The filtrate was concentrated under vacuum to give a yellow oil, 2.1 g, which was used directly for the next step without further purification. ESI-MS m/z 287 (MH)⁺.

Step 4: Synthesis of (R)-2-(4-((3-mercaptopyrrolidin-1-yl)methyl)piperidin-1-yl)ethan-1-ol

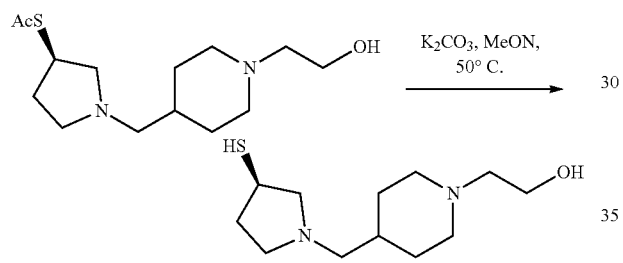

To a solution of the above product (2.1 g, 7.32 mmol) in methanol (60 mL) was added potassium carbonate (2.0 g, 14.63 mmol). The reaction mixture was stirred at 50° C. under Argon for 2 h, then cooled in ice-bath, acidified with 1 N HCl to pH 4-5, extracted with EtOAc. The aqueous phase was lyophilized to afford the crude product, 1.6 g. ESI-MS m/z 245 (MH)⁺.

Step 5: Synthesis of (4R,5S,6S)-6-((R)-1-hydroxyethyl)-3-(((R)-1-((1-(2-hydroxyethyl)piperidin-4-yl)methyl)pyrrolidin-3-yl)thio)-4-methyl-7-oxo-1-azabicyclo[3.2.0]hept-2-ene-2-carboxylic acid

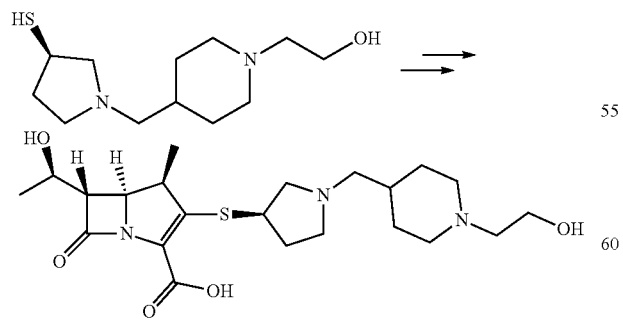

By following the same reaction procedures as described in Steps 7 and 8 of Example 1, the above product was converted to the target compound. ESI-MS m/z 454 (MH)⁺.

Example 41: (4R,5S,6S)-3-(((R)-1-((1-(2-amino-2-oxoethyl)piperidin-4-yl)methyl)pyrrolidin-3-yl)thio)-6-((R)-1-hydroxyethyl)-4-methyl-7-oxo-1-azabicyclo[3.2.0]hept-2-ene-2-carboxylic acid

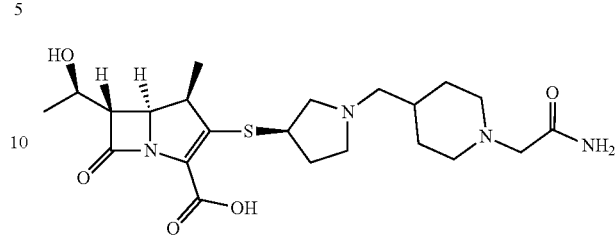

By following the same reaction procedures as described in Steps 3, 4 and 5 of Example 40, utilizing 2-bromoacetamide in place of 2-bromoethan-1-ol in Step 2, the target compound was prepared. ESI-MS m/z 467 (MH)⁺.

Example 42: (4R,5S,6S)-6-((R)-1-hydroxyethyl)-4-methyl-7-oxo-3-((1-(piperidin-4-ylmethyl)azetidin-3-yl)thio)-1-azabicyclo[3.2.0]hept-2-ene-2-carboxylic acid

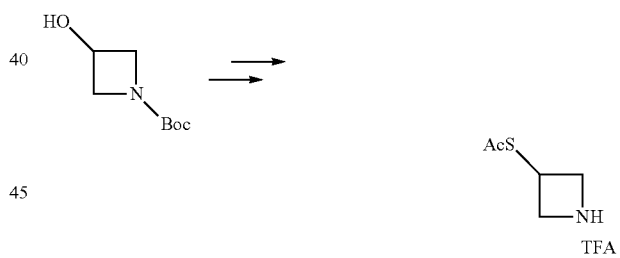

Step 1: Synthesis of S-(azetidin-3-yl) ethanethioate

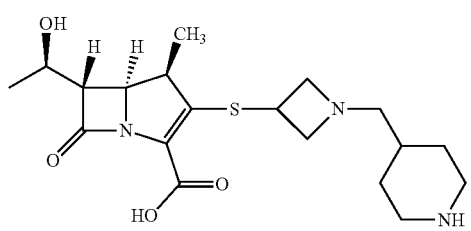 [SMILES: C[C@@H](O)[C@H]1C(=O)N2C(C(=O)O)=C(SC3CN(CC4CCNCC4)C3)[C@H](C)[C@H]12]

By following the same reaction procedures as described in Steps 1, 2 and 4 of Example 1, tert-butyl 3-hydroxyazetidine-1-carboxylate was converted to S-(azetidin-3-yl) ethanethioate, 10 g. ESI-MS m/z 132 (MH)⁺.

Step 2: Synthesis of 4-nitrobenzyl 4-formylpiperidine-1-carboxylate

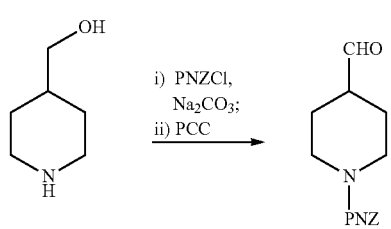

By following the same reaction procedures as described in Steps 1 of Example 7, 4-piperidinemethanol was converted to the crude aldehyde product, 5 g. ESI-MS m/z 293 (MH)+.

Step 3: Synthesis of 4-nitrobenzyl 4-((3-(acetylthio)azetidin-1-yl)methyl)piperidine-1-carboxylate

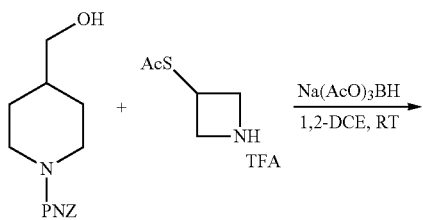

By following the same reaction procedures as described in Step 1 of Example 40, 4-nitrobenzyl 4-formylpiperidine-1-carboxylate (intermediate from Step 1 of Example 7) was reacted with the above product in the presence of sodium triacetoxyborohydride to yield the title compound. ESI-MS m/z 408 (MH)+.

Step 4: Synthesis of (4R,5S,6S)-6-((R)-1-hydroxyethyl)-4-methyl-7-oxo-3-((1-(piperidin-4-ylmethyl)azetidin-3-yl)thio)-1-azabicyclo[3.2.0]hept-2-ene-2-carboxylic acid

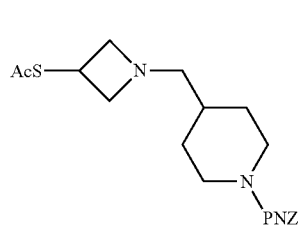

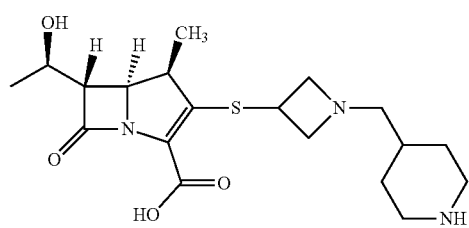

By following the same reaction procedures as described in Steps 4 and 5 of Example 40, the above product was converted to the target compound. ESI-MS m/z 396 (MH)+.

Example 43: Synthesis of (4R,5S,6S)-6-((R)-1-hydroxyethyl)-4-methyl-7-oxo-3-(((R)-1-(piperidin-4-ylmethyl)piperidin-3-yl)thio)-1-azabicyclo[3.2.0]hept-2-ene-2-carboxylic acid

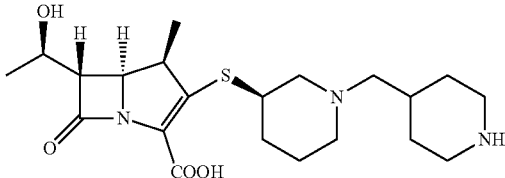 [SMILES: C[C@@H](O)[C@H]1C(=O)N2C(C(=O)O)=C(S[C@@H]3CCCN(CC4CCNCC4)C3)[C@H](C)[C@H]12]

Step 1: Synthesis of tert-butyl (R)-3-((methylsulfonyl)oxy)piperidine-1-carboxylate

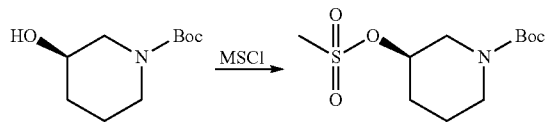

A mixture of tert-butyl (R)-3-hydroxypiperidine-1-carboxylate (5.15 g, 25 mmol) and Et₃N (7.6 g, 77 mmol) in DCM (50 mL) was stirred at 0° C., MsCl (5.8 g, 52 mmol) was added to solution in dropwise, keep stirred for 3 h. The solvent was washed by saturated aqueous NaHCO₃ (50 mL/2) then brine (50 mL), dried over Na₂SO₄, purified by flash chromatography on silica gel (DCM: 100%) to afford product as yellow solid, 3.06 g. ESI-MS m/z 280 (MH)+.

Step 2: Synthesis of tert-butyl (R)-3-(acetylthio)piperidine-1-carboxylate

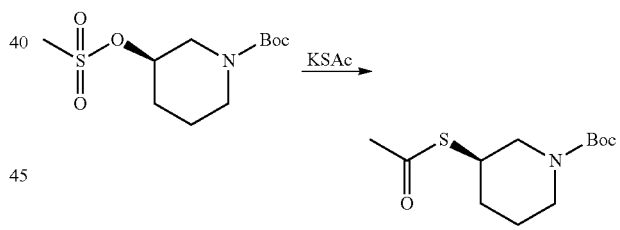

A mixture of tert-butyl (R)-3-((methylsulfonyl)oxy)piperidine-1-carboxylate (3 g, 10.7 mmol) and KSAc (3.1 g, 26.8 mmol) was in DMF (30 mL) protected with N₂. Warmed the solution to 100-105° C. for 4 h. Cooled the solution to r.t. Saturated aqueous NaHCO₃ (200 mL) was added to solution, extracted by DCM (100 mL×2), dried over Na₂SO₄, purified by flash chromatography on silica gel (PE/EA=90/10) to afford product as brown oil, 900 mg. ESI-MS m/z 260 (MH)+.

Step 3: Synthesis of (R)—S-(piperidin-3-yl) ethanethioate hydrochloride

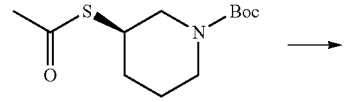

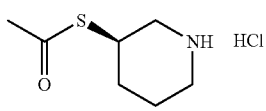

To a mixture of tert-butyl (R)-3-(acetylthio)piperidine-1-carboxylate (900 mg, 3.4 mmol) in DCM (5 mL) at 0° C. was added HCl-EtOH (5 mL, 33%) dropwise, the reaction mixture was stirred for 10 min then warmed to r.t. for 1 h. The solvent was concentrated in vacuo at 40-50° C., H₂O (15 mL) was added to the residue, extracted with EtOAc (15 mL/2). The aqueous phase was lyophilized to yield the product as yellow oil. ESI-MS m/z 160 (MH)⁺.

Step 4: Synthesis of 4-nitrobenzyl (R)-4-((3-mercaptopiperidin-1-yl)methyl)piperidine-1-carboxylate

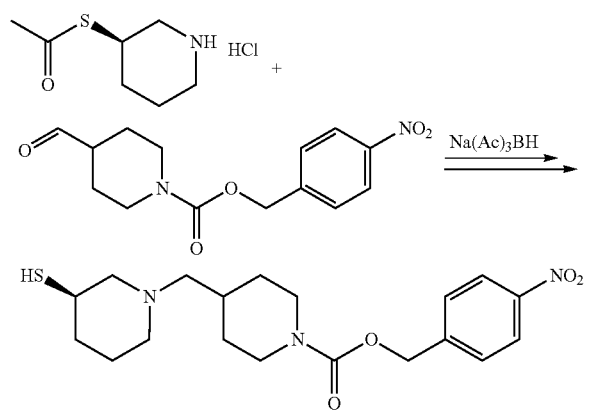

To a solution of the above product (460 mg, 2.35 mmol) and 4-nitrobenzyl 4-formylpiperidine-1-carboxylate (intermediate from Step 1 of Example 7, 678 mg, 2.35 mmol) in DCE (10 mL) at r.t. was added Na(OAc)₃BH (747.2 mg, 3.52 mmol) in portions. The reaction was stirred at rt overnight, then quenched with saturated aqueous NaHCO₃ (50 mL) the organic layer was separated, dried, concentrated, and the residue purified by preparative TLC (DCM/MeOH=12/1) to afford product as colourless oil 264 mg. ESI-MS m/z 436 (MH)⁺.

Step 5: Synthesis of 4-nitrobenzyl (4R,5S,6S)-6-((R)-1-hydroxyethyl)-4-methyl-3-(((R)-1-((1-(((4-nitrobenzyl)oxy)carbonyl)piperidin-4-yl)methyl)piperidin-3-yl)thio)-7-oxo-1-azabicyclo[3.2.0]hept-2-ene-2-carboxylate

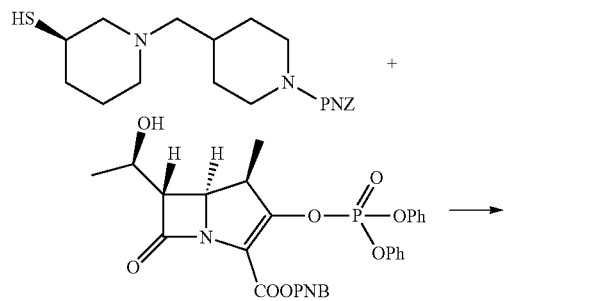

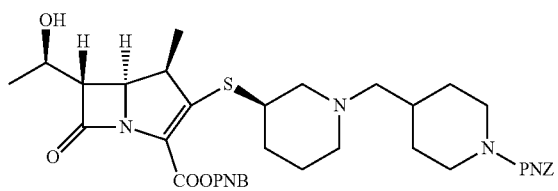

To a mixture of the above product (240 mg, 0.6 mmol) and 4-nitrobenzyl (4R,5R,6S)-3-((diphenoxyphosphoryl)oxy)-6-((R)-1-hydroxyethyl)-4-methyl-7-oxo-1-azabicyclo[3.2.0]hept-2-ene-2-carboxylate (398 mg, 0.67 mmol) was in MeCN (20 mL) under nitrogen atmosphere was added DIPEA (102 mg, 0.79 mmol) the reaction mixture was stirred at 0° C. for 24 h, concentrated, purified by preparative TLC (DCM/MeOH=10/1) to afford the title compound as yellow solid 190 mg. ESI-MS m/z 738 (MH)⁺.

Step 6: Synthesis of (4R,5S,6S)-6-((R)-1-hydroxyethyl)-4-methyl-7-oxo-3-(((R)-1-(piperidin-4-ylmethyl)piperidin-3-yl)thio)-1-azabicyclo[3.2.0]hept-2-ene-2-carboxylic acid

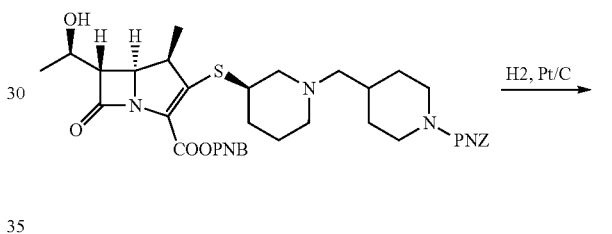

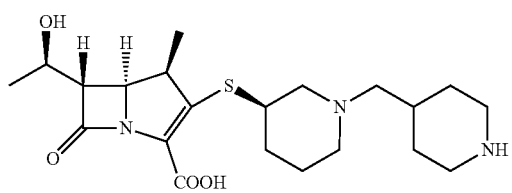

By following the same reaction procedures as described in Step 8 of Example 1, the target compound was prepared. ESI-MS m/z 424 (MH)⁺.

Example 44: (4R,5S,6S)-6-((R)-1-hydroxyethyl)-4-methyl-7-oxo-3-((1-(piperidin-4-ylmethyl)piperidin-4-yl)thio)-1-azabicyclo[3.2.0]hept-2-ene-2-carboxylic acid

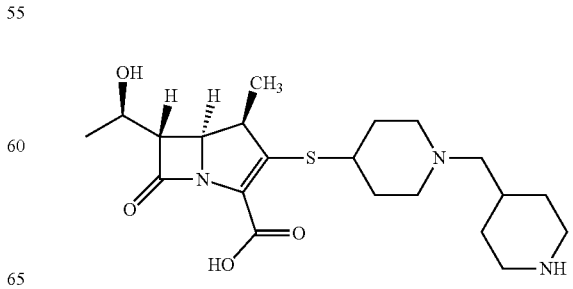

Step 1: Synthesis of A-(piperidin-4-yl) ethanethioate

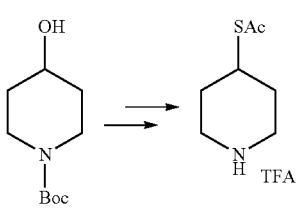

By following the same reaction procedures as described in Steps 1, 2 and 4 of Example 1, tert-butyl 4-hydroxypiperidine-1-carboxylate was converted to S-(piperidin-4-yl) ethanethioate as a TFA salt, 8 g. ESI-MS m/z 160 (MH)+.

Step 2: Synthesis of (4R,5S,6S)-6-((R)-1-hydroxyethyl)-4-methyl-7-oxo-3-((1-(piperidin-4-ylmethyl)piperidin-4-yl)thio)-1-azabicyclo[3.2.0]hept-2-ene-2-carboxylic acid

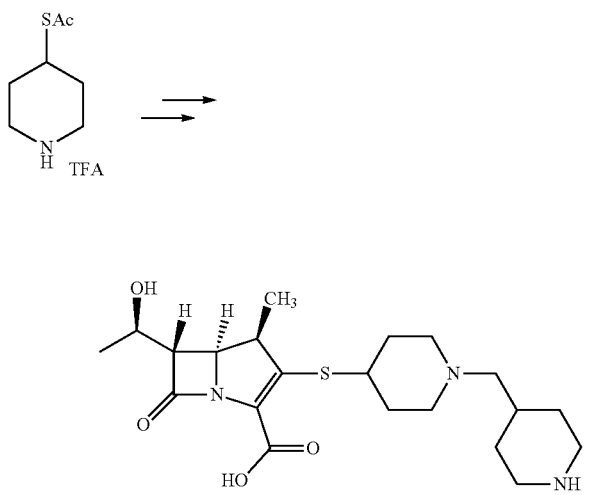

By following the same reaction procedures as described in Steps 2 and 3 of Example 42, using S-(piperidin-4-yl) ethanethioate in place of S-(azetidin-3-yl) ethanethioate as starting material, the target compound was prepared. ESI-MS m/z 424 (MH)+.

Example 45: (4R,5S,6S)-3-(((3R)-1-((3-fluoropiperidin-4-yl)methyl)pyrrolidin-3-yl)thio)-6-((R)-1-hydroxyethyl)-4-methyl-7-oxo-1-azabicyclo[3.2.0]hept-2-ene-2-carboxylic acid

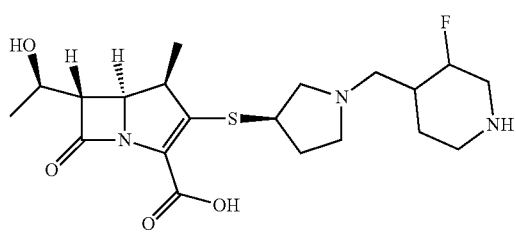 [SMILES: C[C@@H](O)[C@H]1C(=O)N2C(C(=O)O)=C(S[C@@H]3CCN(CC4CCNCC4F)C3)[C@H](C)[C@H]12]

Step 1: Synthesis of tert-butyl 3-fluoro-4-(hydroxymethyl)piperidine-1-carboxylate

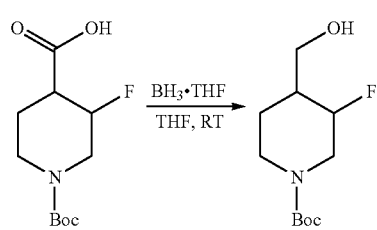 [SMILES: CC(C)(C)OC(=O)N1CCC(C(=O)O)C(F)C1 ; CC(C)(C)OC(=O)N1CCC(CO)C(F)C1 ; "BH3·THF"]

To a solution of 1-(tert-butoxycarbonyl)-3-fluoropiperidine-4-carboxylic acid (1.95 g, 7.89 mmol) in THF (50 mL) was added BH₃·THF (15.7 mL, 23.67 mmol). The reaction mixture was stirred at rt for 5 h. The resulting mixture was quenched by NaHCO₃ (aq), extracted with EtOAc, dried over Na₂SO₄, and concentrated under vacuum. The residue was purified by flash chromatography on silica gel to afford a white solid, 1.7 g. ESI-MS m/z 234 (MH)+.

Step 2: Synthesis of (3-fluoropiperidin-4-yl)methanol hydrochloride

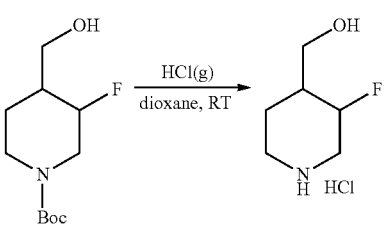 [SMILES: CC(C)(C)OC(=O)N1CCC(CO)C(F)C1 ; OCC1CCNCC1F ; Cl]

The above crude product was dissolved in dioxane saturated with HCl (g) (35 mL) at 0° C., and was stirred for 2 h at rt, and then concentrated in vacuo to give the crude product as a HCl salt, which was used directly for the next step without further purification.

Step 3: Synthesis of (4R,5S,6S)-3-(((3R)-1-((3-fluoropiperidin-4-yl)methyl)pyrrolidin-3-yl)thio)-6-((R)-1-hydroxyethyl)-4-methyl-7-oxo-1-azabicyclo[3.2.0]hept-2-ene-2-carboxylic acid

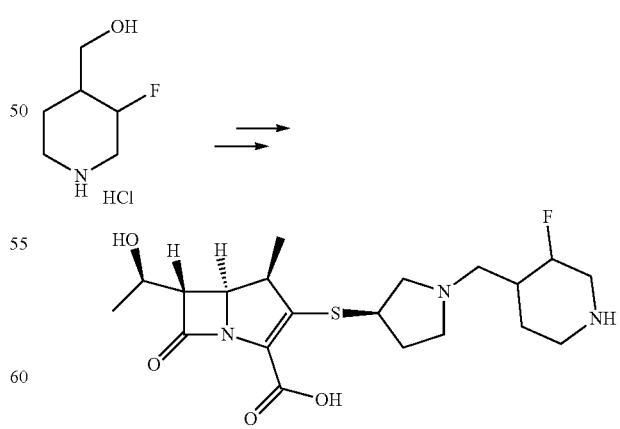

By following the same reaction procedures as described in Steps 1 and 2 of Example 7, (3-fluoropiperidin-4-yl)methanol hydrochloride was converted to the target compound. ESI-MS m/z 428 (MH)+.

Example 46: (4R,5S,6S)-3-(((3R)-1-((3,3-difluoropiperi-din-4-yl)methyl)pyrrolidin-3-yl)thio)-6-((R)-1-hy-droxyethyl)-4-methyl-7-oxo-1-azabicyclo[3.2.0]hept-2-ene-2-carboxylic acid

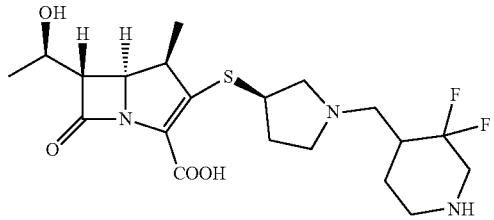 [SMILES: C[C@@H](O)[C@H]1C(=O)N2C(C(=O)O)=C(S[C@@H]3CCN(CC4CCNCC4(F)F)C3)[C@H](C)[C@H]12]

Step 1: Synthesis of (R)-pyrrolidine-3-thiol

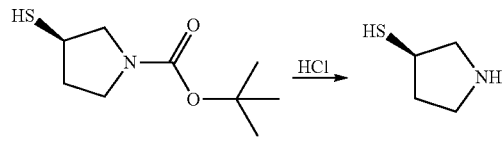

To a mixture of tert-butyl (R)-3-mercaptopyrrolidine-1-carboxylate (intermediate from Step 3 of Example 1, 2 g, 9.8 mmol) in DCM (20 mL) at 0° C. was added EtOH/HCl (1.25 M, 20 mL) dropwise. The reaction mixture was warmed to rt, stirred for 1 h, then concentrated in vacuo. Water (20 mL) was added to the residue, and the mixture was extracted with EtOAc (20 mL/2), then the aqueous was lyophilized to afford product as brown oil.

Step 2: Synthesis of 4-nitrobenzyl 3,3-difluoro-4-form-ylpiperidine-1-carboxylate

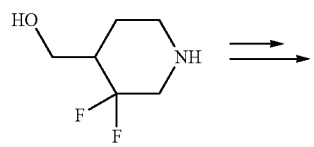

By using the same reaction procedures as described in Step 1 of Example 7, the target compound was prepared from (3,3-difluoropiperidin-4-yl)methanol. ESI-MS m/z 329 (MH)+.

Step 3: Synthesis of 4-nitrobenzyl 3,3-difluoro-4-(((R)-3-mercaptopyrrolidin-1-yl)methyl)piperidine-1-carboxylate

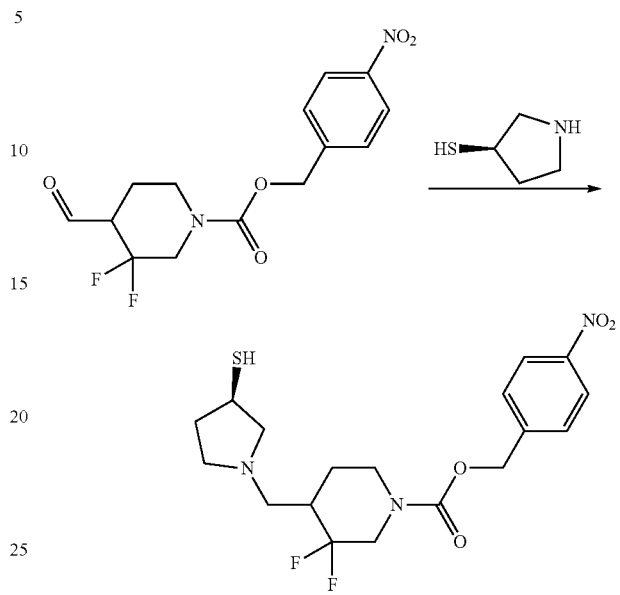

By using the same reaction procedures as described in Step 6 of Example 1 using 4-nitrobenzyl 3,3-difluoro-4-formylpiperidine-1-carboxylate in place of 4-nitrobenzyl 4-oxopiperidine-1-carboxylate as starting material, the target compound was prepared. ESI-MS m/z 416 (MH)+.

Step 5: Synthesis of (4R,5S,6S)-3-(((3R)-1-((3,3-difluo-ropiperidin-4-yl)methyl)pyrrolidin-3-yl)thio)-6-((R)-1-hydroxyethyl)-4-methyl-7-oxo-1-azabicyclo[3.2.0] hept-2-ene-2-carboxylic acid

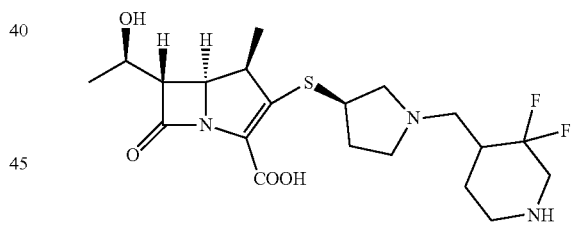

By using the same reaction procedures as described in Step 5 and Step 6 of Example 43, the above product was converted to the target compound. ESI-MS m/z 446 (MH)+.

Example 47: (4R,5S,6S)-3-(((R)-1-((1-glycylpiperidin-4-yl)methyl)pyrrolidin-3-yl)thio)-6-((R)-1-hydroxy-ethyl)-4-methyl-7-oxo-1-azabicyclo[3.2.0]hept-2-ene-2-carboxylic acid

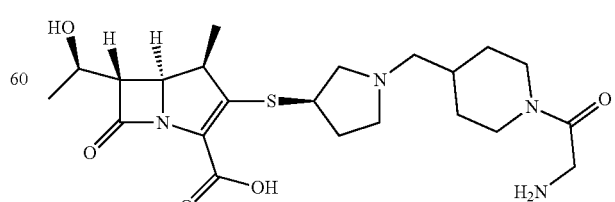

Step 1: Synthesis of (((4-nitrobenzyl)oxy)carbonyl)glycine

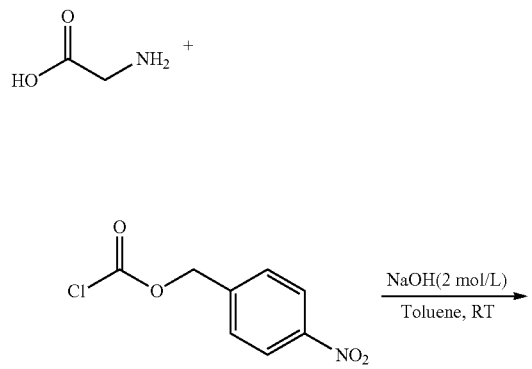

To a solution of glycine (3 g, 40 mmol) in NaOH (aq, 2 mol/L, 20 mL) was added simultaneously from two dropping funnels under stirring NaOH (4 M in water, 10 mL) and a solution of 4-nitrobenzyl carbonochloridate (10.32 g, 48 mmol) in toluene over 10 min. The reaction mixture was stirred for 3 hrs at rt. The resulting mixture was extracted with EtOAc. The aqueous phase was acidified to pH 1 with HCl (4 M in water), extracted with DCM. The organic layer was dried over Na$_2$SO$_4$, evaporated under vacuum to afford a colorless oil, 8.6 g. ESI-MS m/z 253 (M-H).

Step 2: Synthesis of 4-nitrobenzyl (2-(4-(hydroxymethyl)piperidin-1-yl)-2-oxoethyl)carbamate

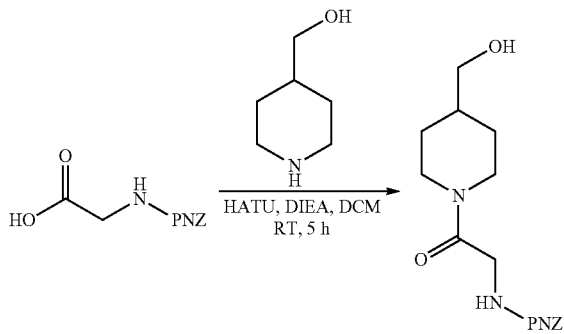

To a solution of the above product in DCM (250 mL) was added HATU (12.8 g, 33.8 mmol) and DIPEA (13.1 g, 101.5 mmol), followed by piperidin-4-ylmethanol (3.88 g, 33.8 mmol). The reaction mixture was stirred at rt for 8 h. The resulting mixture was diluted with DCM, washed with water, dried over Na$_2$SO$_4$, and concentrated under vacuum. The residue was purified by flash chromatography on silica gel to afford a yellow oil, 10 g. ESI-MS m/z 352 (MH)$^+$.

Step 3: Synthesis of 4-nitrobenzyl (2-(4-formylpiperidin-1-yl)-2-oxoethyl)carbamate

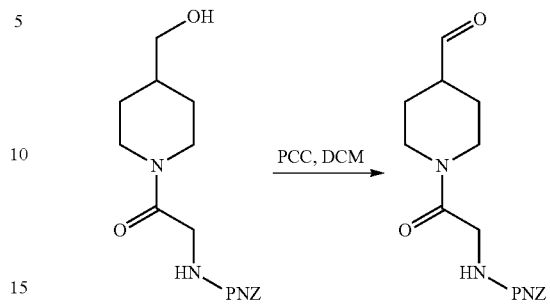

By following the same reaction procedures as described in Step 1, Part (ii) of Example 7, the above alcohol was converted to the crude aldehyde product, 5 g. ESI-MS m/z 350 (MH)$^+$.

Step 4: Synthesis of (4R,5S,6S)-3-(((R)-1-((1-glycylpiperidin-4-yl)methyl)pyrrolidin-3-yl)thio)-6-((R)-1-hydroxyethyl)-4-methyl-7-oxo-1-azabicyclo[3.2.0]hept-2-ene-2-carboxylic acid

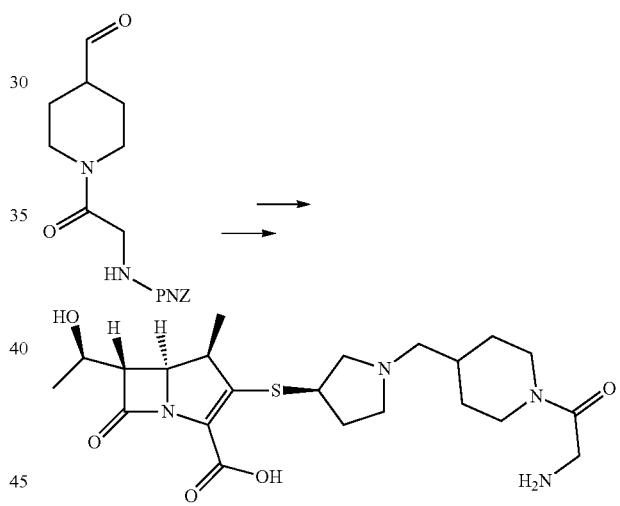

By following the same reaction procedures as described in Steps 6, 7 and 8 of Example 1, 4-nitrobenzyl (2-(4-(hydroxymethyl)piperidin-1-yl)-2-oxoethyl)carbamate was converted to the target compound. ESI-MS m/z 467 (MH)$^+$.

Example 48: (4R,5S,6S)-6-((R)-1-hydroxyethyl)-4-methyl-3-(((R)-1-((1-(methylglycyl)piperidin-4-yl)methyl)pyrrolidin-3-yl)thio)-7-oxo-1-azabicyclo[3.2.0]hept-2-ene-2-carboxylic acid

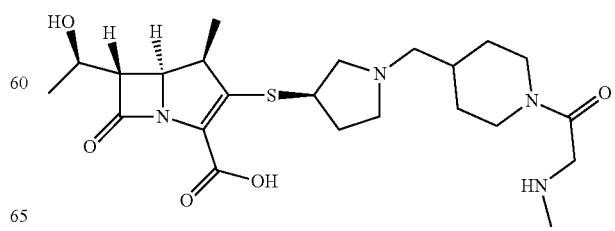

By following the same reaction procedures as described in Example 47, utilizing methylglycine instead of glycine as starting material, the target compound was prepared. ESI-MS m/z 481 (MH)+.

Example 49: (4R,5S,6S)-6-((R)-1-hydroxyethyl)-4-methyl-3-(((R)-1-(((S)-morpholin-2-yl)methyl)pyrrolidin-3-yl)thio)-7-oxo-1-azabicyclo[3.2.0]hept-2-ene-2-carboxylic acid

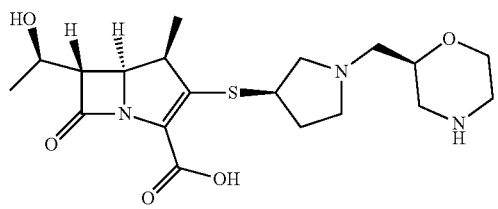 [SMILES: C[C@@H](O)[C@H]1C(=O)N2C(C(=O)O)=C(S[C@@H]3CCN(C[C@@H]4CNCCO4)C3)[C@H](C)[C@H]12]

Step 1: Synthesis of 4-nitrobenzyl (S)-2-(hydroxymethyl)morpholine-4-carboxylate

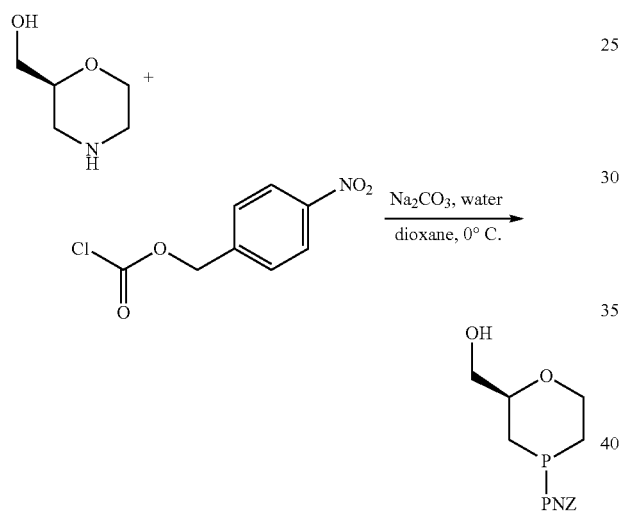

By using the same reaction procedures as described in Step 5 of Example 1, (S)-morpholin-2-ylmethanol (700 mg, 4.56 mmol) was converted to the PNZ carbamate, 1.2 g. ESI-MS m/z 297 (MH)+.

Step 2: Synthesis of 4-nitrobenzyl (S)-2-formylmorpholine-4-carboxylate

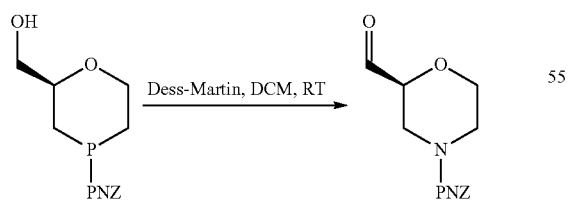

To a solution of 4-nitrobenzyl (S)-2-(hydroxymethyl)morpholine-4-carboxylate (1.0 g, 3.37 mmol) in DCM (30 mL) was added Dess-Martin reagent (2.86 g, 6.75 mmol). The reaction mixture was stirred at rt for 5 h. The resulting mixture was quenched by NaHCO$_3$ (aq), extracted with DCM, dried over Na$_2$SO$_4$, and concentrated under vacuum. The residue was purified by flash chromatography on silica gel (EA/PE=1:10-1:1) to afford a yellow solid, 850 mg. ESI-MS m/z 295 (MH)+.

Step 3: Synthesis of (S)—S-(pyrrolidin-3-yl) ethanethioate

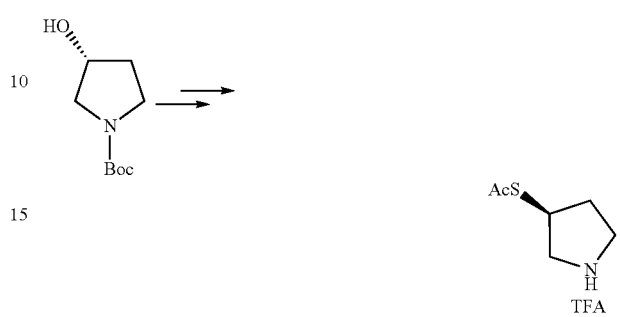

By following the same reaction procedures as described in Steps 1, 2 and 4 of Example 1, (S)-Boc-3-pyrrolidinol was converted to (S)—S-(pyrrolidin-3-yl) ethanethioate, 7.5 g. ESI-MS m/z 146 (MH)+.

Step 4: Synthesis of (4R,5S,6S)-6-((R)-1-hydroxyethyl)-4-methyl-3-(((R)-1-(((S)-morpholin-2-yl)methyl)pyrrolidin-3-yl)thio)-7-oxo-1-azabicyclo[3.2.0]hept-2-ene-2-carboxylic acid

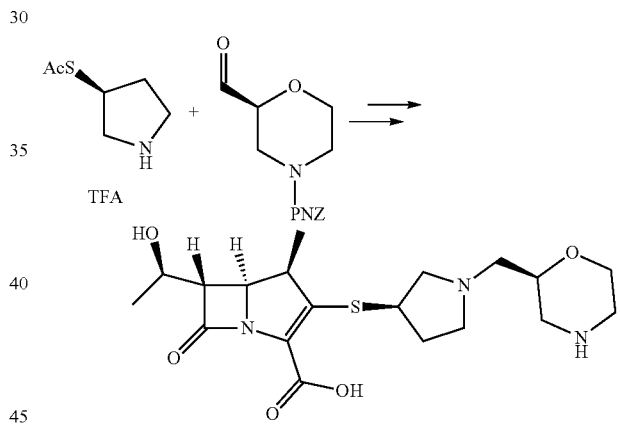

By using the same reaction procedures as described in Step 2 and 3 of Example 42, 4-nitrobenzyl (S)-2-formylmorpholine-4-carboxylate and (S)—S-(pyrrolidin-3-yl) ethanethioate were converted to the target compound, ESI-MS m/z 412 (MH)+.

Example 50: (4R,5S,6S)-6-((R)-1-hydroxyethyl)-4-methyl-3-(((R)-1-(((R)-morpholin-2-yl)methyl)pyrrolidin-3-yl)thio)-7-oxo-1-azabicyclo[3.2.0]hept-2-ene-2-carboxylic acid

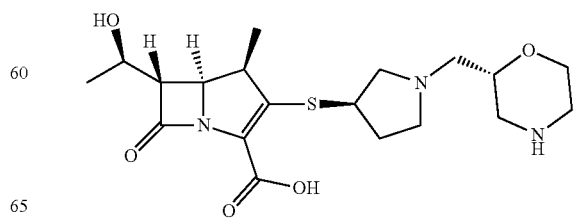

By following the same reaction procedures as described in Example 49, utilizing (R)-morpholin-2-ylmethanol in place of (S)-morpholin-2-ylmethanol as starting material, the target compound was prepared. ESI-MS m/z 481 (MH)⁺.

Example 51: (4R,5S,6S)-6-((R)-1-hydroxyethyl)-4-methyl-7-oxo-3-(((R)-1-(((S)-pyrrolidin-3-yl)methyl)pyrrolidin-3-yl)thio)-1-azabicyclo[3.2.0]hept-2-ene-2-carboxylic acid

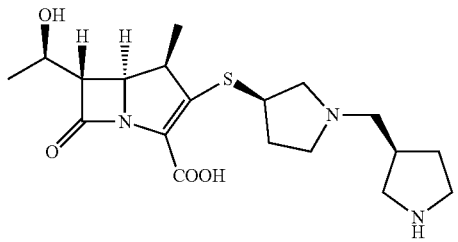 [SMILES: C[C@@H](O)[C@H]1C(=O)N2C(C(=O)O)=C(S[C@@H]3CCN(C[C@H]4CCNC4)C3)[C@H](C)[C@H]12]

By following the same reaction procedures as described in Example 46, except in Step 2 using (S)-pyrrolidin-3-ylmethanol place of (3,3-difluoropiperidin-4-yl)methanol as starting material, the target compound was prepared. ESI-MS m/z 396 (MH)⁺.

Example 52: (4R,5S,6S)-3-(((R)-1-(((R)-1-carbamimidoylpyrrolidin-3-yl)methyl)pyrrolidin-3-yl)thio)-6-((R)-1-hydroxyethyl)-4-methyl-7-oxo-1-azabicyclo[3.2.0]hept-2-ene-2-carboxylic acid

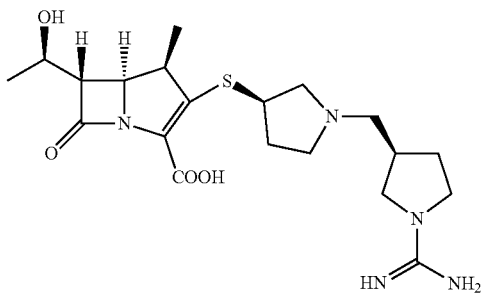 [SMILES: C[C@@H](O)[C@H]1C(=O)N2C(C(=O)O)=C(S[C@@H]3CCN(C[C@H]4CCN(C(=N)N)C4)C3)[C@H](C)[C@H]12]

By following the same reaction procedures as described in Example 35, except in Step 1 using (S)-pyrrolidin-3-ylmethanol instead of 4-piperidinemethanol as starting material, the target compound was prepared. ESI-MS m/z 438 (MH)⁺.

Example 53: (4R,5S,6S)-6-((R)-1-hydroxyethyl)-4-methyl-7-oxo-3-(((R)-1-(((R)-pyrrolidin-3-yl)methyl)pyrrolidin-3-yl)thio)-1-azabicyclo[3.2.0]hept-2-ene-2-carboxylic acid

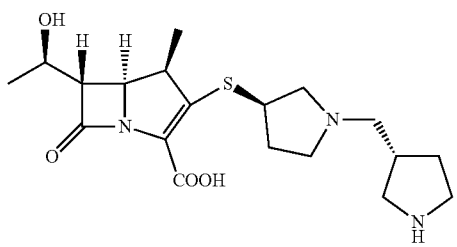 [SMILES: C[C@@H](O)[C@H]1C(=O)N2C(C(=O)O)=C(S[C@@H]3CCN(C[C@@H]4CCNC4)C3)[C@H](C)[C@H]12]

By following the same reaction procedures as described in Example 51, using (R)-pyrrolidin-3-ylmethanol as starting material, the target compound was prepared. ESI-MS m/z 396 (MH)⁺.

Example 54: (4R,5S,6S)-3-(((R)-1-(((S)-1-carbamimidoylpyrrolidin-3-yl)methyl)pyrrolidin-3-yl)thio)-6-((R)-1-hydroxyethyl)-4-methyl-7-oxo-1-azabicyclo[3.2.0]hept-2-ene-2-carboxylic acid

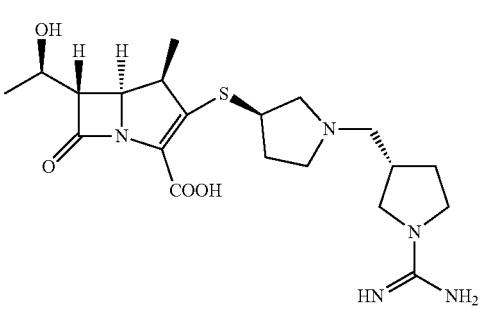 [SMILES: C[C@@H](O)[C@H]1C(=O)N2C(C(=O)O)=C(S[C@@H]3CCN(C[C@@H]4CCN(C(=N)N)C4)C3)[C@H](C)[C@H]12]

By following the same reaction procedures as described in Example 52, using (R)-pyrrolidin-3-ylmethanol as starting material, the target compound was prepared. ESI-MS m/z 438 (MH)⁺.

Example 55: (4R,5S,6S)-6-((R)-1-hydroxyethyl)-4-methyl-7-oxo-3-((1-(piperidin-4-yl)azetidin-3-yl)thio)-1-azabicyclo[3.2.0]hept-2-ene-2-carboxylic acid

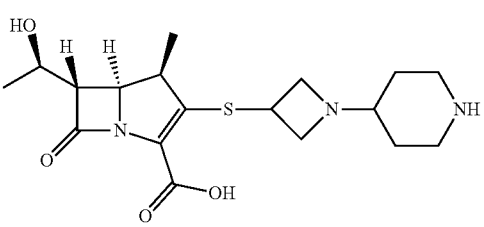 [SMILES: C[C@@H](O)[C@H]1C(=O)N2C(C(=O)O)=C(SC3CN(C4CCNCC4)C3)[C@H](C)[C@H]12]

Step 1: Synthesis of 4-nitrobenzyl 4-oxopiperidine-1-carboxylate

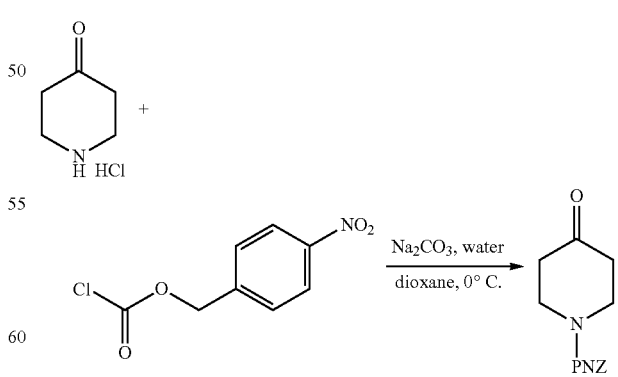

By using the same reaction procedures as described in Step 5 of Example 1, piperidin-4-one hydrochloride (3.9 g, 25.4 mmol) was converted to the PNZ carbamate, 7.3 g. ESI-MS m/z 279 (MH)⁺.

Step 2: Synthesis of (4R,5S,6S)-6-((R)-1-hydroxyethyl)-4-methyl-7-oxo-3-((1-(piperidin-4-yl)azetidin-3-yl)thio)-1-azabicyclo[3.2.0]hept-2-ene-2-carboxylic acid

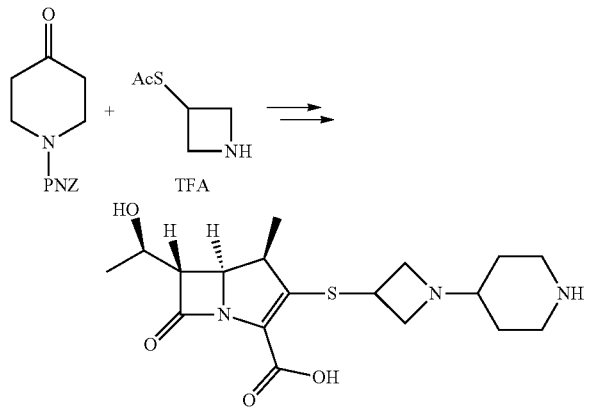

By following the same reaction procedures as described in Steps 2 and 3 of Example 42, 4-nitrobenzyl 4-(3-mercaptoazetidin-1-yl)piperidine-1-carboxylate was converted to the target compound. ESI-MS m/z 382 (MH)+.

Example 56: (4R,5S,6S)-6-((R)-1-hydroxyethyl)-4-methyl-7-oxo-3-((1-(2-(piperidin-4-yl)ethyl)azetidin-3-yl)thio)-1-azabicyclo[3.2.0]hept-2-ene-2-carboxylic acid

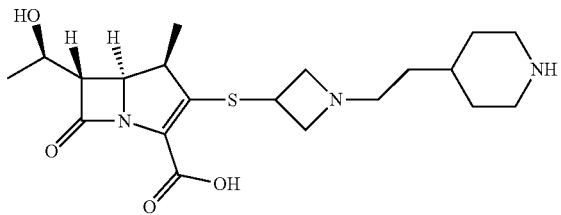 [SMILES: C[C@@H](O)[C@H]1C(=O)N2C(C(=O)O)=C(SC3CN(CCC4CCNCC4)C3)[C@H](C)[C@H]12]

By following the same reaction procedures as described in Steps 2 and 3 of Example 42, 4-nitrobenzyl 4-(2-oxoethyl)piperidine-1-carboxylate (intermediate of Example 11) was converted to the target compound. ESI-MS m/z 410 (MH)+.

Example 57: (4R,5S,6S)-6-((R)-1-hydroxyethyl)-4-methyl-7-oxo-3-((1-(piperidin-3-ylmethyl)azetidin-3-yl)thio)-1-azabicyclo[3.2.0]hept-2-ene-2-carboxylic acid

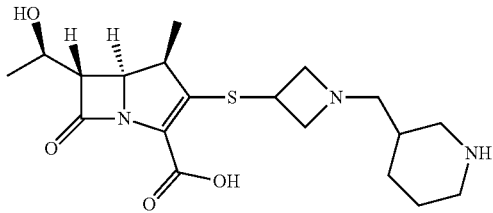 [SMILES: C[C@@H](O)[C@H]1C(=O)N2C(C(=O)O)=C(SC3CN(CC4CCCNC4)C3)[C@H](C)[C@H]12]

By following the same reaction procedures as described in Steps 2 and 3 of Example 42, piperidin-3-ylmethanol 4-nitrobenzyl 3-formylpiperidine-1-carboxylate (intermediate of Example 12) was converted to the target compound. ESI-MS m/z 396 (MH)+.

Example 58: (4R,5S,6S)-6-((R)-1-hydroxyethyl)-4-methyl-7-oxo-3-((1-(((R)-pyrrolidin-3-yl)methyl)azetidin-3-yl)thio)-1-azabicyclo[3.2.0]hept-2-ene-2-carboxylic acid

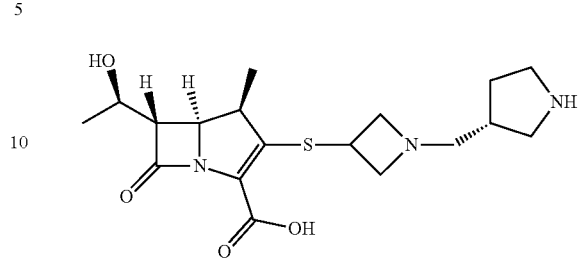

By following the same reaction procedures as described in Steps 2 and 3 of Example 42, 4-nitrobenzyl (R)-3-formylpyrrolidine-1-carboxylate was converted to the target compound. ESI-MS m/z 382 (MH)+.

Example 59: (4R,5S,6S)-6-((R)-1-hydroxyethyl)-4-methyl-7-oxo-3-((1-(((S)-pyrrolidin-3-yl)methyl)azetidin-3-yl)thio)-1-azabicyclo[3.2.0]hept-2-ene-2-carboxylic acid

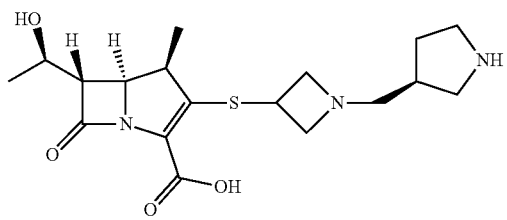 [SMILES: C[C@@H](O)[C@H]1C(=O)N2C(C(=O)O)=C(SC3CN(C[C@H]4CCNC4)C3)[C@H](C)[C@H]12]

By following the same reaction procedures as described in Steps 2 and 3 of Example 42, 4-nitrobenzyl (S)-3-formylpyrrolidine-1-carboxylate (intermediate of Example 51) was converted to the target compound. ESI-MS m/z 382 (MH)+.

Example 60: (4R,5S,6S)-6-((R)-1-hydroxyethyl)-4-methyl-3-((1-(((R)-morpholin-2-yl)methyl)azetidin-3-yl)thio)-7-oxo-1-azabicyclo[3.2.0]hept-2-ene-2-carboxylic acid

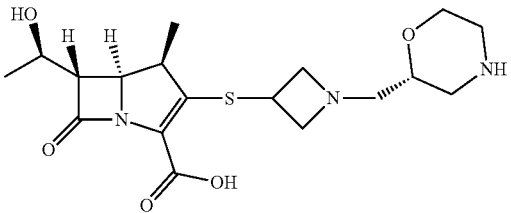 [SMILES: C[C@@H](O)[C@H]1C(=O)N2C(C(=O)O)=C(SC3CN(C[C@H]4CNCCO4)C3)[C@H](C)[C@H]12]

Step 1: Synthesis of 4-nitrobenzyl (R)-2-formylmorpholine-4-carboxylate

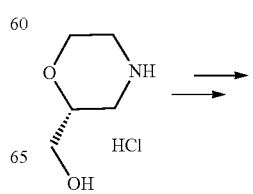

-continued

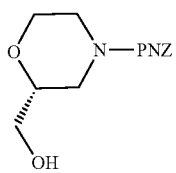

By following the same reaction procedures as described in Steps 1 and 2 of Example 49, utilizing (R)-morpholin-2-ylmethanol instead of (S)-morpholin-2-ylmethanol as starting material, 4-nitrobenzyl (R)-2-formylmorpholine-4-carboxylate was prepared. ESI-MS m/z 295 (MH)$^+$.

Step 2: Synthesis of (4R,5S,6S)-6-((R)-1-hydroxyethyl)-4-methyl-3-((1-(((R)-morpholin-2-yl)methyl)azetidin-3-yl)thio)-7-oxo-1-azabicyclo[3.2.0]hept-2-ene-2-carboxylic acid

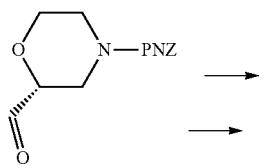

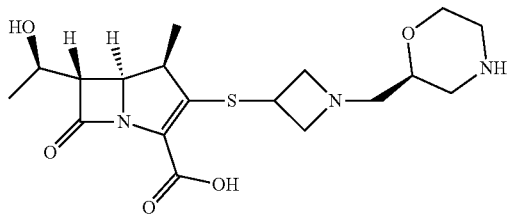 [SMILES: C[C@@H](O)[C@H]1C(=O)N2C(C(=O)O)=C(SC3CN(C[C@@H]4CNCCO4)C3)[C@H](C)[C@H]12]

By following the same reaction procedures as described in Steps 2 and 3 of Example 42, 4-nitrobenzyl (R)-2-formylmorpholine-4-carboxylate was converted to the target compound. ESI-MS m/z 398 (MH)$^+$.

Example 61: (4R,5S,6S)-6-((R)-1-hydroxyethyl)-4-methyl-3-((1-(((S)-morpholin-2-yl)methyl)azetidin-3-yl)thio)-7-oxo-1-azabicyclo[3.2.0]hept-2-ene-2-carboxylic acid By following the same reaction procedures as described in Steps 1 and 2 of Example 60, (S)-morpholin-2-ylmethanol as starting material, the target compound was prepared. ESI-MS m/z 398 (MH)$^+$.

Example 62: (4R,5S,6S)-3-((1-(((1r,4R)-4-aminocyclohexyl)methyl)azetidin-3-yl)thio)-6-((R)-1-hydroxyethyl)-4-methyl-7-oxo-1-azabicyclo[3.2.0]hept-2-ene-2-carboxylic acid

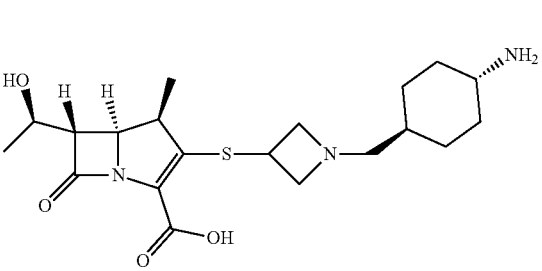 [SMILES: C[C@@H](O)[C@H]1C(=O)N2C(C(=O)O)=C(SC3CN(C[C@H]4CC[C@H](N)CC4)C3)[C@H](C)[C@H]12]

By following the same reaction procedures as described in Steps 2 and 3 of Example 42, 4-nitrobenzyl ((1r,4r)-4-formylcyclohexyl)carbamate (prepared from ((1r,4r)-4-aminocyclohexyl)methanol in a similar manner to 4-nitrobenzyl 4-formylpiperidine-1-carboxylate as described in Step 1 of Example 7) was converted to the target compound. ESI-MS m/z 410 (MH)$^+$.

Example 63: (4R,5S,6S)-6-((R)-1-hydroxyethyl)-4-methyl-7-oxo-3-(((3R)-1-(thiomorpholin-2-ylmethyl)pyrrolidin-3-yl)thio)-1-azabicyclo[3.2.0]hept-2-ene-2-carboxylic acid

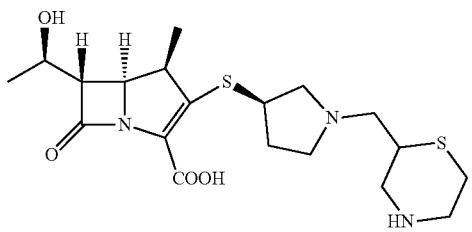 [SMILES: C[C@@H](O)[C@H]1C(=O)N2C(C(=O)O)=C(S[C@@H]3CCN(CC4CNCCS4)C3)[C@H](C)[C@H]12]

Step 1: Synthesis of 4-(((4-nitrobenzyl)oxy)carbonyl)thiomorpholine-2-carboxylic acid

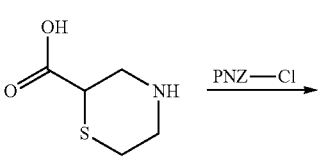

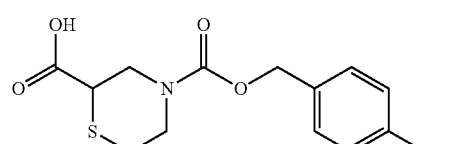

By following the same reaction procedures as described in Step 1 of Example 7, using thiomorpholine-2-carboxylic acid hydrochloride in place of piperidin-4-ylmethanol as starting material, the target compound was prepared. ESI-MS m/z 327 (MH)$^+$.

Step 2: Synthesis of 4-nitrobenzyl 2-(hydroxymethyl)thiomorpholine-4-carboxylate

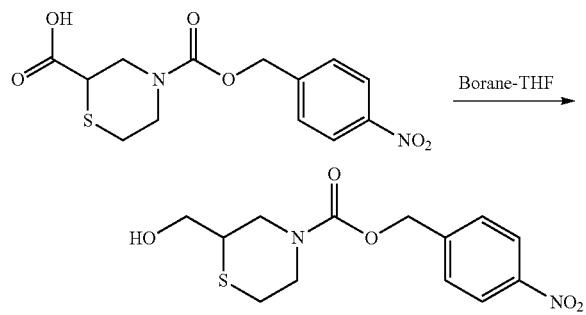

To a solution of 4-(((4-nitrobenzyl)oxy)carbonyl)thiomorpholine-2-carboxylic acid (4.4 g, 13.48 mmol) in THF (10 mL) at 0° C. was added borane-THF (1 M, 40 mL) dropwise. The reaction mixture was stirred at 0° C. for 2 h, quenched with MeOH (10 mL), then concentrated and the residue was purified by flash chromatography on silica gel (petroleum ether/EtOAc, 1:1) to afford the title compound as yellow solid, 3.47 g. ESI-MS m/z 313 (MH)$^+$.

Step 3: Synthesis of 4-nitrobenzyl 2-formylthiomorpholine-4-carboxylate

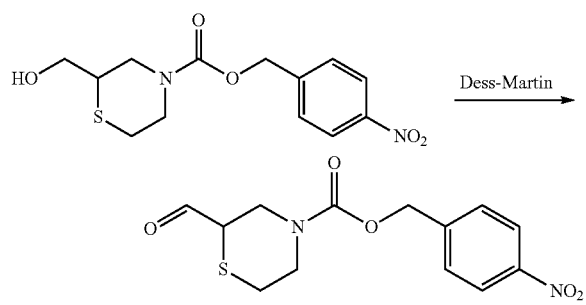

To a mixture of 4-nitrobenzyl 2-(hydroxymethyl)thiomorpholine-4-carboxylate (1.73 g, 5.5 mmol) and NaHCO$_3$ (1.4 g, 16.6 mmol) in DCM (50 mL) at rt was added Dess-Martin reagent (3.0 g, 7.2 mmol) in portions. The mixture was stirred at rt for 3 h, NaHCO$_3$ (saturated, 50 mL) was added, the organic layer was separated, washed with saturated Na$_2$SO$_3$, dried over Na$_2$SO$_4$, concentrationed and then purified by flash column chromatography on silica gel ((petroleum ether/EtOAc, 3:7) to afford the title compound as a colorless oil 1.051 g. ESI-MS m/z 311 (MH)$^+$.

Step 4: Synthesis of (4R,5S,6S)-6-((R)-1-hydroxyethyl)-4-methyl-7-oxo-3-(((3R)-1-(thiomorpholin-2-ylmethyl)pyrrolidin-3-yl)thio)-1-azabicyclo[3.2.0]hept-2-ene-2-carboxylic acid

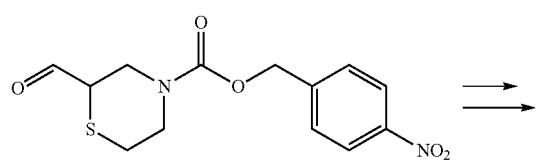

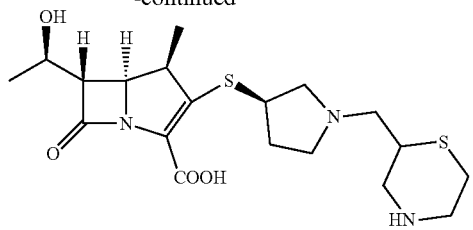

By using the same reaction procedures as described in Steps 3 and 4 of Example 46 using 4-nitrobenzyl 2-formylthiomorpholine-4-carboxylate instead of 4-nitrobenzyl 3,3-difluoro-4-formylpiperidine-1-carboxylate as starting material, the target compound was prepared. ESI-MS m/z 428 (MH)$^+$.

Example 64: (4R,5S,6S)-3-((1-(((1s,4S)-4-aminocyclohexyl)methyl)azetidin-3-yl)thio)-6-((R)-1-hydroxyethyl)-4-methyl-7-oxo-1-azabicyclo[3.2.0]hept-2-ene-2-carboxylic acid

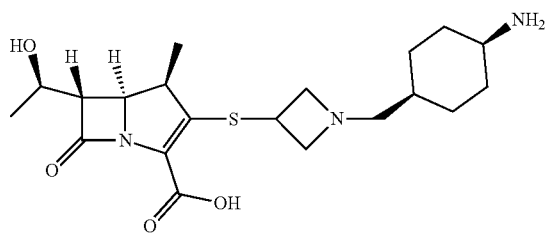 [SMILES: C[C@@H](O)[C@H]1C(=O)N2C(C(=O)O)=C(SC3CN(C[C@H]4CC[C@@H](N)CC4)C3)[C@H](C)[C@H]12]

By following the same reaction procedures as described in Steps 2 and 3 of Example 42, 4-nitrobenzyl ((1s,4s)-4-formylcyclohexyl)carbamate (prepared from ((1s,4S)-4-aminocyclohexyl)methanol in a similar manner to 4-nitrobenzyl 4-formylpiperidine-1-carboxylate as described in Step 1 of Example 7) was converted to the target compound. ESI-MS m/z 410 (MH)$^+$.

Example 65: (4R,5S,6S)-3-(((3R)-1-((3,3-dimethylpiperidin-4-yl)methyl)pyrrolidin-3-yl)thio)-6-((R)-1-hydroxyethyl)-4-methyl-7-oxo-1-azabicyclo[3.2.0]hept-2-ene-2-carboxylic acid

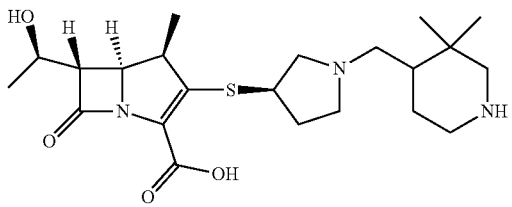 [SMILES: C[C@@H](O)[C@H]1C(=O)N2C(C(=O)O)=C(S[C@@H]3CCN(CC4CCNCC4(C)C)C3)[C@H](C)[C@H]12]

Step 1: Synthesis of 4-methyl 1-(4-nitrobenzyl) 3,3-dimethylpiperidine-1,4-dicarboxylate

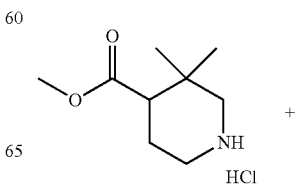

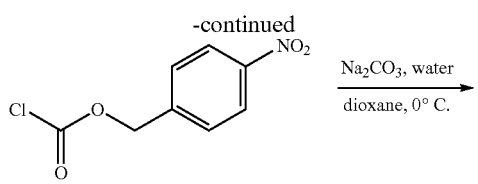

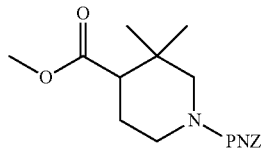

By using the same reaction procedures as described in Step 5 of Example 1, methyl 3,3-dimethylpiperidine-4-carboxylate hydrochloride (1.0 g, 4.8 mmol) instead of piperidin-4-one hydrochloride was converted to the PNZ carbamate, 1.48 g. ESI-MS m/z 351 (MH)⁺.

Step 2: Synthesis of 4-nitrobenzyl 4-(hydroxymethyl)-3,3-dimethylpiperidine-1-carboxylate

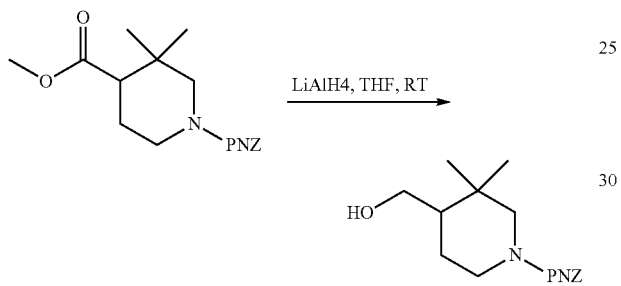

To a solution of 4-methyl 1-(4-nitrobenzyl) 3,3-dimethylpiperidine-1,4-dicarboxylate (1.48 g, 4.2 mmol) in THF (15 mL) was added LiAlH₄ (320 mg, 8.4 mmol) portionwise at 0° C. The reaction mixture was stirred at rt for 6 h. The resulting mixture was quenched by NaOH (aq, 10%), filtered through a pad of celite. The filtrate was extracted with EtOAc, dried over Na₂SO₄, and concentrated under vacuum. The residue was purified by flash chromatography on silica gel (EA/PE=1:10-1:1) to afford a yellow solid, 650 mg. ESI-MS m/z 323 (MH)⁺.

Step 3: Synthesis of (4R,5S,6S)-3-(((3R)-1-((3,3-dimethylpiperidin-4-yl)methyl)pyrrolidin-3-yl)thio)-6-((R)-1-hydroxyethyl)-4-methyl-7-oxo-1-azabicyclo[3.2.0]hept-2-ene-2-carboxylic acid

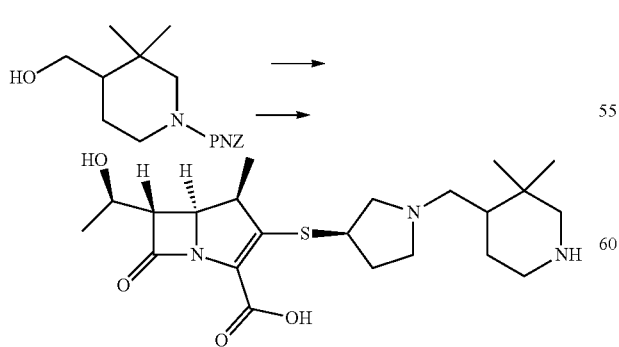

By following the same reaction procedures as described in Steps 3 and 4 of Example 47, 4-nitrobenzyl 4-(hydroxymethyl)-3,3-dimethylpiperidine-1-carboxylate was converted to the target compound. ESI-MS m/z 438 (MH)⁺.

Example 66: (4R,5S,6S)-6-((R)-1-hydroxyethyl)-4-methyl-3-((1-(((1s,4S)-4-(methylamino)cyclohexyl)methyl)azetidin-3-yl)thio)-7-oxo-1-azabicyclo[3.2.0]hept-2-ene-2-carboxylic acid

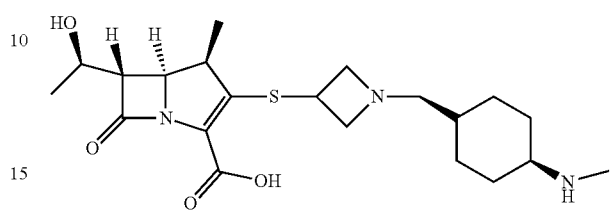

Step 1: Synthesis of methyl (1s,4s)-4-(methylamino)cyclohexane-1-carboxylate

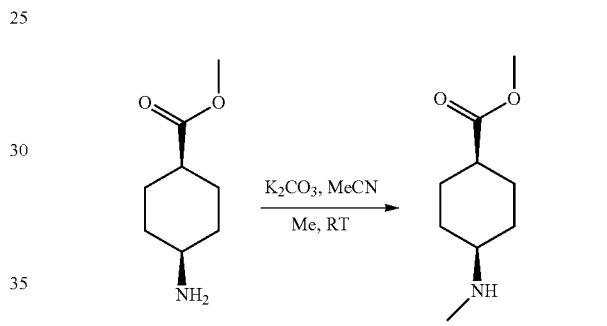

To a solution of methyl (1s,4s)-4-aminocyclohexane-1-carboxylate (2 g, 10 mmol) in MeCN (30 mL) was added K₂CO₃ (2.85 g, 20 mmol), followed by MeI (1.61 g, 11 mmol) dropwise at 0° C. The reaction mixture was stirred at rt for 6 h. The resulting mixture was quenched by water, extracted with EtOAc, dried over Na₂SO₄, and concentrated under vacuum to afford a white solid, 1.2 g. ESI-MS m/z 172 (MH)⁺.

Step 2: Synthesis of 4-nitrobenzyl ((1s,4s)-4-(hydroxymethyl)cyclohexyl)(methyl)carbamate

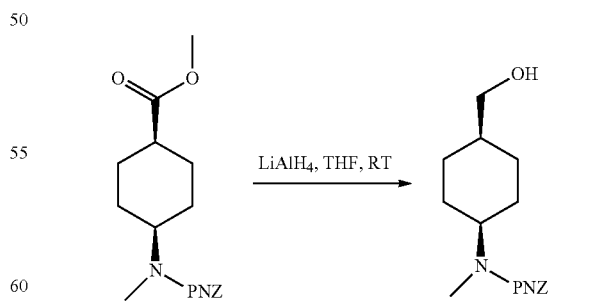

By following the same reaction procedures as described in Step 2 of Example 65, methyl (1s,4s)-4-(methylamino)cyclohexane-1-carboxylate was converted to 4-nitrobenzyl ((1s,4s)-4-(hydroxymethyl) cyclohexyl)(methyl)carbamate. ESI-MS m/z 323 (MH)⁺.

Step 3: Synthesis of 4-nitrobenzyl ((1s,4s)-4-formylcyclohexyl)(methyl)carbamate

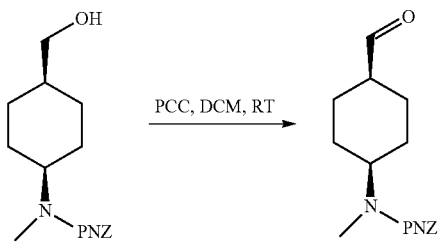

By following the same reaction procedures as described in Steps 1, Part (ii) of Example 7, 4-nitrobenzyl ((1s,4s)-4-(hydroxymethyl) cyclohexyl)(methyl)carbamate was converted to the crude aldehyde product, 5 g. ESI-MS m/z 321 (MH)$^+$.

Step 4: Synthesis of azetidine-3-thiol

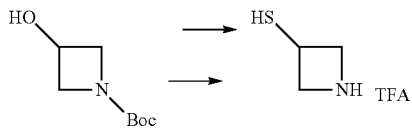

By following the same reaction procedures as described in Steps 1, 2, 3 and 4 of Example 1, tert-butyl 3-hydroxyazetidine-1-carboxylate was converted to azetidine-3-thiol, 7 g. ESI-MS m/z 90 (MH)$^+$.

Step 5: Synthesis of (4R,5S,6S)-6-((R)-1-hydroxyethyl)-4-methyl-3-((1-(((1s,4S)-4-(methylamino)cyclohexyl)methyl)azetidin-3-yl)thio)-7-oxo-1-azabicyclo[3.2.0]hept-2-ene-2-carboxylic acid

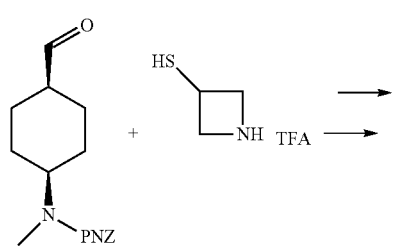

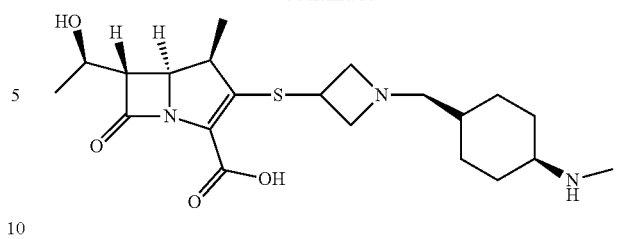

By following the same reaction procedures as described in Steps 6, 7 and 8 of Example 1, 4-nitrobenzyl ((1s,4s)-4-formylcyclohexyl)(methyl)carbamate and azetidine-3-thiol were converted to the target compound, 12 mg. ESI-MS m/z 424 (MH)$^+$.

Example 67: (4R,5S,6S)-3-((1-(((1r,4R)-4-guanidinocyclohexyl)methyl)azetidin-3-yl)thio)-6-((R)-1-hydroxyethyl)-4-methyl-7-oxo-1-azabicyclo[3.2.0]hept-2-ene-2-carboxylic acid

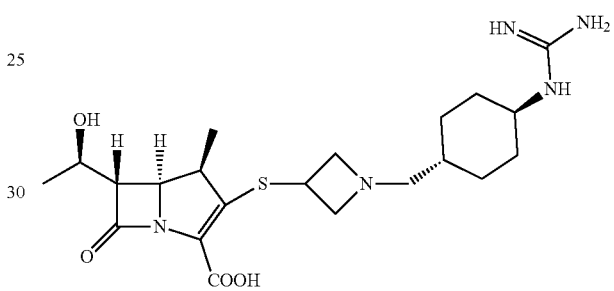

Step 1: Synthesis of Carbamic acid, N-[(methylthio)[[(4-nitrophenylmethoxy)carbonyl]amino]methylene]-, (4-nitrophenyl)methyl ester

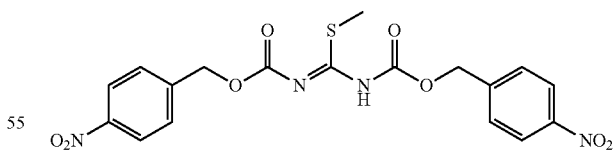

A solution of methyl carbamimidothioate (10 g, 71.8 mmol) and NaOH (6.25N, 5.7 mL) in DCM (600 mL) was stirred at 0° C. for 10 min, NaOH (1N, 150 mL) and PNZ—Cl (31.7 g in DCM-(200 mL) were both added to the methyl carbamimidothioate solution dropwise, while maintaining pH=11. The reaction mixture was stirred at rt. for 24 h, the organic layer was separated, washed with brine, dried over Na$_2$SO$_4$, and concentrated to afford the title compound as white solid, 27.49 g. ESI-MS m/z 449 (MH)$^+$.

Step 2: Synthesis of carbamic acid, [[(4-hydroxymethyl)cyclohexyl]carbonimidoyl]bis-, bis(4-nitrophenylmethyl) ester

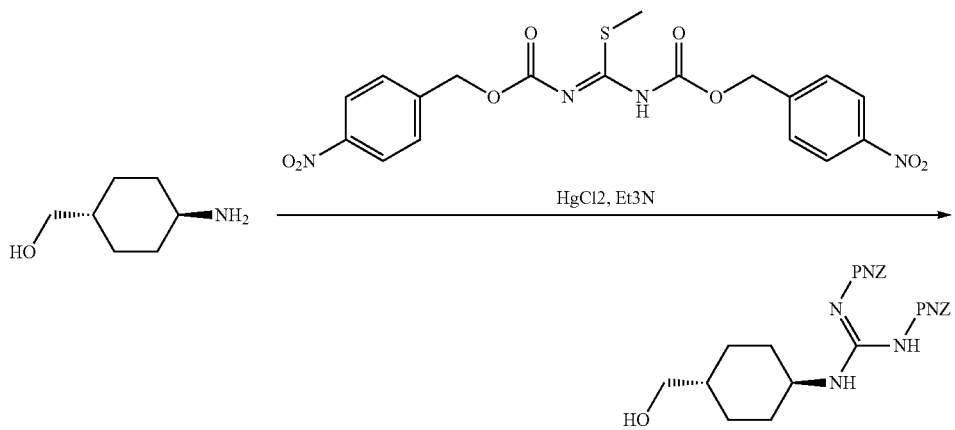

To a mixture of (4-aminocyclohexyl)methanol hydrochloride hydrate (911.13 mg, 5.5 mmol) and the resulting product from Step 1 (2.24 g, 5 mmol), and Et$_3$N (2.0 g, 20 mmol) in DCM (100 mL) at rt was added HgCl$_2$ (1.5 g, 5.5 mmol) in portions, then the reaction mixture was stirred at rt overnight. The mixture was filtered, the filtrate was concentrated to a residue, which was purified by flash chromatography on silica gel (DCM/MeOH, 95/5) to afford the title compound as white solid, 2.437 g. ESI-MS m/z 530 (MH)$^+$.

Step 3: Synthesis of carbamic acid, [[(4-formyl)cyclohexyl]carbonimidoyl]bis-, bis(4-nitrophenylmethyl) ester

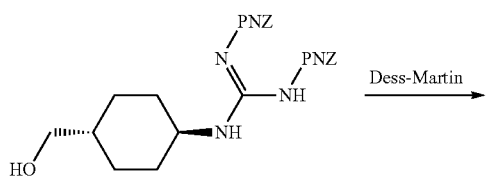

By using the same reaction procedures as described in Step 3 of Example 63, the target compound was prepared from the above product. ESI-MS m/z 528 (MH)$^+$.

Step 4: Synthesis of carbamic acid, [[(4-(3-mercaptoazetidin-1-yl)cyclohexyl]carbonimidoyl]bis-, bis(4-nitrophenylmethyl) ester

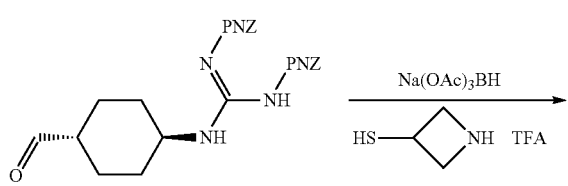

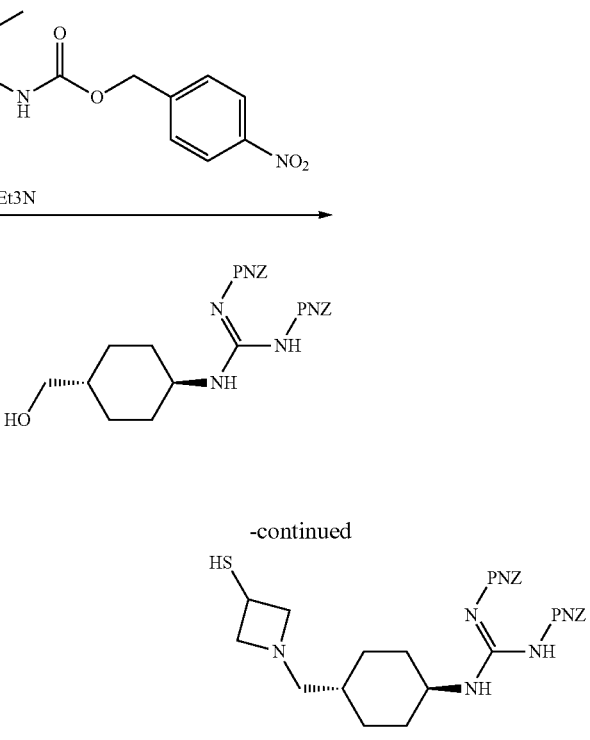

By using the same reaction procedures as described in Step 6 of Example 1, the target compound was prepared from the above aldehyde and azetidine-3-thiol. ESI-MS m/z 601 (MH)$^+$.

Step 5: Synthesis of (4R,5S,6S)-3-((1-(((1r,4R)-4-guanidinocyclohexyl)methyl)azetidin-3-yl)thio)-6-((R)-1-hydroxyethyl)-4-methyl-7-oxo-1-azabicyclo[3.2.0]hept-2-ene-2-carboxylic acid

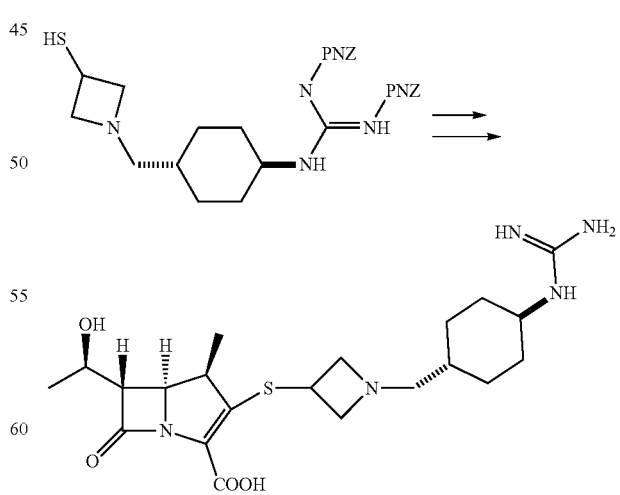

By following the same reaction procedures as described in Steps 7 and 8 of Example 1, the above product was converted to the target compound. ESI-MS m/z 452 (MH)$^+$.

Example 68: (4R,5S,6S)-6-((R)-1-hydroxyethyl)-4-methyl-3-((1-(((1r,4R)-4-(methylamino)cyclohexyl)methyl)azetidin-3-yl)thio)-7-oxo-1-azabicyclo[3.2.0]hept-2-ene-2-carboxylic acid

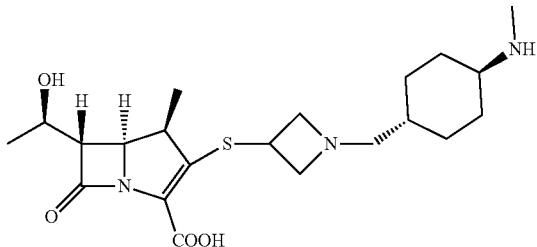 [SMILES: CN[C@H]1CC[C@H](CN2CC(SC3=C(C(=O)O)N4C(=O)[C@H]([C@@H](C)O)[C@H]4[C@H]3C)C2)CC1]

Step 1: Synthesis of (4-(methylamino)cyclohexyl)methanol

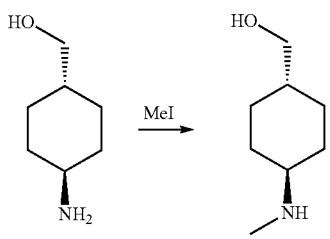

To a mixture of (4-aminocyclohexyl)methanol (6.62 g, 40 mmol) and $K_2CO_3$ (11.04 g, 80 mmol) was in MeCN (60 mL) at 0° C. was added MeI (5.6 g, 40 mmol) dropwise, the reaction mixture was stirred at rt for 7 h, filtered, and the filtrate was concentrated to afford the crude title compound. ESI-MS m/z 144 (MH)+.

Step 2: Synthesis of (4R,5S,6S)-6-((R)-1-hydroxyethyl)-4-methyl-3-((1-(((1r,4R)-4-(methylamino)cyclohexyl)methyl)azetidin-3-yl)thio)-7-oxo-1-azabicyclo[3.2.0]hept-2-ene-2-carboxylic acid

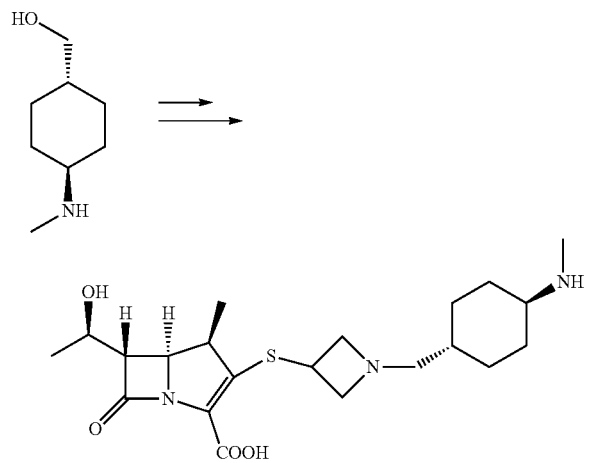

By following the same reaction procedures as described in Step 5 of Example 1, and Steps 3, 4, and 5 of Example 66, the above product was converted to the target compound. ESI-MS m/z 424 (MH)+.

Example 69: (4R,5S,6S)-3-((1-(((1r,4R)-4-(ethylamino)cyclohexyl)methyl)azetidin-3-yl)thio)-6-((R)-1-hydroxyethyl)-4-methyl-7-oxo-1-azabicyclo[3.2.0]hept-2-ene-2-carboxylic acid

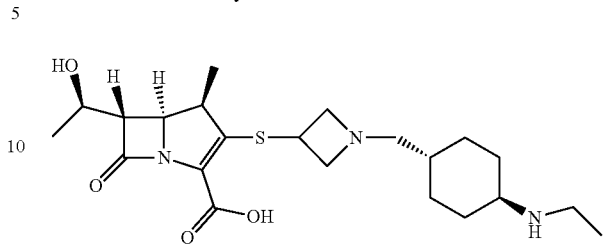

Step 1: Synthesis of methyl (1r,4r)-4-(ethylamino)cyclohexane-1-carboxylate

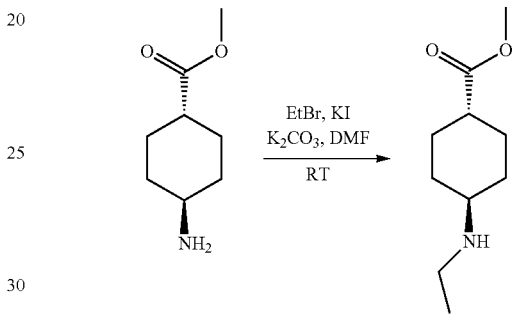

To a solution of methyl (1r,4r)-4-aminocyclohexane-1-carboxylate (3.2 g, 16.5 mmol) in DMF (30 mL) was added $K_2CO_3$ 6.8 g, 49.5 mmol) and KI (1.6 g, 9.9 mmol), followed by EtBr (2.2 g, 19.8 mmol) dropwise at 0° C. The reaction mixture was stirred at rt for 12 h. The resulting mixture was quenched by water, extracted with EtOAc, dried over $Na_2SO_4$, and concentrated under vacuum to afford a yellow oil, 2.5 g. ESI-MS m/z 186 (MH)+.

Step 2: Synthesis of (4R,5S,6S)-3-((1-(((1r,4R)-4-(ethylamino)cyclohexyl)methyl)azetidin-3-yl)thio)-6-((R)-1-hydroxyethyl)-4-methyl-7-oxo-1-azabicyclo[3.2.0]hept-2-ene-2-carboxylic acid

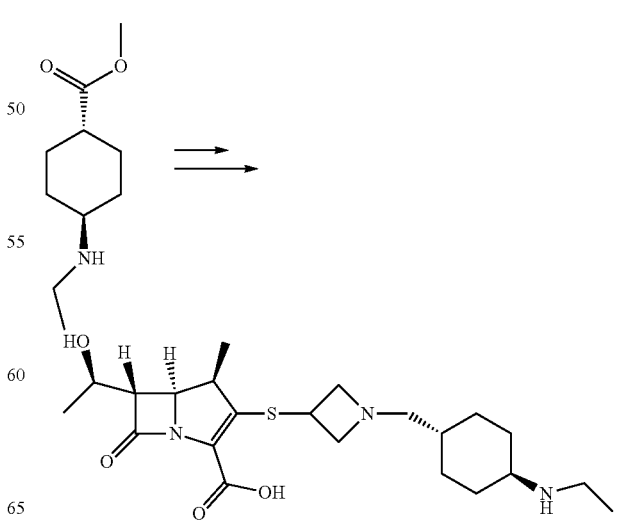

By following the same reaction procedures as described in Steps 2, 3, 4 and 5 of Example 66, methyl (1r,4r)-4-(ethylamino)cyclohexane-1-carboxylate was converted to the target compound, 20 mg. ESI-MS m/z 438 (MH)+.

Example 70: (4R,5S,6S)-3-((1-(((1s,4S)-4-(ethylamino)cyclohexyl)methyl)azetidin-3-yl)thio)-6-((R)-1-hydroxyethyl)-4-methyl-7-oxo-1-azabicyclo[3.2.0]hept-2-ene-2-carboxylic acid

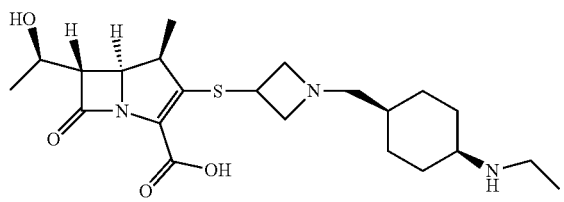 [SMILES: CCN[C@H]1CC[C@@H](CN2CC(SC3=C(C(=O)O)N4C(=O)[C@H]([C@@H](C)O)[C@H]4[C@H]3C)C2)CC1]

By following the same reaction procedures as described in Steps 1 and 2 of Example 69, methyl (1s,4s)-4-aminocyclohexane-1-carboxylate was converted to the target compound, 15 mg. ESI-MS m/z 438 (MH)+.

Example 71: (4R,5S,6S)-3-((1-(2-(1-carbamimidoylpiperidin-4-yl)ethyl)azetidin-3-yl)thio)-6-((R)-1-hydroxyethyl)-4-methyl-7-oxo-1-azabicyclo[3.2.0]hept-2-ene-2-carboxylic acid

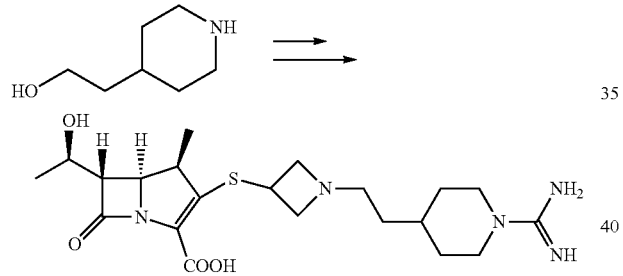

By using the same reaction procedures as described in Example 67 using 2-(piperidin-4-yl)ethan-1-ol instead of (4-aminocyclohexyl)methanol as starting material, the target compound was prepared. ESI-MS m/z 452 (MH)+.

Example 72: (4R,5S,6S)-6-((R)-1-hydroxyethyl)-4-methyl-3-((1-(((1r,4R)-4-(1-methylguanidino)cyclohexyl)methyl)azetidin-3-yl)thio)-7-oxo-1-azabicyclo[3.2.0]hept-2-ene-2-carboxylic acid

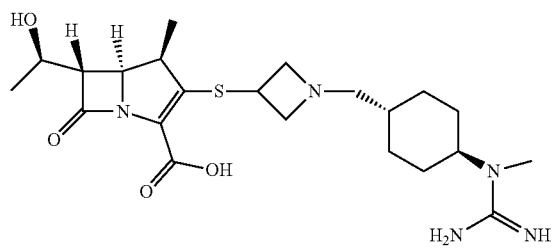 [SMILES: C[C@@H](O)[C@H]1C(=O)N2C(C(=O)O)=C(SC3CN(C[C@H]4CC[C@H](N(C)C(=N)N)CC4)C3)[C@H](C)[C@H]12]

Step 1: Synthesis of methyl (1r,4r)-4-(methylamino)cyclohexane-1-carboxylate

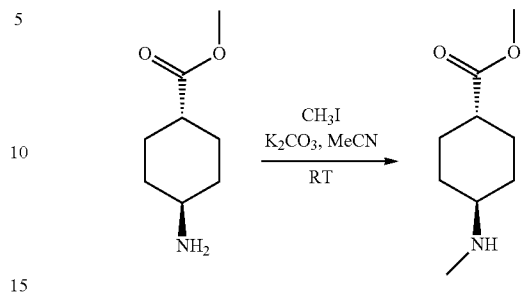

By following the same reaction procedures as described in Step 1 of Example 66, methyl (1r,4r)-4-aminocyclohexane-1-carboxylate was converted to methyl (1r,4r)-4-(methylamino)cyclohexane-1-carboxylate, 4.2 g. ESI-MS m/z 172 (MH)+.

Step 2: Synthesis of methyl (1r,4r)-4-((E)-1-methyl-2,3-bis(((4-nitrobenzyl)oxy)carbonyl)guanidino) cyclohexane-1-carboxylate

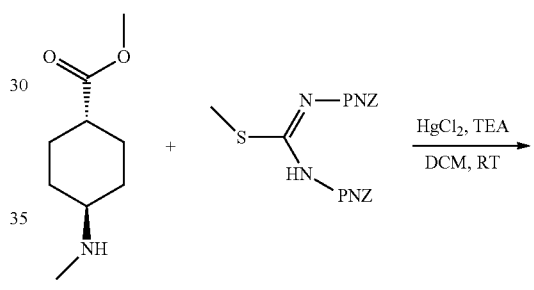

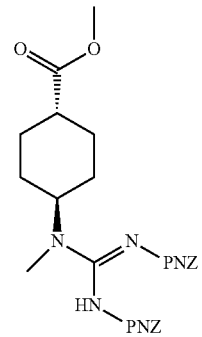

To a solution of methyl (1r,4r)-4-(methylamino)cyclohexane-1-carboxylate (3.88 g, 22.5 mmol) in DCM (150 mL) was added 2-methyl-2-thiopseudourea protected by PNZ (10.1 g, 22.5 mmol), thiethylamine (9.77 mL, 67.5 mmol), and HgCl2 (6.13 g, 24.7 mmol). The reaction mixture was stirred at rt overnight, filtered, the filtrate was washed with saturated aqueous NH4Cl, water and brine, dried over Na2SO4, concentrated in vacuo. The residue was purified by flash chromatography on silica gel (PE/EA=10:1-2:1) to afford the product, 2.4 g. ESI-MS m/z 572 (MH)+.

Step 3: Synthesis of (4R,5S,6S)-6-((R)-1-hydroxyethyl)-4-methyl-3-((1-(((1r,4R)-4-(1-methylguanidino)cyclohexyl)methyl)azetidin-3-yl)thio)-7-oxo-1-azabicyclo[3.2.0]hept-2-ene-2-carboxylic acid

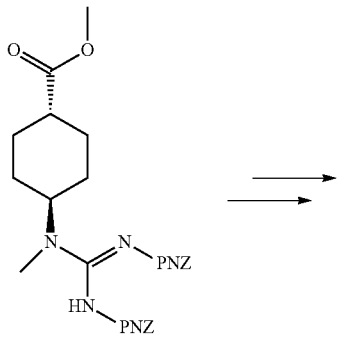

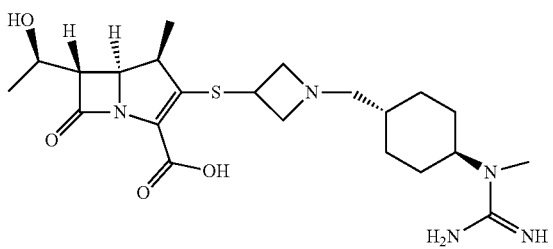

By following the same reaction procedures as described in Steps 2 (ii), 3, 4 and 5 of Example 66, methyl (1r,4r)-4-((E)-1-methyl-2,3-bis(((4-nitrobenzyl)oxy)carbonyl)guanidino)cyclohexane-1-carboxylate was converted to the target compound, 10 mg. ESI-MS m/z 466 (MH)+.

Example 73: (4R,5S,6S)-3-((1-(((1s,4S)-4-guanidinocyclohexyl)methyl)azetidin-3-yl)thio)-6-((R)-1-hydroxyethyl)-4-methyl-7-oxo-1-azabicyclo[3.2.0]hept-2-ene-2-carboxylic acid

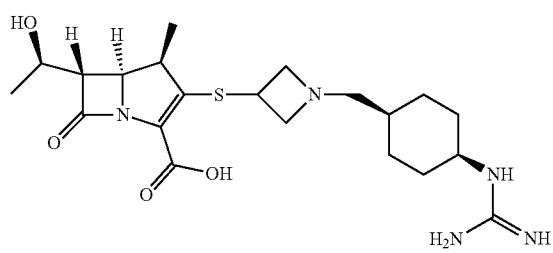 [SMILES: C[C@@H](O)[C@H]1C(=O)N2C(C(=O)O)=C(SC3CN(C[C@H]4CC[C@@H](NC(=N)N)CC4)C3)[C@H](C)[C@H]12]

By following the same reaction procedures as described in Steps 2 and 3 of Example 72, methyl (1s,4s)-4-aminocyclohexane-1-carboxylate hydrochloride was converted to the target compound, 10 mg. ESI-MS m/z 452 (MH)+.

Example 74: (4R,5S,6S)-6-((R)-1-hydroxyethyl)-4-methyl-3-((1-(((1s,4S)-4-(1-methylguanidino)cyclohexyl)methyl)azetidin-3-yl)thio)-7-oxo-1-azabicyclo[3.2.0]hept-2-ene-2-carboxylic acid

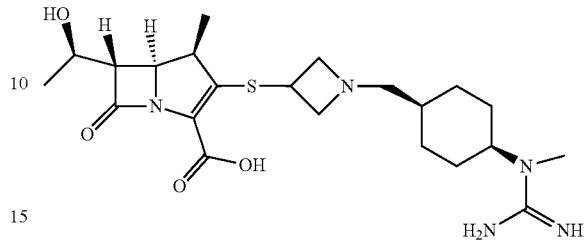

By following the same reaction procedures as described in Steps 1, 2 and 3 of Example 72, methyl (1s,4s)-4-aminocyclohexane-1-carboxylate hydrochloride was converted to the target compound, 10 mg. ESI-MS m/z 466 (MH)+.

Example A1: Parenteral Composition of a Compound Described Herein, or a Pharmaceutically Acceptable Salt, Solvate, or Stereoisomer Thereof To prepare a parenteral pharmaceutical composition suitable for administration by injection, 100 mg of a compound of Formula (I), Formula (Ia), Formula (Ia-1), Formula (II), Formula (IIa), Formula (IIa-1), Formula (III), Formula (IIIa), Formula (IIIa-1), or a pharmaceutically acceptable salt, solvate, or stereoisomer thereof, or a water soluble pharmaceutically acceptable salt thereof, is dissolved in DMSO and then mixed with 10 mF of 0.9% sterile saline solution. The mixture is incorporated into a dosage unit suitable for administration by injection.

Example A2: Oral Composition of a Compounds Described Herein, or a Pharmaceutically Acceptable Salt, Solvate, or Stereoisomer Thereof To prepare a pharmaceutical composition for oral delivery, 400 mg of compound described herein, or a pharmaceutically acceptable salt, solvate, or stereoisomer thereof and the following ingredients are mixed intimately and pressed into single scored tablets.

Tablet Formulation

| Ingredient | Quantity per tablet (mg) |
| --- | --- |
| compound | 400 |
| cornstarch | 50 |
| croscarmellose sodium | 25 |
| lactose | 120 |
| magnesium stearate | 5 |

The following ingredients are mixed intimately and loaded into a hard-shell gelatin capsule.

Capsule Formulation

| Ingredient | Quantity per capsule (mg) |
|---|---|
| compound | 200 |
| lactose spray dried | 148 |
| magnesium stearate | 2 |

Biological Examples

Example B1: In vitro Antibacterial Assays

To determine the ability of test compounds to potentiate the inhibition of the growth of bacterial strains, classic cell-based broth microdilution MIC assays were employed. MIC assays are performed according to CLSI methods except where otherwise noted (CLSI, 2011 and CLSI, 2009). The reference strains S. aureus ATCC 29213 (methicillin sensitive), S. aureus ATCC 33591 (methicillin-resistant), E. coli ATCC 25922 (wild-type/QC strain), P. aeruginosa ATCC 27853 (wild-type/QC strain), and the clinical isolate P. aeruginosa PA 8 were used to determine the ability of the exemplary carbapenem compounds to inhibit bacterial growth. An expanded panel of methicillin resistance S. aureus (MRSA) and Pseudomonas was also used to determine the ability of exemplary carbapenem compounds to inhibit bacterial growth across a broader representation of those species. To determine activity in MRSA and in addition to S. aureus ATCC 33591, S. aureus USA 300, USA 400 and USA 600, some of the most common clones found to cause human infection, were also used. To further gauge the impact on the carbapenem compounds due to various resistance mechanisms in Pseudomonas, the following strains were included: P. aeruginosa 35151 (hyper-permeable strain), P. aeruginosa AmexAB-OprM (an efflux pump knockout), and P. aeruginosa PA 3 (a clinical isolate of reduced carbapenem susceptibility). Briefly, cryo-preserved bacterial cultures of clinical strains are streaked for isolation on appropriate agar medium, in this case Mueller Hinton II agar. Following incubation to allow formation of colonies, these plates are sealed with parafilm and stored refrigerated for up to two weeks. For preparation of assay inocula and to ensure low variability, at least 5 colonies are picked from the agar plates with an inoculating loop and aseptically transferred to a culture tube containing 3 mL of Mueller-Hinton Broth (supplemented with divalent cations to required levels based on Manufacturers' specification). The broth culture is grown for 3-5 hours at 37° C. with shaking at 200 rpm. Meanwhile, 2-fold serial dilutions of test compounds are conducted in a 96 well plate with a final volume of 75 µL per well at 2-fold the final desired concentration. After the dilution plates are set up the growing cultures are then diluted in a cuvette containing MH II broth and the optical density is measured at 600 nm. Inocula are diluted such that 75 µL of this culture in Mueller-Hinton Broth results in a starting bacterial concentration of $5 \times 10^5$ CFU/mL when added to the dilution plates. The plates are incubated 16-20 hours at 37° C. The MIC is read visually as the lowest concentration well with no bacterial growth.

Representative results are shown in Tables 3, 4, and 5 where A represents an MIC>32 µg/mL, B represents an MIC between 8 and 32 µg/mL inclusive, C represents an MIC between 1 and 4 µg/mL inclusive, and D represents an MIC of <1 µg/mL. NT=Not Tested.

TABLE 3

Inhibition of bacterial growth. Minimum Inhibitory Concentrations of Exemplary Compounds.

| Example | S. aureus 29213 (MSSA) MIC (µg/mL) | S. aureus 33591 (MRSA) MIC (µg/mL) | E. coli 25922 MIC (µg/mL) | P. aeruginosa 27853 MIC (µg/mL) | P. aeruginosa PA8 MIC (µg/mL) |
|---|---|---|---|---|---|
| 1 | D | B | D | C | NT |
| 2 | D | B | D | C | A |
| 3 | NT | B | D | B | B |
| 4 | D | B | D | C | B |
| 5 | D | B | D | C | NT |
| 6 | D | B | D | C | C |
| 7 | D | C | D | C | C |
| 8 | D | C | D | B | B |
| 9 | D | B | D | B | B |
| 10 | D | B | D | B | NT |
| 11 | D | C | D | C | C |
| 12 | D | B | D | B | NT |
| 13 | D | B | D | B | NT |
| 14 | D | B | D | B | NT |
| 15 | D | B | D | B | NT |
| 16 | D | B | D | B | NT |
| 17 | NT | B | D | C | C |
| 18 | NT | B | D | C | C |
| 19 | C | B | D | C | C |
| 20 | NT | B | D | C | C |
| 21 | NT | B | D | C | C |
| 22 | C | B | D | C | C |
| 23 | NT | B | D | C | C |
| 24 | C | B | D | C | B |
| 25 | NT | B | D | B | C |
| 26 | NT | A | D | C | C |
| 27 | NT | B | D | C | C |
| 28 | NT | B | D | B | C |
| 29 | NT | B | D | B | C |
| 30 | NT | B | D | B | C |
| 31 | NT | C | D | B | B |

TABLE 3-continued

Inhibition of bacterial growth. Minimum Inhibitory Concentrations of Exemplary Compounds.

| Example | S. aureus 29213 (MSSA) MIC (μg/mL) | S. aureus 33591 (MRSA) MIC (μg/mL) | E. coli 25922 MIC (μg/mL) | P. aeruginosa 27853 MIC (μg/mL) | P. aeruginosa PA8 MIC (μg/mL) |
|---|---|---|---|---|---|
| 32 | NT | B | B | B | B |
| 33 | NT | B | D | C | C |
| 34 | NT | C | D | B | B |
| 35 | C | C | D | C | C |
| 36 | NT | A | D | B | B |
| 37 | NT | B | D | C | B |
| 38 | NT | B | D | B | B |

TABLE 4

Inhibition of bacterial growth for methicillin-resistant S. aureus and E. coli strains. Minimum Inhibitory Concentrations of exemplary compounds (MIC, in μg/mL).

| Example | S. aureus 33591 | S. aureus USA300 | S. aureus USA400 | S. aureus USA600 | E. coli 25922 |
|---|---|---|---|---|---|
| 35 | C | D | C | D | D |
| 36 | A | B | B | NT | D |
| 37 | B | B | C | NT | D |
| 38 | B | B | C | NT | D |
| 39 | C | C | NT | C | D |
| 40 | B | C | NT | C | D |
| 41 | B | C | NT | C | D |
| 42 | C | C | C | C | D |
| 43 | B | C | NT | C | D |
| 44 | B | C | C | NT | C |
| 45 | C | C | NT | C | D |
| 46 | B | C | NT | C | D |
| 47 | B | C | NT | C | D |
| 48 | B | C | NT | C | D |
| 49 | B | C | NT | C | D |
| 50 | C | C | NT | C | D |
| 51 | C | C | NT | C | D |
| 52 | C | D | NT | D | D |
| 53 | C | C | NT | C | D |
| 54 | C | D | NT | C | D |
| 55 | C | C | NT | D | D |
| 56 | C | C | NT | C | D |
| 57 | B | C | NT | C | D |
| 58 | C | C | NT | C | D |
| 59 | C | C | NT | C | D |
| 60 | B | C | NT | C | D |
| 61 | B | C | NT | C | D |
| 62 | C | C | NT | D | D |
| 63 | C | C | NT | C | D |
| 64 | C | D | NT | D | D |
| 65 | C | C | NT | C | D |
| 66 | C | C | NT | C | D |
| 67 | C | C | NT | D | D |
| 68 | C | C | NT | C | D |
| 69 | C | C | NT | C | D |
| 70 | C | C | NT | C | D |
| 71 | C | C | NT | D | D |
| 72 | C | C | NT | D | D |
| 73 | C | C | NT | D | D |
| 74 | C | C | NT | C | D |

TABLE 5

Inhibition of bacterial growth for *P. aeruginosa* strains. Minimum Inhibitory Concentrations of exemplary compounds (MIC, in µg/mL).

| Example | *P. aeruginosa* 27853 | *P. aeruginosa* 35151 | *P. aeruginosa* ΔmexAB-OprM | *P. aeruginosa* PA3 | *P. aeruginosa* PA8 |
|---|---|---|---|---|---|
| 35 | C | D | D | B | C |
| 36 | B | NT | NT | A | B |
| 37 | C | NT | NT | B | C |
| 38 | B | NT | NT | B | B |
| 39 | C | D | C | NT | NT |
| 40 | C | D | C | NT | NT |
| 41 | B | D | C | NT | NT |
| 42 | C | D | C | B | C |
| 43 | B | D | B | A | A |
| 44 | B | D | C | B | B |
| 45 | C | D | C | NT | NT |
| 46 | B | D | C | NT | NT |
| 47 | C | D | C | NT | NT |
| 48 | C | D | C | NT | NT |
| 49 | B | D | C | B | C |
| 50 | C | D | C | B | C |
| 51 | C | D | C | B | C |
| 52 | C | D | D | NT | NT |
| 53 | C | D | C | B | C |
| 54 | C | D | D | NT | NT |
| 55 | C | D | C | NT | NT |
| 56 | C | D | C | NT | NT |
| 57 | C | D | C | NT | NT |
| 58 | C | D | C | NT | NT |
| 59 | C | D | C | NT | NT |
| 60 | B | D | C | NT | NT |
| 61 | C | D | C | NT | NT |
| 62 | C | D | C | NT | NT |
| 63 | B | D | C | NT | NT |
| 64 | C | D | C | NT | NT |
| 65 | B | D | C | NT | NT |
| 66 | C | D | C | NT | NT |
| 67 | C | D | C | NT | NT |
| 68 | C | D | C | NT | NT |
| 69 | C | D | C | NT | NT |
| 70 | C | D | C | NT | NT |
| 71 | C | D | C | NT | NT |
| 72 | B | D | C | NT | NT |
| 73 | C | D | D | NT | NT |
| 74 | B | D | C | NT | NT |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

The invention claimed is:

1. A compound of Formula (IVa-1), or a pharmaceutically acceptable salt, solvate, or stereoisomer thereof:

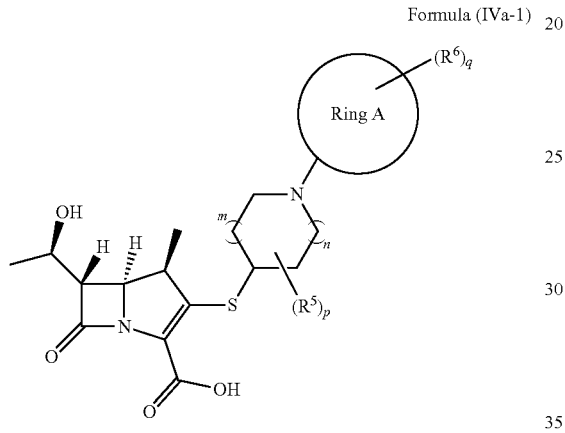

Formula (IVa-1)

wherein:
Ring A is cyclohexyl;
$R^5$ is hydrogen;
each $R^6$ is independently —$NR^{60}R^{61}$, —$NR^{60}(CR^{62}R^{63})_{w6}NR^{60}R^{61}$, —$NR^{60}C(=NR^{61})NR^{60}R^{61}$, —$C(=NR^{60})NR^{60}R^{61}$, —$C(=NR^{60})R^{60}$, —$N(R^{60})C(=NR^{61})R^{60}$, —$(CR^{62}R^{63})\ NR^{60}R^{61}$, —$C(=O)NR^{60}R^{61}$—$C(=O)(CR^{62}R^{63})_{v6}NR^{60}R^{61}$, —$(CR^{62}R^{63})\backslash N(R^{60})C(=NR^{61})NR^{60}R^{61}$, or
each $R^{60}$ and $R^{61}$ is independently selected from the group consisting of hydrogen and $C_1$-$C_6$ alkyl;
each $R^{62}$ and $R^{63}$ is independently selected from the group consisting of hydrogen, halogen, and $C_1$-$C_6$ alkyl;
v6 is 1 or 2:
w6 is 2;
n is 0 or 1;
m is 0 or 1;
p is 1; and
q is 1 or 2.

2. The compound of claim 1, wherein each $R^6$ is independently —$NR^{60}R^{61}$, —$NR^{60}(CR^{62}R^{63})_{w6}NR^{60}R^{61}$, —$NR^{60}C(=NR^{61})NR^{60}R^{61}$, —$C(=NR^{60})NR^{60}R^{61}$, —$N(R^{60})C(=NR^{61})R^{60}$, or —$(CR^{62}R^{63})_{v6}NR^{60}R^{61}$.

3. The compound of claim 2, wherein each $R^6$ is independently —$NR^{60}R^{61}$ or —$NR^{60}C(=NR^{61})NR^{60}R^{61}$.

4. The compound of claim 1, wherein q is 1.

5. The compound of claim 1, wherein n is 0 and m is 0 or 1.

6. The compound of claim 1, wherein n is 0 and m is 0.

7. The compound of claim 1, wherein n is 0 and m is 1.

8. The compound of claim 1, wherein p is 1.

9. A compound of Formula (IIa-1), or a pharmaceutically acceptable salt, solvate, or stereoisomer thereof:

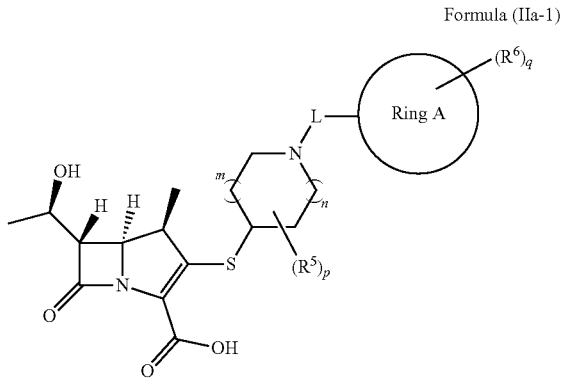

Formula (IIa-1)

wherein:
Ring A is cyclohexyl;
L is —$(CR^8R^9)_z$—;
each $R^8$ and $R^9$ are independently hydrogen or $C_1$-$C_6$ alkyl;
$R^5$ is hydrogen;
each $R^6$ is independently —$NR^{60}R^{61}$, —$NR^{60}(CR^{62}R^{63})_{w6}NR^{60}R^{61}$, —$NR^{60}C(=NR^{61})NR^{60}R^{61}$, —$C(=NR^{60})NR^{60}R^{61}$, —$C(=NR^{60})R^{60}$, —$N(R^{60})C(=NR^{61})R^{60}$, —$(CR^{62}R^{63})_{v6}NR^{60}R^{61}$, —$C(=O)NR^{60}R^{61}$, —$C(=O)(CR^{62}R^{63})_{v6}NR^{60}R^{61}$, —$(CR^{62}R^{63})_{v6}N(R^{60})C(=NR^{61})NR^{60}R^{61}$, or —$(CR^{62}R^{63})_{v6}C(=NR^{61})NR^{60}R^{61}$;
each $R^{60}$ and $R^{61}$ is independently selected from the group consisting of hydrogen and $C_1$-$C_6$ alkyl;
each $R^{62}$ and $R^{63}$ is independently selected from the group consisting of hydrogen, halogen, and $C_1$-$C_6$ alkyl;
v6 is 1 or 2;
w6 is 2;
n is 1;
m is 0 or 1;
p is 1;
q is 1 or 2; and
z is 1 or 2.

10. A compound of Formula (IIIa-1), or a pharmaceutically acceptable salt, solvate, or stereoisomer thereof:

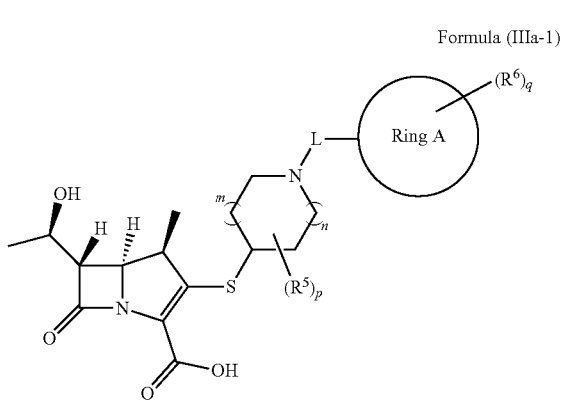

Formula (IIIa-1)

wherein:
Ring A is cyclohexyl;
L is —(CR$^8$R$^9$)$_z$—;
each R$^8$ and R$^9$ is independently hydrogen or C$_1$-C$_6$ alkyl;
R$^5$ is hydrogen;
each R$^6$ is independently —NR$^{60}$R$^{61}$, —NR$^{60}$(CR$^{62}$R$^{63}$)$_{w6}$NR$^{60}$R$^{61}$, —NR$^{60}$C(=NR$^{61}$)NR$^{60}$R$^{61}$, —C(=NR$^{60}$)NR$^{60}$R$^{61}$, —C(=NR$^{60}$) R$^{60}$, —N(R$^{60}$)C(=NR$^{61}$) R$^{60}$, —(CR$^{62}$R$^{63}$)$_{v6}$NR$^{60}$R$^{61}$, —C(=O)NR$^{60}$R$^{61}$, —C(=O)(CR$^{62}$R$^{63}$)$_{v6}$NR$^{60}$R$^{61}$, —(CR$^{62}$R$^{63}$)$_{v6}$N(R$^{60}$)C(=NR$^{61}$)NR$^{60}$R$^{61}$, or —(CR$^{62}$R$^{63}$)v6C(=NR$^{61}$)NR$^{60}$R$^{61}$;
each R$^{60}$ and R$^{61}$ is independently selected from the group consisting of hydrogen and C$_1$-C$_6$ alkyl;
each R$^{62}$ and R$^{63}$ is independently selected from the group consisting of hydrogen, halogen, and C$_1$-C$_6$ alkyl;
v6 is 1 or 2:
w6 is 2;
n is 0 or 1;
m is 0 or 1;
p is 1;
q is 1 or 2; and
z is 1 or 2.

11. A compound selected from the group consisting of:

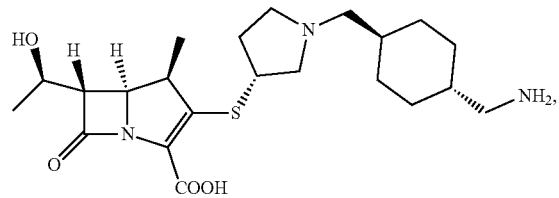

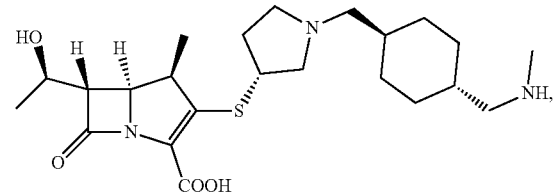

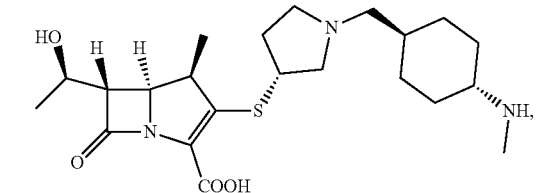

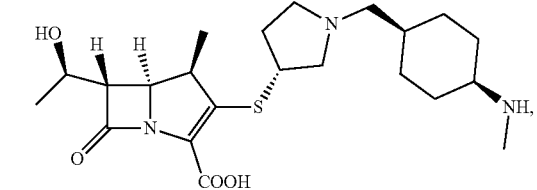

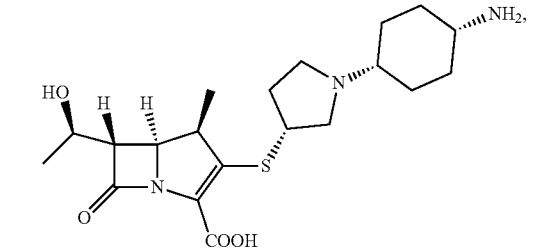

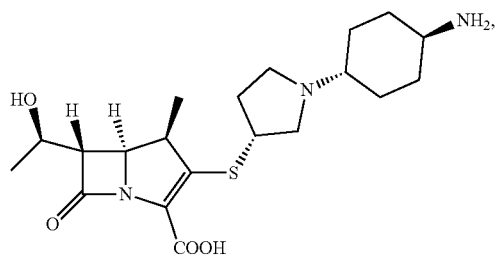

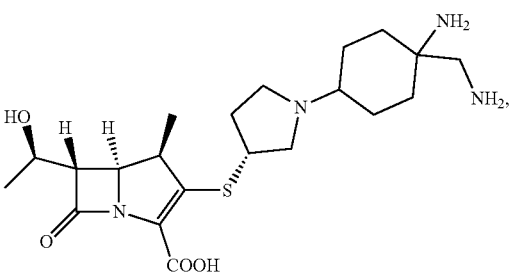

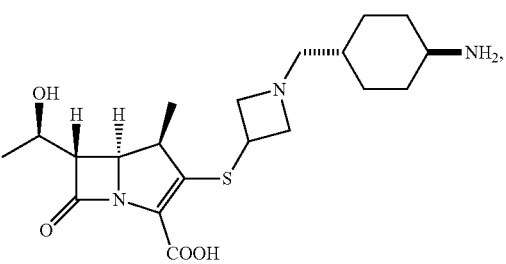

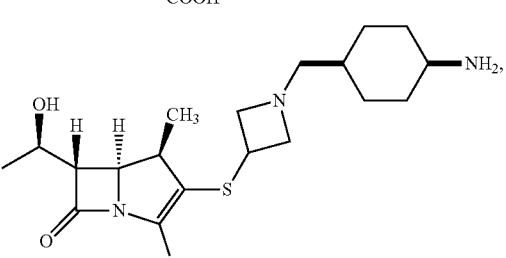

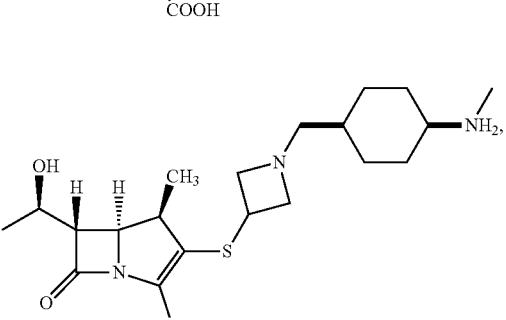

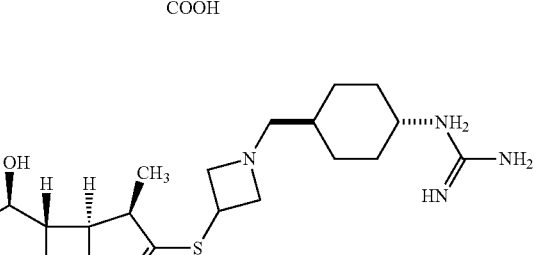

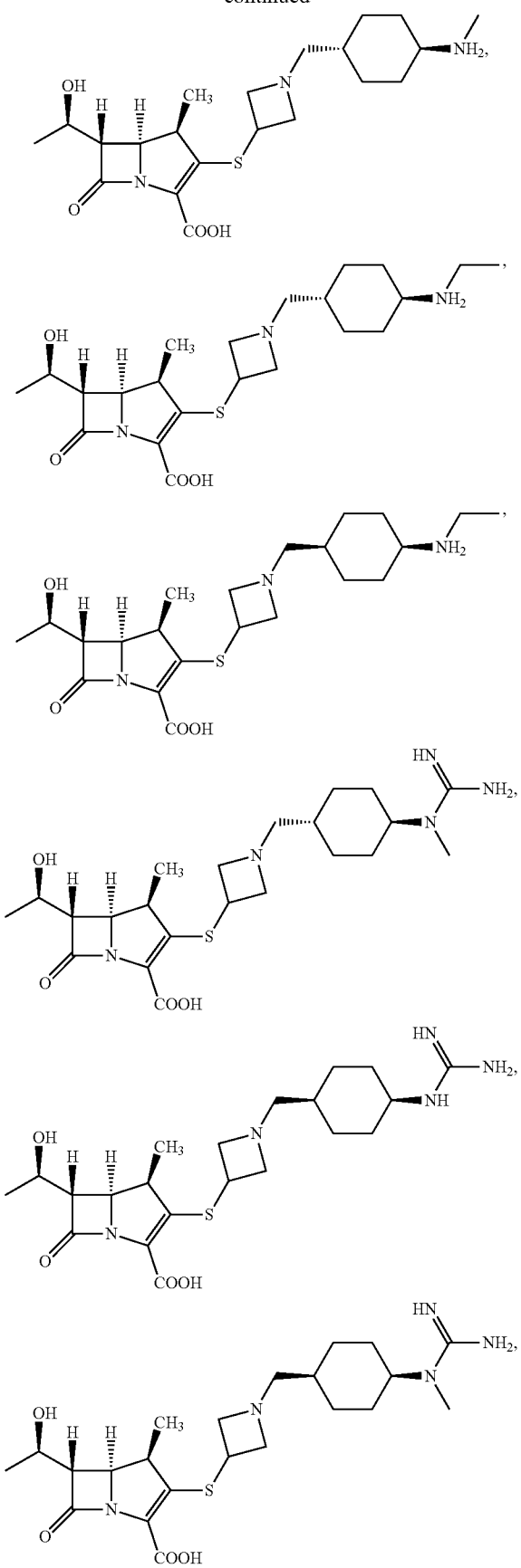
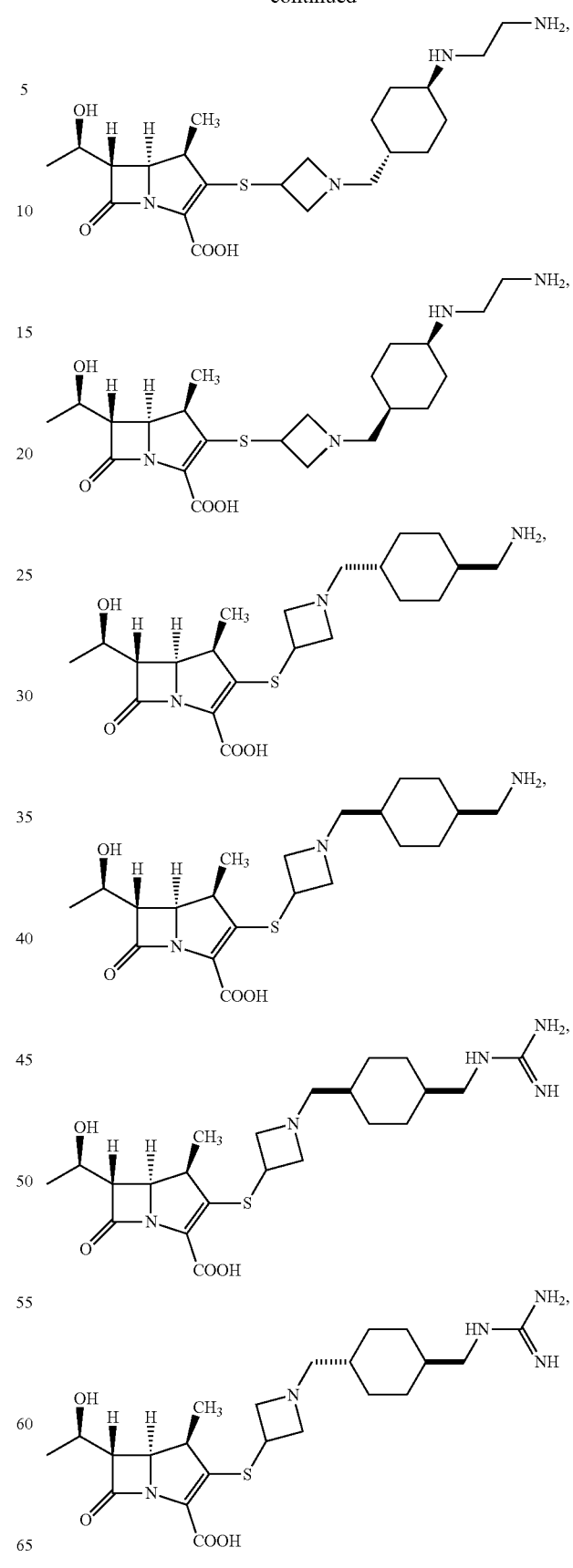

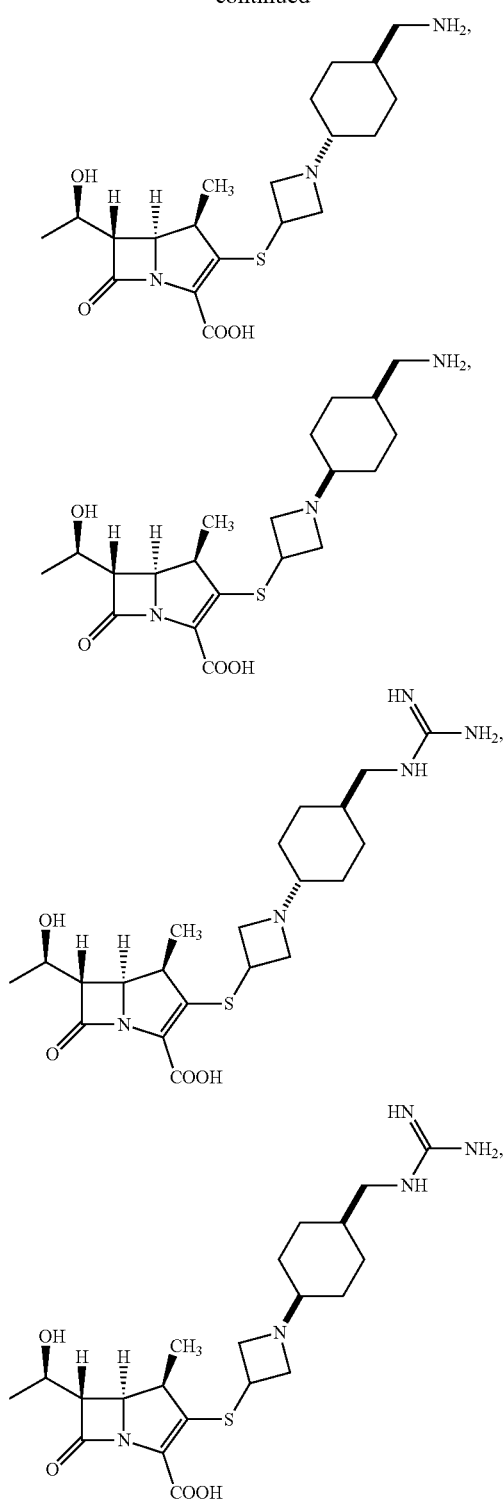
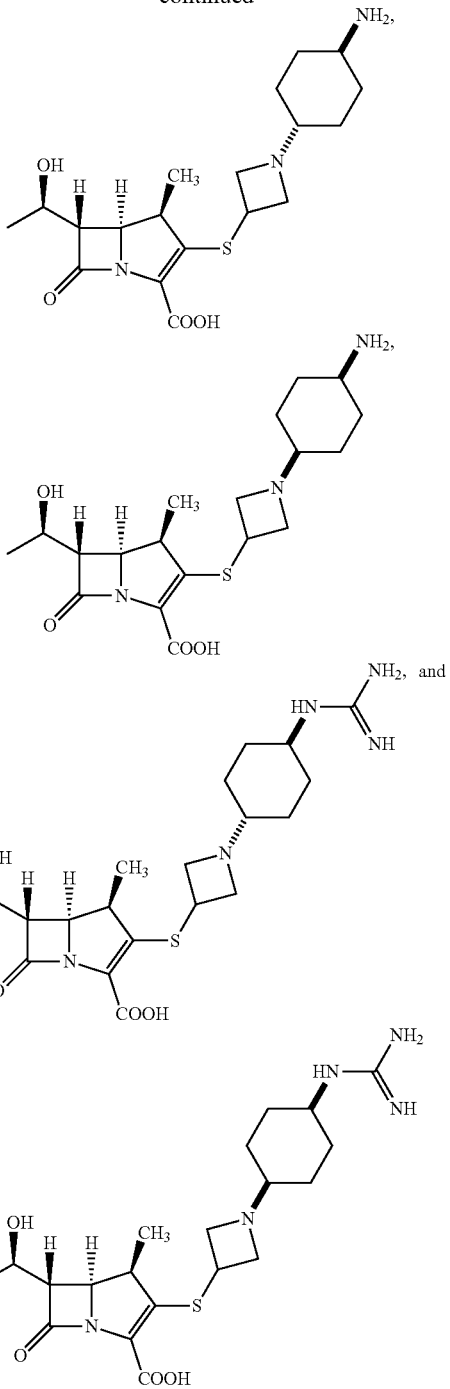
or a pharmaceutically acceptable salt, solvate, or stereoisomer thereof.
12. A pharmaceutical composition comprising a compound of claim 1, or a pharmaceutically acceptable salt, solvate, or stereoisomer thereof and a pharmaceutically acceptable excipient.
* * * * *

UNITED STATES PATENT AND TRADEMARK OFFICE
CERTIFICATE OF CORRECTION

PATENT NO. : 12,084,445 B2
APPLICATION NO. : 17/057594
DATED : September 10, 2024
INVENTOR(S) : Christopher J. Burns et al.

It is certified that error appears in the above-identified patent and that said Letters Patent is hereby corrected as shown below:

In the Claims

Column 177, Lines 40-45:
In Claim 1, replace: "each $R^6$ is independently —$NR^{60}R^{61}$, —$NR^{60}(CR^{62}R^{63})_{w6}NR^{60}R^{61}$, —$NR^{60}C(=NR^{61})NR^{60}R^{61}$, —$C(=NR^{60})NR^{60}R^{61}$, —$C(=NR^{60}) R^{60}$, —$N(R^{60})C(=NR^{61}) R^{60}$, —$(CR^{62}R^{63}) NR^{60}R^{61}$, —$C(=O)NR^{60}R^{61}$—$C(=O)(CR^{62}R^{63})_{v6}NR^{60}R^{61}$, —$(CR^{62}R^{63})\backslash N(R^{60})C(=NR^{61})NR^{60}R^{61}$, or" with --each $R^6$ is independently —$NR^{60}R^{61}$, —$NR^{60}(CR^{62}R^{63})_{w6}NR^{60}R^{61}$, —$NR^{60}C(=NR^{61})NR^{60}R^{61}$, —$C(=NR^{60})NR^{60}R^{61}$, —$C(=NR^{60})R^{60}$, —$N(R^{60})C(=NR^{61})R^{60}$, —$(CR^{62}R^{63})_{v6}NR^{60}R^{61}$, —$C(=O)NR^{60}R^{61}$,—$C(=O)(CR^{62}R^{63})_{v6}NR^{60}R^{61}$, —$(CR^{62}R^{63})_{v6}N(R^{60})C(=NR^{61})NR^{60}R^{61}$, or —$(CR^{62}R^{63})_{v6}C(=NR^{61})NR^{60}R^{61}$;--

Column 179, Line 12:
In Claim 10, replace: "—$(CR^{62}R^{63})v6C(=NR^{61})NR^{60}R^{61}$" with -- —$(CR^{62}R^{63})_{v6}C(=NR^{61})NR^{60}R^{61}$--

Column 180, Lines 44-54:
In Claim 11, replace: " 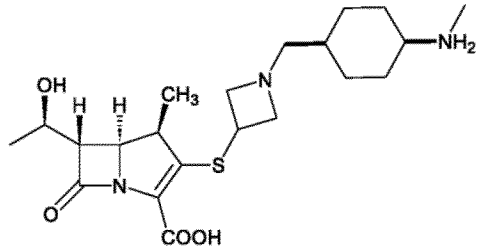 " with -- 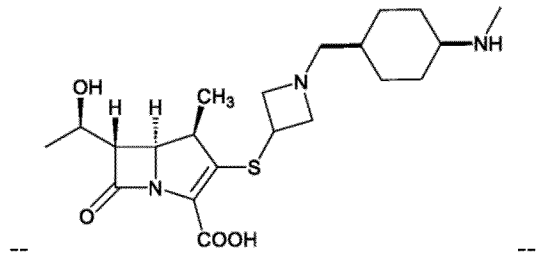 --

Signed and Sealed this
Twelfth Day of November, 2024

Katherine Kelly Vidal
*Director of the United States Patent and Trademark Office*

CERTIFICATE OF CORRECTION (continued)
U.S. Pat. No. 12,084,445 B2

Column 180, Lines 56-65:

In Claim 11, replace: " 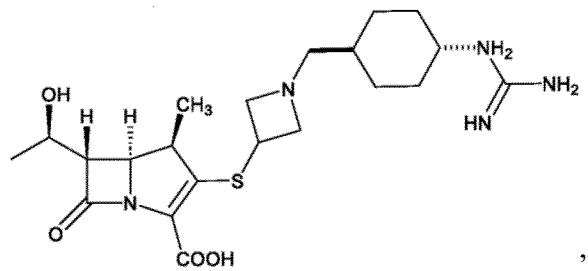 " with

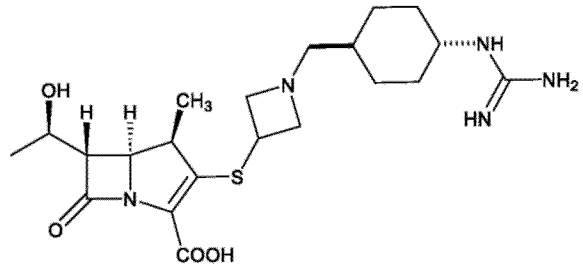

--                                   --

Column 181, Lines 1-11:

In Claim 11, replace: " 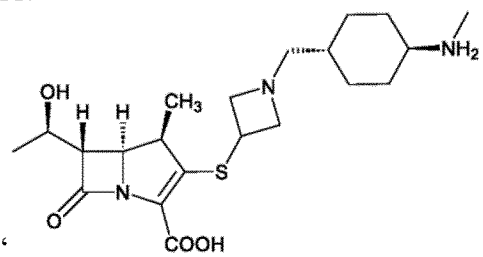 " with

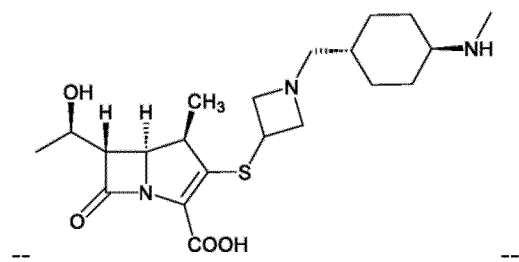

--                                   --

Column 181, Lines 12-21:

In Claim 11, replace: " 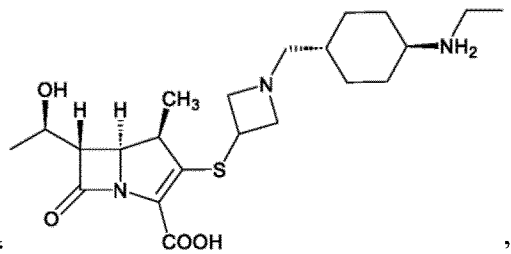 " with

CERTIFICATE OF CORRECTION (continued)
U.S. Pat. No. 12,084,445 B2

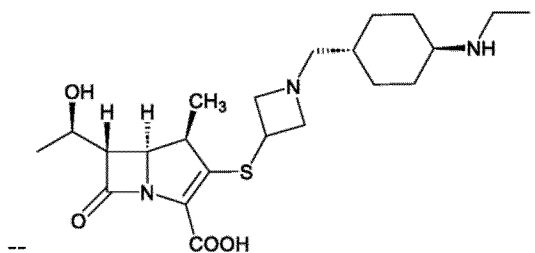

Column 181, Lines 22-32:

In Claim 11, replace: " 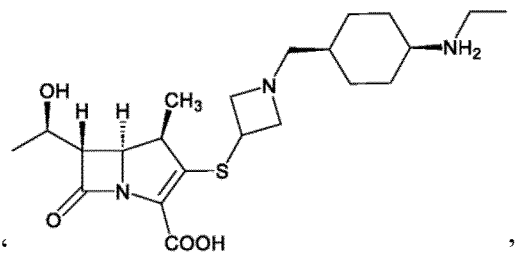 " with

" 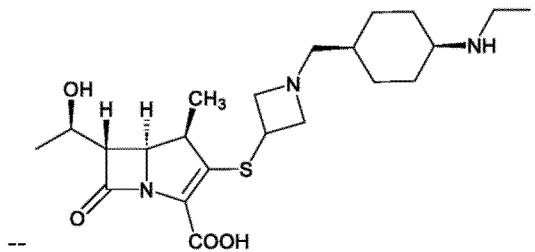 "